US010995149B2

(12) United States Patent
Chen et al.

(10) Patent No.: US 10,995,149 B2
(45) Date of Patent: May 4, 2021

(54) ANTIBODIES THAT SPECIFICALLY BIND PD-1 AND METHODS OF USE

(71) Applicant: Janssen Biotech, Inc., Horsham, PA (US)

(72) Inventors: Qiang Chen, San Diego, CA (US); Suzanne Cole, Spring House, PA (US); Karen Duffy, Spring House, PA (US); Yanxia Guo, Spring House, PA (US); Debra Gardner, Spring House, PA (US); Damon Hamel, San Diego, CA (US); Shannon Hitchcock, Spring House, PA (US); Ann Lacombe, San Diego, CA (US); Jinquan Luo, Spring House, PA (US); Ravi Malaviya, Spring House, PA (US); Yevgeniya Orlovsky, Spring House, PA (US); Pejman Soroosh, San Diego, CA (US); Melissa Swiecki, Spring House, PA (US); Deepti Wilkinson, San Diego, CA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 15/997,148

(22) Filed: Jun. 4, 2018

(65) Prior Publication Data

US 2018/0355061 A1 Dec. 13, 2018

Related U.S. Application Data

(60) Provisional application No. 62/673,185, filed on May 18, 2018, provisional application No. 62/648,114, filed on Mar. 26, 2018, provisional application No. 62/515,188, filed on Jun. 5, 2017.

(51) Int. Cl.
| | | |
|---|---|---|
| *C07K 16/40* | (2006.01) | |
| *A61P 37/06* | (2006.01) | |
| *C07K 16/06* | (2006.01) | |
| *A61K 39/395* | (2006.01) | |
| *C07K 16/18* | (2006.01) | |
| *C07K 16/28* | (2006.01) | |
| *A61K 39/00* | (2006.01) | |

(52) U.S. Cl.
CPC .......... *C07K 16/40* (2013.01); *A61K 39/3955* (2013.01); *A61P 37/06* (2018.01); *C07K 16/065* (2013.01); *C07K 16/18* (2013.01); *C07K 16/2818* (2013.01); *A61K 2039/505* (2013.01); *A61K 2039/57* (2013.01); *C07K 2317/24* (2013.01); *C07K 2317/33* (2013.01); *C07K 2317/73* (2013.01); *C07K 2317/732* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 5,225,539 | A | 7/1993 | Winter |
| 5,635,483 | A | 6/1997 | Pettit et al. |
| 5,780,588 | A | 7/1998 | Pettit et al. |
| 6,150,584 | A | 11/2000 | Kucherlapati et al. |
| 6,180,370 | B1 | 1/2001 | Queen et al. |
| 6,818,749 | B1 | 11/2004 | Kashmiri et al. |
| 7,709,226 | B2 | 5/2010 | Foote |
| 8,242,247 | B2 | 8/2012 | Klein et al. |
| 8,748,356 | B2 | 6/2014 | Raghunathan |
| 2007/0014796 | A1 | 1/2007 | Carr et al. |
| 2009/0182127 | A1 | 7/2009 | Kjaergaard et al. |
| 2010/0015133 | A1 | 1/2010 | Igawa et al. |
| 2010/0028637 | A1 | 2/2010 | Tavsanli et al. |
| 2010/0261620 | A1 | 10/2010 | Almagro et al. |
| 2011/0123532 | A1 | 5/2011 | Gurney et al. |
| 2012/0149876 | A1 | 6/2012 | Von Kreudenstein et al. |
| 2013/0195849 | A1 | 8/2013 | Spreter Von Kreudenstein et al. |
| 2014/0273092 | A1 | 9/2014 | Flikweert et al. |
| 2017/0015742 | A1 | 1/2017 | Gu et al. |
| 2017/0029530 | A1 | 2/2017 | Saunders et al. |

FOREIGN PATENT DOCUMENTS

| | | |
|---|---|---|
| WO | WO1988/01649 A1 | 3/1988 |
| WO | WO1990/04036 A1 | 4/1990 |
| WO | WO1990/007861 A1 | 7/1990 |
| WO | WO1992/01047 A1 | 1/1992 |
| WO | WO1992/22653 A1 | 12/1992 |
| WO | WO1994/13804 A1 | 6/1994 |
| WO | WO1998/44001 A1 | 10/1998 |
| WO | WO1999/45962 A1 | 9/1999 |
| WO | WO2002/066630 A1 | 2/2001 |
| WO | WO2002/43478 A2 | 11/2001 |

(Continued)

OTHER PUBLICATIONS

Mariuzza, R.A. etal. The Structural Basis of Antigen-Antibody Recognition1 Annu. Rev. Biophys. Biphys. Chem. 16:139-159, 1987.*
MacCallum et al. "Antibody-antigen interactions: contact analysis and binding site topography", Journal of Molecular Biology, 1996. vol. 262, pp. 732-745.*

(Continued)

*Primary Examiner* — Nora M Rooney
(74) *Attorney, Agent, or Firm* — Eric Dichter

(57) ABSTRACT

Antibodies that specifically bind PD-1 or antigen binding fragments thereof, polynucleotides encoding the antibodies or fragments, and methods of making and using the foregoing are useful in the treatment of an inflammatory or immune disorder.

19 Claims, 28 Drawing Sheets

Specification includes a Sequence Listing.

(56) References Cited

FOREIGN PATENT DOCUMENTS

| WO | WO02/088172 A2 | 11/2002 |
| --- | --- | --- |
| WO | WO2008/077546 A1 | 7/2008 |
| WO | WO2009/018386 A1 | 2/2009 |
| WO | WO2009/080251 A1 | 7/2009 |
| WO | WO2009/080252 A1 | 7/2009 |
| WO | WO2009/080254 A1 | 7/2009 |
| WO | WO2009/085462 A1 | 7/2009 |
| WO | WO2011/131746 A2 | 10/2011 |
| WO | WO 2015/058573 A1 | 4/2014 |
| WO | WO 2015/148984 A2 | 10/2015 |

OTHER PUBLICATIONS

De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*

Goel et al. Plasticity within the Antigen-Combining Site May Manifest as Molecular Mimicry in the Humoral Immune Response.1 J. Immunol. 173(12)7358-7367, 2004.*

Kahn et al. 'Adjustable Locks and Flexible Keys: Plasticity of Epitope-Paratope Interactions in Germline Antibodies.' J. Immunol. 192:5398-5405, 2014.*

Poosarla et al. 'Computational De Novo Design of Antibodies Binding to a Peptide With High Affinity.' Biotech. Bioeng. 114(6): 1331-1342, 2017.*

Baert et al., "Influence of Immunogenicity on the Long-Term Efficacy of Infliximab in Crohn's Disease," New England Journal of Medicine, 348: 602-608 (2003).

Bedu-Addo et al., "Use of Biophysical Characterization in Preformulation Development of a Heavy-Chain Fragment of Botulinum Serotype B: Evaluation of Suitable Purification Process Conditions," Pharmaceutical Research, 21(8): 1353-1361 (2004).

Cai et al., "C-Terminal Lysine Processing of Human Immunoglobulin G2 Heavy Chain In Vivo," Biotechnology and Bioengineering, 108: 404-412 (2011).

Chothia et al., "Canonical Structures for the Hypervariable Regions of Immunoglobulins," Journal of Molecular Bioogy, 126: 901-917 (1987).

Felson et al. "American College of Rheumatology Preliminary Definition of Improvement in Rheumatoid Arthritis," Arthritis & Rheumatology 38: 727-735 (1995).

Ferrara et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi α-mannosidase II," Biotechnology and Bioengineering, 93(5): 851-861 (2006).

Ferrara et al., "The Carbohydrate at FcγRIIIa Asn-162" The Journal of Biological Chemistry, 281(8): 5032-5036 (2006).

Gupta et al., Development of a Multidose Formulation for a Humanized Monoclonal Antibody Using Experimental Design Techniques, AAPS PharmSci, 5(2): 1-9 (2003).

He et al., "Circulating Precursor CCR7$^{lo}$PD-1$^{hi}$ CXCR5$^+$ CD4$^+$ T Cells Indicate Tfh Cell Activity and Promote Antibody Responses upon Antigen Reexposure," Immunity, 39: 770-781 (2013).

Honda et al., "Tuning of Antigen Sensitivity by T Cell Receptor-Dependent Negative Feedback Controls T Cell Effector Function in Inflamed Tissues," Immunity, 40(2):235-247 (2014).

Honegger, et al., "Yet Another Numbering Scheme for Immunoglobulin Variable Domains: An Automatic Modeling and Analysis Tool," Journal of Molecular Biology, 309: 657-670 (2001).

Knappik et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2000).

Kobayashi et al., Enhanced Expression of Programmed Death-1 (PD-1)/PD-L1 in Salivary Glands of Patients with Sjogren's Syndrome, Journal of Rheumatology, 32(11): 2156-2163 (2005).

Konno et al., "Fucose content of monoclonal antibodies can be controlled by culture medium osmolality for high-antibody-dependent cellular cytotoxicity," Cytotechnology 64: 249-265 (2012).

Lefranc et al., "IMGT unique numbering for immunologlobulin and T cell receptor variable domains and Ig superfamily V-like domains," Developmental & Comparative Immunology, 27: 55-77 (2003).

Maa et al., "Aggregation of recombinant human growth hormone induced by phenolic compounds," International Journal of Pharmaceutics, 140: 155-168 (1996).

MacLennan et al., "Structure-Function Relationships in the Ca$^{2+}$-Binding and Translocation Domain of SERCA1: physiological correlates in Brody disease," Acta Physiol. Scan. 163, Suppl. 643: 55-67 (1998).

Martin, et al., "Structural Families in Loops of Homologous Proteins: Automatic Classification, Modelling and Application to Antibodies," Journal of Molecular Biology, 263: 800-815 (1996).

Mori et al., "Engineering Chinese Hamster Ovary Cells to Maximize Effector Function of Produced Antibodies Using FUT8 siRNA," Biotechnology and Bioengineering, 88(7): 901-908 (2004).

Needleman, et al., "A General Method Applicable for the Search for Similarities In the Amino Acid Sequence of Two Proteins," Journal of Molecular Biology, 48: 443-453 (1970).

Nishimura, et al., "Development of Lupus-like Autoimmune Diseases by Disruption of the PD-1 Gene Encoding and ITIM Motif-Carrying Immunoreceptor," Immunity, 11: 141-151 (1999).

Olivier et al., "EB66 cell line, a duck embryonic stem cell-derived substrate for the industrial production of therapeutic monoclonal antibodies with enhanced ADCC activity," mAbs 2(4): 405-415 (2010).

Padlan, et al., "A Possible Procedure for Reducing the Immunogenicity of Antibody Variable Domains While Preserving Their Ligand-Binding Properties," Molecular Immunology, 28(4/5): 489-498 (1991).

Pauken, et al., "Overcoming T cell exhaustion in infection and cancer," Trends in Immunology, 36(4): 265-276 (2015).

Rao et al., "Pathologically expanded peripheral T helper cell subset drives B cells in rheumatoid arthritis," Nature, 542: 110-114 (2017).

Remmele et al., "Interleukin-1 Receptor (IL-1R) Liquid Formulation Development Using Differential Scanning Calorimetry," Pharmaceutical Research, 15(2): 200-208 (1997).

Remmele et al., Differential Scanning Calorimetry A Practical Tool for Elucidating Stability of Liquid Biopharmaceuticals, *Biopharm*, 13:36-46 (2000).

Sasaki et al., "Structure-Mutation Analysis of the ATPase Site of *Dictyostelium Discoidum* Myosin II," Adv Biophys., 35:1-24 (1988).

Shi et al., "De Novo Selection of High-Affinity Antibodies from Synthetic Fab Libraries Displayed on Phage as pIX Fusion Proteins," Journal of Molecular Biology, 397: 385-396 (2010).

Shields et al., "High Resolution Mapping of the Binding Site on Human IgG1 for FcγRI, FcγRII, FcγRIII and FcRn and Design of IgG1 Variants with Improved Binding to the FcγR," The Journal of Biological Chemistry, 277:26733-26740 (2002).

Shinkawa, et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular cytotoxicity," The Journal of Biological Chemistry, 278(5): 3466-3473 (2003).

Stickler et al., "The human G1m1 allotype associates with CD4+ T-cell responsiveness to a highly conserved IgG1 constant region peptide and confers an asparaginyl endopeptidase cleavage site," Genes and Immunity, 12: 213-221 (2011).

Tornetta, et al., "Antibody Fab display and selection through fusion to the pIX coat protein of filamentous phage," Journal of Immunological Methods, 360: 39-46 (2010).

van Gestel, et al., "Development and Validation of the European League Against Rheumatism Response Criteria for Rheumatoid Arthritis," Arthritis & Rheumatism 39(1): 34-40 (1996).

Verstappen, et al., "Attenuation of Follicular Helper T Cell-Dependent B Cell Hyperactivity by Abatacept Treatment in Primary Sjogren's Syndrome," Arthritis & Rheumatology, 69(9): 1850-1861 (2017).

Wan, et al., "Aberrant Regulation of Synovial T Cell Activation by Soluble Costimulatory Molecules in Rheumatoid Arthritis," Journal of Immunology, 177(12):8844-8850 (2006).

(56) References Cited

OTHER PUBLICATIONS

Worn, et al., "Stability Engineering of Antibody Single-chain Fv Fragments," Journal of Molecular Biology, 305:989-1010 (2001).
Woyke et al., "In Vitro Activities and Postantifungal Effects of the Potent Dolastatin 10 Derivative Auristatin PHE," Antimicrobial Agents and Chemotherapy, 45(12): 3580-3584 (2001).
Zhou et al., "Development of A Simple and Rapid Method for Producing Non-Fucosylated Oligonamannose Containing Antibodies With Increased Effector Function," Biotechnology and Bioengineering, 99:652-665 (2008).
Zamani et al., "PD-1/PD-L and autoimmunity: A growing relationship," Cellular Immunology, 310: 27-41 (2016).
Zhang et al., "Mechanism for Benzyl Alcohol-Induced Aggregation of Recombinant Human Interleukin-1 Receptor Antagonist in Aqueous Solution," Journal of Pharmaceutical Science, 93(12): 3076-3089 (2004).

* cited by examiner

Figure 2A.

```
                            1
PD1H93_8        DVQLQESGPELKKPGETVKISCKASGYTFT
PD1H384_9       QVQLVQSGSELKKPGASVKVSCKASGYTFT
PD1H405_10      QVQLVQSGSELKKPGASVKVSCKASGYTFT
PD1H585_140     QVQLVQSGSELKKPGASVKVSCKASGYTFT
PD1H586_141     QVQLVQSGSELKKPGASVKVSCKASGYTFT
PD1H587_142     QVQLVQSGSELKKPGASVKVSCKASGYTFT
                :***  :**.******  :**:**********

PD1H93_8        DYSMHWVKQAPGKGLKWMGWINIETGEPTY
PD1H384_9       DYSMHWVRQAPGQGLEWMGWINIETGEPTY
PD1H405_10      DYSMHWVRQAPGQGLEWMGWINIETGEPTY
PD1H585_140     DYSMHWVRQAPGQGLEWMGWINIETGYPTY
PD1H586_141     DYSMHWVRQAPGQGLEWMGWINIETGHPTY
PD1H587_142     DYSMHWVRQAPGQGLEWMGWINIETGWPTY
                *******:****:**:********** ***

PD1H93_8        ADDFKGRFAFSLETSASTAYLQINNLKNED
PD1H384_9       AQGFTGRFVFSLDTSVSTAYLQICSLKAED
PD1H405_10      AQGFTGRFVFSLDTSVSTAYLQISSLKAED
PD1H585_140     AQGFTGRFVFSLDTSVSTAYLQISSLKAED
PD1H586_141     AQGFTGRFVFSLDTSVSTAYLQISSLKAED
PD1H587_142     AQGFTGRFVFSLDTSVSTAYLQISSLKAED
                *:.*.***.***:**.*******.**.**

121
PD1H93_8        TATYFCARDYYGTYFYAMDYWGQGTTLTVSS
PD1H384_9       TAVYFCARDYYGTYFYAMDYWGQGTLVTVSS
PD1H405_10      TAVYFCARDYYGTYFYAMDYWGQGTLVTVSS
PD1H585_140     TAVYFCARDYYGTYFYAMDYWGQGTLVTVSS
PD1H586_141     TAVYFCARDYYGTYFYAMDYWGQGTLVTVSS
PD1H587_142     TAVYFCARDYYGTYFYAMDYWGQGTLVTVSS
                **.*********************** :****
```

Figure 2B.

```
                    1
PD1L30_14      QIVLTQSPAIMSASLGERVTMTCTASSSVS
PD1L468_15     EIVLTQSPATLSLSPGERATLSCTASSSVS
PD1L469_16     EIVLTQSPATLSLSPGERATLSCTASSSVS
PD1L651_143    EIVLTQSPATLSLSPGERATLSCTASSSFS
PD1L652_144    EIVLTQSPATLSLSPGERATLSCTASSSVP
               :********  :*  *  ***.*::******..

PD1L30_14      SSYLHWYQQKPGSSPKLWIYSTSNLASGVP
PD1L468_15     SSYLHWYQQKPGLAPRLLIYSTSNLASGIP
PD1L469_16     SSYLHWYQQKPGLAPRLLIYSTSNLASGIP
PD1L651_143    SSYLHWYQQKPGLAPRLLIYSTSNLASGIP
PD1L652_144    SSYLHWYQQKPGLAPRLLIYSTSNLASGIP
               ************ :*:*  **********:*

PD1L30_14      ARFSGSGSGTSYSLTISSMEAEDAATYYCH
PD1L468_15     DRFSGSGSGTDFTLTISRLEPEDFAVYYCH
PD1L469_16     DRFSGSGSGTDYTLTISRLEPEDFAVYYCH
PD1L651_143    DRFSGSGSGTDYTLTISRLEPEDFAVYYCH
PD1L652_144    DRFSGSGSGTDYTLTISRLEPEDFAVYYCH
               *********.::****  :*.**  *.****

108
PD1L30_14      QYHRSPLTFGAGTKLELK
PD1L468_15     QYHRSPLTFGQGTKLEIK
PD1L469_16     QYHRSPLTFGQGTKLEIK
PD1L651_143    QYHRSPLTFGQGTKLEIK
PD1L652_144    QYHRSPLTFGQGTKLEIK
               ********** *****:*
```

Figure 3A.

```
                         1
PD1H90      QVQLQQPGAELVKPGASVKLSCKASGYTFT
PD1H388     QVQLVQSGAEVKKPGASVKVSCKASGYTFT
PD1H399     QVQLVQSGAEVKKPGASVKVSCKASGYTFT
PD1H400     QVQLVQSGAEVKKPGASVKVSCKASGYTFT
PD1H401     QVQLVQSGAEVKKPGASVKVSCKASGYTFT
PD1H402     QVQLVQSGAEVKKPGASVKVSCKASGYTFT
PD1H403     QVQLVQSGAEVKKPGASVKVSCKASGYTFT
PD1H404     QVQLVQSGAEVKKPGASVKVSCKASGYTFT
            **** *.***: *******:**********

PD1H90      TYWMHWVKQRPGQGLEWIGEINPNNGGINY
PD1H388     TYWMHWVRQAPGQGLEWMGEINPNNGGINY
PD1H399     TYWMHWVRQAPGQGLEWMGEINPNNAGINY
PD1H400     TYWMHWVRQAPGQGLEWMGEINPNDAGINY
PD1H401     TYWMHWVRQAPGQGLEWMGEINPNQGGINY
PD1H402     TYWMHWVRQAPGQGLEWMGEINPNKGGINY
PD1H403     TYWMHWVRQAPGQGLEWMGEINPNEGGINY
PD1H404     TYWMHWVRQAPGQGLEWMGEINPNNIGINY
            *******:* *******:******. ****

PD1H90      NEKFKKKATLTVDKSSSTAYMQLSSLTSED
PD1H388     AQKFQGRVTLTVDKSISTAYMELSRLRSDD
PD1H399     AQKFQGRVTLTVDKSISTAYMELSRLRSDD
PD1H400     AQKFQGRVTLTVDKSISTAYMELSRLRSDD
PD1H401     AQKFQGRVTLTVDKSISTAYMELSRLRSDD
PD1H402     AQKFQGRVTLTVDKSISTAYMELSRLRSDD
PD1H403     AQKFQGRVTLTVDKSISTAYMELSRLRSDD
PD1H404     AQKFQGRVTLTVDKSISTAYMELSRLRSDD
            :**: :.******* ****:** * *:*

117
PD1H90      SAVYYCTIDYYDYGGYWGQGTTLTVSS
PD1H388     TAVYYCTIDYYDYGGYWGQGTLVTVSS
PD1H399     TAVYYCTIDYYDYGGYWGQGTLVTVSS
PD1H400     TAVYYCTIDYYDYGGYWGQGTLVTVSS
PD1H401     TAVYYCTIDYYDYGGYWGQGTLVTVSS
PD1H402     TAVYYCTIDYYDYGGYWGQGTLVTVSS
PD1H403     TAVYYCTIDYYDYGGYWGQGTLVTVSS
PD1H404     TAVYYCTIDYYDYGGYWGQGTLVTVSS
            :******************* :****
```

Figure 3B.

```
                    1
PD1L28     DIVMTQSQKFMSTSVRDRVSVTCKASQNVG
PD1L470    DIQMTQSPSSLSASVGDRVTITCKASQNVG
PD1L471    DIQMTQSPSSLSASVGDRVTITCKASQNVG
           **  ****  .  :*:**  ***::*********

PD1L28     TNVAWYQQKPGQSPKALIYSASYRYSGVPD
PD1L470    TNVAWYQQKPEKAPKSLIYSASYRYSGVPS
PD1L471    TNVAWYQQKPEKAPKALIYSASYRYSGVPS
           *********   ::**:*************.

PD1L28     RFTGSGSGTDFTLTITNVQSEDLAEYFCQQ
PD1L470    RFSGSGSGTDFTLTISSLQPEDFATYYCQQ
PD1L471    RFSGSGSGTDFTLTISSLQPEDFATYFCQQ
           **:*************:..:*.**:*  *:***

107
PD1L28     YNIYPYTFGSGTKLEMK
PD1L470    YNIYPYTFGQGTKLEIK
PD1L471    YNIYPYTFGQGTKLEIK
           *********.*****:*
```

Figure 4A.

```
            1
PD1H81      QVTLKESGPGLLQPSQTLSLTCSFSGFSLS
PD1H389     QITLKESGPTLVKPTQTLTLTCTFSGFSLS
            *:******* *::*:***:***:*******

PD1H81      TSGMGVSWIRQPSGKGLEWLAHIYWDDDKR
PD1H389     TSGMGVSWIRQPPGKALEWLAHIYWDDDKR
            ************.**.*************

PD1H81      YNPSLKSRLTISKDTSSNQVFLKITSVDTA
PD1H389     YSPSLKSRLTITKDTSKNQVVLTMTNMDPV
            *.*********:****.***.*.:*.:*..

122
PD1H81      DTGTYYCVRKGYYDYGYVMDYWGQGTTVTVSS
PD1H389     DTGTYYCVRKGYYDYGYVMDYWGQGTLVTVSS
            ************************** *****
```

Figure 4B.

```
                  1
PD1L43      DIVMTQAALSNPVTLGTSASISCRSSKSLL
PD1L472     DIVMTQSPLSLPVTPGEPASISCRSSKSLL
PD1L473     DIVMTQSPLSLPVTPGEPASISCRSSKSLL
            ******:.** *** * .************

PD1L43      HSNGITYLNWYLQKPGQSPQLLIYQMSNLA
PD1L472     HSNGITYLNWYLQKPGQSPQLLIYQMSNLA
PD1L473     HSNGITYLNWYLQKPGQSPQLLIYQMSNLA
            ******************************

PD1L43      SGVPDRFSSSGSGTDFTLRISRVEAEDVGV
PD1L472     SGVPDRFSGSGSGTDFTLKISRVEAEDVGV
PD1L473     SGVPDRFSSSGSGTDFTLKISRVEAEDVGV
            *******.********:************

112
PD1L43      YYCAQNLELPLTFGSGTKLEMK
PD1L472     YYCAQNLELPLTFGGGTKVEIK
PD1L473     YYCAQNLELPLTFGGGTKVEIK
            *************.***:*:*
```

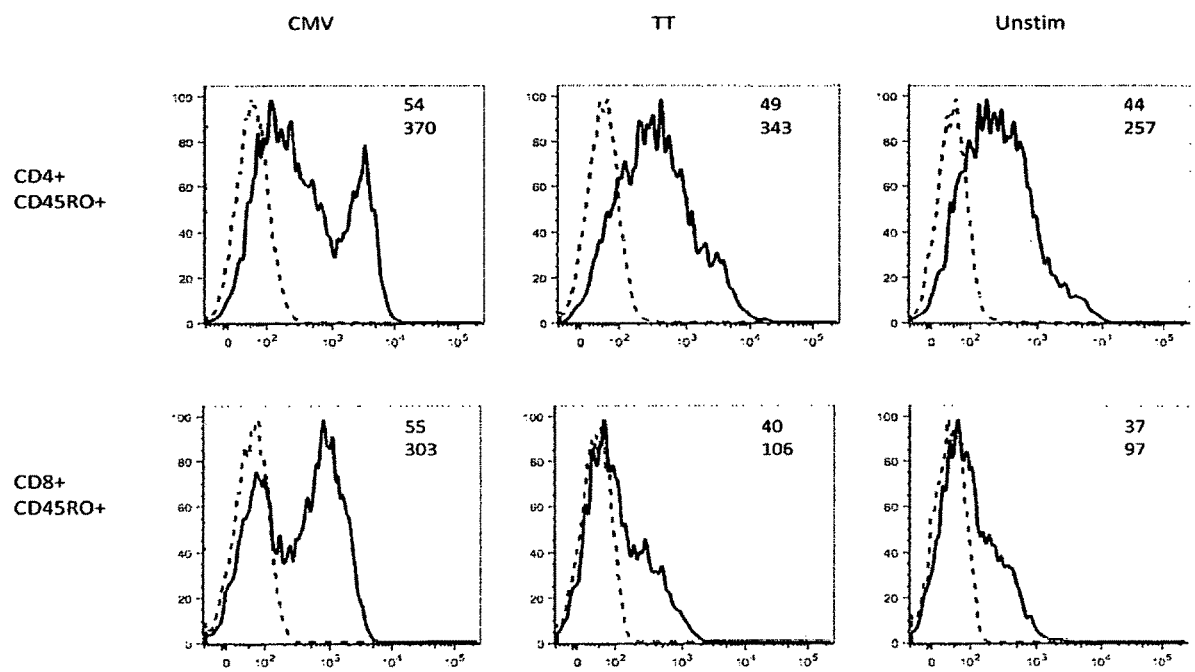

SEQUENCE LISTING

```
<160> NUMBER OF SEQ ID NOS: 166

<210> SEQ ID NO 1
<211> LENGTH: 150
<212> TYPE: PRT
<213> ORGANISM: Homo sapiens

<400> SEQUENCE: 1

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 2

Gly Tyr Thr Phe Thr Asp Tyr Ser Met His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Trp Ile Asn Ile Glu Thr Gly Glu Pro Thr
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Tyr Tyr Gly Thr Tyr Phe Tyr Ala Met Asp Tyr
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ala Ser Ser Ser Val Ser Ser Tyr Leu His
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Thr Ser Asn Leu Ala Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Gln Tyr His Arg Ser Pro Leu Thr
1               5

<210> SEQ ID NO 8

<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

Asp Val Gln Leu Gln Glu Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Ile Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Tyr Tyr Gly Thr Tyr Phe Tyr Ala Met Asp Tyr Trp Gly
            100                 105                 110

Gln Gly Thr Thr Leu Thr Val Ser Ser
        115                 120

<210> SEQ ID NO 9
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Phe Cys
                85                  90                  95

Ala Arg Asp Tyr Tyr Gly Thr Tyr Phe Tyr Ala Met Asp Tyr Trp Gly
            100                 105                 110

Gln Gly Thr Leu Val Thr Val Ser Ser
        115                 120

<210> SEQ ID NO 10
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

-continued

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Tyr Tyr Gly Thr Tyr Phe Tyr Ala Met Asp Tyr Trp Gly
            100                 105                 110

Gln Gly Thr Leu Val Thr Val Ser Ser
            115                 120
```

<210> SEQ ID NO 11
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
gatgtacagc ttcaggagtc aggacctgag ctgaagaagc ctggagagac agtcaagatc      60
tcctgcaagg cttctggtta taccttcaca gactattcaa tgcactgggt gaagcaggct     120
ccaggaaagg gtttaaagtg gatgggctgg ataaacattg agactggtga gccaacatat     180
gcagatgact tcaagggacg gtttgccttc tctttggaaa cctctgccag cactgcctat     240
ttgcagatca acaacctcaa aaatgaggac acggctacat atttctgtgc tagagattac     300
tacggtactt acttctatgc tatggactac tggggtcaag gcaccactct cacagtctcc     360
tca                                                                    363
```

<210> SEQ ID NO 12
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
caggtgcagc tggtgcagtc tggaagcgaa ctgaagaaac ctggagcctc tgtgaaagtg      60
tcttgtaagg ccagcggcta caccttcacc gactacagca tgcactgggt gcggcaggcc     120
cctggacagg gcctggaatg gatgggctgg atcaacatcg agaccggcga gcccacctac     180
gcccagggct taccggacg gttcgtgttc agcctggata catctgtgtc tacagcctat     240
ctgcagatct gctctctgaa ggccgaagat acagccgtgt acttctgcgc ccgggactac     300
tacggcacct acttctacgc catggactac tggggccagg gaacactggt gacagtgtct     360
tct                                                                    363
```

<210> SEQ ID NO 13
<211> LENGTH: 363
<212> TYPE: DNA
<213> ORGANISM: Artificial Sequence -continued
<220> FEATURE:
<223> OTHER INFORMATION: Description of Artificial Sequence: Synthetic
      polynucleotide

<400> SEQUENCE: 13

| | | |
|---|---|---|
| caagtgcagc tggtgcagtc tggcagcgag ctgaaaaaac ctggcgcctc cgtgaaggtg | 60 |
| tcctgcaagg ctagcggcta cacctttacc gactacagca tgcactgggt ccgacaggct | 120 |
| ccaggacaag gcttggaatg gatgggctgg atcaacatcg agacaggcga gcccacatac | 180 |
| gcccagggct ttaccggcag attcgtgttc agcctggaca cctctgtgtc caccgcctac | 240 |
| ctgcagatca gctctctgaa ggccgaggat accgccgtgt acttctgcgc cagagactac | 300 |
| tacggcaccct acttctacgc catggattac tggggccagg gcaccctggt taccgtttct | 360 |
| tct | 363 |

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
                20                  25                  30

Tyr Leu His Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Leu Thr Phe Gly Ala Gly Thr Lys Leu Glu Leu Lys
            100                 105
```

<210> SEQ ID NO 15
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Ser Ser Ser
                20                  25                  30

Tyr Leu His Trp Tyr Gln Gln Lys Pro Gly Leu Ala Pro Arg Leu Leu
            35                  40                  45

Ile Tyr Ser Thr Ser Asn Leu Ala Ser Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Pro
```

```
                85                  90                  95
Leu Thr Phe Gly Gln Gly Thr Lys Leu Glu Ile Lys
            100                 105

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Ser Ser Ser
            20                  25                  30

Tyr Leu His Trp Tyr Gln Gln Lys Pro Gly Leu Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Tyr Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Leu Thr Phe Gly Gln Gly Thr Lys Leu Glu Ile Lys
            100                 105

<210> SEQ ID NO 17
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
caaattgttc tcacccagtc tccagcaatc atgtctgcat ctctagggga acgggtcacc    60
atgacctgca ctgccagctc aagtgtaagt tccagttact tgcactggta ccagcagaag   120
ccaggatcct cccccaaact ctggatttat agcacatcca acctggcttc tggagtccca   180
gctcgcttca gtggcagtgg gtctgggacc tcttactctc tcacaatcag cagcatggag   240
gctgaagatg ctgccactta ttactgccac cagtatcatc gttccccgct cacgttcggt   300
gctgggacca agctggagct gaaa                                          324

<210> SEQ ID NO 18
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gagatcgtgc tgacacagtc tcctgccaca ctgtctctgt ctcctggaga acgggccaca    60
ctgagctgca ccgccagcag cagcgtgagc agcagctacc tgcactggta ccagcagaaa   120
cctggactgg cccctcggct gctgatctac agcaccagca acctggccag cggcatccct   180
gatcggtttt ctggcagcgg atctggcaca gattttacac tgaccatcag ccggctggaa   240
```

```
cctgaggatt tgccgtgta ctactgccac cagtaccacc ggagccccct gaccttcggc    300
cagggaacaa agctggaaat caag                                         324
```

<210> SEQ ID NO 19
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
gagatcgtgc tgacacagtc tcctgccaca ctgtctctgt ctcctggaga acgggccaca     60
ctgagctgca ccgccagcag cagcgtgagc agcagctacc tgcactggta ccagcagaaa    120
cctggactgg cccctcggct gctgatctac agcaccagca acctggccag cggcatccct    180
gatcggtttt ctggcagcgg atctggcaca gattacacac tgaccatcag ccggctggaa    240
cctgaggatt tgccgtgta ctactgccac cagtaccacc ggagccccct gaccttcggc    300
cagggaacaa agctggaaat caag                                         324
```

<210> SEQ ID NO 20
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Val Gln Leu Gln Glu Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Ile Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Tyr Tyr Gly Thr Tyr Phe Tyr Ala Met Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450

<210> SEQ ID NO 21
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Phe Cys
                85                  90                  95

Ala Arg Asp Tyr Tyr Gly Thr Tyr Phe Tyr Ala Met Asp Tyr Trp Gly
            100                 105                 110

Gln Gly Thr Leu Val Thr Val Ser Ser Ala Ser Thr Lys Gly Pro Ser

```
                 115                 120                 125
Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 22
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Gln Ser Gly Ser Glu Leu Lys Lys Pro Gly Ala
1               5                   10                  15
```

```
Ser Val Lys Val Ser Cys Lys Ala Ser Gly Tyr Thr Phe Thr Asp Tyr
            20                  25                  30
Ser Met His Trp Val Arg Gln Ala Pro Gly Gln Gly Leu Glu Trp Met
            35                  40                  45
Gly Trp Ile Asn Ile Glu Thr Gly Glu Pro Thr Tyr Ala Gln Gly Phe
50                  55                  60
Thr Gly Arg Phe Val Phe Ser Leu Asp Thr Ser Val Ser Thr Ala Tyr
65                  70                  75                  80
Leu Gln Ile Ser Ser Leu Lys Ala Glu Asp Thr Ala Val Tyr Phe Cys
                85                  90                  95
Ala Arg Asp Tyr Tyr Gly Thr Tyr Phe Tyr Ala Met Asp Tyr Trp Gly
                100                 105                 110
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Lys Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
```

```
                    435                 440                 445
Pro Gly Lys
    450

<210> SEQ ID NO 23
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gatgtacagc ttcaggagtc aggacctgag ctgaagaagc ctggagagac agtcaagatc      60
tcctgcaagg cttctggtta taccttcaca gactattcaa tgcactgggt gaagcaggct     120
ccaggaaagg gtttaaagtg gatgggctgg ataaacattg agactggtga gccaacatat     180 gcagatgact␣caagggacg gtttgccttc tctttggaaa cctctgccag cactgcctat     240
ttgcagatca acaacctcaa aaatgaggac acggctacat atttctgtgc tagagattac     300
tacggtactt acttctatgc tatggactac tggggtcaag gcaccactct cacagtctcc     360
tcagcctcca ccaagggccc atcggtcttc cccctggcac cctcctccaa gagcacctct     420
gggggcacag cggccctggg ctgcctggtc aaggactact ccccgaacc ggtgacggtg      480 tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc      780 cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag cccccatcga gaaaaccatc    1020
tccaaagcca aagggcagcc ccgagaacca caggtgtaca ccctgccccc atcccgggag    1080 gagatgacca␣agaaccaggt␣cagcctgacc␣tgcctggtca␣aaggcttcta␣tcccagcgac    1140 atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                 1353

<210> SEQ ID NO 24
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
caggtgcagc tggtgcagtc tggaagcgaa ctgaagaaac ctggagcctc tgtgaaagtg      60
tcttgtaagg ccagcggcta caccttcacc gactacagca tgcactgggt gcggcaggcc     120
cctggacagg gcctggaatg gatgggctgg atcaacatcg agaccggcga gcccacctac     180
```

| | |
|---|---|
| gcccagggct ttaccggacg gttcgtgttc agcctggata catctgtgtc tacagcctat | 240 |
| ctgcagatct gctctctgaa ggccgaagat acagccgtgt acttctgcgc ccgggactac | 300 |
| tacggcacct acttctacgc catggactac tggggccagg aacactggt gacagtgtct | 360 |
| tctgcctcca ccaagggccc atcggtcttc cccctggcac cctcctccaa gagcacctct | 420 |
| gggggcacag cggccctggg ctgcctggtc aaggactact ccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca cctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgtgtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca aagggcagcc ccgagaacca caggtgtaca ccctgccccc atcccgggag | 1080 |
| gagatgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 25
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

| | |
|---|---|
| caagtgcagc tggtgcagtc tggcagcgag ctgaaaaaac ctggcgcctc cgtgaaggtg | 60 |
| tcctgcaagg ctagcggcta cacctttacc gactacagca tgcactgggt ccgacaggct | 120 |
| ccaggacaag gcttggaatg gatgggctgg atcaacatcg agacaggcga gcccacatac | 180 |
| gcccagggct ttaccggcag attcgtgttc agcctggaca cctctgtgtc caccgcctac | 240 |
| ctgcagatca gctctctgaa ggccgaggat accgccgtgt acttctgcgc cagagactac | 300 |
| tacggcacct acttctacgc catggattac tggggccagg gcaccctggt taccgttct | 360 |
| tctgcctcca ccaagggccc atcggtcttc cccctggcac cctcctccaa gagcacctct | 420 |
| gggggcacag cggccctggg ctgcctggtc aaggactact ccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca cctcatgat ctcccggacc | 780 |
| cctgaggtca catgcgtggt ggtggacgtg agccacgaag accctgaggt caagttcaac | 840 |

```
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggag   1080
gagatgacca gaaccaggt cagcctgacc tgcctggtca aaggcttcta tcccagcgac    1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353
```

<210> SEQ ID NO 26
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Gln Ile Val Leu Thr Gln Ser Pro Ala Ile Met Ser Ala Ser Leu Gly
 1               5                  10                  15

Glu Arg Val Thr Met Thr Cys Thr Ala Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys His Gln Tyr His Arg Ser Pro
                85                  90                  95

Leu Thr Phe Gly Ala Gly Thr Lys Leu Glu Leu Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 27
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Val Ser Ser Ser
            20                  25                  30

Tyr Leu His Trp Tyr Gln Gln Lys Pro Gly Leu Ala Pro Arg Leu Leu
                35                  40                  45

Ile Tyr Ser Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Leu Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 28
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Val Ser Ser Ser
            20                  25                  30

Tyr Leu His Trp Tyr Gln Gln Lys Pro Gly Leu Ala Pro Arg Leu Leu
                35                  40                  45

Ile Tyr Ser Thr Ser Asn Leu Ala Ser Gly Ile Pro Asp Arg Phe Ser
    50                  55                  60

Gly Ser Gly Ser Gly Thr Asp Tyr Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Leu Thr Phe Gly Gln Gly Thr Lys Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

```
Gly Thr Ala Ser Val Val Cys Leu Leu Asn Asn Phe Tyr Pro Arg Glu
        130                 135                 140
Ala Lys Val Gln Trp Lys Val Asp Asn Ala Leu Gln Ser Gly Asn Ser
145                 150                 155                 160
Gln Glu Ser Val Thr Glu Gln Asp Ser Lys Asp Ser Thr Tyr Ser Leu
                165                 170                 175
Ser Ser Thr Leu Thr Leu Ser Lys Ala Asp Tyr Glu Lys His Lys Val
                180                 185                 190
Tyr Ala Cys Glu Val Thr His Gln Gly Leu Ser Ser Pro Val Thr Lys
            195                 200                 205
Ser Phe Asn Arg Gly Glu Cys
        210                 215

<210> SEQ ID NO 29
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
caaattgttc tcacccagtc tccagcaatc atgtctgcat ctctagggga cgggtcacc      60 atgacctgca ctgccagctc aagtgtaagt tccagttact gcactgta ccagcagaaa    120 ccaggatcct cccccaaact ctggatttat agcacatcca acctggcttc tggagtccca    180
gctcgcttca gtggcagtgg gtctgggacc tcttactctc tcacaatcag cagcatggag    240
gctgaagatg ctgccactta ttactgccac cagtatcatc gttccccgct cacgttcggt    300
gctgggacca agctggagct gaaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac aaagtctacg cctgcgaagt cacccatcag    600
ggcctgagct cgcccgtcac aaagagcttc aacaggggag agtgt                   645

<210> SEQ ID NO 30
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gagatcgtgc tgacacagtc tcctgccaca ctgtctctgt ctcctggaga cgggccaca      60 ctgagctgca ccgccagcag cagcgtgagc agcagctacc tgcactgta ccagcagaaa    120 cctggactgg cccctcggct gctgatctac agcaccagca acctggccag cggcatccct    180
gatcggtttt ctggcagcgg atctggcaca gattttacac tgaccatcag ccggctggaa    240
cctgaggatt ttgccgtgta ctactgccac cagtaccacc ggagccccct gaccttcggc    300
cagggaacaa agctggaaat caagcgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
```

-continued

```
caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgt                   645
```

<210> SEQ ID NO 31
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
gagatcgtgc tgacacagtc tcccgccaca ctgtcactgt ctccaggcga aagagccaca    60
ctgagctgta ccgccagcag ctctgtgtcc agcagctacc tgcactggta tcagcagaag   120
cctggactgg cccctcggct gctgatctac agcacaagca atctggccag cggcatcccc   180
gatagatttt ccggctctgg aagcggcacc gactacaccc tgacaatcag cagactggaa   240
cccgaggact cgccgtgta ctactgccac cagtaccaca gaagccctct gacctttggc    300
cagggcacca agctggaaat caagcgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagacta cgagaaacac aaagtctacg cctgcgaagt cacccatcag   600
ggcctgagct cgcccgtcac aaagagcttc aacaggggag agtgt                  645
```

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Tyr Thr Phe Thr Thr Tyr Trp Met His
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Ile Asn Pro Asn Asn Gly Gly Ile Asn
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Ile Asn Pro Asn Asn Ala Gly Ile Asn

```
1               5                   10
```

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Glu Ile Asn Pro Asn Asp Ala Gly Ile Asn
1               5                   10
```

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Glu Ile Asn Pro Asn Gln Gly Gly Ile Asn
1               5                   10
```

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Glu Ile Asn Pro Asn Lys Gly Gly Ile Asn
1               5                   10
```

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Glu Ile Asn Pro Asn Glu Gly Gly Ile Asn
1               5                   10
```

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Glu Ile Asn Pro Asn Asn Ile Gly Ile Asn
1               5                   10
```

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic

```
                                   peptide

<400> SEQUENCE: 40

Asp Tyr Tyr Asp Tyr Gly Gly Tyr
1               5

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Ala Ser Gln Asn Val Gly Thr Asn Val Ala
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Ala Ser Tyr Arg Tyr Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Gln Tyr Asn Ile Tyr Pro Tyr Thr
1               5

<210> SEQ ID NO 44
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Glu Ile Asn Pro Asn Asn Gly Ile Asn Tyr Asn Glu Lys Phe
    50                  55                  60

Lys Lys Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Cys
                85                  90                  95

Thr Ile Asp Tyr Tyr Asp Tyr Gly Gly Tyr Trp Gly Gln Gly Thr Thr
```

-continued

```
                   100                 105                 110

Leu Thr Val Ser Ser
            115

<210> SEQ ID NO 45
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asn Pro Asn Asn Gly Gly Ile Asn Tyr Ala Gln Lys Phe
    50                  55                  60

Gln Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ile Asp Tyr Tyr Asp Tyr Gly Gly Tyr Trp Gly Gln Gly Thr Leu
                100                 105                 110

Val Thr Val Ser Ser
            115

<210> SEQ ID NO 46
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asn Pro Asn Asn Ala Gly Ile Asn Tyr Ala Gln Lys Phe
    50                  55                  60

Gln Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ile Asp Tyr Tyr Asp Tyr Gly Gly Tyr Trp Gly Gln Gly Thr Leu
                100                 105                 110

Val Thr Val Ser Ser
            115

<210> SEQ ID NO 47
<211> LENGTH: 117
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 47

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asn Pro Asn Asp Ala Gly Ile Asn Tyr Ala Gln Lys Phe
    50                  55                  60

Gln Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ile Asp Tyr Tyr Asp Tyr Gly Gly Tyr Trp Gly Gln Gly Thr Leu
            100                 105                 110

Val Thr Val Ser Ser
        115
```

<210> SEQ ID NO 48
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asn Pro Asn Gln Gly Ile Asn Tyr Ala Gln Lys Phe
    50                  55                  60

Gln Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ile Asp Tyr Tyr Asp Tyr Gly Gly Tyr Trp Gly Gln Gly Thr Leu
            100                 105                 110

Val Thr Val Ser Ser
        115
```

<210> SEQ ID NO 49
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asn Pro Asn Lys Gly Gly Ile Asn Tyr Ala Gln Lys Phe
    50                  55                  60

Gln Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ile Asp Tyr Tyr Asp Tyr Gly Gly Tyr Trp Gly Gln Gly Thr Leu
                100                 105                 110

Val Thr Val Ser Ser
            115

<210> SEQ ID NO 50
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asn Pro Asn Glu Gly Gly Ile Asn Tyr Ala Gln Lys Phe
    50                  55                  60

Gln Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ile Asp Tyr Tyr Asp Tyr Gly Gly Tyr Trp Gly Gln Gly Thr Leu
                100                 105                 110

Val Thr Val Ser Ser
            115

<210> SEQ ID NO 51
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asn Pro Asn Asn Ile Gly Ile Asn Tyr Ala Gln Lys Phe
    50                  55                  60
```

Gln Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ile Asp Tyr Tyr Asp Tyr Gly Gly Tyr Trp Gly Gln Gly Thr Leu
            100                 105                 110

Val Thr Val Ser Ser
        115

<210> SEQ ID NO 52
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
caggtccaac tgcagcagcc tggggctgaa cttgtgaagc ctggggcttc agtgaagttg      60
tcctgcaagg cttctggcta caccttcacc acctactgga tgcactgggt gaagcagagg     120
cctggacaag gccttgagtg gattggagag attaatccta acaatggtgg tattaattac     180
aatgagaagt tcaagaagaa ggccacactg actgtagaca atcctccag cacagcctac      240 atgcagctca gcagcctgac atctgaggac tctgcggtct attactgtac aatagactac     300
tatgattacg ggggctactg gggccaaggc accactctca cagtctcctc a              351

<210> SEQ ID NO 53
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
caggtgcagc tggtgcagtc tggagccgaa gtgaagaaac ctggagcctc tgtgaaagtg      60
tcttgtaagg ccagcggcta caccttcacc acctactgga tgcactgggt gcggcaggcc     120
cctggacagg gcctgaatg gatgggcgag atcaacccca acaacggcgg catcaactac      180
gcccagaaat tcagggacg ggtgaccctg acagtggata gagcatctc tacagcctac       240 atggaactgt ctcggctgcg gagcgatgac acagccgtgt actactgcac catcgactac     300
tacgactacg gcggctactg gggccaggga acactggtga cagtgtcttc t              351

<210> SEQ ID NO 54
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
caggtgcagc tggtgcagtc tggagccgaa gtgaagaaac ctggagcctc tgtgaaagtg      60
tcttgtaagg ccagcggcta caccttcacc acctactgga tgcactgggt gcggcaggcc     120
cctggacagg gcctgaatg gatgggcgag atcaacccca acaacggcgg catcaactac      180
gcccagaaat tcagggacg ggtgaccctg acagtggata gagcatctc tacagcctac       240 atggaactgt ctcggctgcg gagcgatgac acagccgtgt actactgcac catcgactac     300

```
tacgactacg gcggctactg gggccaggga acactggtga cagtgtcttc t            351
```

<210> SEQ ID NO 55
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
caggtgcagc tggtgcagtc tggagccgaa gtgaagaaac ctggagcctc tgtgaaagtg    60
tcttgtaagg ccagcggcta caccttcacc acctactgga tgcactgggt gcggcaggcc   120
cctggacagg gcctggaatg gatgggcgag atcaaccccc acgacgccgg catcaactac   180
gcccagaaat tcagggacg ggtgaccctg acagtggata agagcatctc tacagcctac   240
atggaactgt ctcggctgcg gagcgatgac acagccgtgt actactgcac catcgactac   300
tacgactacg gcggctactg gggccaggga acactggtga cagtgtcttc t            351
```

<210> SEQ ID NO 56
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
caggtgcagc tggtgcagtc tggagccgaa gtgaagaaac ctggagcctc tgtgaaagtg    60
tcttgtaagg ccagcggcta caccttcacc acctactgga tgcactgggt gcggcaggcc   120
cctggacagg gcctggaatg gatgggcgag atcaaccccca accagggcgg catcaactac   180
gcccagaaat tcagggacg ggtgaccctg acagtggata agagcatctc tacagcctac   240
atggaactgt ctcggctgcg gagcgatgac acagccgtgt actactgcac catcgactac   300
tacgactacg gcggctactg gggccaggga acactggtga cagtgtcttc t            351
```

<210> SEQ ID NO 57
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
caggtgcagc tggtgcagtc tggagccgaa gtgaagaaac ctggagcctc tgtgaaagtg    60
tcttgtaagg ccagcggcta caccttcacc acctactgga tgcactgggt gcggcaggcc   120
cctggacagg gcctggaatg gatgggcgag atcaaccccca acaagggcgg catcaactac   180
gcccagaaat tcagggacg ggtgaccctg acagtggata agagcatctc tacagcctac   240
atggaactgt ctcggctgcg gagcgatgac acagccgtgt actactgcac catcgactac   300
tacgactacg gcggctactg gggccaggga acactggtga cagtgtcttc t            351
```

<210> SEQ ID NO 58
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
caggtgcagc tggtgcagtc tggagccgaa gtgaagaaac ctggagcctc tgtgaaagtg      60
tcttgtaagg ccagcggcta caccttcacc acctactgga tgcactgggt gcggcaggcc     120
cctggacagg gcctggaatg gatgggcgag atcaaccccc acgagggcgg catcaactac     180
gcccagaaat ttcagggacg ggtgaccctg acagtggata gagcatctc tacagcctac     240
atggaactgt ctcggctgcg gagcgatgac acagccgtgt actactgcac catcgactac     300
tacgactacg gcggctactg gggccaggga acactggtga cagtgtcttc t              351
```

<210> SEQ ID NO 59
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
caggtgcagc tggtgcagtc tggagccgaa gtgaagaaac ctggagcctc tgtgaaagtg      60
tcttgtaagg ccagcggcta caccttcacc acctactgga tgcactgggt gcggcaggcc     120
cctggacagg gcctggaatg gatgggcgag atcaaccccc acaacatcgg catcaactac     180
gcccagaaat ttcagggacg ggtgaccctg acagtggata gagcatctc tacagcctac     240
atggaactgt ctcggctgcg gagcgatgac acagccgtgt actactgcac catcgactac     300
tacgactacg gcggctactg gggccaggga acactggtga cagtgtcttc t              351
```

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Asp Ile Val Met Thr Gln Ser Gln Lys Phe Met Ser Thr Ser Val Arg
1               5                   10                  15
Asp Arg Val Ser Val Thr Cys Lys Ala Ser Gln Asn Val Gly Thr Asn
            20                  25                  30
Val Ala Trp Tyr Gln Gln Lys Pro Gly Gln Ser Pro Lys Ala Leu Ile
        35                  40                  45
Tyr Ser Ala Ser Tyr Arg Tyr Ser Gly Val Pro Asp Arg Phe Thr Gly
    50                  55                  60
Ser Gly Ser Gly Thr Asp Phe Thr Leu Thr Ile Thr Asn Val Gln Ser
65                  70                  75                  80
Glu Asp Leu Ala Glu Tyr Phe Cys Gln Gln Tyr Asn Ile Tyr Pro Tyr
                85                  90                  95
Thr Phe Gly Ser Gly Thr Lys Leu Glu Met Lys
            100                 105
```

<210> SEQ ID NO 61
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Glu Lys Ala Pro Lys Ser Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys
            100                 105

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Glu Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Ile Tyr Pro Tyr
                85                  90                  95

Thr Phe Gly Gln Gly Thr Lys Leu Glu Ile Lys
            100                 105

<210> SEQ ID NO 63
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gacattgtga tgacccagtc tcaaaaattc atgtccacat cagtaagaga cagggtcagc      60
gtcacctgca aggccagtca gaatgtgggc actaatgtag cctggtatca acagaaacca     120
gggcaatctc ctaaagcact gatttactcg gcatcctacc ggtacagtgg agtccctgat     180
cgcttcacag gcagtggatc tgggacagat ttcactctca ccatcaccaa tgtgcagtct     240
gaagacttgg cagaatattt ctgtcagcaa tataacatct atccgtacac gttcggatcg     300
gggaccaagc tggaaatgaa a                                               321

<210> SEQ ID NO 64
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64
gacatccaga tgacacagtc tcctagctct ctgagcgcct ctgtgggaga tcgggtgaca    60
atcacctgca aggccagcca gaacgtgggc accaacgtgg cctggtacca gcagaaacct   120
gaaaaagccc ctaagagcct gatctacagc gccagctacc ggtacagcgg cgtgccttct   180
cggtttagcg gctctggaag cggaacagat ttcacactga ccatctctag cctgcagcct   240
gaagattttg ccacatacta ctgccagcag tacaacatct accccTACAC cttcggccag   300
ggaacaaagc tggaaatcaa g                                             321

<210> SEQ ID NO 65
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gacatccaga tgacacagtc tcctagctct ctgagcgcct ctgtgggaga tcgggtgaca    60
atcacctgca aggccagcca gaacgtgggc accaacgtgg cctggtacca gcagaaacct   120
gaaaaagccc ctaaggccct gatctacagc gccagctacc ggtacagcgg cgtgccttct   180
cggtttagcg gctctggaag cggaacagat ttcacactga ccatctctag cctgcagcct   240
gaagattttg ccacatactt ttgccagcag tacaacatct accccTACAC cttcggccag   300
ggaacaaagc tggaaatcaa g                                             321

<210> SEQ ID NO 66
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Glu Ile Asn Pro Asn Asn Gly Gly Ile Asn Tyr Asn Glu Lys Phe
    50                  55                  60

Lys Lys Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Ile Asp Tyr Tyr Asp Tyr Gly Gly Tyr Trp Gly Gln Gly Thr Thr
            100                 105                 110

Leu Thr Val Ser Ser Ala Ser Thr Lys Gly Pro Ser Val Phe Pro Leu

```
            115                 120                 125
Ala Pro Ser Ser Lys Ser Thr Ser Gly Gly Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 67
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Thr Tyr
            20                  25                  30
```

```
Trp Met His Trp Val Arg Gln Ala Pro Gly Gln Gly Leu Glu Trp Met
        35                  40                  45
Gly Glu Ile Asn Pro Asn Asn Gly Gly Ile Asn Tyr Ala Gln Lys Phe
 50                  55                  60
Gln Gly Arg Val Thr Leu Thr Val Asp Lys Ser Ile Ser Thr Ala Tyr
 65                  70                  75                  80
Met Glu Leu Ser Arg Leu Arg Ser Asp Asp Thr Ala Val Tyr Tyr Cys
                 85                  90                  95
Thr Ile Asp Tyr Tyr Asp Tyr Gly Gly Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445
```

-continued

<210> SEQ ID NO 68
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asn Pro Asn Asn Ala Gly Ile Asn Tyr Ala Gln Lys Phe
    50                  55                  60

Gln Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ile Asp Tyr Tyr Asp Tyr Gly Gly Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 69
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Trp Met His Trp Val Arg Gln Ala Pro Gly Gln Gly Leu Glu Trp Met
            35                  40                  45

Gly Glu Ile Asn Pro Asn Asp Ala Gly Ile Asn Tyr Ala Gln Lys Phe
50                  55                  60

Gln Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ile Asp Tyr Tyr Asp Tyr Gly Gly Tyr Trp Gly Gln Gly Thr Leu
            100                 105                 110

Val Thr Val Ser Ser Ala Ser Thr Lys Gly Pro Ser Val Phe Pro Leu
115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

```
Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 70
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asn Pro Asn Gln Gly Gly Ile Asn Tyr Ala Gln Lys Phe
    50                  55                  60

Gln Gly Arg Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Ile Asp Tyr Tyr Asp Tyr Gly Gly Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

195                 200                 205

Thr Lys Val Asp Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 71
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asn Pro Asn Lys Gly Gly Ile Asn Tyr Ala Gln Lys Phe
    50                  55                  60

Gln Gly Arg Val Thr Leu Thr Val Asp Lys Ser Ile Ser Thr Ala Tyr
65                  70                  75                  80

Met Glu Leu Ser Arg Leu Arg Ser Asp Thr Ala Val Tyr Tyr Cys
                85                  90                  95

Thr Ile Asp Tyr Tyr Asp Tyr Gly Gly Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 72
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
            35                  40                  45

Gly Glu Ile Asn Pro Asn Glu Gly Gly Ile Asn Tyr Ala Gln Lys Phe
 50                  55                  60

Gln Gly Arg Val Thr Leu Thr Val Asp Lys Ser Ile Ser Thr Ala Tyr
 65                  70                  75                  80

Met Glu Leu Ser Arg Leu Arg Ser Asp Thr Ala Val Tyr Tyr Cys
                 85                  90                  95

Thr Ile Asp Tyr Tyr Asp Tyr Gly Gly Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 73
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Met
        35                  40                  45

Gly Glu Ile Asn Pro Asn Asn Ile Gly Ile Asn Tyr Ala Gln Lys Phe
    50                  55                  60

Gln Gly Arg Val Thr Leu Thr Val Asp Lys Ser Ile Ser Thr Ala Tyr
65                  70                  75                  80

Met Glu Leu Ser Arg Leu Arg Ser Asp Thr Ala Val Tyr Tyr Cys
                85                  90                  95

Thr Ile Asp Tyr Tyr Asp Tyr Gly Gly Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

```
Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 74
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
caggtccaac tgcagcagcc tggggctgaa cttgtgaagc ctggggcttc agtgaagttg      60
tcctgcaagg cttctggcta caccttcacc acctactgga tgcactgggt gaagcagagg    120
cctggacaag ccttgagtg gattggagag attaatccta caatggtgg tattaattac      180 aatgagaagt tcaagaagaa ggccacactg actgtagaca atcctccag cacagcctac     240 atgcagctca gcagcctgac atctgaggac tctgcggtct attactgtac aatagactac    300
tatgattacg ggggctactg gggccaaggc accactctca cagtctcctc agcctccacc    360
aagggcccat cggtcttccc cctggcaccc tcctccaaga gcacctctgg ggcacagcg    420 gccctgggct gcctggtcaa ggactacttc cccgaaccgg tgacggtgtc gtggaactca    480
ggcgccctga ccagcggcgt gcacaccttc cggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gacaaaactc acacatgccc accgtgccca gcacctgaac tcctggggg accgtcagtc    720 ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc ccatcgaga aaccatctc caaagccaaa     1020 gggcagcccc gagaaccaca ggtgtacacc ctgccccat cccggagga tgaccaag       1080 aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca gagcaggtg gcagcagggg    1260 aacgtcttct catgctccgt gatgcatgag gctctgcaca accactacac gcagaagagc    1320 ctctcccctgt ctccgggtaa a                                             1341

<210> SEQ ID NO 75
<211> LENGTH: 1341
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 75

```
caggtgcagc tggtgcagtc tggagccgaa gtgaagaaac ctggagcctc tgtgaaagtg      60
tcttgtaagg ccagcggcta caccttcacc acctactgga tgcactgggt gcggcaggcc     120
cctggacagg gcctggaatg gatgggcgag atcaacccca acaacggcgg catcaactac     180
gcccagaaat ttcagggacg ggtgaccctg acagtggata agagcatctc tacagcctac     240
atggaactgt ctcggctgcg gagcgatgac acagccgtgt actactgcac catcgactac     300
tacgactacg gcggctactg gggccaggga acactggtga cagtgtcttc tgcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagccc aaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga gatgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa a                                              1341
```

<210> SEQ ID NO 76
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
caggtgcagc tggtgcagtc tggagccgaa gtgaagaaac ctggagcctc tgtgaaagtg      60
tcttgtaagg ccagcggcta caccttcacc acctactgga tgcactgggt gcggcaggcc     120
cctggacagg gcctggaatg gatgggcgag atcaacccca acaacgccgg catcaactac     180
gcccagaaat ttcagggacg ggtgaccctg acagtggata agagcatctc tacagcctac     240
atggaactgt ctcggctgcg gagcgatgac acagccgtgt actactgcac catcgactac     300
tacgactacg gcggctactg gggccaggga acactggtga cagtgtcttc tgcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
```

```
tccctcagca gcgtggtgac cgtgccctcc agcagcttgg gcacccagac ctacatctgc      600
aacgtgaatc acaagcccag caacaccaag gtggacaaga agttgagcc caaatcttgt       660 gacaaaactc acacatgccc accgtgccca gcacctgaac tcctgggggg accgtcagtc      720
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga tgaccaag       1080 aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca agagcaggtg gcagcagggg     1260
aacgtcttct catgctccgt gatgcatgag gctctgcaca accactacac gcagaagagc     1320
ctctccctgt ctccgggtaa a                                               1341
```

<210> SEQ ID NO 77
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

```
caggtgcagc tggtgcagtc tggagccgaa gtgaagaaac ctggagcctc tgtgaaagtg       60
tcttgtaagg ccagcggcta caccttcacc acctactgga tgcactgggt gcggcaggcc      120
cctggacagg gcctggaatg gatgggcgag atcaaccca acgacgccgg catcaactac      180
gcccagaaat tcagggacg ggtgaccctg acagtggata gagcatctc tacagcctac        240 atggaactgt ctcggctgcg gagcgatgac acagccgtgt actactgcac catcgactac      300
tacgactacg gcggctactg gggccaggga acactggtga cagtgtcttc tgcctccacc      360
aagggcccat cggtcttccc cctggcaccc tcctccaaga gcacctctgg gggcacagcg      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacccagac ctacatctgc      600
aacgtgaatc acaagcccag caacaccaag gtggacaaga agttgagcc caaatcttgt       660 gacaaaactc acacatgccc accgtgccca gcacctgaac tcctgggggg accgtcagtc      720
ttcctcttcc ccccaaaacc caaggacacc ctcatgatct cccggacccc tgaggtcaca      780
tgcgtggtgg tggacgtgag ccacgaagac cctgaggtca agttcaactg gtacgtggac      840
ggcgtggagg tgcataatgc caagacaaag ccgcgggagg agcagtacaa cagcacgtac      900
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga tgaccaag       1080 aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
```

```
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa a                                              1341
```

<210> SEQ ID NO 78
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78

```
caggtgcagc tggtgcagtc tggagccgaa gtgaagaaac ctggagcctc tgtgaaagtg      60
tcttgtaagg ccagcggcta caccttcacc acctactgga tgcactgggt gcggcaggcc     120
cctggacagg gcctggaatg gatgggcgag atcaaccccaa ccagggcgg catcaactac     180 gcccagaaat tcagggacg ggtgaccctg acagtggata gagcatctc tacagcctac     240 atggaactgt ctcggctgcg gagcgatgac acagccgtgt actactgcac catcgactac     300
tacgactacg gcggctactg gggccaggga acactggtga cagtgtcttc tgcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tcccttagca gcgtggtgac cgtgccctcc agcagcttgg gcacccagac ctacatctgc     600
aacgtgaatc acaagcccag caacaccaag gtggacaaga agttgagcc caaatcttgt     660 gacaaaactc acacatgccc accgtgccca gcacctgaac tcctggggg accgtcagtc     720 ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgtgtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggagga tgaccaag    1080 aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa a                                              1341
```

<210> SEQ ID NO 79
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

```
caggtgcagc tggtgcagtc tggagccgaa gtgaagaaac ctggagcctc tgtgaaagtg      60
tcttgtaagg ccagcggcta caccttcacc acctactgga tgcactgggt gcggcaggcc     120
```

| | |
|---|---|
| cctggacagg gcctggaatg gatgggcgag atcaacccca caagggcgg catcaactac | 180 |
| gcccagaaat tcagggacg ggtgaccctg acagtggata agagcatctc tacagcctac | 240 |
| atggaactgt ctcggctgcg gagcgatgac acagccgtgt actactgcac catcgactac | 300 |
| tacgactacg gcggctactg gggccaggga acactggtga cagtgtcttc tgcctccacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctggggg accgtcagtc | 720 |
| ttcctcttcc ccccaaaacc caaggacacc ctcatgatct cccggacccc tgaggtcaca | 780 |
| tgcgtggtgg tggacgtgag ccacgaagac cctgaggtca agttcaactg gtacgtggac | 840 |
| ggcgtggagg tgcataatgc caagacaaag ccgcgggagg agcagtacaa cagcacgtac | 900 |
| cgtgtggtca gcgtcctcac cgtcctgcac caggactggc tgaatggcaa ggagtacaag | 960 |
| tgcaaggtct ccaacaaagc cctcccagcc cccatcgaga aaaccatctc caaagccaaa | 1020 |
| gggcagcccc gagaaccaca ggtgtacacc ctgcccccat cccgggagga tgaccaag | 1080 |
| aaccaggtca gcctgacctg cctggtcaaa ggcttctatc ccagcgacat cgccgtggag | 1140 |
| tgggagagca atgggcagcc ggagaacaac tacaagacca cgcctcccgt gctggactcc | 1200 |
| gacggctcct tcttcctcta cagcaagctc accgtggaca agagcaggtg gcagcagggg | 1260 |
| aacgtcttct catgctccgt gatgcatgag gctctgcaca accactacac gcagaagagc | 1320 |
| ctctcccctgt ctccgggtaa a | 1341 |

<210> SEQ ID NO 80
<211> LENGTH: 1341
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 80

| | |
|---|---|
| caggtgcagc tggtgcagtc tggagccgaa gtgaagaaac ctggagcctc tgtgaaagtg | 60 |
| tcttgtaagg ccagcggcta caccttcacc acctactgga tgcactgggt gcggcaggcc | 120 |
| cctggacagg gcctggaatg gatgggcgag atcaacccca cgagggcgg catcaactac | 180 |
| gcccagaaat tcagggacg ggtgaccctg acagtggata agagcatctc tacagcctac | 240 |
| atggaactgt ctcggctgcg gagcgatgac acagccgtgt actactgcac catcgactac | 300 |
| tacgactacg gcggctactg gggccaggga acactggtga cagtgtcttc tgcctccacc | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc aggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| gacaaaactc acacatgccc accgtgccca gcacctgaac tcctggggg accgtcagtc | 720 |
| ttcctcttcc ccccaaaacc caaggacacc ctcatgatct cccggacccc tgaggtcaca | 780 |

```
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa a                                             1341

<210> SEQ ID NO 81
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
caggtgcagc tggtgcagtc tggagccgaa gtgaagaaac ctggagcctc tgtgaaagtg     60
tcttgtaagg ccagcggcta caccttcacc acctactgga tgcactgggt gcggcaggcc    120
cctggacagg gcctggaatg gatgggcgag atcaacccca caacatcgg catcaactac    180 gcccagaaat tcagggacg ggtgaccctg acagtggata gagcatctc tacagcctac    240 atggaactgt ctcggctgcg gagcgatgac acagccgtgt actactgcac catcgactac    300
tacgactacg gcggctactg gggccaggga acactggtga cagtgtcttc tgcctccacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa a                                             1341

<210> SEQ ID NO 82
```

```
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Val Met Thr Gln Ser Gln Lys Phe Met Ser Thr Ser Val Arg
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Asn Ile Tyr Pro Tyr
                85                  90                  95

Thr Phe Gly Ser Gly Thr Lys Leu Glu Met Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 83
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Glu Lys Ala Pro Lys Ser Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95
```

```
Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 84
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Glu Lys Ala Pro Lys Ala Leu Ile
        35                  40                  45

Tyr Ser Ala Ser Tyr Arg Tyr Ser Gly Val Pro Ser Arg Phe Ser Gly
 50                 55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Ile Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 85
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
gacattgtga tgacccagtc tcaaaaattc atgtccacat cagtaagaga cagggtcagc      60
gtcacctgca aggccagtca gaatgtgggc actaatgtag cctggtatca acagaaacca    120
gggcaatctc ctaaagcact gatttactcg gcatcctacc ggtacagtgg agtccctgat    180
cgcttcacag gcagtggatc tgggacagat ttcactctca ccatcaccaa tgtgcagtct    240
gaagacttgg cagaatattt ctgtcagcaa tataacatct atccgtacac gttcggatcg    300
gggaccaagc tggaaatgaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642

<210> SEQ ID NO 86
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
gacatccaga tgacacagtc tcctagctct ctgagcgcct ctgtgggaga tcgggtgaca      60
atcacctgca aggccagcca gaacgtgggc accaacgtgg cctggtacca gcagaaacct    120
gaaaaagccc ctaagagcct gatctacagc gccagctacc ggtacagcgg cgtgccttct    180
cggtttagcg gctctggaag cggaacagat ttcactctga ccatctctag cctgcagcct    240
gaagattttg ccacatacta ctgccagcag tacaacatct acccctacac cttcggccag    300
ggaacaaagc tggaaatcaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642

<210> SEQ ID NO 87
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
gacatccaga tgacacagtc tcctagctct ctgagcgcct ctgtgggaga tcgggtgaca      60
atcacctgca aggccagcca gaacgtgggc accaacgtgg cctggtacca gcagaaacct    120
```

```
gaaaaagccc ctaaggccct gatctacagc gccagctacc ggtacagcgg cgtgccttct    180
cggtttagcg gctctggaag cggaacagat ttcacactga ccatctctag cctgcagcct    240
gaagattttg ccacatactt ttgccagcag tacaacatct acccctacac cttcggccag    300
ggaacaaagc tggaaatcaa gcgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Phe Ser Leu Ser Thr Ser Gly Met Gly Val Ser
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

His Ile Tyr Trp Asp Asp Asp Lys Arg
1               5

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Gly Tyr Tyr Asp Tyr Gly Tyr Val Met Asp Tyr
1               5                   10

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ser Ser Lys Ser Leu Leu His Ser Asn Gly Ile Thr Tyr Leu Asn
1               5                   10                  15

<210> SEQ ID NO 92
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 92

Gln Met Ser Asn Leu Ala Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Gln Asn Leu Glu Leu Pro Leu Thr
1               5

<210> SEQ ID NO 94
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Thr Leu Lys Glu Ser Gly Pro Gly Leu Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Gly Thr Tyr Tyr
                85                  90                  95

Cys Val Arg Lys Gly Tyr Tyr Asp Tyr Gly Tyr Val Met Asp Tyr Trp
            100                 105                 110

Gly Gln Gly Thr Thr Val Thr Val Ser Ser
        115                 120

<210> SEQ ID NO 95
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45
```

Trp Leu Ala His Ile Tyr Trp Asp Asp Asp Lys Arg Tyr Ser Pro Ser
            50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Gly Thr Tyr Tyr
                 85                  90                  95

Cys Val Arg Lys Gly Tyr Tyr Asp Tyr Gly Tyr Val Met Asp Tyr Trp
            100                 105                 110

Gly Gln Gly Thr Leu Val Thr Val Ser Ser
            115                 120

<210> SEQ ID NO 96
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
caggttactc tgaaagagtc tggccctggg ttattgcagc cctcccagac cctcagtctg      60
acttgttctt tctctgggtt ttcactgagc acttctggta tgggtgtgag ctggattcgt     120
cagccttcag gaaagggtct ggagtggctg gcacacattt actgggatga tgacaagcgc     180
tataacccat ccctgaagag ccggctcaca atctccaaag atacctccag caaccaggta     240
ttcctcaaga tcaccagtgt ggacactgca gatactggca catactactg tgttcgaaag     300
ggctactatg attacggcta tgtaatggac tactggggtc aagggaccac ggtcaccgtc     360
tcctca                                                                366

<210> SEQ ID NO 97
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
cagatcacac tgaaagaatc tggacctaca ctggtgaaac ctacacagac cctgacactg      60
acctgtacct tcagcggctt cagcctgagc accagcggca tgggcgtgag ctggattcgg     120
cagcctcctg gaaaggccct ggaatggctg gcccacatct actgggacga cgacaagcgg     180
tacagcccta gcctgaagtc tcggctgaca atcaccaagg atacctctaa gaaccaggtg     240
gtgctgacaa tgaccaacat ggaccctgtg gacacaggca cctactactg cgtgcggaag     300
ggctactacg actacggcta cgtgatggac tactggggcc agggaacact ggtgacagtg     360
tcttct                                                                366

<210> SEQ ID NO 98
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Val Met Thr Gln Ala Ala Leu Ser Asn Pro Val Thr Leu Gly
 1               5                  10                  15

-continued

Thr Ser Ala Ser Ile Ser Cys Arg Ser Ser Lys Ser Leu Leu His Ser
            20                  25                  30

Asn Gly Ile Thr Tyr Leu Asn Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Ser Gly Thr Lys Leu Glu Met Lys
            100                 105                 110

<210> SEQ ID NO 99
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Asn Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 100
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Asn Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 101
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
gatattgtga tgactcaggc tgcactctcc aatccagtca ctcttggaac atcagcttcc     60
atctcctgca ggtctagtaa gagtctccta catagtaatg gcatcactta tttgaattgg    120
tatctgcaga agccaggcca gtctcctcag ctcctgattt atcagatgtc caaccttgcc    180
tcaggagtcc cagacaggtt cagtagcagt gggtcaggaa ctgatttcac actgagaatc    240
agcagagtgg aggctgagga tgtgggtgtt tattactgtg ctcaaaatct agaacttccg    300
ctcacgttcg gatcggggac caagctggaa atgaaa                              336

<210> SEQ ID NO 102
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gacatcgtga tgacacagtc tcctctgtct ctgcctgtga cacctggcga acctgcctct     60
atcagctgcc ggagcagcaa gagcctgctg cacagcaacg gcatcaccta cctgaactgg    120
tacctgcaga aacctggaca gtctcctcag ctgctgatct accagatgag caacctggcc    180
agcggcgtgc ctgatcggtt tagcggctct ggaagcggca cagacttcac actgaagatc    240
tctcgggtgg aagccgagga cgtgggagtg tactactgcg cccagaacct ggagctgccc    300
ctgaccttcg gaggcggaac aaaggtggag atcaag                              336

<210> SEQ ID NO 103
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
gacatcgtga tgacacagtc tcctctgtct ctgcctgtga cacctggcga acctgcctct     60
atcagctgcc ggagcagcaa gagcctgctg cacagcaacg gcatcaccta cctgaactgg    120
tacctgcaga aacctggaca gtctcctcag ctgctgatct accagatgag caacctggcc    180
agcggcgtgc ctgatcggtt tagcagctct ggaagcggca cagacttcac actgaagatc    240
tctcgggtgg aagccgagga cgtgggagtg tactactgcg cccagaacct ggagctgccc    300
ctgaccttcg gaggcggaac aaaggtggag atcaag                              336

<210> SEQ ID NO 104
<211> LENGTH: 452
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 104

Gln Val Thr Leu Lys Glu Ser Gly Pro Gly Leu Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ser Val Asp Thr Ala Asp Thr Gly Thr Tyr Tyr
                85                  90                  95

Cys Val Arg Lys Gly Tyr Tyr Asp Tyr Gly Tyr Val Met Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

```
Pro Val Leu Asp Ser Asp Gly Ser Phe Phe Leu Tyr Ser Lys Leu Thr
                    405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 105
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Gly Thr Tyr Tyr
                85                  90                  95

Cys Val Arg Lys Gly Tyr Tyr Asp Tyr Gly Tyr Val Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300
```

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 106
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
caggttactc tgaaagagtc tggccctggg ttattgcagc cctcccagac cctcagtctg     60
acttgttctt tctctgggtt ttcactgagc acttctggta tgggtgtgag ctggattcgt    120
cagccttcag gaaagggtct ggagtggctg gcacacattt actgggatga tgacaagcgc    180
tataacccat ccctgaagag ccggctcaca atctccaaag atacctccag caaccaggta    240
ttcctcaaga tcaccagtgt ggacactgca gatactggca catactactg tgttcgaaag    300
ggctactatg attacggcta tgtaatggac tactggggtc aagggaccac ggtcaccgtc    360
tcctcagcct ccaccaaggg cccatcggtc ttccccctgg caccctcctc caagagcacc    420 tctggggggca gcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagaaagtt    660
gagcccaaat cttgtgacaa aactcacaca tgcccaccgt gcccagcacc tgaactcctg    720
gggggaccgt cagtcttcct cttccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaaagggca gccccgagaa ccacaggtgt acaccctgcc cccatcccgg   1080
gaggagatga ccaagaacca ggtcagcctg acctgcctgg tcaaaggctt ctatcccagc   1140

```
gacatcgccg tggagtggga gagcaatggg cagccggaga acaactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga agagcctctc cctgtctccg ggtaaa                              1356

<210> SEQ ID NO 107
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
cagatcacac tgaaagaatc tggacctaca ctggtgaaac ctacacagac cctgacactg      60
acctgtacct tcagcggctt cagcctgagc accagcggca tgggcgtgag ctggattcgg     120
cagcctcctg aaaggccct ggaatggctg gcccacatct actgggacga cgacaagcgg     180
tacagcccta gcctgaagtc tcggctgaca atcaccaagg atacctctaa gaaccaggtg     240
gtgctgacaa tgaccaacat ggaccctgtg acacaggacc ctactactg cgtgcggaag     300 ggctactacg actacggcta cgtgatggac tactggggcc agggaacact ggtgacagtg     360
tcttctgcct ccaccaaggg cccatcggtc ttccccctgg cacctcctc caagagcacc     420 tctgggggca gcgcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagaaagtt     660
gagcccaaat cttgtgacaa aactcacaca tgcccaccgt gcccagcacc tgaactcctg     720
gggggaccgt cagtcttcct cttccccccc aaacccaagg acaccctcat gatctcccgg     780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
gaggagatga ccaagaacca ggtcagcctg acctgcctgg tcaaaggctt ctatcccagc    1140
gacatcgccg tggagtggga gagcaatggg cagccggaga acaactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga agagcctctc cctgtctccg ggtaaa                              1356

<210> SEQ ID NO 108
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Val Met Thr Gln Ala Ala Leu Ser Asn Pro Val Thr Leu Gly
1               5                   10                  15
```

```
Thr Ser Ala Ser Ile Ser Cys Arg Ser Ser Lys Ser Leu Leu His Ser
            20                  25                  30

Asn Gly Ile Thr Tyr Leu Asn Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Ser Gly Thr Lys Leu Glu Met Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 109
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
            20                  25                  30

Asn Gly Ile Thr Tyr Leu Asn Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
```

```
                145                 150                 155                 160
Ser Gly Asn Ser Gln Glu Ser Val Thr Glu Gln Asp Ser Lys Asp Ser
                    165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 110
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Asn Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                    165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 111
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
gatattgtga tgactcaggc tgcactctcc aatccagtca ctcttggaac atcagcttcc      60
```

```
atctcctgca ggtctagtaa gagtctccta catagtaatg gcatcactta tttgaattgg    120
tatctgcaga agccaggcca gtctcctcag ctcctgattt atcagatgtc caaccttgcc    180
tcaggagtcc cagacaggtt cagtagcagt gggtcaggaa ctgatttcac actgagaatc    240
agcagagtgg aggctgagga tgtgggtgtt tattactgtg ctcaaaatct agaacttccg    300
ctcacgttcg gatcggggac caagctggaa atgaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt       657
```

<210> SEQ ID NO 112
<211> LENGTH: 657
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 112

```
gacatcgtga tgacacagtc tcctctgtct ctgcctgtga cacctggcga acctgcctct     60
atcagctgcc ggagcagcaa gagcctgctg cacagcaacg gcatcaccta cctgaactgg    120
tacctgcaga aacctggaca gtctcctcag ctgctgatct accagatgag caacctggcc    180
agcggcgtgc ctgatcggtt tagcggctct ggaagcggca cagacttcac actgaagatc    240
tctcgggtgg aagccgagga cgtgggagtg tactactgcg cccagaacct ggagctgccc    300
ctgaccttcg gaggcggaac aaaggtggag atcaagcgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt       657
```

<210> SEQ ID NO 113
<211> LENGTH: 657
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 113

```
gacatcgtga tgacacagtc tcctctgtct ctgcctgtga cacctggcga acctgcctct     60
atcagctgcc ggagcagcaa gagcctgctg cacagcaacg gcatcaccta cctgaactgg    120
tacctgcaga aacctggaca gtctcctcag ctgctgatct accagatgag caacctggcc    180
agcggcgtgc ctgatcggtt tagcagctct ggaagcggca cagacttcac actgaagatc    240
tctcgggtgg aagccgagga cgtgggagtg tactactgcg cccagaacct ggagctgccc    300
ctgaccttcg gaggcggaac aaaggtggag atcaagcgta cggtggctgc accatctgtc    360
ttcatcttcc cgccatctga tgagcagttg aaatctggaa ctgcctctgt tgtgtgcctg    420
```

```
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct caacagggg agagtgt       657
```

```
<210> SEQ ID NO 114
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Asp Ile Asn Trp Val Arg Gln Arg Pro Glu Gln Gly Leu Glu Trp Ile
        35                  40                  45

Gly Trp Ile Phe Pro Gly Asp Gly Ser Thr Lys Tyr Asn Glu Lys Phe
    50                  55                  60

Lys Gly Lys Ala Thr Leu Thr Thr Asp Lys Ser Ser Thr Ala Tyr
65                  70                  75                  80

Met Gln Phe Ser Arg Leu Thr Ser Glu Asp Ser Ala Val Tyr Phe Cys
                85                  90                  95

Ala Arg Gly Gly Met Arg Gln Leu Gly Arg Phe Val Tyr Trp Gly Gln
            100                 105                 110

Gly Thr Thr Leu Thr Val Ser Ser
        115                 120

<210> SEQ ID NO 115
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Asp Ile Val Leu Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Asn Pro Tyr
                85                  90                  95

Thr Phe Gly Gly Gly Thr Lys Leu Glu Ile Lys
            100                 105

<210> SEQ ID NO 116
<211> LENGTH: 119
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 116

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Val Lys Asp Thr
            20                  25                  30

Tyr Phe His Trp Val Lys Gln Arg Pro Asp Gln Gly Leu Glu Trp Ile
        35                  40                  45

Gly Arg Ile Val Ser Ala Asn Gly Asp Thr Lys Tyr Ala Pro Lys Leu
50                  55                  60

Gln Asp Lys Ala Thr Ile Thr Thr Asp Thr Ser Asn Thr Ala Tyr
65                  70                  75                  80

Leu Gln Leu Ser Arg Leu Thr Ser Glu Asp Thr Ala Val Tyr Tyr Cys
                85                  90                  95

Val Leu Ile Tyr Tyr Gly Phe Glu Glu Gly Asp Phe Trp Gly Gln Gly
            100                 105                 110

Thr Thr Leu Thr Val Ser Ser
        115
```

<210> SEQ ID NO 117
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

```
Asp Ile Val Met Thr Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Val Pro Lys Leu Leu Ile
        35                  40                  45

Tyr Lys Ala Ser Asn Leu His Thr Gly Val Pro Ser Arg Phe Ser Gly
50                  55                  60

Ser Gly Ser Gly Thr Gly Phe Thr Leu Asn Ile Ser Ser Leu Gln Pro
65                  70                  75                  80

Glu Asp Ile Ala Thr Tyr Tyr Cys Gln Gln Gly Gln Ser Phe Pro Leu
                85                  90                  95

Thr Phe Gly Ala Gly Thr Lys Leu Glu Leu Lys
            100                 105
```

<210> SEQ ID NO 118
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: D or Q
<220> FEATURE:
<221> NAME/KEY: MOD_RES
<222> LOCATION: (5)..(5)
<223> OTHER INFORMATION: Q or V

```
-continued

<220> FEATURE:
<221> NAME/KEY: MOD_RES
<222> LOCATION: (6)..(6)
<223> OTHER INFORMATION: E or Q
<220> FEATURE:
<221> NAME/KEY: MOD_RES
<222> LOCATION: (9)..(9)
<223> OTHER INFORMATION: P or S
<220> FEATURE:
<221> NAME/KEY: MOD_RES
<222> LOCATION: (16)..(16)
<223> OTHER INFORMATION: E or A
<220> FEATURE:
<221> NAME/KEY: MOD_RES
<222> LOCATION: (17)..(17)
<223> OTHER INFORMATION: T or S
<220> FEATURE:
<221> NAME/KEY: MOD_RES
<222> LOCATION: (20)..(20)
<223> OTHER INFORMATION: I or V
<220> FEATURE:
<221> NAME/KEY: MOD_RES
<222> LOCATION: (38)..(38)
<223> OTHER INFORMATION: K or R
<220> FEATURE:
<221> NAME/KEY: MOD_RES
<222> LOCATION: (43)..(43)
<223> OTHER INFORMATION: K or Q
<220> FEATURE:
<221> NAME/KEY: MOD_RES
<222> LOCATION: (46)..(46)
<223> OTHER INFORMATION: K or E
<220> FEATURE:
<221> NAME/KEY: MOD_RES
<222> LOCATION: (57)..(57)
<223> OTHER INFORMATION: E, Y, H or W
<220> FEATURE:
<221> NAME/KEY: MOD_RES
<222> LOCATION: (62)..(62)
<223> OTHER INFORMATION: D or Q
<220> FEATURE:
<221> NAME/KEY: MOD_RES
<222> LOCATION: (63)..(63)
<223> OTHER INFORMATION: D or G
<220> FEATURE:
<221> NAME/KEY: MOD_RES
<222> LOCATION: (65)..(65)
<223> OTHER INFORMATION: K or T
<220> FEATURE:
<221> NAME/KEY: MOD_RES
<222> LOCATION: (69)..(69)
<223> OTHER INFORMATION: A or V
<220> FEATURE:
<221> NAME/KEY: MOD_RES
<222> LOCATION: (73)..(73)
<223> OTHER INFORMATION: E or D
<220> FEATURE:
<221> NAME/KEY: MOD_RES
<222> LOCATION: (76)..(76)
<223> OTHER INFORMATION: A or V
<220> FEATURE:
<221> NAME/KEY: MOD_RES
<222> LOCATION: (84)..(84)
<223> OTHER INFORMATION: N, C or S
<220> FEATURE:
<221> NAME/KEY: MOD_RES
<222> LOCATION: (85)..(85)
<223> OTHER INFORMATION: N or S
<220> FEATURE:
<221> NAME/KEY: MOD_RES
<222> LOCATION: (88)..(88)
<223> OTHER INFORMATION: N or A
<220> FEATURE:
<221> NAME/KEY: MOD_RES
<222> LOCATION: (93)..(93)
<223> OTHER INFORMATION: T or V
<220> FEATURE:
<221> NAME/KEY: MOD_RES
<222> LOCATION: (116)..(116)
```

```
<223> OTHER INFORMATION: T or L
<220> FEATURE:
<221> NAME/KEY: MOD_RES
<222> LOCATION: (117)..(117)
<223> OTHER INFORMATION: L or V

<400> SEQUENCE: 118

Xaa Val Gln Leu Xaa Xaa Ser Gly Xaa Glu Leu Lys Lys Pro Gly Xaa
1               5                   10                  15

Xaa Val Lys Xaa Ser Cys Lys Ala Ser Gly Tyr Thr Phe Thr Asp Tyr
            20                  25                  30

Ser Met His Trp Val Xaa Gln Ala Pro Gly Xaa Gly Leu Xaa Trp Met
        35                  40                  45

Gly Trp Ile Asn Ile Glu Thr Gly Xaa Pro Thr Tyr Ala Xaa Xaa Phe
    50                  55                  60

Xaa Gly Arg Phe Xaa Phe Ser Leu Xaa Thr Ser Xaa Ser Thr Ala Tyr
65                  70                  75                  80

Leu Gln Ile Xaa Xaa Leu Lys Xaa Glu Asp Thr Ala Xaa Tyr Phe Cys
                85                  90                  95

Ala Arg Asp Tyr Tyr Gly Thr Tyr Phe Tyr Ala Met Asp Tyr Trp Gly
            100                 105                 110

Gln Gly Thr Xaa Xaa Thr Val Ser Ser
            115                 120

<210> SEQ ID NO 119
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Q or E
<220> FEATURE:
<221> NAME/KEY: MOD_RES
<222> LOCATION: (10)..(10)
<223> OTHER INFORMATION: I or T
<220> FEATURE:
<221> NAME/KEY: MOD_RES
<222> LOCATION: (11)..(11)
<223> OTHER INFORMATION: M or L
<220> FEATURE:
<221> NAME/KEY: MOD_RES
<222> LOCATION: (13)..(13)
<223> OTHER INFORMATION: A or L
<220> FEATURE:
<221> NAME/KEY: MOD_RES
<222> LOCATION: (15)..(15)
<223> OTHER INFORMATION: L or P
<220> FEATURE:
<221> NAME/KEY: MOD_RES
<222> LOCATION: (19)..(19)
<223> OTHER INFORMATION: V or A
<220> FEATURE:
<221> NAME/KEY: MOD_RES
<222> LOCATION: (21)..(21)
<223> OTHER INFORMATION: M or L
<220> FEATURE:
<221> NAME/KEY: MOD_RES
<222> LOCATION: (22)..(22)
<223> OTHER INFORMATION: T or S
<220> FEATURE:
<221> NAME/KEY: MOD_RES
<222> LOCATION: (29)..(29)
<223> OTHER INFORMATION: V or F
<220> FEATURE:
<221> NAME/KEY: MOD_RES
<222> LOCATION: (30)..(30)
```

```
<223> OTHER INFORMATION: S or P
<220> FEATURE:
<221> NAME/KEY: MOD_RES
<222> LOCATION: (43)..(43)
<223> OTHER INFORMATION: S or L
<220> FEATURE:
<221> NAME/KEY: MOD_RES
<222> LOCATION: (44)..(44)
<223> OTHER INFORMATION: S or A
<220> FEATURE:
<221> NAME/KEY: MOD_RES
<222> LOCATION: (46)..(46)
<223> OTHER INFORMATION: K or R
<220> FEATURE:
<221> NAME/KEY: MOD_RES
<222> LOCATION: (48)..(48)
<223> OTHER INFORMATION: W or L
<220> FEATURE:
<221> NAME/KEY: MOD_RES
<222> LOCATION: (59)..(59)
<223> OTHER INFORMATION: V or I
<220> FEATURE:
<221> NAME/KEY: MOD_RES
<222> LOCATION: (61)..(61)
<223> OTHER INFORMATION: A or D
<220> FEATURE:
<221> NAME/KEY: MOD_RES
<222> LOCATION: (71)..(71)
<223> OTHER INFORMATION: S or D
<220> FEATURE:
<221> NAME/KEY: MOD_RES
<222> LOCATION: (72)..(72)
<223> OTHER INFORMATION: Y or F
<220> FEATURE:
<221> NAME/KEY: MOD_RES
<222> LOCATION: (73)..(73)
<223> OTHER INFORMATION: S or T
<220> FEATURE:
<221> NAME/KEY: MOD_RES
<222> LOCATION: (78)..(78)
<223> OTHER INFORMATION: S or R
<220> FEATURE:
<221> NAME/KEY: MOD_RES
<222> LOCATION: (79)..(79)
<223> OTHER INFORMATION: M or L
<220> FEATURE:
<221> NAME/KEY: MOD_RES
<222> LOCATION: (81)..(81)
<223> OTHER INFORMATION: A or P
<220> FEATURE:
<221> NAME/KEY: MOD_RES
<222> LOCATION: (84)..(84)
<223> OTHER INFORMATION: A or F
<220> FEATURE:
<221> NAME/KEY: MOD_RES
<222> LOCATION: (86)..(86)
<223> OTHER INFORMATION: T or V
<220> FEATURE:
<221> NAME/KEY: MOD_RES
<222> LOCATION: (101)..(101)
<223> OTHER INFORMATION: A or Q
<220> FEATURE:
<221> NAME/KEY: MOD_RES
<222> LOCATION: (107)..(107)
<223> OTHER INFORMATION: L or I

<400> SEQUENCE: 119

Xaa Ile Val Leu Thr Gln Ser Pro Ala Xaa Xaa Ser Xaa Ser Xaa Gly
1               5                   10                  15

Glu Arg Xaa Thr Xaa Xaa Cys Thr Ala Ser Ser Ser Xaa Xaa Ser Ser
            20                  25                  30

Tyr Leu His Trp Tyr Gln Gln Lys Pro Gly Xaa Xaa Pro Xaa Leu Xaa
        35                  40                  45

Ile Tyr Ser Thr Ser Asn Leu Ala Ser Gly Xaa Pro Xaa Arg Phe Ser
    50                  55                  60
```

```
Gly Ser Gly Ser Gly Thr Xaa Xaa Xaa Leu Thr Ile Ser Xaa Xaa Glu
 65                  70                  75                  80

Xaa Glu Asp Xaa Ala Xaa Tyr Tyr Cys His Gln Tyr His Arg Ser Pro
                 85                  90                  95

Leu Thr Phe Gly Xaa Gly Thr Lys Leu Glu Xaa Lys
            100                 105
```

```
<210> SEQ ID NO 120
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Q or V
<220> FEATURE:
<221> NAME/KEY: MOD_RES
<222> LOCATION: (7)..(7)
<223> OTHER INFORMATION: S or P
<220> FEATURE:
<221> NAME/KEY: MOD_RES
<222> LOCATION: (11)..(11)
<223> OTHER INFORMATION: L or V
<220> FEATURE:
<221> NAME/KEY: MOD_RES
<222> LOCATION: (12)..(12)
<223> OTHER INFORMATION: V or K
<220> FEATURE:
<221> NAME/KEY: MOD_RES
<222> LOCATION: (20)..(20)
<223> OTHER INFORMATION: L or V
<220> FEATURE:
<221> NAME/KEY: MOD_RES
<222> LOCATION: (38)..(38)
<223> OTHER INFORMATION: K or R
<220> FEATURE:
<221> NAME/KEY: MOD_RES
<222> LOCATION: (40)..(40)
<223> OTHER INFORMATION: R or A
<220> FEATURE:
<221> NAME/KEY: MOD_RES
<222> LOCATION: (48)..(48)
<223> OTHER INFORMATION: I or M
<220> FEATURE:
<221> NAME/KEY: MOD_RES
<222> LOCATION: (55)..(55)
<223> OTHER INFORMATION: N, D, Q, K or E
<220> FEATURE:
<221> NAME/KEY: MOD_RES
<222> LOCATION: (56)..(56)
<223> OTHER INFORMATION: G, A or I
<220> FEATURE:
<221> NAME/KEY: MOD_RES
<222> LOCATION: (61)..(61)
<223> OTHER INFORMATION: N or A
<220> FEATURE:
<221> NAME/KEY: MOD_RES
<222> LOCATION: (62)..(62)
<223> OTHER INFORMATION: E or Q
<220> FEATURE:
<221> NAME/KEY: MOD_RES
<222> LOCATION: (65)..(65)
<223> OTHER INFORMATION: K or Q
<220> FEATURE:
<221> NAME/KEY: MOD_RES
<222> LOCATION: (66)..(66)
<223> OTHER INFORMATION: K or G
<220> FEATURE:
<221> NAME/KEY: MOD_RES
<222> LOCATION: (67)..(67)
<223> OTHER INFORMATION: K or R
<220> FEATURE:
```

```
<221> NAME/KEY: MOD_RES
<222> LOCATION: (68)..(68)
<223> OTHER INFORMATION: A or V
<220> FEATURE:
<221> NAME/KEY: MOD_RES
<222> LOCATION: (76)..(76)
<223> OTHER INFORMATION: S or I
<220> FEATURE:
<221> NAME/KEY: MOD_RES
<222> LOCATION: (82)..(82)
<223> OTHER INFORMATION: Q or E
<220> FEATURE:
<221> NAME/KEY: MOD_RES
<222> LOCATION: (85)..(85)
<223> OTHER INFORMATION: S or R
<220> FEATURE:
<221> NAME/KEY: MOD_RES
<222> LOCATION: (87)..(87)
<223> OTHER INFORMATION: T or R
<220> FEATURE:
<221> NAME/KEY: MOD_RES
<222> LOCATION: (89)..(89)
<223> OTHER INFORMATION: E or D
<220> FEATURE:
<221> NAME/KEY: MOD_RES
<222> LOCATION: (91)..(91)
<223> OTHER INFORMATION: S or T
<220> FEATURE:
<221> NAME/KEY: MOD_RES
<222> LOCATION: (112)..(112)
<223> OTHER INFORMATION: T or L
<220> FEATURE:
<221> NAME/KEY: MOD_RES
<222> LOCATION: (113)..(113)
<223> OTHER INFORMATION: L or V

<400> SEQUENCE: 120

Gln Val Gln Leu Xaa Gln Xaa Gly Ala Glu Xaa Xaa Lys Pro Gly Ala
1               5                   10                  15

Ser Val Lys Xaa Ser Cys Lys Ala Ser Gly Tyr Thr Phe Thr Thr Tyr
            20                  25                  30

Trp Met His Trp Val Xaa Gln Xaa Pro Gly Gln Gly Leu Glu Trp Xaa
        35                  40                  45

Gly Glu Ile Asn Pro Asn Xaa Xaa Gly Ile Asn Tyr Xaa Xaa Lys Phe
    50                  55                  60

Xaa Xaa Xaa Xaa Thr Leu Thr Val Asp Lys Ser Xaa Ser Thr Ala Tyr
65                  70                  75                  80

Met Xaa Leu Ser Xaa Leu Xaa Ser Xaa Asp Xaa Ala Val Tyr Tyr Cys
                85                  90                  95

Thr Ile Asp Tyr Tyr Asp Tyr Gly Gly Tyr Trp Gly Gln Gly Thr Xaa
            100                 105                 110

Xaa Thr Val Ser Ser
        115

<210> SEQ ID NO 121
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: V or Q
<220> FEATURE:
<221> NAME/KEY: MOD_RES
<222> LOCATION: (8)..(8)
<223> OTHER INFORMATION: Q or P
<220> FEATURE:
```

```
<221> NAME/KEY: MOD_RES
<222> LOCATION: (9)..(9)
<223> OTHER INFORMATION: K or S
<220> FEATURE:
<221> NAME/KEY: MOD_RES
<222> LOCATION: (10)..(10)
<223> OTHER INFORMATION: F or S
<220> FEATURE:
<221> NAME/KEY: MOD_RES
<222> LOCATION: (11)..(11)
<223> OTHER INFORMATION: M or L
<220> FEATURE:
<221> NAME/KEY: MOD_RES
<222> LOCATION: (13)..(13)
<223> OTHER INFORMATION: T or A
<220> FEATURE:
<221> NAME/KEY: MOD_RES
<222> LOCATION: (16)..(16)
<223> OTHER INFORMATION: R or G
<220> FEATURE:
<221> NAME/KEY: MOD_RES
<222> LOCATION: (20)..(20)
<223> OTHER INFORMATION: S or T
<220> FEATURE:
<221> NAME/KEY: MOD_RES
<222> LOCATION: (21)..(21)
<223> OTHER INFORMATION: V or I
<220> FEATURE:
<221> NAME/KEY: MOD_RES
<222> LOCATION: (41)..(41)
<223> OTHER INFORMATION: G or E
<220> FEATURE:
<221> NAME/KEY: MOD_RES
<222> LOCATION: (42)..(42)
<223> OTHER INFORMATION: Q or K
<220> FEATURE:
<221> NAME/KEY: MOD_RES
<222> LOCATION: (43)..(43)
<223> OTHER INFORMATION: S or A
<220> FEATURE:
<221> NAME/KEY: MOD_RES
<222> LOCATION: (46)..(46)
<223> OTHER INFORMATION: A or S
<220> FEATURE:
<221> NAME/KEY: MOD_RES
<222> LOCATION: (60)..(60)
<223> OTHER INFORMATION: D or S
<220> FEATURE:
<221> NAME/KEY: MOD_RES
<222> LOCATION: (63)..(63)
<223> OTHER INFORMATION: T or S
<220> FEATURE:
<221> NAME/KEY: MOD_RES
<222> LOCATION: (76)..(76)
<223> OTHER INFORMATION: T or S
<220> FEATURE:
<221> NAME/KEY: MOD_RES
<222> LOCATION: (77)..(77)
<223> OTHER INFORMATION: N or S
<220> FEATURE:
<221> NAME/KEY: MOD_RES
<222> LOCATION: (78)..(78)
<223> OTHER INFORMATION: V or L
<220> FEATURE:
<221> NAME/KEY: MOD_RES
<222> LOCATION: (80)..(80)
<223> OTHER INFORMATION: S or P
<220> FEATURE:
<221> NAME/KEY: MOD_RES
<222> LOCATION: (83)..(83)
<223> OTHER INFORMATION: L or F
<220> FEATURE:
<221> NAME/KEY: MOD_RES
<222> LOCATION: (85)..(85)
<223> OTHER INFORMATION: E or T
<220> FEATURE:
<221> NAME/KEY: MOD_RES
<222> LOCATION: (87)..(87)
<223> OTHER INFORMATION: F or Y
```

-continued

```
<220> FEATURE:
<221> NAME/KEY: MOD_RES
<222> LOCATION: (100)..(100)
<223> OTHER INFORMATION: S or Q
<220> FEATURE:
<221> NAME/KEY: MOD_RES
<222> LOCATION: (106)..(106)
<223> OTHER INFORMATION: M or I

<400> SEQUENCE: 121

Asp Ile Xaa Met Thr Gln Ser Xaa Xaa Xaa Xaa Ser Xaa Ser Val Xaa
1               5                   10                  15

Asp Arg Val Xaa Xaa Thr Cys Lys Ala Ser Gln Asn Val Gly Thr Asn
            20                  25                  30

Val Ala Trp Tyr Gln Gln Lys Pro Xaa Xaa Xaa Pro Lys Xaa Leu Ile
        35                  40                  45

Tyr Ser Ala Ser Tyr Arg Tyr Ser Gly Val Pro Xaa Arg Phe Xaa Gly
    50                  55                  60

Ser Gly Ser Gly Thr Asp Phe Thr Leu Thr Ile Xaa Xaa Xaa Gln Xaa
65                  70                  75                  80

Glu Asp Xaa Ala Xaa Tyr Xaa Cys Gln Gln Tyr Asn Ile Tyr Pro Tyr
                85                  90                  95

Thr Phe Gly Xaa Gly Thr Lys Leu Glu Xaa Lys
            100                 105

<210> SEQ ID NO 122
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: V or I
<220> FEATURE:
<221> NAME/KEY: MOD_RES
<222> LOCATION: (10)..(10)
<223> OTHER INFORMATION: G or T
<220> FEATURE:
<221> NAME/KEY: MOD_RES
<222> LOCATION: (12)..(12)
<223> OTHER INFORMATION: L or V
<220> FEATURE:
<221> NAME/KEY: MOD_RES
<222> LOCATION: (13)..(13)
<223> OTHER INFORMATION: Q or K
<220> FEATURE:
<221> NAME/KEY: MOD_RES
<222> LOCATION: (15)..(15)
<223> OTHER INFORMATION: S or T
<220> FEATURE:
<221> NAME/KEY: MOD_RES
<222> LOCATION: (19)..(19)
<223> OTHER INFORMATION: S or T
<220> FEATURE:
<221> NAME/KEY: MOD_RES
<222> LOCATION: (23)..(23)
<223> OTHER INFORMATION: S or T
<220> FEATURE:
<221> NAME/KEY: MOD_RES
<222> LOCATION: (43)..(43)
<223> OTHER INFORMATION: S or P
<220> FEATURE:
<221> NAME/KEY: MOD_RES
<222> LOCATION: (46)..(46)
<223> OTHER INFORMATION: G or A
<220> FEATURE:
<221> NAME/KEY: MOD_RES
<222> LOCATION: (62)..(62)
```

<223> OTHER INFORMATION: N or S
<220> FEATURE:
<221> NAME/KEY: MOD_RES
<222> LOCATION: (72)..(72)
<223> OTHER INFORMATION: S or T
<220> FEATURE:
<221> NAME/KEY: MOD_RES
<222> LOCATION: (77)..(77)
<223> OTHER INFORMATION: S or K
<220> FEATURE:
<221> NAME/KEY: MOD_RES
<222> LOCATION: (81)..(81)
<223> OTHER INFORMATION: F or V
<220> FEATURE:
<221> NAME/KEY: MOD_RES
<222> LOCATION: (83)..(83)
<223> OTHER INFORMATION: K or T
<220> FEATURE:
<221> NAME/KEY: MOD_RES
<222> LOCATION: (84)..(84)
<223> OTHER INFORMATION: I or M
<220> FEATURE:
<221> NAME/KEY: MOD_RES
<222> LOCATION: (86)..(86)
<223> OTHER INFORMATION: S or N
<220> FEATURE:
<221> NAME/KEY: MOD_RES
<222> LOCATION: (87)..(87)
<223> OTHER INFORMATION: V or M
<220> FEATURE:
<221> NAME/KEY: MOD_RES
<222> LOCATION: (89)..(89)
<223> OTHER INFORMATION: T or P
<220> FEATURE:
<221> NAME/KEY: MOD_RES
<222> LOCATION: (90)..(90)
<223> OTHER INFORMATION: A or V
<220> FEATURE:
<221> NAME/KEY: MOD_RES
<222> LOCATION: (117)..(117)
<223> OTHER INFORMATION: T or L

<400> SEQUENCE: 122

Gln Xaa Thr Leu Lys Glu Ser Gly Pro Xaa Leu Xaa Xaa Pro Xaa Gln
1               5                   10                  15

Thr Leu Xaa Leu Thr Cys Xaa Phe Ser Gly Phe Ser Leu Ser Thr Ser
            20                  25                  30

Gly Met Gly Val Ser Trp Ile Arg Gln Pro Xaa Gly Lys Xaa Leu Glu
        35                  40                  45

Trp Leu Ala His Ile Tyr Trp Asp Asp Lys Arg Tyr Xaa Pro Ser
    50                  55                  60

Leu Lys Ser Arg Leu Thr Ile Xaa Lys Asp Thr Ser Xaa Asn Gln Val
65                  70                  75                  80

Xaa Leu Xaa Xaa Thr Xaa Xaa Asp Xaa Xaa Asp Thr Gly Thr Tyr Tyr
                85                  90                  95

Cys Val Arg Lys Gly Tyr Tyr Asp Tyr Gly Tyr Val Met Asp Tyr Trp
            100                 105                 110

Gly Gln Gly Thr Xaa Val Thr Val Ser Ser
        115                 120

<210> SEQ ID NO 123
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)

<223> OTHER INFORMATION: A or S
<220> FEATURE:
<221> NAME/KEY: MOD_RES
<222> LOCATION: (8)..(8)
<223> OTHER INFORMATION: A or P
<220> FEATURE:
<221> NAME/KEY: MOD_RES
<222> LOCATION: (11)..(11)
<223> OTHER INFORMATION: N or L
<220> FEATURE:
<221> NAME/KEY: MOD_RES
<222> LOCATION: (15)..(15)
<223> OTHER INFORMATION: L or P
<220> FEATURE:
<221> NAME/KEY: MOD_RES
<222> LOCATION: (17)..(17)
<223> OTHER INFORMATION: T or E
<220> FEATURE:
<221> NAME/KEY: MOD_RES
<222> LOCATION: (18)..(18)
<223> OTHER INFORMATION: S or P
<220> FEATURE:
<221> NAME/KEY: MOD_RES
<222> LOCATION: (69)..(69)
<223> OTHER INFORMATION: S or G
<220> FEATURE:
<221> NAME/KEY: MOD_RES
<222> LOCATION: (79)..(79)
<223> OTHER INFORMATION: R or K
<220> FEATURE:
<221> NAME/KEY: MOD_RES
<222> LOCATION: (105)..(105)
<223> OTHER INFORMATION: S or G
<220> FEATURE:
<221> NAME/KEY: MOD_RES
<222> LOCATION: (109)..(109)
<223> OTHER INFORMATION: L or V
<220> FEATURE:
<221> NAME/KEY: MOD_RES
<222> LOCATION: (111)..(111)
<223> OTHER INFORMATION: M or I

<400> SEQUENCE: 123

Asp Ile Val Met Thr Gln Xaa Xaa Leu Ser Xaa Pro Val Thr Xaa Gly
1               5                   10                  15

Xaa Xaa Ala Ser Ile Ser Cys Arg Ser Ser Lys Ser Leu Leu His Ser
            20                  25                  30

Asn Gly Ile Thr Tyr Leu Asn Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Xaa Ser Gly Ser Gly Thr Asp Phe Thr Leu Xaa Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Xaa Gly Thr Lys Xaa Glu Xaa Lys
            100                 105                 110

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N, D, Q, K or E
<220> FEATURE:
<221> NAME/KEY: MOD_RES

```
<222> LOCATION: (7)..(7)
<223> OTHER INFORMATION: G, A or I

<400> SEQUENCE: 124

Glu Ile Asn Pro Asn Xaa Xaa Gly Ile Asn
1               5                   10

<210> SEQ ID NO 125
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg

<210> SEQ ID NO 126
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Ile Val Leu Thr Gln Ser Pro Ala Thr Leu Ser Leu Ser Pro Gly
1               5                   10                  15

Glu Arg Ala Thr Leu Ser Cys Gly Ala Ser Gln Ser Val Ser Ser Ser
            20                  25                  30

Tyr Leu Ala Trp Tyr Gln Gln Lys Pro Gly Leu Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

<210> SEQ ID NO 127
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asn Ser Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg

<210> SEQ ID NO 128
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
            85                  90                  95

<210> SEQ ID NO 129
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
            35                  40                  45

Trp Leu Ala Leu Ile Tyr Trp Asn Asp Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Gly Thr Tyr Tyr
            85                  90                  95

Cys Val

```
<210> SEQ ID NO 130
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 131
<211> LENGTH: 268
<212> TYPE: PRT
<213> ORGANISM: Homo sapiens

<400> SEQUENCE: 131

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205
```

Gln Trp Arg Glu Lys Thr Pro Glu Pro Pro Val Pro Cys Val Pro Glu
    210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265

<210> SEQ ID NO 132
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132
caagtgcagc tggtgcagtc tggcagcgag ctgaaaaaac tggcgcctc cgtgaaggtg      60 tcctgcaagg ctagcggcta cccttttacc gactacagca tgcactgggt ccgacaggct    120
ccaggacaag gcttggaatg gatgggctgg atcaacatcg agacaggcga gcccacatac    180
gcccagggct taccggcag attcgtgttc agcctggaca cctctgtgtc caccgcctac    240
ctgcagatca gctctctgaa ggccgaggat accgccgtgt acttctgcgc cagagactac    300
tacggcacct acttctacgc catggattac tggggccagg gcaccctggt taccgtttct    360
tct                                                                   363

<210> SEQ ID NO 133
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
gagatcgtgc tgacacagtc tcccgccaca ctgtcactgt ctccaggcga aagagccaca     60
ctgagctgta ccgccagcag ctctgtgtcc agcagctacc tgcactggta tcagcagaag    120
cctggactgg cccctcggct gctgatctac agcacaagca atctggccag cggcatcccc    180
gatagatttt ccggctctgg aagcggcacc gactacaccc tgacaatcag cagactggaa    240
cccgaggact cgccgtgta ctactgccac cagtaccaca aagccctct gacctttggc     300 cagggcacca agctggaaat caag                                            324

<210> SEQ ID NO 134
<211> LENGTH: 1353
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
caagtgcagc tggtgcagtc tggcagcgag ctgaaaaaac tggcgcctc cgtgaaggtg      60 tcctgcaagg ctagcggcta cccttttacc gactacagca tgcactgggt ccgacaggct    120
ccaggacaag gcttggaatg gatgggctgg atcaacatcg agacaggcga gcccacatac    180
gcccagggct taccggcag attcgtgttc agcctggaca cctctgtgtc caccgcctac    240

```
ctgcagatca gctctctgaa ggccgaggat accgccgtgt acttctgcgc cagagactac    300
tacggcacct acttctacgc catggattac tggggccagg gcaccctggt taccgtttct    360
tctgcctcca ccaagggccc atcggtcttc cccctggcac cctcctccaa gagcacctct    420
gggggcacag cggccctggg ctgcctggtc aaggactact ccccgaacc ggtgacggtg     480 tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt cccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag ccccatcga gaaaaccatc     1020 tccaaagcca agggcagcc ccgagaacca caggtgtaca ccctgccccc atcccgggag    1080
gagatgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                 1353
```

<210> SEQ ID NO 135
<211> LENGTH: 645
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 135

```
gagatcgtgc tgacacagtc tcccgccaca ctgtcactgt ctccaggcga aagagccaca    60
ctgagctgta ccgccagcag ctctgtgtcc agcagctacc tgcactggta tcagcagaag    120
cctggactgg cccctcggct gctgatctac agcacaagca atctggccag cggcatcccc    180
gatagatttt ccggctctgg aagcggcacc gactacaccc tgacaatcag cagactggaa    240
cccgaggact tcgccgtgta ctactgccac cagtaccaca gaagccctct gacctttggc    300
cagggcacca gctggaaat caagcgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgt                   645
```

<210> SEQ ID NO 136
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

```
caagtgcagc tggtgcaatc tggcgccgaa gtgaaaaagc ctggcgcctc tgtgaaggtg    60
tcctgcaagg ccagcggcta ccctttacc acctactgga tgcactgggt ccgacaggct   120
ccaggacaag gcttggagtg gatgggcgag atcaacccca atgaaggcgg catcaactac   180
gcccagaaat tccagggcag agtgaccctg accgtggaca gagcatcag caccgcctac   240
atggaactga ccggctgag atccgatgac accgccgtgt actactgcac catcgactac   300
tacgactacg gcggctattg gggccagggc acactggtta cagtgtcctc t           351
```

<210> SEQ ID NO 137
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 137

```
gacatccaga tgacacagag ccctagcagc ctgtctgcct ctgtgggcga tagagtgacc    60
atcacatgca aggccagcca gaacgtgggc accaatgtgg cctggtatca gcagaagcct   120
gagaaggccc ctaagagcct gatctacagc gccagctaca gatacagcgg cgtgccaagc   180
agatttctg gaagcggcag cggcaccgac ttcaccctga caattagtag cctgcagcct   240
gaggacttcg ccacctacta ctgccagcag tacaacatct acccctacac cttcggccag   300
ggcaccaagc tggaaatcaa g                                              321
```

<210> SEQ ID NO 138
<211> LENGTH: 1341
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 138

```
caagtgcagc tggtgcaatc tggcgccgaa gtgaaaaagc ctggcgcctc tgtgaaggtg    60
tcctgcaagg ccagcggcta ccctttacc acctactgga tgcactgggt ccgacaggct   120
ccaggacaag gcttggagtg gatgggcgag atcaacccca atgaaggcgg catcaactac   180
gcccagaaat tccagggcag agtgaccctg accgtggaca gagcatcag caccgcctac   240
atggaactga ccggctgag atccgatgac accgccgtgt actactgcac catcgactac   300
tacgactacg gcggctattg gggccagggc acactggtta cagtgtcctc tgcctccacc   360
aagggcccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtggacaaga agttgagcc caaatcttgt   660
gacaaaactc acacatgccc accgtgccca gcacctgaac tcctggggg accgtcagtc   720
ttcctcttcc ccccaaaacc caaggacacc ctcatgatct cccggacccc tgaggtcaca   780
tgcgtggtgg tggacgtgag ccacgaagac cctgaggtca agttcaactg gtacgtggac   840
ggcgtggagg tgcataatgc caagacaaag ccgcgggagg agcagtacaa cagcacgtac   900
```

```
cgtgtggtca gcgtcctcac cgtcctgcac caggactggc tgaatggcaa ggagtacaag      960
tgcaaggtct ccaacaaagc cctcccagcc cccatcgaga aaaccatctc caaagccaaa     1020
gggcagcccc gagaaccaca ggtgtacacc ctgcccccat cccgggagga gatgaccaag     1080
aaccaggtca gcctgacctg cctggtcaaa ggcttctatc ccagcgacat cgccgtggag     1140
tgggagagca atgggcagcc ggagaacaac tacaagacca cgcctcccgt gctggactcc     1200
gacggctcct tcttcctcta cagcaagctc accgtggaca gagcaggtg gcagcagggg     1260 aacgtcttct catgctccgt gatgcatgag gctctgcaca accactacac gcagaagagc     1320 ctctcccctgt ctccgggtaa a                                              1341
```

<210> SEQ ID NO 139
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 139

```
gacatccaga tgacacagag ccctagcagc ctgtctgcct ctgtgggcga tagagtgacc       60
atcacatgca aggccagcca gaacgtgggc accaatgtgg cctggtatca gcagaagcct      120
gagaaggccc ctaagagcct gatctacagc gccagctaca gatacagcgg cgtgccaagc      180 agatttctg gaagcggcag cggcaccgac ttcaccctga caattagtag cctgcagcct      240
gaggacttcg ccacctacta ctgccagcag tacaacatct accctacac cttcggccag      300 ggcaccaagc tggaaatcaa gcgtacggtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gt                         642
```

<210> SEQ ID NO 140
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 140

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Gly Tyr Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95
```

Ala Arg Asp Tyr Tyr Gly Thr Tyr Phe Tyr Ala Met Asp Tyr Trp Gly
            100                 105                 110

Gln Gly Thr Leu Val Thr Val Ser Ser
        115                 120

<210> SEQ ID NO 141
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Gly His Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Tyr Tyr Gly Thr Tyr Phe Tyr Ala Met Asp Tyr Trp Gly
            100                 105                 110

Gln Gly Thr Leu Val Thr Val Ser Ser
        115                 120

<210> SEQ ID NO 142
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Gly Trp Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Tyr Tyr Gly Thr Tyr Phe Tyr Ala Met Asp Tyr Trp Gly
            100                 105                 110

Gln Gly Thr Leu Val Thr Val Ser Ser
        115                 120

<210> SEQ ID NO 143
<211> LENGTH: 108

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Phe Ser Ser Ser
            20                  25                  30

Tyr Leu His Trp Tyr Gln Gln Lys Pro Gly Leu Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Tyr Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Leu Thr Phe Gly Gln Gly Thr Lys Leu Glu Ile Lys
            100                 105

<210> SEQ ID NO 144
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Pro Ser Ser
            20                  25                  30

Tyr Leu His Trp Tyr Gln Gln Lys Pro Gly Leu Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Tyr Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Leu Thr Phe Gly Gln Gly Thr Lys Leu Glu Ile Lys
            100                 105

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Trp Ile Asn Ile Glu Thr Gly Tyr Pro Thr
1               5                   10

<210> SEQ ID NO 146
<211> LENGTH: 10
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 146

Trp Ile Asn Ile Glu Thr Gly His Pro Thr
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Trp Ile Asn Ile Glu Thr Gly Trp Pro Thr
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Thr Ala Ser Ser Ser Phe Ser Ser Ser Tyr Leu His
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Thr Ala Ser Ser Ser Val Pro Ser Ser Tyr Leu His
1               5                   10

<210> SEQ ID NO 150
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Gly Tyr Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys 85                  90                  95
Ala Arg Asp Tyr Tyr Gly Thr Tyr Phe Tyr Ala Met Asp Tyr Trp Gly
                    100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 151
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Gly His Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Tyr Tyr Gly Thr Tyr Phe Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val

```
                    405                 410                 415
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
        450

<210> SEQ ID NO 152
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Glu Trp Met
        35                  40                  45

Gly Trp Ile Asn Ile Glu Thr Gly Trp Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Asp Tyr Tyr Gly Thr Tyr Phe Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 153
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Phe Ser Ser Ser
            20                  25                  30

Tyr Leu His Trp Tyr Gln Gln Lys Pro Gly Leu Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Tyr Thr Leu Thr Ile Ser Arg Leu Glu
65                  70                  75                  80

Pro Glu Asp Phe Ala Val Tyr Tyr Cys His Gln Tyr His Arg Ser Pro
            85                  90                  95

Leu Thr Phe Gly Gln Gly Thr Lys Leu Glu Ile Lys Arg Thr Val Ala
        100                 105                 110

Ala Pro Ser Val Phe Ile Phe Pro Pro Ser Asp Glu Gln Leu Lys Ser
    115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
        180                 185                 190

Tyr Ala Cys Glu Val Thr His Gln Gly Leu Ser Ser Pro Val Thr Lys
    195                 200                 205
```

```
Ser Phe Asn Arg Gly Glu Cys
    210                 215
```

<210> SEQ ID NO 154
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

```
Glu Ile Val Leu Thr Gln Ser Pro Ala Thr Leu Ser Leu Ser Pro Gly
1               5                   10                  15

Glu Arg Ala Thr Leu Ser Cys Thr Ala Ser Ser Ser Val Pro Ser Ser
            20                  25                  30

Tyr Leu His Trp Tyr Gln Gln Lys Pro Gly Leu Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Tyr Thr Leu Thr Ile Ser Arg Leu Glu
65                  70                  75                  80

Pro Glu Asp Phe Ala Val Tyr Tyr Cys His Gln Tyr His Arg Ser Pro
                85                  90                  95

Leu Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 155
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 155

```
caggtgcagc tggtgcagtc tggaagcgaa ctgaagaaac tggagcctc tgtgaaagtg      60 tcttgtaagg ccagcggcta caccttcacc gactacagca tgcactgggt gcggcaggcc    120
cctggacagg gcctggaatg gatgggctgg atcaacatcg agaccggcta tcccacctac    180
gcccagggct ttaccggacg gttcgtgttc agcctggata catctgtgtc tacagcctat    240
ctgcagatca gctctctgaa ggccgaagat acagccgtgt acttctgcgc ccggactac     300 tacggcaccct acttctacgc catggactac tggggccagg gaacactggt gacagtgtct    360
``` tct                                                                         363

<210> SEQ ID NO 156
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
caggtgcagc tggtgcagtc tggaagcgaa ctgaagaaac ctggagcctc tgtgaaagtg      60
tcttgtaagg ccagcggcta caccttcacc gactacagca tgcactgggt gcggcaggcc     120
cctggacagg gcctggaatg gatgggctgg atcaacatcg agaccggcca tcccacctac     180
gcccagggct ttaccggacg gttcgtgttc agcctggata catctgtgtc tacagcctat     240
ctgcagatca gctctctgaa ggccgaagat acagccgtgt acttctgcgc ccgggactac     300 tacggcaccct acttctacgc catggactac tggggccagg gaacactggt gacagtgtct     360
tct                                                                         363

<210> SEQ ID NO 157
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
caggtgcagc tggtgcagtc tggaagcgaa ctgaagaaac ctggagcctc tgtgaaagtg      60
tcttgtaagg ccagcggcta caccttcacc gactacagca tgcactgggt gcggcaggcc     120
cctggacagg gcctggaatg gatgggctgg atcaacatcg agaccggctg cccacctac     180 gcccagggct ttaccggacg gttcgtgttc agcctggata catctgtgtc tacagcctat     240
ctgcagatca gctctctgaa ggccgaagat acagccgtgt acttctgcgc ccgggactac     300 tacggcaccct acttctacgc catggactac tggggccagg gaacactggt gacagtgtct     360
tct                                                                         363

<210> SEQ ID NO 158
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158
gagatcgtgc tgacacagtc tcctgccaca ctgtctctgt ctcctggaga acgggccaca      60
ctgagctgca ccgccagcag cagcttcagc agcagctacc tgcactggta ccagcagaaa     120
cctggactgg cccctcggct gctgatctac agcaccagca acctggccag cggcatccct     180
gatcggtttt ctggcagcgg atctggcaca gattacacac tgaccatcag ccggctggaa     240
cctgaggatt ttgccgtgta ctactgccac cagtaccacc ggagcccct gaccttcggc      300 cagggaacaa agctggaaat caag                                                 324

<210> SEQ ID NO 159
<211> LENGTH: 324

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 159
gagatcgtgc tgacacagtc tcctgccaca ctgtctctgt ctcctggaga acgggccaca      60
ctgagctgca ccgccagcag cagcgtgcca agcagctacc tgcactggta ccagcagaaa    120
cctggactgg cccctcggct gctgatctac agcaccagca acctggccag cggcatccct    180
gatcggtttt ctggcagcgg atctggcaca gattacacac tgaccatcag ccggctggaa    240
cctgaggatt ttgccgtgta ctactgccac cagtaccacc ggagccccct gaccttcggc    300
cagggaacaa agctggaaat caag                                           324

<210> SEQ ID NO 160
<211> LENGTH: 1813
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 160
tctgataaga gtcagaggta actcccgttg cggtgctgtt aacggtggag ggcagtgtag     60
tctgagcagt actcgttgct gccgcgcgcg ccaccagaca taatagctga cagactaaca   120
gactgttcct ttccatgggt cttttctgca gtcaccgtcc ttagatccac tagtccagtg   180
tggtgaagct tgccgccacc atggcttggg tgtggaccct gctattcctg atggcagctg   240
cccaaagtat acaggcccag gtgcagctgg tgcagtctgg aagcgaactg aagaaacctg   300
gagcctctgt gaaagtgtct tgtaaggcca gcggctacac cttcaccgac tacagcatgc   360
actgggtgcg gcaggcccct ggacagggcc tggaatggat gggctggatc aacatcgaga   420
ccggctatcc cacctacgcc cagggcttta ccggacggtt cgtgttcagc ctggatacat   480
ctgtgtctac agcctatctg cagatcagct ctctgaaggc cgaagataca gccgtgtact   540
tctgcgcccg ggactactac ggcacctact tctacgccat ggactactgg ggccagggaa   600
cactggtgac agtgtcttct gcctccacca agggcccatc ggtcttcccc ctggcaccct   660
cctccaagag cacctctggg ggcacagcgg ccctgggctg cctggtcaag gactacttcc   720
ccgaaccggt gacggtgtcg tggaactcag gcgccctgac cagcggcgtg cacaccttcc   780
cggctgtcct acagtcctca ggactctact ccctcagcag cgtggtgacc gtgccctcca   840
gcagcttggg cacccagacc tacatctgca acgtgaatca caagcccagc aacaccaagg   900
tggacaagaa agttgagccc aaatcttgtg acaaaactca cacatgccca ccgtgcccag   960
cacctgaact cctggggggga ccgtcagtct tcctcttccc cccaaaaccc aaggacaccc  1020
tcatgatctc ccggacccct gaggtcacat gcgtggtggt ggacgtgagc cacgaagacc  1080
ctgaggtcaa gttcaactgg tacgtggacg gcgtggaggt gcataatgcc aagacaaagc  1140
cgcgggagga gcagtacaac agcacgtacc gtgtggtcag cgtcctcacc gtcctgcacc  1200
aggactggct gaatggcaag gagtacaagt gcaaggtctc caacaaagcc ctcccagccc  1260
ccatcgagaa aaccatctcc aaagccaaag ggcagccccg agaaccacag gtgtacaccc  1320
tgcccccatc ccgggaggag atgaccaaga accaggtcag cctgacctgc ctggtcaaag  1380
gcttctatcc cagcgacatc gccgtggagt gggagagcaa tgggcagccg gagaacaact  1440
```

```
acaagaccac gcctcccgtg ctggactccg acggctcctt cttcctctac agcaagctca    1500
ccgtggacaa gagcaggtgg cagcagggga acgtcttctc atgctccgtg atgcatgagg    1560
ctctgcacaa ccactacacg cagaagagcc tctccctgtc tccgggtaaa tgatagttcg    1620
aattcctaga agacatgata agatacattg atgagtttgg acaaaccaca actagaatgc    1680
agtgaaaaaa atgctttatt tgtgaaattt gtgatgctat tgctttattt gtaaccatta    1740
taagctgcaa taaacaagtt aacaacaaca attgcattca ttttatgttt caggttcagg    1800
gggaggtgtg gga                                                      1813

<210> SEQ ID NO 161
<211> LENGTH: 1813
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
tctgataaga gtcagaggta actcccgttg cggtgctgtt aacggtggag ggcagtgtag      60
tctgagcagt actcgttgct gccgcgcgcg ccaccagaca taatagctga cagactaaca    120
gactgttcct ttccatgggt cttttctgca gtcaccgtcc ttagatccac tagtccagtg    180
tggtgaagct tgccgccacc atggcttggg tgtggacctt gctattcctg atggcagctg    240
cccaaagtat acaggcccag gtgcagctgg tgcagtctgg aagcgaactg aagaaacctg    300
gagcctctgt gaaagtgtct tgtaaggcca gcggctacac cttcaccgac tacagcatgc    360
actgggtgcg gcaggcccct ggacagggcc tggaatggat gggctggatc aacatcgaga    420
ccggccatcc cacctacgcc cagggcttta ccggacggtt cgtgttcagc ctggatacat    480
ctgtgtctac agcctatctg cagatcagct ctctgaaggc cgaagataca gccgtgtact    540
tctgcgcccg ggactactac ggcacctact tctacgccat ggactactgg ggccagggaa    600
cactggtgac agtgtcttct gcctccacca agggcccatc ggtcttcccc ctggcaccct    660
cctccaagag cacctctggg ggcacagcgg ccctgggctg cctggtcaag gactacttcc    720
ccgaaccggt gacggtgtcg tggaactcag gcgccctgac cagcggcgtg cacaccttcc    780
cggctgtcct acagtcctca ggactctact ccctcagcag cgtggtgacc gtgccctcca    840
gcagcttggg cacccagacc tacatctgca acgtgaatca caagcccagc aacaccaagg    900
tggacaagaa agttgagccc aaatcttgtg acaaaactca cacatgccca ccgtgcccag    960
cacctgaact cctgggggga ccgtcagtct tcctcttccc cccaaaaccc aaggacaccc    1020
tcatgatctc ccggaccccct gaggtcacat gcgtggtggt ggacgtgagc cacgaagacc    1080
ctgaggtcaa gttcaactgg tacgtggacg gcgtggaggt gcataatgcc aagacaaagc    1140
cgcgggagga gcagtacaac agcacgtacc gtgtggtcag cgtcctcacc gtcctgcacc    1200
aggactggct gaatggcaag gagtacaagt gcaaggtctc caacaaagcc ctcccagccc    1260
ccatcgagaa aaccatctcc aaagccaaag gcagccccg agaaccacag gtgtacaccc    1320
tgcccccatc ccgggaggag atgaccaaga accaggtcag cctgacctgc ctggtcaaag    1380
gcttctatcc cagcgacatc gccgtggagt gggagagcaa tgggcagccg gagaacaact    1440
acaagaccac gcctcccgtg ctggactccg acggctcctt cttcctctac agcaagctca    1500
ccgtggacaa gagcaggtgg cagcagggga acgtcttctc atgctccgtg atgcatgagg    1560
ctctgcacaa ccactacacg cagaagagcc tctccctgtc tccgggtaaa tgatagttcg    1620
```

| | |
|---|---|
| aattcctaga agacatgata agatacattg atgagtttgg acaaaccaca actagaatgc | 1680 |
| agtgaaaaaa atgctttatt tgtgaaattt gtgatgctat tgctttattt gtaaccatta | 1740 |
| taagctgcaa taaacaagtt aacaacaaca attgcattca ttttatgttt caggttcagg | 1800 |
| gggaggtgtg gga | 1813 |

<210> SEQ ID NO 162
<211> LENGTH: 1813
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 162

| | |
|---|---|
| tctgataaga gtcagaggta actcccgttg cggtgctgtt aacggtggag ggcagtgtag | 60 |
| tctgagcagt actcgttgct gccgcgcgcg ccaccagaca taatagctga cagactaaca | 120 |
| gactgttcct ttccatgggt cttttctgca gtcaccgtcc ttagatccac tagtccagtg | 180 |
| tggtgaagct tgccgccacc atggcttggg tgtggacctt gctattcctg atggcagctg | 240 |
| cccaaagtat acaggcccag gtgcagctgg tgcagtctgg aagcgaactg aagaaacctg | 300 |
| gagcctctgt gaaagtgtct tgtaaggcca gcggctacac cttcaccgac tacagcatgc | 360 |
| actgggtgcg gcaggcccct ggacagggcc tggaatggat gggctggatc aacatcgaga | 420 |
| ccggctggcc cacctacgcc cagggcttta ccggacggtt cgtgttcagc ctggatacat | 480 |
| ctgtgtctac agcctatctg cagatcagct ctctgaaggc cgaagataca gccgtgtact | 540 |
| tctgcgcccg ggactactac ggcacctact tctacgccat ggactactgg ggccagggaa | 600 |
| cactggtgac agtgtcttct gcctccacca agggcccatc ggtcttcccc ctggcaccct | 660 |
| cctccaagag cacctctggg ggcacagcgg ccctgggctg cctggtcaag gactacttcc | 720 |
| ccgaaccggt gacggtgtcg tggaactcag gcgccctgac cagcggcgtg cacaccttcc | 780 |
| cggctgtcct acagtcctca ggactctact ccctcagcag cgtggtgacc gtgccctcca | 840 |
| gcagcttggg cacccagacc tacatctgca acgtgaatca caagcccagc aacaccaagg | 900 |
| tggacaagaa agttgagccc aaatcttgtg acaaaactca cacatgccca ccgtgcccag | 960 |
| cacctgaact cctgggggga ccgtcagtct tcctcttccc cccaaaaccc aaggacaccc | 1020 |
| tcatgatctc ccggaccect gaggtcacat gcgtggtggt ggacgtgagc cacgaagacc | 1080 |
| ctgaggtcaa gttcaactgg tacgtggacg gcgtggaggt gcataatgcc aagacaaagc | 1140 |
| cgcgggagga gcagtacaac agcacgtacc gtgtggtcag cgtcctcacc gtcctgcacc | 1200 |
| aggactggct gaatggcaag gagtacaagt gcaaggtctc caacaaagcc ctcccagccc | 1260 |
| ccatcgagaa aaccatctcc aaagccaaag gcagccccg agaaccacag gtgtacaccc | 1320 |
| tgcccccatc ccgggaggag atgaccaaga accaggtcag cctgacctgc ctggtcaaag | 1380 |
| gcttctatcc cagcgacatc gccgtggagt gggagagcaa tgggcagccg gagaacaact | 1440 |
| acaagaccac gcctcccgtg ctggactccg acggctcctt cttcctctac agcaagctca | 1500 |
| ccgtggacaa gagcaggtgg cagcagggga acgtcttctc atgctccgtg atgcatgagg | 1560 |
| ctctgcacaa ccactacacg cagaagagcc tctccctgtc tccgggtaaa tgatagttcg | 1620 |
| aattcctaga agacatgata agatacattg atgagtttgg acaaaccaca actagaatgc | 1680 |
| agtgaaaaaa atgctttatt tgtgaaattt gtgatgctat tgctttattt gtaaccatta | 1740 |
| taagctgcaa taaacaagtt aacaacaaca attgcattca ttttatgttt caggttcagg | 1800 | gggaggtgtg gga                                                              1813

<210> SEQ ID NO 163
<211> LENGTH: 1105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 163
tctgataaga gtcagaggta actcccgttg cggtgctgtt aacggtggag ggcagtgtag    60
tctgagcagt actcgttgct gccgcgcgcg ccaccagaca taatagctga cagactaaca   120
gactgttcct ttccatgggt cttttctgca gtcaccgtcc ttagatccac tagtccagtg   180
tggtgaagct gccgccacc atggcttggg tgtggacctt gctattcctg atggcggccg    240
cccaaagtat acaggccgag atcgtgctga cacagtctcc tgccacactg tctctgtctc   300
ctggagaacg ggccacactg agctgcaccg ccagcagcag cttcagcagc agctacctgc   360
actggtacca gcagaaacct ggactggccc ctcggctgct gatctacagc accagcaacc   420
tggccagcgg catccctgat cggttttctg gcagcggatc tggcacagat tacacactga   480
ccatcagccg gctggaacct gaggattttg ccgtgtacta ctgccaccag taccaccgga   540 gcccctgac cttcggccag ggaacaaagc tggaaatcaa cgtacggtg gctgcaccat    600 ctgtcttcat cttcccgcca tctgatgagc agttgaaatc tggaactgcc tctgttgtgt   660
gcctgctgaa taacttctat cccagagagg ccaaagtaca gtggaaggtg gataacgccc   720
tccaatcggg taactcccag gagagtgtca cagagcagga cagcaaggac agcacctaca   780
gcctcagcag caccctgacg ctgagcaaag cagactacga gaaacacaaa gtctacgcct   840
gcgaagtcac ccatcagggc ctgagctcgc ccgtcacaaa gagcttcaac aggggagagt   900
gttagtgatt cgaattccta gaagacatga taagatacat tgatgagttt ggacaaacca   960
caactagaat gcagtgaaaa aaatgcttta tttgtgaaat ttgtgatgct attgctttat  1020
ttgtaaccat tataagctgc aataaacaag ttaacaacaa caattgcatt catttatgt   1080 ttcaggttca gggggaggtg tggga                                        1105

<210> SEQ ID NO 164
<211> LENGTH: 1105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 164
tctgataaga gtcagaggta actcccgttg cggtgctgtt aacggtggag ggcagtgtag    60
tctgagcagt actcgttgct gccgcgcgcg ccaccagaca taatagctga cagactaaca   120
gactgttcct ttccatgggt cttttctgca gtcaccgtcc ttagatccac tagtccagtg   180
tggtgaagct gccgccacc atggcttggg tgtggacctt gctattcctg atggcggccg    240
cccaaagtat acaggccgag atcgtgctga cacagtctcc tgccacactg tctctgtctc   300
ctggagaacg ggccacactg agctgcaccg ccagcagcag cgtgccaagc agctacctgc   360
actggtacca gcagaaacct ggactggccc ctcggctgct gatctacagc accagcaacc   420
tggccagcgg catccctgat cggttttctg gcagcggatc tggcacagat tacacactga   480
ccatcagccg gctggaacct gaggattttg ccgtgtacta ctgccaccag taccaccgga   540

```
gcccctgac cttcggccag ggaacaaagc tggaaatcaa gcgtacggtg gctgcaccat    600
ctgtcttcat cttcccgcca tctgatgagc agttgaaatc tggaactgcc tctgttgtgt    660
gcctgctgaa taacttctat cccagagagg ccaaagtaca gtggaaggtg gataacgccc    720
tccaatcggg taactcccag gagagtgtca cagagcagga cagcaaggac agcacctaca    780
gcctcagcag caccctgacg ctgagcaaag cagactacga gaaacacaaa gtctacgcct    840
gcgaagtcac ccatcagggc ctgagctcgc ccgtcacaaa gagcttcaac aggggagagt    900
gttagtgatt cgaattccta gaagacatga taagatacat tgatgagttt ggacaaacca    960
caactagaat gcagtgaaaa aaatgcttta tttgtgaaat ttgtgatgct attgctttat   1020
ttgtaaccat tataagctgc aataaacaag ttaacaacaa caattgcatt cattttatgt   1080
ttcaggttca gggggaggtg tggga                                         1105
```

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: E, Y, H or W

<400> SEQUENCE: 165

Trp Ile Asn Ile Glu Thr Gly Xaa Pro Thr
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: V or F
<220> FEATURE:
<221> NAME/KEY: MOD_RES
<222> LOCATION: (7)..(7)
<223> OTHER INFORMATION: S or P

<400> SEQUENCE: 166

Thr Ala Ser Ser Ser Xaa Xaa Ser Ser Tyr Leu His
1               5                   10

ANTIBODIES THAT SPECIFICALLY BIND PD-1 AND METHODS OF USE

CROSS-REFERENCE TO RELATED APPLICATIONS

This application claims the benefit of the U.S. Provisional Application Ser. No. 62/673,185, filed 18 May 2018, the U.S. Provisional Application Ser. No. 62/648,114, filed 26 Mar. 2018, and the U.S. Provisional Application Ser. No. 62/515,188, filed 5 Jun. 2017, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on May 30, 2018, is named JBI5131USNPST25.txt and is 220 kilobytes in size.

FIELD OF THE INVENTION

The present invention relates to antibodies that specifically bind PD-1, polynucleotides encoding the antibodies or antigen binding fragments, and methods of making and using the foregoing.

BACKGROUND OF THE INVENTION

PD-1 (Programmed Death-1; PDCD1) is an inhibitory receptor the belongs to the CD28/CTLA-4 family. PD-1 is a type I transmembrane glycoprotein that contains a single extracellular domain, and a cytoplasmic domain containing both an immunoreceptor tyrosine-based inhibitory motif (ITIM) and an immunoreceptor tyrosine-based switch motif (ITSM). PD-1 is expressed on activated T cells, B cells, NK cells, and thymocytes, and on resting memory T cells including follicular helper T cells ($T_{FH}$) and peripheral helper T cells ($T_{PH}$). PD-1, upon engagement by its ligands PD-L1 or PD-L2, suppresses T cell functions through multiple mechanisms (Pauken & Wherry (2015) *Trends in Immunology* 36(4): 265-276). PD-1 engagement directly inhibits T cell receptor (TCR) signaling through co-localization with the TCR and subsequent induction of dephosphorylation of TCR proximal signaling molecules, inhibition of Ras/MEK/ERK pathway leading to inhibition of the cell cycle progression and T cell proliferation, inhibition of cell growth and survival and reprogramming of T cell metabolism through suppression of PI3K/AKT pathway, leading to the upregulation of the BATF transcription factor, and modulation of development, maintenance and function of regulatory T cells. PD-1 has also been proposed to increase T cell motility and to limit duration of interaction between T cells and target cells, thereby reducing the extent of T cell activation (Honda et al., (2014) *Immunity* 40(2): 235-47).

Studies in PD-1-deficient mice have indicated that this pathway is important for both central and peripheral tolerance. PD-1 deficient mice on a C57Bl/6 background can develop spontaneous autoimmune disease symptoms including autoantibody production, glomerulonephritis and arthritis (Nishimura et al., Immunity 1999). These data indicate that PD-1 is negatively regulating immune responses.

Monoclonal antibodies against PD-1 and PD-L1 are approved therapies for the treatment of cancers such as advanced melanoma, advanced non-small cell lung cancer, and classical Hodgkin lymphoma. PD-L1 has been found to be upregulated on many different tumor types, and is able to inhibit the tumor-infiltrating PD-1+ T cells. Antagonist PD-1 or PD-L1 monoclonal antibodies reverse this suppression, allowing the T cells to become activated and attack the tumor. Thus, immune checkpoint blockade provides a way to enhance anti-tumor immune responses.

Although biologic anti-inflammatory therapeutics are available, there remains a need for improved anti-inflammatory drugs that can effectively suppress inflammation for the treatment of various immune disorders, for example rheumatoid arthritis, in which a significant portion of patients still do not respond adequately to therapy.

SUMMARY OF THE INVENTION

The invention provides an isolated antibody that specifically binds PD-1 or an antigen binding fragment thereof, comprising a heavy chain complementarity determining region 1 (HCDR1), a HCDR2, a HCDR3, a light chain complementarity determining region 1 (LCDR1), a LCDR2 and a LCDR3 of SEQ ID NOs: 2, 165, 4, 166, 6 and 7, respectively.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 3, 4, 5, 6 and 7, respectively; the VH of SEQ ID NOs: 8, 9 or 10 and the VL of SEQ ID NOs: 14, 15 or 16; and/or a heavy chain (HC) of SEQ ID NO: 20, 21 or 22 and a light chain (LC) of SEQ ID NO: 26, 27 or 28.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 145, 4, 5, 6, and 7, respectively; the VH of SEQ ID NO: 140 and the VL of SEQ ID NO: 16; and/or the HC of SEQ ID NO: 150 and the LC of SEQ ID NO: 28.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 146, 4, 5, 6, and 7, respectively; the VH of SEQ ID NO: 141 and the VL of SEQ ID NO: 16; and/or the HC of SEQ ID NO: 151 and the LC of SEQ ID NO: 28.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 147, 4, 5, 6, and 7, respectively; the VH of SEQ ID NO: 142 and the VL of SEQ ID NO: 16; and/or the HC of SEQ ID NO: 152 and the LC of SEQ ID NO: 28.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 3, 4, 148, 6 and 7, respectively; the VH of SEQ ID NO: 10 and the VL of SEQ ID NO: 143; and/or the HC of SEQ ID NO: 22 and the LC of SEQ ID NO: 153.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 3, 4, 149, 6 and 7, respectively; the VH of SEQ ID NO: 10 and the VL of SEQ ID NO: 144; and/or the HC of SEQ ID NO: 22 and the LC of SEQ ID NO: 154.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 145, 4, 148, 6 and 7, respectively; the VH of SEQ ID NO: 140 and the VL of SEQ ID NO: 143; and/or the HC of SEQ ID NO: 150 and the LC of SEQ ID NO: 153.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 146, 4, 148, 6 and 7, respectively; the VH of SEQ ID NO: 141 and the VL of SEQ ID NO: 143; and/or the HC of SEQ ID NO: 151 and the LC of SEQ ID NO: 153.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 147, 4, 148, 6 and 7, respectively; the VH of SEQ ID NO: 142 and the VL of SEQ ID NO: 143; and/or the HC of SEQ ID NO: 152 and the LC of SEQ ID NO: 153.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 145, 4, 149, 6 and 7, respectively; the VH of SEQ ID NO: 140 and the VL of SEQ ID NO: 144; and/or the HC of SEQ ID NO: 150 and the LC of SEQ ID NO: 154.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 146, 4, 149, 6 and 7, respectively; the VH of SEQ ID NO: 141 and the VL of SEQ ID NO: 144; and/or the HC of SEQ ID NO: 151 and the LC of SEQ ID NO: 154.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 2, 147, 4, 149, 6 and 7, respectively, the VH of SEQ ID NO: 142 and the VL of SEQ ID NO: 144; and/or the HC of SEQ ID NO: 152 and the LC of SEQ ID NO: 154.

The invention also provides an isolated antibody that specifically binds PD-1 or an antigen binding fragment thereof, comprising a heavy chain complementarity determining region 1 (HCDR1), a HCDR2, a HCDR3, a light chain complementarity determining region 1 (LCDR1), a LCDR2 and a LCDR3 of SEQ ID NOs: 32, 124, 40, 41, 42 and 43, respectively.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: SEQ ID NOs: 32, 33, 40, 41, 42 and 43, respectively; the VH of SEQ ID NOs: 44 or 45 and the VL of SEQ ID NOs: 60, 61 or 62; and/or the HC of SEQ ID NOs: 66 or 67 and the LC of SEQ ID NOs: 82, 83 or 84.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 32, 34, 40, 41, 42 and 43, respectively; the VH of SEQ ID NO: 46 and the VL of SEQ ID NO: 61; and/or the HC of SEQ ID NO: 68 and the LC of SEQ ID NO: 83.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 32, 35, 40, 41, 42 and 43, respectively; the VH of SEQ ID NO: 47 and the VL of SEQ ID NO: 61; and/or the HC of SEQ ID NO: 69 and the LC of SEQ ID NO: 83.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 32, 36, 40, 41, 42 and 43, respectively; the VH of SEQ ID NO: 48 and the VL of SEQ ID NO: 61; and/or the HC of SEQ ID NO: 70 and the LC of SEQ ID NO: 83.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 32, 37, 40, 41, 42 and 43, respectively; the VH of SEQ ID NO: 49 and the VL of SEQ ID NO: 61; and/or the HC of SEQ ID NO: 71 and the LC of SEQ ID NO: 83.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 32, 38, 40, 41, 42 and 43, respectively; the VH of SEQ ID NO: 50 and the VL of SEQ ID NO: 61; and/or the HC of SEQ ID NO: 72 and the LC of SEQ ID NO: 83.

The invention also provides an isolated antibody that specifically binds PD-1 or an antigen binding fragment thereof, comprising the HCDR1, the HCDR2, the HCDR3, the LCDR1, the LCDR2 and the LCDR3 of SEQ ID NOs: 32, 39, 40, 41, 42 and 43, respectively; the VH of SEQ ID NO: 51 and the VL of SEQ ID NO: 61; and/or the HC of SEQ ID NO: 73 and the LC of SEQ ID NO: 83.

The invention also provides an isolated antibody that specifically binds PD-1 or an antigen binding fragment thereof, comprising a heavy chain complementarity determining region 1 (HCDR1), a HCDR2, a HCDR3, a light chain complementarity determining region 1 (LCDR1), a LCDR2 and a LCDR3 of SEQ ID NOs: 88, 89, 90, 91, 92 and 93, respectively.

The invention also provides an isolated antibody that specifically binds PD-1 or an antigen binding fragment thereof, wherein the antibody or the antigen binding fragment thereof competes for binding to PD-1 with the antibody of the invention.

The invention also provides an isolated antibody that specifically binds PD-1 or an antigen binding fragment thereof, wherein the antibody or the antigen binding fragment thereof binds to the same PD-1 epitope as the antibody of the invention.

The invention also provides an isolated antibody that specifically binds PD-1 or an antigen binding fragment thereof, wherein the antibody VH and the antibody VL or the antibody HC and the antibody LC are encoded by certain polynucleotides recited herein.

The invention also provides a polynucleotide encoding the antibody of the invention.

The invention also provides a vector comprising at least one polynucleotide of the invention The invention also provides a host cell comprising the vector of the invention.

The invention also provides a method of making the antibody or the antigen binding fragment thereof of the invention, comprising culturing the host cell of the invention in conditions that the antibody or the antigen binding fragment thereof is expressed, and isolating the antibody or the antigen binding fragment thereof.

The invention also provides a pharmaceutical composition comprising the antibody or the antigen binding fragment thereof of the invention.

The invention also provides a kit comprising the antibody or the antigen binding fragment thereof of the invention.

The invention also provides a method of suppressing activation of a PD-1 expressing T cell in a subject, comprising administering to a subject the isolated antibody or the antigen binding fragment thereof of the invention for a time sufficient to suppress activation of the PD-1 expressing T cell.

The invention also provides a method of downmodulating an immune response comprising administering to a subject in need thereof a therapeutically effective amount of the isolated antibody or the antigen binding fragment thereof of the invention for a time sufficient to downmodulate the immune response.

The invention also provides a method of treating an immune disorder comprising administering to a subject in need thereof a therapeutically effective amount of the isolated antibody or the antigen binding fragment thereof of the invention for a time sufficient to treat the immune disorder.

The invention also provides an anti-idiotypic antibody that specifically binds the antibody or the antigen-binding fragment of the invention.

The invention also provides an immunoconjugate comprising the antibody or the antigen binding fragment of the invention conjugated to a heterologous molecule.

BRIEF DESCRIPTION OF THE FIGURES

FIG. 2A shows the alignment of PD1B505 mAb lineage VH regions PD1H93 (SEQ ID NO: 8) PD1H384 (SEQ ID NO: 9), PD1H405 (SEQ ID NO: 10), PD1H585 (SEQ ID NO: 140), PD1H586 (SEQ ID NO: 141) and PD1H587 (SEQ ID NO: 142). CDR regions are underlined. The SEQ ID NOs: of the VH chains are shown after the chain name in the Figure (e.g. PD1H93_8; _8 indicates the SEQ ID NO: 8)

FIG. 2B shows the alignment of PD1B505 mAb lineage VL regions PD1L30 (SEQ ID NO: 14) PD1L468 (SEQ ID NO: 15), PD1L469 (SEQ ID NO: 16), PD1L651 (SEQ ID NO: 143) and PD1L652 (SEQ ID NO: 144). CDR regions are underlined. The SEQ ID NOs: of the VL chains are shown after the chain name in the Figure (e.g. PD1L30_14; _14 indicates the SEQ ID NO: 14)

FIG. 3A shows the alignment of PD1B506 mAb lineage VH regions PD1H90 (SEQ ID NO: 44) PD1H388 (SEQ ID NO: 45), PD1H399 (SEQ ID NO: 46), PD1H400 (SEQ ID NO: 47), PD1H401 (SEQ ID NO: 48), PD1H402 (SEQ ID NO: 49), PD1H403 (SEQ ID NO: 50) and PD1H404 (SEQ ID NO: 51). CDR regions are underlined.

FIG. 3B shows the alignment of PD1B506 mAb lineage VL regions PD1L28 (SEQ ID NO: 60) PD1L470 (SEQ ID NO: 61) and PD1L471 (SEQ ID NO: 62). CDR regions are underlined.

FIG. 4A shows the alignment of PD1B512 mAb lineage VH regions PD1H81 (SEQ ID NO: 94) and PD1H389 (SEQ ID NO: 95). CDR regions are underlined.

FIG. 4B shows the alignment of PD1B512 mAb lineage VL regions PD1L43 (SEQ ID NO: 98) PD1L472 (SEQ ID NO: 99) and PD1L473 (SEQ ID NO: 100). CDR regions are underlined.

FIG. 8A shows that PD-1 expression was higher on the $CD4^+$ $CD45RO^+$ or $CD8^+$ $CD45RO^+$ memory T cells stimulated with CMV as compared to the T cells stimulated with TT (inset, geometric mean fluorescent intensity). PD-1 antibody: solid lines; isotype control: dashed lines.

DETAILED DESCRIPTION OF THE INVENTION

Figure 1A:
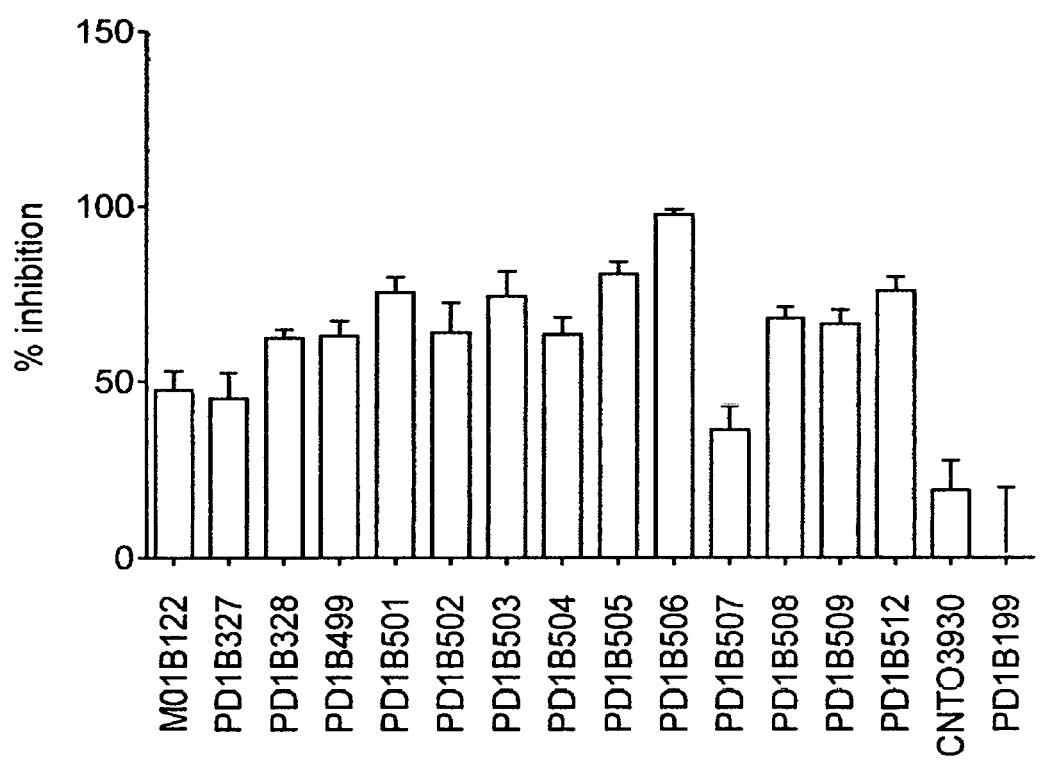
FIG. 1A shows that select generated antibodies inhibited T cell activation in CMV recall assay at a level of over 50% or more. CNT03930: isotype control. PD1B199: an antagonistic PD-1 mAb.

All publications, including but not limited to patents and patent applications cited in this specification are herein incorporated by reference as though fully set forth.

It is to be understood that the terminology used herein is for the purpose of describing embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

As used herein and in the claims, the singular forms "a," "and," and "the" include plural reference unless the context clearly dictates otherwise.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

"Specifically binds," "specific binding" or "binds" refers to antibody binding to an antigen or an epitope within the antigen with greater affinity than for other antigens or epitopes. Typically, the antibody binds to the antigen or the epitope within the antigen with an equilibrium dissociation constant ($K_D$) of about $1 \times 10^{-7}$ M or less, for example about $1 \times 10^{-8}$ M or less, about $1 \times 10^{-9}$ M or less, about $1 \times 10^{10}$ M or less, about $1 \times 10^{11}$ M or less, or about $1 \times 10^{12}$ M or less, typically with a $K_D$ that is at least one hundred-fold less than its $K_D$ for binding to a non-specific antigen (e.g., BSA, casein). The $K_D$ may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset). While a monospecific antibody specifically binds one antigen or one epitope, a bispecific antibody specifically binds two distinct antigens or two distinct epitopes.

"Agonist" or "agonistic" refers to an antibody which upon binding to PD-1 induces at least one biological activity that is induced by PD-1 ligand PD-L1. The antibody is an agonist when the at least one biological activity is induced by at least about 20%, 30%, 40%, 45%, 50%, 55%, 60%, 65%, 70%, 75%, 80%, 85%, 90%, 95%, or 100% greater than in the absence of the agonist (e.g., negative control), or when the induction is statistically significant when compared to the induction in the absence of the agonist. A typical biological activity that is induced by PD-L1 binding to PD-1 is inhibition of antigen-specific CD4$^+$ and/or CD8$^+$ T cells, resulting in suppression of immune responses.

PD-1 refers to human programmed cell death protein 1, PD-1. PD-1 is also known as CD279 or PDCD1. The amino acid sequence of the mature human PD-1 (without signal sequence) is shown in SEQ ID NO: 131. The extracellular domain spans residues 1-150, the transmembrane domain spans residues 151-171 and the cytoplasmic domain spans residues 172-268 of SEQ ID NO: 1. Throughout the specification "the extracellular domain of human PD-1" or "huPD1-ECD" refers to protein having amino acid sequence of residues 1-150 of SEQ ID NO: 1.

"Antibodies" is meant in a broad sense and includes immunoglobulin molecules belonging to any class, IgA, IgD, IgE, IgG and IgM, or sub-class IgA$_1$, IgA$_2$, IgG$_1$, IgG$_2$, IgG$_3$ and IgG$_4$ and including either kappa (κ) and lambda (λ) light chain. Antibodies include monoclonal antibodies, full length antibodies, antigen binding fragments, bispecific or multispecific antibodies, dimeric, tetrameric or multimeric antibodies, single chain antibodies, domain antibodies and any other modified configuration of the immunoglobulin molecule that comprises an antigen binding fragment of the required specificity. "Full length antibodies" are comprised of two heavy chains (HC) and two light chains (LC) interconnected by disulfide bonds as well as multimers thereof (e.g. IgM). Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL may be further subdivided into regions of hypervariability, termed complementarity determining regions (CDR), interspersed with framework regions (FR). Each VH and VL is composed of three CDRs and four FR segments, arranged from amino-terminus to carboxy-terminus in the following order: FR1, CDR1, FR2, CDR2, FR3, CDR3, and FR4.

"Complementarity determining regions (CDR)" are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu et al. (1970) J Exp Med 132: 211-50) (Kabat et al., Sequences of Proteins of Immunological Interest, 5th Ed. Public Health Service, National Institutes of Health, Bethesda, Md., 1991), Chothia (Chothia et al. (1987) J Mol Biol 196: 901-17), IMGT (Lefranc et al. (2003) Dev Comp Immunol 27: 55-77) and AbM (Martin and Thornton J Bmol Biol 263: 800-15, 1996). The correspondence between the various delineations and variable region numbering are described (see e.g. Lefranc et al. (2003) Dev Comp Immunol 27: 55-77; Honegger and Pluckthun, J Mol Biol (2001) 309:657-70; International ImMunoGeneTics (IMGT) database; Web resources, http://www_imgt_org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

"Antigen binding fragment" refers to a portion of an immunoglobulin molecule that binds an antigen. Antigen binding fragments may be synthetic, enzymatically obtainable or genetically engineered polypeptides and include the VH, the VL, the VH and the VL, Fab, F(ab')2, Fd and Fv fragments, domain antibodies (dAb) consisting of one VH domain or one VL domain, shark variable IgNAR domains, camelized VH domains, minimal recognition units consisting of the amino acid residues that mimic the CDRs of an antibody, such as FR3-CDR3-FR4 portions, the HCDR1, the HCDR2 and/or the HCDR3 and the LCDR1, the LCDR2 and/or the LCDR3. VH and VL domains may be linked together via a synthetic linker to form various types of single chain antibody designs where the VH/VL domains may pair intramolecularly, or intermolecularly in those cases when the VH and VL domains are expressed by separate single chain antibody constructs, to form a monovalent antigen binding site, such as single chain Fv (scFv) or diabody; described for example in Int. Patent Publ. Nos. WO1998/44001, WO1988/01649, WO1994/13804 and WO1992/01047.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Antibodies" include antibodies generated using various technologies, including antibodies generated from immunized animals such as mice, rats, rabbits or chickens, or identified from phage or mammalian display libraries as described herein.

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a human subject. Variable regions of human antibody are derived from human germline immunoglobulin sequences. If the antibody contains a constant region or a portion of the constant region, the constant region is also derived from human germline immunoglobulin sequences.

Human antibody comprises heavy or light chain variable regions that are "derived from" human germline immunoglobulin sequences if the variable regions of the antibody are obtained from a system that uses human germline immunoglobulin genes. Such exemplary systems are human immunoglobulin gene libraries displayed on phage or mammalian cells, and transgenic non-human animals such as mice, rats or chickens carrying human immunoglobulin loci. "Human antibody" typically contains amino acid differences when compared to the immunoglobulins expressed in humans due to differences between the systems used to obtain the antibody and human immunoglobulin loci, introduction of naturally occurring somatic mutations, intentional introduction of substitutions into the framework or CDRs. "Human antibody" is typically about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin sequences. In some cases, "human antibody" may contain consensus framework sequences derived from human framework sequence analyses, for example as described in (Knappik et al. (2000) J Mol Biol 296: 57-86), or synthetic HCDR3 incorporated into human immunoglobulin gene libraries displayed on phage, for example as described in (Shi et al. (2010) J Mol Biol 397: 385-96), and in Int. Patent Publ. No. WO2009/085462. Antibodies in which CDRs are derived from a non-human species are not included in the definition of "human antibody".

"Recombinant" refers to antibodies and other proteins that are prepared, expressed, created or isolated by recombinant means.

"Epitope" refers to a portion of an antigen to which an antibody specifically binds. Epitopes usually consist of chemically active (such as polar, non-polar or hydrophobic) surface groupings of moieties such as amino acids or polysaccharide side chains and may have specific three-dimensional structural characteristics, as well as specific charge characteristics. An epitope may be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

"Multispecific" refers to a protein, such as an antibody, that specifically binds two or more distinct antigens or two or more distinct epitopes within the same antigen. The multispecific protein may have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset), or may bind an epitope that is shared between two or more distinct antigens.

"Bispecific" refers to a protein, such as an antibody, that specifically binds two distinct antigens or two distinct epitopes within the same antigen. The bispecific protein may have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset), or may bind an epitope that is shared between two or more distinct antigens.

"In combination with" means that the drugs or therapeutics are administered to a subject such as human together in a mixture, concurrently as single agents or sequentially as single agents in any order.

"Treat" or "treatment" refers to both therapeutic treatment and prophylactic or preventative measures, wherein the object is to prevent or slow down (lessen) an undesired physiological change or disorder. Beneficial or desired clinical results include alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those already with the condition or disorder as well as those prone to have the condition or disorder or those in which the condition or disorder is to be prevented.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages.

"Downmodulate" or "downmodulating" refers to a detectable decrease in the level of an immune response in a subject compared with the level of a response in the subject in the absence of a treatment or compound, and/or compared with the level of a response in an otherwise identical but untreated subject.

"Immune disorder" refers to any disease, disorder or disease symptom caused by an activity of the immune system, including autoimmune diseases, inflammatory diseases and allergies.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

"Vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" means a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is an exemplary synthetic polynucleotide.

"Polypeptide" or "protein" means a molecule that comprises at least two amino acid residues linked by a peptide bond to form a polypeptide. Small polypeptides of less than 50 amino acids may be referred to as "peptides".

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Sample" refers to a collection of similar fluids, cells, or tissues isolated from a subject, as well as fluids, cells, or tissues present within a subject. Exemplary samples are biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium, lavage fluids and the like, tissue biopsies, fine needle aspirations, surgically resected tissue, organ cultures or cell cultures.

Conventional one and three-letter amino acid codes are used herein as shown in Table 1.

TABLE 1

| Amino acid | Three-letter code | One-letter code |
| --- | --- | --- |
| Alanine | Ala | A |
| Arginine | Arg | R |
| Asparagine | Asn | N |
| Aspartate | Asp | D |
| Cysteine | Cys | C |
| Glutamate | Gln | E |
| Glutamine | Glu | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Compositions of Matter

Provided herein are antibodies that specifically bind PD-1 or antigen binding fragments thereof, polynucleotides encoding the antibodies provided herein, vectors, host cells and methods of making and using the antibodies. The antibodies or antigen binding fragments thereof may be agonistic antibodies.

Some cancer patients treated with immune checkpoint inhibitors including PD-1 antagonists, develop autoimmune-related adverse events, such as symptoms of arthritis, colitis, or psoriasis. One hypothesis to explain this observation is that self-reactive T cells in these patients were being actively suppressed through PD-1, and were "unleashed" in the presence of a PD-1 antagonist. It is then reasonable to reverse this hypothesis and believe that is it likely that "already-unleashed" T cells in patients who have autoimmune disease could be suppressed through PD-1 ligation/agonism.

SNPs in the PD-1 gene PDCD1 have been found to be associated with a variety of autoimmune diseases including rheumatoid arthritis, lupus, and ankylosing spondylitis (summarized by Zamani et al., Cell Immunol 2016 310:27-41). Though functions have not yet been elucidated for the PD-1 SNPs, these associations may indicate that a reduction in PD-1 activity may lead to a reduction in T cell suppression, which could increase susceptibility to autoimmune disease.

There is a need for therapeutics to suppress autoreactive T cells in autoimmune diseases. PD-1$^+$ T cells have been found in tissues from patients with autoimmune diseases, including rheumatoid arthritis and Sjogren's Syndrome (Wan et al., J Immunol 2006 177(12):8844-50.; Kobayashi et al., J Rheumatol 2005 32(11):2156-63). An antibody capable of agonizing PD-1 could be used to suppress T cell proliferation and cytokine release, to limit damage within tissues and restore immune homeostasis. A PD-1 agonist mAb would target activated instead of resting naïve and memory T cells and B cells. In this way the therapeutic would suppress immune responses towards self-antigens in patients with autoimmune diseases without compromising immune memory responses to pathogens. Two T cell types that express high levels of PD-1, $T_{FH}$ and $T_{PH}$, promote B cell responses and antibody production (Rao et al., Nature 2017; 542: 110-114). The frequency of these cells is increased in autoimmune diseases driven by autoantibody production, including rheumatoid arthritis, systemic lupus erythematosus, and Sjogren's Syndrome (Rao et al., Nature 2017; 542: 110-114; He et al., Immunity 2013; 39: 770-781; Verstappen et al., Arthr & Rheum 2017; 69(9): 1850-1861). The antibodies of the invention, in addition to providing suppression of activated T cells may selectively deplete cells exhibiting high PD-1 expression, such as $T_{FH}$ and $T_{PH}$ cells.

The invention provides an isolated antibody that specifically binds PD-1 or an antigen binding fragment thereof.

The invention also provides an isolated antibody that specifically binds PD-1 or an antigen binding fragment thereof comprising a heavy chain complementarity determining region 1 (HCDR1), a HCDR2, and HCDR3, a light chain complementarity determining region 1 (LCDR1), a LCDR2 and/or a LCDR3 of any one of antibodies PD1B505, PD1B742, PD1B743, PD1B878, PD1B506, PD1B750, PD1B751, PD1B845, PD1B846, PD1B847, PD1B848, PD1B849, PD1B850, PD1B512, PD1B756, PD1B757, PD1B1085, PD1B1086, PD1B1087, PD1B1088, PD1B1089, PD1B1090, PD1B1091, PD1B1092, PD1B1093, PD1B1094 or PD1B1095.

The invention also provides an isolated antibody that specifically binds PD-1 or an antigen binding fragment thereof comprising a heavy chain variable region (VH) framework and/or a light chain variable region (VL) framework of any one of antibodies PD1B505, PD1B742, PD1B743, PD1B878, PD1B506, PD1B750, PD1B751, PD1B845, PD1B846, PD1B847, PD1B848, PD1B849, PD1B850, PD1B512, PD1B756, PD1B757, PD1B1085, PD1B1086, PD1B1087, PD1B1088, PD1B1089, PD1B1090, PD1B1091, PD1B1092, PD1B1093, PD1B1094 or PD1B1095.

The invention also provides an isolated antibody that specifically binds PD-1 or an antigen binding fragment thereof comprising the VH and/or the VL of any one of antibodies PD1B505, PD1B742, PD1B743, PD1B878, PD1B506, PD1B750, PD1B751, PD1B845, PD1B846, PD1B847, PD1B848, PD1B849, PD1B850, PD1B512, PD1B756, PD1B757, PD1B1085, PD1B1086, PD1B1087, PD1B1088, PD1B1089, PD1B1090, PD1B1091, PD1B1092, PD1B1093, PD1B1094 or PD1B1095.

In some embodiments, the antibody that specifically binds PD-1 or the antigen binding fragment thereof is an agonistic antibody.

In some embodiments, the antibody that specifically binds PD-1 or the antigen binding fragment thereof mediates ADCC of PD-1 expressing cells.

In some embodiments, PD-1 expressing cells are activated memory T cells, T follicular helper cells ($T_{FH}$) or T peripheral helper cells ($T_{PH}$), or any combination thereof.

$T_{FH}$ cells may be identified as: live, CD19−CD56−/CD4+CD45RO+/HLADR+/CXCR5+/ICOS+PD1+;

$T_{PH}$ cells may be identified as: live, CD19−CD56−/CD4+CD45RO+/HLADR+/CXCR5−/ICOS+PD1+; combination of $T_{FH}$/$T_{PH}$ cells may be identified as: live, CD19−CD56−/CD4+CD45RO+/HLADR+/ICOS+PD1+.

Memory T cells may be identified as CD4$^+$ CD45RO$^+$ or CD8$^+$ CD45RO$^+$.

PD1B505 Lineage Antibodies mAbs PD1B505, PD1B742, PD1B743, PD1B878, PD1B1085, PD1B1086, PD1B1087, PD1B1088, PD1B1089, PD1B1090, PD1B1091, PD1B1092, PD1B1093, PD or PD are exemplary antibodies of PD1B505 mAb lineage. These mAbs have identical CDR regions except that some antibodies have one amino acid difference in the HCDR2 and one or two amino acid differences in the LCDR1. The VH region identity is between 82-100% and the VL region identity between 78-100%. PD1B505 lineage mAbs are ligand non-blocking.

The lineage is characterized by the HCDR1, the HCDR2, the HCDR3, the LCDR1, the LCDR2 and the LCDR3 of SEQ ID NOs: 2, 165, 4, 166, 6 and 7, respectively, and by the VH genus sequence of SEQ ID NO: 118 and the VL genus sequence of SEQ ID NO: 119.

```
                                        SEQ ID NO: 165
            (HCDR2 genus)
            WINIETGXPT;
``` wherein X is E, Y, H or W.

```
                                        SEQ ID NO: 166
            (LCDR1 genus)
            TASSSX₁X₂SSYLH;
``` wherein
$X_1$ is V or F; and
$X_2$ is S or P.

The invention also provides and isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 165, 4, 166, 6 and 7, respectively.

In some embodiments, the isolated antibody that specifically binds PD-1 or the antigen binding fragment thereof comprises the HCDR2 of SEQ ID NOs: 3, 145, 146 or 147 and/or the LCDR1 of SEQ ID NOs: 5, 148 or 149.

In some embodiments, the antibody or the antigen binding fragment thereof has one, two, three, four or five of the following properties:

does not block PD-L1 binding to PD-1, wherein lack of blocking is measured by inability of the antibody to inhibit clustering of PD-L1 expressing and PD-1 expressing cells as described in Example 1;

binds PD-1 with an equilibrium dissociation constant ($K_D$) of about $5 \times 10^{-8}$ M or less, wherein the $K_D$ is measured using a ProteOn XPR36 system at +25° C.;

binds PD-1 with an association constant (ka) of about $3 \times 10^4$ l/Ms or more, wherein the ka is measured using a ProteOn XPR36 system at +25° C.;

binds PD-1 with a dissociation constant (kd) of about $3 \times 10^{-3}$ l/s or less, wherein the kd is measured using a ProteOn XPR36 system at +25° C.; or inhibits proliferation of antigen specific T cells; wherein proliferation is assessed in a CMV-PBMC assay.

In some embodiments, the antibody that specifically binds PD-1 or the antigen binding fragment thereof comprises the VH framework derived from IGHV7-4-1*1 (SEQ ID NO: 125).

In some embodiments, the antibody that specifically binds PD-1 or the antigen binding fragment thereof comprises the VL framework derived from IGKV3D-20*1 (SEQ ID NO: 126).

In some embodiments, the antibody that specifically binds PD-1 or the antigen binding fragment thereof comprises the VH framework derived from IGHV7-4-1*1 (SEQ ID NO: 125) and the VL framework derived from IGKV3D-20*1 (SEQ ID NO: 126).

```
                                SEQ ID NO: 125
IGHV7-4-1*1
QVQLVQSGSELKKPGASVKVSCKASGYTFTSYAMNWVRQAPGQGLEWMGW

INTNTGNPTYAQGFTGRFVFSLDTSVSTAYLQICSLKAEDTAVYYCAR

SEQ ID NO: 126
IGKV3D-20*1
EIVLTQSPATLSLSPGERATLSCGASQSVSSSYLAWYQQKPGLAPRLLIY

DASSRATGIPDRFSGSGSGTDFTLTISRLEPEDFAVYYCQQYGSSP
```

The invention also provides an isolated antibody that specifically binds PD-1 or an antigen binding fragment thereof comprising a heavy chain variable region (VH) of SEQ ID NO: 118. SEQ ID NO: 118 is a VH genus sequence of PD1B505 lineage mAbs.

The invention also provides an isolated antibody that specifically binds PD-1 or an antigen binding fragment thereof comprising a light chain variable region (VL) of SEQ ID NO: 119. SEQ ID NO: 118 is a VL genus sequence of PD1B505 lineage mAbs.

The invention also provides an isolated antibody that specifically binds PD-1 or an antigen binding fragment thereof comprising the VH of SEQ ID NO: 118 and the VL of SEQ ID NO: 119. The CDRs are shown in bold in SEQ ID NO: 118 and SEQ ID NO: 119.

```
SEQ ID NO: 118
(PD1B505 lineage VH genus)
X1VQLX2X3SGX4ELKKPGX5X6VKX7SCKASGYTFTDYSMHWVX8QAPG

X9GLX10WMGWINIETGX11PTYAX12X13FX14GRFX15FSLX16TS

X17STAYLQIX18X19LKX20EDTAX21YFCARDYYGTYFYAMDYWGQGT

X22X23TVSS;
``` wherein
$X_1$ is D or Q;
$X_2$ is Q or V;
$X_3$ is E or Q;
$X_4$ is P or S;
$X_5$ is E or A;
$X_6$ is T or S;
$X_7$ is I or V;
$X_8$ is K or R;
$X_9$ is K or Q;
$X_{10}$ is K or E;
$X_{11}$ is E, Y, H or W;
$X_{12}$ is D or Q;
$X_{13}$ is D or G;
$X_{14}$ is K or T;
$X_{15}$ is A or V;
$X_{16}$ is E or D;
$X_{17}$ is A or V;
$X_{18}$ is N, C or S;
$X_{19}$ is N or S;
$X_{20}$ is N or A;
$X_{21}$ is T or V;
$X_{22}$ is T or L; or
$X_{23}$ is L or V.

```
                                SEQ ID NO: 119
(PD1B505 lineage VL genus)
X1IVLTQSPAX2X3SX4SX5GERX6TX7X8CTASSSX9X10SSYLHWYQQ

KPGX11X12PX13LX14IYSTSNLASGX15PX16RFSGSGSGTX17X18

X19LTISX20X21EX22EDX23AX24YYCHQYHRSPLTFGX25GTKLE

X26K;
``` wherein
$X_1$ is Q or E;
$X_2$ is I or T;
$X_3$ is M or L;
$X_4$ is A or L;
$X_5$ is L or P;
$X_6$ is V or A;
$X_7$ is M or L;
$X_8$ is T or S;
$X_9$ is V or F;
$X_{10}$ is S or P;
$X_{11}$ is S or L;
$X_{12}$ is S or A;
$X_{13}$ is K or R;
$X_{14}$ is W or L;
$X_{15}$ is V or I;
$X_{16}$ is A or D;
$X_{17}$ is S or D;
$X_{18}$ is Y or F;
$X_{19}$ is S or T;
$X_{20}$ is S or R;
$X_{21}$ is M or L;
$X_{22}$ is A or P;
$X_{23}$ is A or F;

$X_{24}$ is T or V;
$X_{25}$ is A or Q; and
$X_{26}$ is L or I.

In some embodiments, the antibody that specifically binds PD-1 or the antigen binding fragment thereof comprises the VH of SEQ ID NOs: 8, 9, 10, 140, 141 or 142.

In some embodiments, the antibody that specifically binds PD-1 or the antigen binding fragment thereof comprises the VL of SEQ ID NOs: 14, 15, 16, 143 or 144. In some embodiments, the antibody that specifically binds PD-1 or the antigen binding fragment thereof comprises the VH of SEQ ID NOs: 8, 9, 10, 140, 141 or 142 and the VL of SEQ ID NOs: 14, 15, 16, 143 or 144.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 3, 4, 5, 6 and 7, respectively.

In some embodiments, the antibody comprises the VH of SEQ ID NOs: 8, 9 or 10 and the VL of SEQ ID NOs: 14, 15 or 16.

In some embodiments, the antibody comprises a heavy chain (HC) of SEQ ID NO: 20, 21 or 22 and a light chain (LC) of SEQ ID NO: 26, 27 or 28.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 145, 4, 5, 6, and 7, respectively. In some embodiments, the antibody comprises the VH of SEQ ID NO: 140 and the VL of SEQ ID NO: 16. In some embodiments, the antibody comprises the HC of SEQ ID NO: 150 and the LC of SEQ ID NO: 28. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 146, 4, 5, 6, and 7, respectively. In some embodiments, the antibody comprises the VH of SEQ ID NO: 141 and the VL of SEQ ID NO: 16. In some embodiments, the antibody comprises the HC of SEQ ID NO: 151 and the LC of SEQ ID NO: 28. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 147, 4, 5, 6, and 7, respectively. In some embodiments, the antibody comprises the VH of SEQ ID NO: 142 and the VL of SEQ ID NO: 16. In some embodiments, the antibody comprises the HC of SEQ ID NO: 152 and the LC of SEQ ID NO: 28. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 3, 4, 148, 6 and 7, respectively. In some embodiments, the antibody comprises the VH of SEQ ID NO: 10 and the VL of SEQ ID NO: 143. In some embodiments, the antibody comprises the HC of SEQ ID NO: 22 and the LC of SEQ ID NO: 153. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 3, 4, 149, 6 and 7, respectively. In some embodiments, the antibody comprises the VH of SEQ ID NO: 10 and the VL of SEQ ID NO: 144. In some embodiments, the antibody comprises the HC of SEQ ID NO: 22 and the LC of SEQ ID NO: 154. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 145, 4, 148, 6 and 7, respectively. In some embodiments, the antibody comprises the VH of SEQ ID NO: 140 and the VL of SEQ ID NO: 143. In some embodiments, the antibody comprises the HC of SEQ ID NO: 150 and the LC of SEQ ID NO: 153. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 146, 4, 148, 6 and 7, respectively. In some embodiments, the antibody comprises the VH of SEQ ID NO: 141 and the VL of SEQ ID NO: 143. In some embodiments, the antibody comprises the HC of SEQ ID NO: 151 and the LC of SEQ ID NO: 153. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 147, 4, 148, 6 and 7, respectively. In some embodiments, the antibody comprises the VH of SEQ ID NO: 142 and the VL of SEQ ID NO: 143. In some embodiments, the antibody comprises the HC of SEQ ID NO: 152 and the LC of SEQ ID NO: 153. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 145, 4, 149, 6 and 7, respectively. In some embodiments, the antibody comprises the VH of SEQ ID NO: 140 and the VL of SEQ ID NO: 144. In some embodiments, the antibody comprises the HC of SEQ ID NO: 150 and the LC of SEQ ID NO: 154. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 146, 4, 149, 6 and 7, respectively. In some embodiments, the antibody comprises the VH of SEQ ID NO: 141 and the VL of SEQ ID NO: 144. In some embodiments, the antibody comprises the HC of SEQ ID NO: 151 and the LC of SEQ ID NO: 154. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 2, 147, 4, 149, 6 and 7, respectively. In some embodiments, the antibody comprises the VH of SEQ ID NO: 142 and the VL of SEQ ID NO: 144. In some embodiments, the antibody comprises the HC of SEQ ID NO: 152 and the LC of SEQ ID NO: 154. The antibody is also provided for use in therapy, such as in treatment of an immune disorder, rheumatoid arthritis, lupus, systemic lupus erythematosus or graft versus host disease.

In some embodiments, the antibody that specifically binds PD-1 or the antigen binding fragment thereof is an agonistic antibody.

The invention also provides an isolated antibody that specifically binds PD-1 or an antigen binding fragment thereof, wherein the antibody competes for binding to PD-1 with the antibody or the antigen binding fragment comprising the VH of SEQ ID NO: 8 and the VL of SEQ ID NO: 14;
the VH of SEQ ID NO: 9 and the VL of SEQ ID NO: 15;
the VH of SEQ ID NO: 9 and the VL of SEQ ID NO: 16;
the VH of SEQ ID NO: 10 and the VL of SEQ ID NO: 16;
the VH of SEQ ID NO: 140 and the VL of SEQ ID NO: 16;
the VH of SEQ ID NO: 141 and the VL of SEQ ID NO: 16;
the VH of SEQ ID NO: 142 and the VL of SEQ ID NO: 16;
the VH of SEQ ID NO: 10 and the VL of SEQ ID NO: 143;
the VH of SEQ ID NO: 10 and the VL of SEQ ID NO: 144;
the VH of SEQ ID NO: 140 and the VL of SEQ ID NO: 143;
the VH of SEQ ID NO: 141 and the VL of SEQ ID NO: 143;
the VH of SEQ ID NO: 142 and the VL of SEQ ID NO: 143;
the VH of SEQ ID NO: 140 and the VL of SEQ ID NO: 144;
the VH of SEQ ID NO: 141 and the VL of SEQ ID NO: 144; or
the VH of SEQ ID NO: 142 and the VL of SEQ ID NO: 144.

The invention also provides herein an isolated antibody that specifically binds PD-1 or an antigen binding fragment thereof, wherein the antibody binds the same epitope that is bound by the antibody comprising the VH of SEQ ID NO: 8 and the VL of SEQ ID NO: 14;
the VH of SEQ ID NO: 9 and the VL of SEQ ID NO: 15;
the VH of SEQ ID NO: 9 and the VL of SEQ ID NO: 16;
the VH of SEQ ID NO: 10 and the VL of SEQ ID NO: 16;
the VH of SEQ ID NO: 140 and the VL of SEQ ID NO: 16;
the VH of SEQ ID NO: 141 and the VL of SEQ ID NO: 16;
the VH of SEQ ID NO: 142 and the VL of SEQ ID NO: 16;
the VH of SEQ ID NO: 10 and the VL of SEQ ID NO: 143;
the VH of SEQ ID NO: 10 and the VL of SEQ ID NO: 144;
the VH of SEQ ID NO: 140 and the VL of SEQ ID NO: 143;
the VH of SEQ ID NO: 141 and the VL of SEQ ID NO: 143;
the VH of SEQ ID NO: 142 and the VL of SEQ ID NO: 143;
the VH of SEQ ID NO: 140 and the VL of SEQ ID NO: 144;
the VH of SEQ ID NO: 141 and the VL of SEQ ID NO: 144; or
the VH of SEQ ID NO: 142 and the VL of SEQ ID NO: 144.

In some embodiments, the VH and the VL or the HC and the LC of the antibody that specifically binds PD-1 or the antigen binding fragment thereof provided herein are encoded by polynucleotide comprising the polynucleotide sequence of SEQ ID NOs: 11 and 17, respectively;
SEQ ID NOs: 12 and 18, respectively;
SEQ ID NOs: 12 and 19, respectively;
SEQ ID NOs: 13 and 19, respectively;
SEQ ID NOs: 23 and 29, respectively;
SEQ ID NOs: 24 and 30, respectively;
SEQ ID NOs: 24 and 31, respectively;
SEQ ID NOs: 25 and 31, respectively;
SEQ ID NOs: 132 and 133, respectively; or
SEQ ID NOs: 134 and 135, respectively;
SEQ ID NOs: 155 and 19, respectively;
SEQ ID NOs: 156 and 19, respectively;
SEQ ID NOs: 157 and 19, respectively;
SEQ ID NOs: 13 and 158, respectively;
SEQ ID NOs: 13 and 159, respectively;
SEQ ID NOs: 155 and 158, respectively;
SEQ ID NOs: 156 and 158, respectively;
SEQ ID NOs: 157 and 158, respectively;
SEQ ID NOs: 155 and 159, respectively;
SEQ ID NOs: 156 and 159, respectively;
SEQ ID NOs: 157 and 159, respectively;
SEQ ID NOs: 160 and 31, respectively;
SEQ ID NOs: 161 and 31, respectively;
SEQ ID NOs: 162 and 31, respectively;
SEQ ID NOs: 25 and 163, respectively;
SEQ ID NOs: 25 and 164, respectively;
SEQ ID NOs: 160 and 163, respectively;
SEQ ID NOs: 161 and 163, respectively;
SEQ ID NOs: 162 and 163, respectively;
SEQ ID NOs: 160 and 164, respectively;
SEQ ID NOs: 161 and 164, respectively; or
SEQ ID NOs: 162 and 164, respectively.

PD1B506 Lineage Antibodies mAbs PD1B506, PD1B750, PD1B751, PD1B845, PD1B846, PD1B847, PD1B848, PD1B849 and PD1B850 are exemplary antibodies of the PD1B506 mAb lineage. These mAbs have identical HCDR1, HCDR3, LCDR1, LCDR2 and LCDR3, and a variant HCDR2. The VH region identity is between 80-100% and the VL region identity about 98%. PD1B506 lineage mAbs are ligand blocking. The lineage is characterized by the HCDR1, the HCDR2, the HCDR3, the LCDR1, the LCDR2 and the LCDR3 of SEQ ID NOs: 32, 124, 40, 41, 42 and 43, respectively, and by the VH genus sequence of SEQ ID NO: 120 and the VL genus sequence of SEQ ID NO: 121.

The invention also provides an isolated antibody that specifically binds PD-1 or an antigen binding fragment thereof comprising the HCDR1, the HCDR2 and the HCDR3 of SEQ ID NOs: 32, 124, 40, 41, 42 and 43, respectively.

```
                                         SEQ ID NO: 124
       (PD1B506 lineage HCDR2 genus)
       EINPNX₁X₂GIN;
``` wherein $X_1$ is N, D, Q, K or E; and $X_2$ is G, A or I.

In some embodiments, the isolated antibody that specifically binds PD-1 or the antigen binding fragment thereof comprises the HCDR2 of SEQ ID NOs: 33, 34, 35, 36, 37, 38 or 39.

In some embodiments, the antibody or the antigen binding fragment thereof provided herein has one, two, three, four or five of the following properties: blocks PD-L1 binding to PD-1, wherein blocking is measured by ability of the antibody to inhibit clustering of PD-L1 expressing and PD-1 expressing cells as described in Example 1;

binds PD-1 with an equilibrium dissociation constant ($K_D$) of about $5 \times 10^{-8}$ M or less, wherein the $K_D$ is measured using a ProteOn XPR36 system at +25° C.;

binds PD-1 with an association constant (ka) of about $4 \times 10^5$ l/Ms or more, wherein the ka is measured using a ProteOn XPR36 system at +25° C.;

binds PD-1 with a dissociation constant (kd) of about $1 \times 10^{-2}$ l/s or less, wherein the kd is measured using a ProteOn XPR36 system at +25° C.; or inhibit proliferation of antigen specific T cells; wherein proliferation is assessed in a CMV-PBMC assay as described in Example 1.

In some embodiments, the antibody that specifically binds PD-1 or the antigen binding fragment thereof comprises the VH framework derived from IGHV1-2*02 (SEQ ID NO: 127).

In some embodiments, the antibody that specifically binds PD-1 or the antigen binding fragment thereof comprises the VL framework derived from IGKV1D-16*1 (SEQ ID NO: 128).

In some embodiments, the antibody that specifically binds PD-1 or the antigen binding fragment thereof comprises the VH framework derived from IGHV1-2*02 (SEQ ID NO: 127) and the VL framework derived from IG IGKV1D-16*1 (SEQ ID NO: 128).

```
IGHV1-2*02
                                         SEQ ID NO: 127
QVQLVQSGAEVKKPGASVKVSCKASGYTFTGYYMHWVRQAPGQGLEWMGW

INPNSGGTNYAQKFQGRVTMTRDTSISTAYMELSRLRSDDTAVYYCAR

IGKV1D-16*1
                                         SEQ ID NO: 128
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYP
```

The invention also provides an isolated antibody that specifically binds PD-1 or an antigen binding fragment thereof comprising a heavy chain variable region (VH) of SEQ ID NO: 120. SEQ ID NO: 120 is a VH genus sequence of PD1B506 lineage mAbs.

The invention also provides an isolated antibody that specifically binds PD-1 or an antigen binding fragment thereof comprising a light chain variable region (VL) of SEQ ID NO: 121. SEQ ID NO: 121 is a VL genus sequence of PD1B506 lineage mAbs.

The invention also provides an isolated antibody that specifically binds PD-1 or an antigen binding fragment thereof comprising the VH of SEQ ID NO: 120 and the VL of SEQ ID NO: 121. The CDRs are bolded in SEQ ID NO: 120 and SEQ ID NO: 121.

```
(PD1B506 lineage VH genus)
                                         SEQ ID NO: 120
QVQLX₁QX₂GAEX₃X₄KPGASVKX₅SCKASGYTFTTYWMHWVX₆QX₇PGQ

GLEWX₈GEINPNX₉X₁₀GINY X₁₁X₁₂KFX₁₃X₁₄X₁₅X₁₆TLTVDKSX₁₇

STAYMX₁₈LSX₁₉LX₂₀SX₂₁DX₂₂AVYYCTIDYYDYGGYWGQGTX₂₃X₂₄

TVSS;
``` wherein $X_1$ is Q or V;
$X_2$ is S or P;
$X_3$ is L or V;
$X_4$ is V or K;
$X_5$ is L or V;
$X_6$ is K or R;
$X_7$ is R or A;
$X_8$ is I or M;
$X_9$ is N, D, Q, K or E;
$X_{10}$ is G, A or I;
$X_{11}$ is N or A;
$X_{12}$ is E or Q;
$X_{13}$ is K or Q;
$X_{14}$ is K or G;
$X_{15}$ is K or R;
$X_{16}$ is A or V;
$X_{17}$ is S or I;
$X_{18}$ is Q or E;
$X_{19}$ is S or R;
$X_{20}$ is T or R;
$X_{21}$ is E or D;
$X_{22}$ is S or T;
$X_{23}$ is T or L; and
$X_{24}$ is L or V.

```
(PD1B506 lineage VL genus)
                                         SEQ ID NO: 121
DIX₁MTQSX₂X₃X₄X₅SX₆SVX₇DRVX₈X₉TCKASQNVGTNVAWYQQKP

X₁₀X₁₁X₁₂PKX₁₃LIYSASYRYSGVPX₁₄RFX₁₅GSGSGTDFTLTIX₁₆

X₁₇X₁₈QX₁₉EDX₂₀AX₂₁YX₂₂CQQYNIYPYTFGX₂₃GTKLEX₂₄K;
``` wherein $X_1$ is V or Q;
$X_2$ is Q or P;
$X_3$ is K or S;
$X_4$ is F or S;
$X_5$ is M or L;
$X_6$ is T or A;
$X_7$ is R or G;
$X_8$ is S or T;
$X_9$ is V or I;
$X_{10}$ is G or E;
$X_{11}$ is Q or K;
$X_{12}$ is S or A;
$X_{13}$ is A or S;

$X_{14}$ is D or S;
$X_{15}$ is T or S;
$X_{16}$ is T or S;
$X_{17}$ is N or S;
$X_{18}$ is V or L;
$X_{19}$ is S or P;
$X_{20}$ is L or F;
$X_{21}$ is E or T;
$X_{22}$ is F or Y;
$X_{23}$ is S or Q; and
$X_{24}$ is M or I.

In some embodiments, the antibody that specifically binds PD-1 or the antigen binding fragment thereof comprises the VH of SEQ ID NOs: 44, 45, 46, 47, 48, 49, 50 or 51.

In some embodiments, the antibody that specifically binds PD-1 or the antigen binding fragment thereof comprises the VL of SEQ ID NOs: 60, 61 or 62.

In some embodiments, the antibody that specifically binds PD-1 or the antigen binding fragment thereof comprises the VH of SEQ ID NOs: 44, 45, 46, 47, 48, 49, 50 or 51 and the VL of SEQ ID NOs: 60, 61 or 62.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 32, 33, 40, 41, 42 and 43, respectively. In some embodiments, the antibody comprises the VH of SEQ ID NOs: 44 or 45 and the VL of SEQ ID NOs: 60, 61 or 62. In some embodiments, the antibody comprises the HC of SEQ ID NOs: 66 or 67 and the LC of SEQ ID NOs: 82, 83 or 84. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 32, 34, 40, 41, 42 and 43, respectively. In some embodiments, the antibody comprises the VH of SEQ ID NO: 46 and the VL of SEQ ID NO: 61. In some embodiments, the antibody comprises the HC of SEQ ID NO: 68 and the LC of SEQ ID NO: 83. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 32, 35, 40, 41, 42 and 43, respectively. In some embodiments, the antibody comprises the VH of SEQ ID NO: 47 and the VL of SEQ ID NO: 61. In some embodiments, the antibody comprises the HC of SEQ ID NO: 69 and the LC of SEQ ID NO: 83. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 32, 36, 40, 41, 42 and 43, respectively. In some embodiments, the antibody comprises the VH of SEQ ID NO: 48 and the VL of SEQ ID NO: 61. In some embodiments, the antibody comprises the HC of SEQ ID NO: 70 and the LC of SEQ ID NO: 83. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 32, 37, 40, 41, 42 and 43, respectively. In some embodiments, the antibody comprises the VH of SEQ ID NO: 49 and the VL of SEQ ID NO: 61. In some embodiments, the antibody comprises the HC of SEQ ID NO: 71 and the LC of SEQ ID NO: 83. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 32, 38, 40, 41, 42 and 43, respectively. In some embodiments, the antibody comprises the VH of SEQ ID NO: 50 and the VL of SEQ ID NO: 61. In some embodiments, the antibody comprises the HC of SEQ ID NO: 72 and the LC of SEQ ID NO: 83. The antibody is also provided for use in therapy, such as in treatment of an immune disorder, rheumatoid arthritis, lupus, systemic lupus erythematosus or graft versus host disease.

The invention also provides an isolated antibody that specifically binds PD-1 or an antigen binding fragment thereof comprising the HCDR1, the HCDR2, the HCDR3, the LCDR1, the LCDR2 and the LCDR3 of SEQ ID NOs: 32, 39, 40, 41, 42 and 43, respectively. In some embodiments, the antibody comprises the VH of SEQ ID NO: 51 and the VL of SEQ ID NO: 61. In some embodiments, the antibody comprises the HC of SEQ ID NO: 73 and the LC of SEQ ID NO: 83. The antibody is also provided for use in therapy, such as in treatment of an immune disorder, rheumatoid arthritis, lupus, systemic lupus erythematosus or graft versus host disease.

In some embodiments, the antibody is an agonistic antibody.

The invention also provides herein an isolated antibody that specifically binds PD-1 or an antigen binding fragment thereof, wherein the antibody competes for binding to PD-1 with the antibody or the antigen binding fragment comprising the VH of SEQ ID NO: 44 and the VL of SEQ ID NO: 60;
the VH of SEQ ID NO: 45 and the VL of SEQ ID NO: 61;
the VH of SEQ ID NO: 45 and the VL of SEQ ID NO: 62;
the VH of SEQ ID NO: 46 and the VL of SEQ ID NO: 61;
the VH of SEQ ID NO: 47 and the VL of SEQ ID NO: 61;
the VH of SEQ ID NO: 48 and the VL of SEQ ID NO: 61;
the VH of SEQ ID NO: 49 and the VL of SEQ ID NO: 61;
the VH of SEQ ID NO: 50 and the VL of SEQ ID NO: 61; or
the VH of SEQ ID NO: 51 and the VL of SEQ ID NO: 61.

The invention also provides herein an isolated antibody that specifically binds PD-1 or an antigen binding fragment thereof, wherein the antibody binds the same epitope that is bound by the antibody comprising the VH of SEQ ID NO: 44 and the VL of SEQ ID NO: 60;
the VH of SEQ ID NO: 45 and the VL of SEQ ID NO: 61;
the VH of SEQ ID NO: 45 and the VL of SEQ ID NO: 62;
the VH of SEQ ID NO: 46 and the VL of SEQ ID NO: 61;
the VH of SEQ ID NO: 47 and the VL of SEQ ID NO: 61;
the VH of SEQ ID NO: 48 and the VL of SEQ ID NO: 61;
the VH of SEQ ID NO: 49 and the VL of SEQ ID NO: 61;

the VH of SEQ ID NO: 50 and the VL of SEQ ID NO: 61; or the VH of SEQ ID NO: 51 and the VL of SEQ ID NO: 61.

In some embodiments, the VH and the VL or the HC and the LC of the antibody that specifically binds PD-1 or the antigen binding fragment thereof provided herein are encoded by polynucleotide comprising the polynucleotide sequence of SEQ ID NOs: 52 and 63, respectively;
SEQ ID NOs: 53 and 64, respectively;
SEQ ID NOs: 53 and 65, respectively;
SEQ ID NOs: 54 and 64, respectively;
SEQ ID NOs: 55 and 64, respectively;
SEQ ID NOs: 56 and 64, respectively;
SEQ ID NOs: 57 and 64, respectively;
SEQ ID NOs: 58 and 64, respectively;
SEQ ID NOs: 59 and 64, respectively;
SEQ ID NOs: 74 and 85, respectively;
SEQ ID NOs: 75 and 86, respectively;
SEQ ID NOs: 75 and 87, respectively;
SEQ ID NOs: 76 and 86, respectively;
SEQ ID NOs: 77 and 86, respectively;
SEQ ID NOs: 78 and 86, respectively;
SEQ ID NOs: 79 and 86, respectively;
SEQ ID NOs: 80 and 86, respectively;
SEQ ID NOs: 81 and 86, respectively;
SEQ ID NOs: 136 and 137, respectively; or
SEQ ID NOs: 138 and 139, respectively.

PD1B512 Lineage Antibodies mAbs PD1B505, PD1B756 and PD1B757 are exemplary antibodies of PD1B512 mAb lineage. These mAbs have identical CDR regions with the VH region identity of about 84% and the VL region identity between 90-99%. PD1B512 lineage mAbs are ligand non-blocking. The lineage is characterized by the HCDR1, the HCDR2, the HCDR3, the LCDR1, the LCDR2 and the LCDR3 of SEQ ID NOs: 88, 89, 90, 91, 92 and 93, respectively, and by the VH genus sequence of SEQ ID NO: 122 and the VL genus sequence of SEQ ID NO: 123.

The invention also provides and isolated antibody that specifically binds PD-1 or an antigen binding fragment thereof comprising the HCDR1, the HCDR2, the HCDR3, the LCDR1, the LCDR2 and the LCDR3 of SEQ ID NOs: 88, 89, 90, 91, 92 and 93, respectively.

In some embodiments, the antibody or the antigen binding fragment thereof does not block PD-L1 binding to PD-1, wherein lack of blocking is measured by inability of the antibody to inhibit clustering of PD-L1 expressing and PD-1 expressing cells as described in Example 1.

In some embodiments, the antibody that specifically binds PD-1 or the antigen binding fragment thereof provided herein comprises the VH framework derived from IGHV2-5*04 (SEQ ID NO: 129).

In some embodiments, the antibody that specifically binds PD-1 or the antigen binding fragment thereof provided herein comprises the VL framework derived from IGKV2-28*01 (SEQ ID NO: 130).

In some embodiments, the antibody that specifically binds PD-1 or the antigen binding fragment thereof provided herein comprises the VH framework derived from IGHV2-5*04 (SEQ ID NO: 129) and the VL framework derived from IGKV2-28*01 (SEQ ID NO: 130).

IGHV2-5*04
SEQ ID NO: 129
QITLKESGPTLVKPTQTLTLTCTFSGFSLSTSGVGVGWIRQPPGKALEWL

ALIYWNDDKRYSPSLKSRLTITKDTSKNQVVLTMTNMDPVDTGTYYCV

IGKV2-28*01
SEQ ID NO: 130
DIVMTQSPLSLPVTPGEPASISCRSSQSLLHSNGYNYLDWYLQKPGQSPQ

LLIYLGSNRASGVPDRFSGSGSGTDFTLKISRVEAEDVGVYYCMQALQTP

The invention also provides an isolated antibody that specifically binds PD-1 or an antigen binding fragment thereof comprising a heavy chain variable region (VH) of SEQ ID NO: 122. SEQ ID NO: 122 is a VH genus sequence of PD1B512 lineage mAbs.

The invention also provides an isolated antibody that specifically binds PD-1 or an antigen binding fragment thereof comprising a light chain variable region (VL) of SEQ ID NO: 123. SEQ ID NO: 123 is a VL genus sequence of PD1B512 lineage mAbs.

The invention also provides an isolated antibody that specifically binds PD-1 or an antigen binding fragment thereof comprising the VH of SEQ ID NO: 122 and the VL of SEQ ID NO: 123. The CDRs are bolded in SEQ ID NO: 122 and SEQ ID NO: 123.

(PD1B112 lineage VH genus)
SEQ ID NO: 122
QX$_1$TLKESGPX$_2$LX$_3$X$_4$PX$_5$QTLX$_6$LTCX$_7$FSGFSLSTSGMGVSWIRQP

X$_8$GKX$_9$LEWLAHIYWDDDKRYX$_{10}$PSLKSRLTIX$_{11}$KDTSX$_{12}$NQVX$_{13}$L

X$_{14}$X$_{15}$TX$_{16}$X$_{17}$DX$_{18}$X$_{19}$DTGTYYCVRKGYYDYGYVMDYWGQGTX$_{20}$V

TVSS, wherein
X$_1$ is V or I;
X$_2$ is G or T;
X$_3$ is L or V;
X$_4$ is Q or K;
X$_5$ is S or T;
X$_6$ is S or T;
X$_7$ is S or T;
X$_8$ is S or P;
X$_9$ is G or A;
X$_{10}$ is N or S;
X$_{11}$ is S or T;
X$_{12}$ is S or K;
X$_{13}$ is F or V;
X$_{14}$ is K or T;
X$_{15}$ is I or M;
X$_{16}$ is S or N;
X$_{17}$ is V or M;
X$_{18}$ is T or P;
X$_{19}$ is A or V; and
X$_{20}$ is T or L.

(PD1B112 lineage VL genus)
SEQ ID NO: 123
DIVMTQX$_1$X$_2$LSX$_3$PVTX$_4$GX$_5$X$_6$ASISCRSSKSLLHSNGITYLNWYLQK

PGQSPQLLIYQMSNLASGVPDRFSX$_7$SGSGTDFTLX$_8$ISRVEAEDVGVYY

CAQNLELPLTFGX$_9$GTKX$_{10}$EX$_{11}$K, wherein $X_1$ is A or S;
$X_2$ is A or P;
$X_3$ is N or L;
$X_4$ is L or P;
$X_5$ is T or E;
$X_6$ is S or P;
$X_7$ is S or G;
$X_8$ is R or K;
$X_9$ is S or G;
$X_{10}$ is L or V; and
$X_{11}$ is M or I.

In some embodiments, the antibody that specifically binds PD-1 or the antigen binding fragment thereof comprises the VH of SEQ ID NOs: 94 or 95.

In some embodiments, the antibody that specifically binds PD-1 or the antigen binding fragment thereof comprises the VL of SEQ ID NOs: 98, 99 or 100.

The invention also provides an isolated antibody that specifically binds PD-1 or an antigen binding fragment thereof comprising the VH of SEQ ID NOs: 94 or 95 and the VL of SEQ ID NOs: 98, 99 or 100.

The invention also provides an isolated antibody that specifically binds PD-1 or an antigen binding fragment thereof comprising the VH of SEQ ID NO: 94 and the VL of SEQ ID NO: 98. In some embodiments, the antibody comprises the HC of SEQ ID NO: 104 and the LC of SEQ ID NO: 108. The antibody is also provided for use in therapy, such as in treatment of an immune disorder, rheumatoid arthritis, lupus, systemic lupus erythematosus or graft versus host disease.

In some embodiments, the antibody that specifically binds PD-1 or the antigen binding fragment thereof provided herein comprises the VH of SEQ ID NO: 95 and the VL of SEQ ID NO: 99. In some embodiments, the antibody comprises the HC of SEQ ID NO: 105 and the LC of SEQ ID NO: 109. The antibody is also provided for use in therapy, such as in treatment of an immune disorder, rheumatoid arthritis, lupus, systemic lupus erythematosus or graft versus host disease.

In some embodiments, the antibody that specifically binds PD-1 or the antigen binding fragment thereof provided herein comprises the VH of SEQ ID NO: 95 and the VL of SEQ ID NO: 100. In some embodiments, the antibody comprises the HC of SEQ ID NO: 105 and the LC of SEQ ID NO: 110. The antibody is also provided for use in therapy, such as in treatment of an immune disorder, rheumatoid arthritis, lupus, systemic lupus erythematosus or graft versus host disease.

In some embodiments, the antibody is an agonistic antibody.

The invention also provides herein an isolated antibody that specifically binds PD-1 or an antigen binding fragment thereof, wherein the antibody competes for binding to PD-1 with the antibody or the antigen binding fragment comprising the VH of SEQ ID NO: 94 and the VL of SEQ ID NO: 98;
the VH of SEQ ID NO: 95 and the VL of SEQ ID NO: 99; or
the VH of SEQ ID NO: 95 and the VL of SEQ ID NO: 100.

The invention also provides herein an isolated antibody that specifically binds PD-1 or an antigen binding fragment thereof, wherein the antibody binds the same epitope that is bound by the antibody comprising the VH of SEQ ID NO: 94 and the VL of SEQ ID NO: 98;
the VH of SEQ ID NO: 95 and the VL of SEQ ID NO: 99; or
the VH of SEQ ID NO: 95 and the VL of SEQ ID NO: 100.

In some embodiments, the VH and the VL or the HC and the LC of the antibody that specifically binds PD-1 or the antigen binding fragment thereof provided herein are encoded by polynucleotide comprising the polynucleotide sequence of SEQ ID NOs: 96 and 101, respectively;
SEQ ID NOs: 97 and 102, respectively;
SEQ ID NOs: 97 and 103, respectively;
SEQ ID NOs: 106 and 111, respectively;
SEQ ID NOs: 107 and 112, respectively; or
SEQ ID NOs: 107 and 113, respectively.

Homologous Antibodies and Antibodies with Conservative Mutations

Variants of the antibodies that specifically bind PD-1 or the antigen binding fragments thereof provided herein are within the scope of the invention. For example, variants may comprise 1, 2, 3, 4, 5, 6, 7, 8, 9, 10, 11, 12, 13, 14, 15, 16, 17, 18, 19, 20, 21, 22, 23, 24, 25, 26, 27, 28 or 29 amino acid substitutions in the VH and/or the VL as long as the variant antibodies retain or have improved functional properties when compared to the parental antibodies. In some embodiments, the sequence identity may be about 80%, 81%, 82%, 83%, 84%, 85%, 86%, 87%, 88%, 89%, 90%, 91%, 92%, 93%, 94%, 95%, 96%, 97%, 98% or 99% to the VH and/or the VL amino acid sequence of the invention. In some embodiments, the variation is in the framework regions. In some embodiments, variants are generated by conservative substitutions.

For example, PD1B505 lineage antibodies may comprise substitutions at VH residue positions 1, 5, 6, 9, 16, 17, 20, 38, 43, 46, 57, 62, 63, 65, 69, 73, 76, 84, 85, 88, 93, 116 and/or 117 (residue numbering according to SEQ ID NO: 8) and at VL residue positions 1, 10, 11, 13, 15, 19, 21, 22, 29, 30, 43, 44, 46, 48, 59, 61, 71, 72, 73, 78, 79, 81, 84, 86, 101 and/or 107 (residue numbering according to SEQ ID NO: 14). PD1B506 lineage antibodies may comprises substitutions at VH residue positions 5, 7, 11, 12, 20, 38, 40, 48, 55, 56, 61, 62, 65, 66, 67, 68, 76, 82, 85, 87, 89, 91, 112 and/or 113 (residue numbering according to SEQ ID NO: 44) and at VL residue positions 3, 8, 9, 10, 11, 13, 16, 20, 21, 41, 42, 43, 46, 60, 63, 76, 77, 78, 80, 83, 85, 87, 100 and/or 106 (residue numbering according to SEQ ID NO: 60). PD1B512 lineage antibodies may comprise substitutions at VH residue positions 2, 10, 12, 13, 15, 19, 23, 43, 46, 62, 72, 77, 81, 83, 84, 86, 87, 89, 90 and/or 117 and at VL residue positions 7, 8, 11, 15, 17, 18, 69, 79, 105, 109 and/or 111. Conservative substitutions may be made at any indicated positions and the resulting variant antibodies tested for their desired characteristics in the assays described herein. Alternatively, substitutions in one lineage mAb may be made at indicated positions by substitution with corresponding amino acid at the particular position present in the other antibodies within the lineage.

Also provided are antibodies that specifically bind PD-1 or antigen binding fragments thereof comprising the VH and the VL which are at least 80% identical to the VH of SEQ ID NO: 8 and the VL of SEQ ID NO: 14;
the VH of SEQ ID NO: 9 and the VL of SEQ ID NO: 15;
the VH of SEQ ID NO: 9 and the VL of SEQ ID NO: 16;
the VH of SEQ ID NO: 10 and the VL of SEQ ID NO: 16;

the VH of SEQ ID NO: 140 and the VL of SEQ ID NO: 16;
the VH of SEQ ID NO: 141 and the VL of SEQ ID NO: 16;
the VH of SEQ ID NO: 142 and the VL of SEQ ID NO: 16;
the VH of SEQ ID NO: 10 and the VL of SEQ ID NO: 143;
the VH of SEQ ID NO: 10 and the VL of SEQ ID NO: 144;
the VH of SEQ ID NO: 140 and the VL of SEQ ID NO: 143;
the VH of SEQ ID NO: 141 and the VL of SEQ ID NO: 143;
the VH of SEQ ID NO: 142 and the VL of SEQ ID NO: 143;
the VH of SEQ ID NO: 140 and the VL of SEQ ID NO: 144;
the VH of SEQ ID NO: 141 and the VL of SEQ ID NO: 144;
the VH of SEQ ID NO: 142 and the VL of SEQ ID NO: 144;
the VH of SEQ ID NO: 44 and the VL of SEQ ID NO: 60;
the VH of SEQ ID NO: 45 and the VL of SEQ ID NO: 61;
the VH of SEQ ID NO: 45 and the VL of SEQ ID NO: 62;
the VH of SEQ ID NO: 46 and the VL of SEQ ID NO: 61;
the VH of SEQ ID NO: 47 and the VL of SEQ ID NO: 61;
the VH of SEQ ID NO: 48 and the VL of SEQ ID NO: 61;
the VH of SEQ ID NO: 49 and the VL of SEQ ID NO: 61;
the VH of SEQ ID NO: 50 and the VL of SEQ ID NO: 61;
the VH of SEQ ID NO: 51 and the VL of SEQ ID NO: 61;
the VH of SEQ ID NO: 94 and the VL of SEQ ID NO: 98;
the VH of SEQ ID NO: 95 and the VL of SEQ ID NO: 99; or
the VH of SEQ ID NO: 95 and the VL of SEQ ID NO: 100.

In some embodiments, the identity is 85%. In some embodiments, the identity is 90%. In some embodiments, the identity is 91%. In some embodiments, the identity is 91%. In some embodiments, the identity is 92%. In some embodiments, the identity is 93%. In some embodiments, the identity is 94%. In some embodiments, the identity is 94%. In some embodiments, the identity is 96%. In some embodiments, the identity is 97%. In some embodiments, the identity is 98%. In some embodiments, the identity is 99%.

The percent identity between the two sequences is a function of the number of identical positions shared by the sequences (i.e., % identity=number of identical positions/total number of positions×100), taking into account the number of gaps, and the length of each gap, which need to be introduced for optimal alignment of the two sequences.

The percent identity between two amino acid sequences may be determined using the algorithm of E. Meyers and W. Miller (*Comput Appl Biosci* 4:11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch (*J Mol Biol* 48:444-453 (1970)) algorithm which has been incorporated into the GAP program in the GCG software package (available at http_//_www_gcg_com), using either a Blossum 62 matrix or a PAM250 matrix, and a gap weight of 16, 14, 12, 10, 8, 6, or 4 and a length weight of 1, 2, 3, 4, 5, or 6.

In some embodiments, variant antibodies comprise one or two conservative substitutions in any of the CDR regions, wherein the antibodies retain the desired functional properties of the parental antibodies.

"Conservative modifications" refer to amino acid modifications that do not significantly affect or alter the binding characteristics of the antibody containing the amino acid modifications. Conservative modifications include amino acid substitutions, additions and deletions. Conservative amino acid substitutions are those in which the amino acid is replaced with an amino acid residue having a similar side chain. The families of amino acid residues having similar side chains are well defined and include amino acids with acidic side chains (e.g., aspartic acid, glutamic acid), basic side chains (e.g., lysine, arginine, histidine), nonpolar side chains (e.g., alanine, valine, leucine, isoleucine, proline, phenylalanine, methionine), uncharged polar side chains (e.g., glycine, asparagine, glutamine, cysteine, serine, threonine, tyrosine, tryptophan), aromatic side chains (e.g., phenylalanine, tryptophan, histidine, tyrosine), aliphatic side chains (e.g., glycine, alanine, valine, leucine, isoleucine, serine, threonine), amide (e.g., asparagine, glutamine), beta-branched side chains (e.g., threonine, valine, isoleucine) and sulfur-containing side chains (cysteine, methionine). Furthermore, any native residue in the polypeptide may also be substituted with alanine, as has been previously described for alanine scanning mutagenesis (MacLennan et al., (1988) *Acta Physiol Scand Suppl* 643:55-67; Sasaki et al., (1988) *Adv Biophys* 35:1-24). Amino acid substitutions to the antibodies of the invention may be made by known methods for example by PCR mutagenesis (U.S. Pat. No. 4,683,195). Alternatively, libraries of variants may be generated for example using random (NNK) or non-random codons, for example DVK codons, which encode 11 amino acids (Ala, Cys, Asp, Glu, Gly, Lys, Asn, Arg, Ser, Tyr, Trp). The resulting antibody variants may be tested for their characteristics using assays described herein.

Engineered and Modified Antibodies

The antibodies that specifically bind PD-1 or the antigen binding fragments thereof provided herein may be further engineered to generate modified antibodies with similar or altered properties when compared to the parental antibodies. The VH, the VL, the VH and the VL, the constant regions, the heavy chain framework, the light chain framework, or any or all the six CDRs may be engineered in the antibodies of the invention.

The antibodies that specifically bind PD-1 or the antigen binding fragments thereof may be engineered by CDR grafting. One or more CDR sequences of the antibodies of the invention may be grafted to a different framework sequence. CDR grafting may be done using known methods and methods described herein.

The framework sequences that may be used may be obtained from public DNA databases or published references that include germline antibody gene sequences. For example, germline DNA and the encoded protein sequences for human heavy and light chain variable domain genes may be found at IMGT®, the international ImMunoGeneTics Information System® http_//_www-imgt_org. Framework sequences that may be used to replace the existing framework sequences of the antibodies of the invention may be those that show the highest percent (%) identity to the parental variable domains over the entire length of the VH or the VL, or over the length of FR1, FR2, FR3 and FR4. In addition, suitable frameworks may further be selected based on the VH and the VL CDR1 and CDR2 lengths or identical LCDR1, LCDR2, LCDR3, HCDR1 and HCDR2 canonical structure. Suitable frameworks may be selected using known methods, such as human framework adaptation described in U.S. Pat. No. 8,748,356 or superhumanization described in U.S. Pat. No. 7,709,226.

The framework sequences of the parental and engineered antibodies may further be modified, for example by back-mutations to restore and/or improve binding of the generated antibodies to the antigen as described for example in U.S. Pat. No. 6,180,370. The framework sequences of the parental or engineered antibodies may further be modified by mutating one or more residues within the framework region (or alternatively within one or more CDR regions) to remove T-cell epitopes to thereby reduce the potential immunogenicity of the antibody. This approach is also referred to as "deimmunization" and described in further detail in U.S. Patent Publ. No. US20070014796.

The CDR residues of the antibodies or the antigen-binding fragments thereof provided herein may be mutated to improve affinity of the antibodies to PD-1.

The CDR residues of the antibodies or the antigen-binding fragments thereof provided herein may be mutated to minimize risk of post-translational modifications. Amino acid residues of putative motifs for deamination (NS), acid-catalyzed hydrolysis (DP), isomerization (DS), or oxidation (W) may be substituted with any of the naturally occurring amino acids to mutagenize the motifs, and the resulting antibodies may be tested for their functionality and stability using methods described herein.

The antibodies that specifically bind PD-1 or the antigen binding fragments thereof provided herein which are modified to improve stability, selectivity, cross-reactivity, affinity, immunogenicity or other desirable biological or biophysical property are within the scope of the invention. Stability of an antibody is influenced by a number of factors, including (1) core packing of individual domains that affects their intrinsic stability, (2) protein/protein interface interactions that have impact upon the HC and LC pairing, (3) burial of polar and charged residues, (4) H-bonding network for polar and charged residues; and (5) surface charge and polar residue distribution among other intra- and inter-molecular forces (Worn et al., (2001) *J Mol Biol* 305:989-1010). Potential structure destabilizing residues may be identified based upon the crystal structure of the antibody or by molecular modeling in certain cases, and the effect of the residues on antibody stability may be tested by generating and evaluating variants harboring mutations in the identified residues. One of the ways to increase antibody stability is to raise the thermal transition midpoint ($T_m$) as measured by differential scanning calorimetry (DSC). In general, the protein $T_m$ is correlated with its stability and inversely correlated with its susceptibility to unfolding and denaturation in solution and the degradation processes that depend on the tendency of the protein to unfold (Remmele et al., (2000) *Biopharm* 13:36-46). A number of studies have found correlation between the ranking of the physical stability of formulations measured as thermal stability by DSC and physical stability measured by other methods (Gupta et al., (2003) *AAPS PharmSci* 5E8; Zhang et al., (2004) *J Pharm Sci* 93:3076-89; Maa et al., (1996) *Int J Pharm* 140:155-68; Bedu-Addo et al., (2004) *Pharm Res* 21:1353-61; Remmele et al., (1997) *Pharm Res* 15:200-8). Formulation studies suggest that a Fab $T_m$ has implication for long-term physical stability of a corresponding mAb.

Antibody Isotypes, Allotypes and Fc Engineered Antibodies

The antibodies that specifically bind PD-1 or the antigen binding fragments thereof provided herein may be of any known isotype or allotype with wild-type or engineered Fc.

In some embodiments, the antibody that specifically binds PD-1 or the antigen binding fragment thereof provided herein is an IgG1 isotype.

In some embodiments, the antibody that specifically binds PD-1 or the antigen binding fragment thereof provided herein is an IgG2 isotype.

In some embodiments, the antibody that specifically binds PD-1 or the antigen binding fragment thereof provided herein is an IgG3 isotype.

In some embodiments, the antibody that specifically binds PD-1 or the antigen binding fragment thereof provided herein is an IgG4 isotype.

C-terminal lysine (CTL) may be removed from injected antibodies by endogenous circulating carboxypeptidases in the blood stream (Cai et al., (2011) *Biotechnol Bioeng* 108:404-412). During manufacturing, CTL removal may be controlled to less than the maximum level by control of concentration of extracellular $Zn^{2+}$, EDTA or EDTA—$Fe^{3+}$ as described in U.S. Patent Publ. No. US20140273092. CTL content in antibodies may be measured using known methods.

In some embodiments, the antibody that specifically binds PD-1 or the antigen binding fragment thereof provided herein has a C-terminal lysine content from about 10% to about 90%. In some embodiments, the C-terminal lysine content is from about 20% to about 80%. In some embodiments, the C-terminal lysine content is from about 40% to about 70%. In some embodiments, the C-terminal lysine content is from about 55% to about 70%. In some embodiments, the C-terminal lysine content is about 60%.

Immunogenicity of therapeutic antibodies is associated with increased risk of infusion reactions and decreased duration of therapeutic response (Baert et al., (2003) *N Engl J Med* 348:602-08). The extent to which therapeutic antibodies induce an immune response in the host may be determined in part by the allotype of the antibody (Stickler et al., (2011) *Genes and Immunity* 12:213-21). Antibody allotype is related to amino acid sequence variations at specific locations in the constant region sequences of the antibody. Table 2 shows select IgG1, IgG2 and IgG4 allotypes.

In some embodiments, the antibody that specifically binds PD-1 or the antigen binding fragment thereof provided herein is an G2m(n) allotype.

In some embodiments, the antibody that specifically binds PD-1 or the antigen binding fragment thereof provided herein is an G2m(n-) allotype.

In some embodiments, the antibody that specifically binds PD-1 or the antigen binding fragment thereof provided herein is an G2m(n)/(n-) allotype.

In some embodiments, the antibody that specifically binds PD-1 or the antigen binding fragment thereof provided herein is an nG4m(a) allotype.

In some embodiments, the antibody that specifically binds PD-1 or the antigen binding fragment thereof provided herein is an G1m(17,1) allotype.

TABLE 2

| | Amino acid residue at position of diversity (residue numbering: EU Index) | | | | | | |
|---|---|---|---|---|---|---|---|
| | IgG2 | | IgG4 | | IgG1 | | |
| Allotype | 189 | 282 | 309 | 422 | 214 | 356 | 358 | 431 |
| G2m(n) | T | M | | | | | | |
| G2m(n-) | P | V | | | | | | |

TABLE 2-continued

| | Amino acid residue at position of diversity (residue numbering: EU Index) | | | | | | | |
|---|---|---|---|---|---|---|---|---|
| | IgG2 | | IgG4 | | IgG1 | | | |
| Allotype | 189 | 282 | 309 | 422 | 214 | 356 | 358 | 431 |
| G2m(n)/(n−) | T | V | | | | | | |
| nG4m(a) | | | L | R | | | | |
| G1m(17) | | | | | K | E | M | A |
| G1m(17,1) | | | | | K | D | L | A |

Fc mutations may be made to the antibodies that specifically bind PD-1 or the antigen binding fragments thereof provided herein to modulate antibody effector functions such as ADCC, ADCP and/or ADCP and/or pharmacokinetic properties. This may be achieved by introducing mutation(s) into the Fc that modulate binding of the mutated Fc to activating FcγRs (FcγRI, FcγRIIa, FcγRIII), inhibitory FcγRIIb and/or to FcRn.

In some embodiments, the antibody that specifically binds PD-1 or the antigen binding fragment thereof comprise at least one mutation in the antibody Fc.

In some embodiments, the antibody that specifically binds PD-1 or the antigen binding fragment thereof comprise one, two, three, four, five, six, seven, eight, nine, ten, eleven, twelve, thirteen, fourteen or fifteen mutations in the Fc.

In some embodiments, the antibody that specifically binds PD-1 or the antigen binding fragment thereof comprise at least one mutation in the Fc that modulates binding of the antibody to FcRn.

Fc positions that may be mutated to modulate antibody half-life (e.g. binding to FcRn include positions 250, 252, 253, 254, 256, 257, 307, 376, 380, 428, 434 and 435. Exemplary mutations that may be made singularly or in combination are mutations T250Q, M252Y, I253A, S254T, T256E, P257I, T307A, D376V, E380A, M428L, H433K, N434S, N434A, N434H, N434F, H435A and H435R. Exemplary singular or combination mutations that may be made to increase the half-life of the antibodies provided herein are mutations M428L/N434S, M252Y/S254T/T256E, T250Q/M428L, N434A and T307A/E380A/N434A. Exemplary singular or combination mutations that may be made to reduce the half-life of the antibodies provided herein are mutations H435A, P257I/N434H, D376V/N434H, M252Y/S254T/T256E/H433K/N434F, T308P/N434A and H435R.

In some embodiments, the antibody that specifically binds PD-1 or the antigen binding fragment thereof comprises a mutation M252Y/S254T/T256E.

In some embodiments, the antibody that specifically binds PD-1 or the antigen binding fragment thereof comprises at least one mutation in the antibody Fc that reduces binding of the antibody to an activating Fcγ receptor (FcγR) and/or reduces Fc effector functions such as C1q binding, complement dependent cytotoxicity (CDC), antibody-dependent cell-mediated cytotoxicity (ADCC) or phagocytosis (ADCP).

Fc positions that may be mutated to reduce binding of the antibody to the activating FcγR and subsequently to reduce effector function include positions 214, 233, 234, 235, 236, 237, 238, 265, 267, 268, 270, 295, 297, 309, 327, 328, 329, 330, 331 and 365. Exemplary mutations that may be made singularly or in combination are mutations K214T, E233P, L234V, L234A, deletion of G236, V234A, F234A, L235A, G237A, P238A, P238S, D265A, S267E, H268A, H268Q, Q268A, N297A, A327Q, P329A, D270A, Q295A, V309L, A327S, L328F, A330S and P331S in IgG1, IgG2, IgG3 or IgG4. Exemplary combination mutations that result in antibodies with reduced ADCC are mutations L234A/L235A on IgG1, V234A/G237A/P238S/H268AN309L/A330S/P331S on IgG2, F234A/L235A on IgG4, S228P/F234A/L235A on IgG4, N297A on all Ig isotypes, V234A/G237A on IgG2, K214T/E233P/L234V/L235A/G236-deleted/A327G/P331A/D365E/L358M on IgG1, H268Q/V309L/A330S/P331S on IgG2, S267E/L328F on IgG1, L234F/L235E/D265A on IgG1, L234A/L235A/G237A/P238S/H268A/A330S/P331S on IgG1, S228P/F234A/L235A/G237A/P238S on IgG4, and S228P/F234A/L235A/G236-deleted/G237A/P238S on IgG4. Hybrid IgG2/4 Fc domains may also be used, such as Fc with residues 117-260 from IgG2 and residues 261-447 from IgG4.

Exemplary mutation that result in antibodies with reduced CDC is a K322A mutation.

Well-known S228P mutation may be made in IgG4 antibodies to enhance IgG4 stability.

In some embodiments, the antibody that specifically binds PD-1 or the antigen binding fragment thereof comprises a mutation in at least one residue position 214, 233, 234, 235, 236, 237, 238, 265, 267, 268, 270, 295, 297, 309, 322, 327, 328, 329, 330, 331 or 365.

In some embodiments, the antibody that specifically binds PD-1 or the antigen binding fragment thereof comprises at least one mutation selected from the group consisting of K214T, E233P, L234V, L234A, deletion of G236, V234A, F234A, L235A, G237A, P238A, P238S, D265A, S267E, H268A, H268Q, Q268A, N297A, A327Q, P329A, D270A, Q295A, V309L, A327S, L328F, K322, A330S and P331S.

In some embodiments, the antibody that specifically binds PD-1 or the antigen binding fragment thereof comprises a mutation in at least one residue position 228, 234, 235, 237, 238, 268, 322, 330 or 331.

In some embodiments, the antibody that specifically binds PD-1 or the antigen binding fragment thereof comprises a K322A mutation.

In some embodiments, the antibody that specifically binds PD-1 or the antigen binding fragment thereof comprises a S228P mutation.

In some embodiments, the antibody that specifically binds PD-1 or the antigen binding fragment thereof comprises at least one mutation in an antibody Fc that enhances binding of the antibody to an Fcγ receptor (FcγR) and/or enhances Fc effector functions such as C1q binding, complement dependent cytotoxicity (CDC), antibody-dependent cell-mediated cytotoxicity (ADCC) and/or phagocytosis (ADCP).

Fc positions that may be mutated to increase binding of the antibody to the activating FcγR and/or enhance antibody effector functions include positions 236, 239, 243, 256, 290, 292, 298, 300, 305, 312, 326, 330, 332, 333, 334, 345, 360, 339, 378, 396 or 430 (residue numbering according to the EU index). Exemplary mutations that may be made singularly or in combination are a G236A mutation, a S239D mutation, a F243L mutation, a T256A mutation, a K290A mutation, a R292P mutation, a S298A mutation, an Y300L mutation, a V305L mutation, a K326A mutation, an A330K mutation, an I332E mutation, an E333A mutation, a K334A mutation, an A339T mutation and a P396L mutation. Exemplary combination mutations that result in antibodies with increased ADCC or ADCP are a S239D/I332E mutation, a S298A/E333A/K334A mutation, a F243L/R292P/Y300L mutation, a F243L/R292P/Y300L/P396L mutation, a F243L/R292P/Y300L/V305I/P396L mutation and a G236A/S239D/I332E mutation on IgG1.

Fc positions that may be mutated to enhance CDC of the antibody include positions 267, 268, 324, 326, 333, 345 and 430. Exemplary mutations that may be made singularly or in combination are a S267E mutation, a F1268F mutation, a S324T mutation, a K326A mutation, a K326W mutation, an E333A mutation, an E345K mutation, an E345Q mutation, an E345R mutation, an E345Y mutation, an E430S mutation, an E430F mutation and an E430T mutation. Exemplary combination mutations that result in antibodies with increased CDC are a K326A/E333A mutation, a K326W/E333A mutation, a H268F/S324T mutation, a S267E/H268F mutation, a S267E/S324T mutation and a S267E/H268F/S324T mutation on IgG1.

In some embodiments, the antibody that specifically binds PD-1 or the antigen binding fragment thereof comprises at least one mutation in the Fc region that enhances binding of the antibody to FcγRIIb Enhanced binding to FcγRIIb may result in attenuation of FcγRIIb+ B cells, and/or result in clustering of the antibody and subsequent activation of PD-1 downstream signaling pathways.

In some embodiments, the antibody that specifically binds PD-1 or the antigen binding fragment thereof comprises a S267E mutation.

In some embodiments, the antibody that specifically binds PD-1 or the antigen binding fragment thereof comprises a S267D mutation.

In some embodiments, the antibody that specifically binds PD-1 or the antigen binding fragment thereof comprises a S267E/I332E mutation.

In some embodiments, the antibody that specifically binds PD-1 or the antigen binding fragment thereof comprises a S267E/L328F mutation.

In some embodiments, the antibody that specifically binds PD-1 or the antigen binding fragment thereof comprises a G236D/S267E mutation.

In some embodiments, the antibody that specifically binds PD-1 or the antigen binding fragment thereof comprises a P238D/E233D/G237D/H268D/P271G/A330R mutation.

In some embodiments, the antibody that specifically binds PD-1 or the antigen binding fragment thereof comprises a P238D mutation.

"Antibody-dependent cellular cytotoxicity", "antibody-dependent cell-mediated cytotoxicity" or "ADCC" is a mechanism for inducing cell death that depends upon the interaction of antibody-coated target cells with effector cells possessing lytic activity, such as natural killer cells (NK), monocytes, macrophages and neutrophils via Fc gamma receptors (FcγR) expressed on effector cells. For example, NK cells express FcγRIIIa, whereas monocytes express FcγRI, FcγRII and FcγRIIIa. ADCC activity of the antibodies provided herein may be assessed using an in vitro assay using PD-1 expressing cells as target cells and NK cells as effector cells. Cytolysis may be detected by the release of label (e.g. radioactive substrates, fluorescent dyes or natural intracellular proteins) from the lysed cells. In an exemplary assay, target cells are used with a ratio of 1 target cell to 4 effector cells. Target cells are pre-labeled with BATDA and combined with effector cells and the test antibody. The samples are incubated for 2 hours and cell lysis measured by measuring released BATDA into the supernatant. Data is normalized to maximal cytotoxicity with 0.67% Triton X-100 (Sigma Aldrich) and minimal control determined by spontaneous release of BATDA from target cells in the absence of any antibody.

"Antibody-dependent cellular phagocytosis" ("ADCP") refers to a mechanism of elimination of antibody-coated target cells by internalization by phagocytic cells, such as macrophages or dendritic cells. ADCP may be evaluated by using monocyte-derived macrophages as effector cells and Daudi cells (ATCC® CCL-213™) or any other PD-1 expressing cells as target cells engineered to express GFP or other labeled molecule. In an exemplary assay, effector:target cell ratio may be for example 4:1. Effector cells may be incubated with target cells for 4 hours with or without the antibody of the invention. After incubation, cells may be detached using accutase. Macrophages may be identified with anti-CD11b and anti-CD14 antibodies coupled to a fluorescent label, and percent phagocytosis may be determined based on % GFP fluorescence in the $CD11^+CD14^+$ macrophages using standard methods.

"Complement-dependent cytotoxicity", or "CDC", refers to a mechanism for inducing cell death in which the Fc effector domain of a target-bound antibody binds and activates complement component C1q which in turn activates the complement cascade leading to target cell death. Activation of complement may also result in deposition of complement components on the target cell surface that facilitate CDC by binding complement receptors (e.g., CR3) on leukocytes. CDC of cells may be measured for example by plating Daudi cells at $1 \times 10^5$ cells/well (50 µL/well) in RPMI-B (RPMI supplemented with 1% BSA), adding 50 µL of test antibodies to the wells at final concentration between 0-100 µg/mL, incubating the reaction for 15 min at room temperature, adding 11 µL of pooled human serum to the wells, and incubation the reaction for 45 min at 37° C. Percentage (%) lysed cells may be detected as % propidium iodide stained cells in FACS assay using standard methods.

Binding of the antibody to FcγR or FcRn may be assessed on cells engineered to express each receptor using flow cytometry. In an exemplary binding assay, $2 \times 10^5$ cells per well are seeded in 96-well plate and blocked in BSA Stain Buffer (BD Biosciences, San Jose, USA) for 30 min at 4° C. Cells are incubated with a test antibody on ice for 1.5 hour at 4° C. After being washed twice with BSA stain buffer, the cells are incubated with R-PE labeled anti-human IgG secondary antibody (Jackson Immunoresearch Laboratories) for 45 min at 4° C. The cells are washed twice in stain buffer and then resuspended in 150 µL of Stain Buffer containing 1:200 diluted DRAQ7 live/dead stain (Cell Signaling Technology, Danvers, USA). PE and DRAQ7 signals of the stained cells are detected by Miltenyi MACSQuant flow cytometer (Miltenyi Biotec, Auburn, USA) using B2 and B4 channel respectively. Live cells are gated on DRAQ7 exclusion and the geometric mean fluorescence signals are determined for at least 10,000 live events collected. FlowJo software (Tree Star) is used for analysis. Data is plotted as the logarithm of antibody concentration versus mean fluorescence signals. Nonlinear regression analysis is performed.

"Enhance" or "enhanced" refers to enhanced effector function (e.g. ADCC, CDC and/or ADCP) or enhanced binding to an Fcγ receptor (FcγR) or FcRn of the antibody of the invention having at least one mutation in the Fc region when compared to the parental antibody without the mutation "Enhanced" may be an enhancement of about 10%, 20%, 30%, 40%, 50%, 60%, 70%, 80%, 90%, 100% or more, or a statistically significant enhancement.

"Reduce" or "reduced" refers to reduced effector function (e.g. ADCC, CDC and/or ADCP) or reduced binding to an Fcγ receptor (FcγR) or FcRn of the antibody of the invention having at least one mutation in the Fc region when compared to the parental antibody without the mutation. "Reduced"

may be a reduction of about 10%, 20%, 30%, 40%, 50%, 60%, 70%, 80%, 90%, 100% or more, or a statistically significant reduction.

"Modulate" refers to either enhanced or reduced effector function (e.g. ADCC, CDC and/or ADCP) or enhanced or reduced binding to an Fcγ receptor (FcγR) or FcRn of the antibody of the invention having at least one mutation in the Fc region when compared to the parental antibody without the mutation.

Glycoengineered Antibodies

The ability of monoclonal antibodies to induce ADCC can be enhanced by engineering their oligosaccharide component. Human IgG1 or IgG3 are N-glycosylated at Asn297 with the majority of the glycans in the well-known biantennary G0, G0F, G1, G1F, G2 or G2F forms. Antibodies produced by non-engineered CHO cells typically have a glycan fucose content of about at least 85%. The removal of the core fucose from the biantennary complex-type oligosaccharides attached to the Fc regions enhances the ADCC of antibodies via improved FcγRIIIa binding without altering antigen binding or CDC activity. Such mAbs can be achieved using different methods reported to lead to the successful expression of relatively high defucosylated antibodies bearing the biantennary complex-type of Fc oligosaccharides such as control of culture osmolality (Konno et al., Cytotechnology 64(:249-65, 2012), application of a variant CHO line Lec13 as the host cell line (Shields et al., *J Biol Chem* 277:26733-26740, 2002), application of a variant CHO line EB66 as the host cell line (Olivier et al., *MAbs;* 2(4): 405-415, 2010; PMID:20562582), application of a rat hybridoma cell line YB2/0 as the host cell line (Shinkawa et al., *J Biol Chem* 278:3466-3473, 2003), introduction of small interfering RNA specifically against the a 1,6-fucosyltrasferase (FUT8) gene (Mori et al., *Biotechnol Bioeng* 88:901-908, 2004), or coexpression of β-1,4-N-acetylglucosaminyltransferase III and Golgi α-mannosidase II or a potent alpha-mannosidase I inhibitor, kifunensine (Ferrara et al., *J Biol Chem* 281:5032-5036, 2006, Ferrara et al., *Biotechnol Bioeng* 93:851-861, 2006; Xhou et al., *Biotechnol Bioeng* 99:652-65, 2008).

In some embodiments described herein, the antibodies of the invention have a biantennary glycan structure with fucose content of about between 1% to about 15%, for example about 15%, 14%, 13%, 12%, 11% 10%, 9%, 8%, 7%, 6%, 5%, 4%, 3%, 2% or 1%. In some embodiments, the antibodies of the invention have a glycan structure with fucose content of about 50%, 40%, 45%, 40%, 35%, 30%, 25%, or 20%.

"Fucose content" means the amount of the fucose monosaccharide within the sugar chain at Asn297. The relative amount of fucose is the percentage of fucose-containing structures related to all glycostructures. These may be characterized and quantified by multiple methods, for example: 1) using MALDI-TOF of N-glycosidase F treated sample (e.g. complex, hybrid and oligo- and high-mannose structures) as described in Int Pat. Publ. No. WO2008/077546 2); 2) by enzymatic release of the Asn297 glycans with subsequent derivatization and detection/quantitation by HPLC (UPLC) with fluorescence detection and/or HPLC-MS (UPLC-MS); 3) intact protein analysis of the native or reduced mAb, with or without treatment of the Asn297 glycans with Endo S or other enzyme that cleaves between the first and the second GlcNAc monosaccharides, leaving the fucose attached to the first GlcNAc; 4) digestion of the mAb to constituent peptides by enzymatic digestion (e.g., trypsin or endopeptidase Lys-C), and subsequent separation, detection and quantitation by HPLC-MS (UPLC-MS); 5) Separation of the mAb oligosaccharides from the mAb protein by specific enzymatic deglycosylation with PNGase F at Asn 297. The oligosaccharides thus released can be labeled with a fluorophore, separated and identified by various complementary techniques which allow: fine characterization of the glycan structures by matrix-assisted laser desorption ionization (MALDI) mass spectrometry by comparison of the experimental masses with the theoretical masses, determination of the degree of sialylation by ion exchange HPLC (GlycoSep C), separation and quantification of the oligosaccharide forms according to hydrophilicity criteria by normal-phase HPLC (GlycoSep N), and separation and quantification of the oligosaccharides by high performance capillary electrophoresis-laser induced fluorescence (HPCE-LIF).

"Low fucose" or "low fucose content" as used herein refers to antibodies with fucose content of about between 1%-15%.

"Normal fucose" or 'normal fucose content" as used herein refers to antibodies with fucose content of about over 50%, typically about over 80% or over 85%.

Anti-Idiotypic Antibodies

Anti-idiotypic antibodies are antibodies that specifically bind to the antibodies that specifically bind PD-1 disclosed herein.

The invention also provides an anti-idiotypic antibody that specifically binds to the antibodies that specifically bind PD-1 provided herein.

The invention also provides an anti-idiotypic antibody that specifically binds to the antibody comprising the VH of SEQ ID NO: 8 and the VL of SEQ ID NO: 14;
the VH of SEQ ID NO: 9 and the VL of SEQ ID NO: 15;
the VH of SEQ ID NO: 9 and the VL of SEQ ID NO: 16;
the VH of SEQ ID NO: 10 and the VL of SEQ ID NO: 16;
the VH of SEQ ID NO: 140 and the VL of SEQ ID NO: 16;
the VH of SEQ ID NO: 141 and the VL of SEQ ID NO: 16;
the VH of SEQ ID NO: 142 and the VL of SEQ ID NO: 16;
the VH of SEQ ID NO: 10 and the VL of SEQ ID NO: 143;
the VH of SEQ ID NO: 10 and the VL of SEQ ID NO: 144;
the VH of SEQ ID NO: 140 and the VL of SEQ ID NO: 143;
the VH of SEQ ID NO: 141 and the VL of SEQ ID NO: 143;
the VH of SEQ ID NO: 142 and the VL of SEQ ID NO: 143;
the VH of SEQ ID NO: 140 and the VL of SEQ ID NO: 144;
the VH of SEQ ID NO: 141 and the VL of SEQ ID NO: 144;
the VH of SEQ ID NO: 142 and the VL of SEQ ID NO: 144;
the VH of SEQ ID NO: 44 and the VL of SEQ ID NO: 60;
the VH of SEQ ID NO: 45 and the VL of SEQ ID NO: 61;
the VH of SEQ ID NO: 45 and the VL of SEQ ID NO: 62;
the VH of SEQ ID NO: 46 and the VL of SEQ ID NO: 61;
the VH of SEQ ID NO: 47 and the VL of SEQ ID NO: 61;
the VH of SEQ ID NO: 48 and the VL of SEQ ID NO: 61;
the VH of SEQ ID NO: 49 and the VL of SEQ ID NO: 61;
the VH of SEQ ID NO: 50 and the VL of SEQ ID NO: 61;
the VH of SEQ ID NO: 51 and the VL of SEQ ID NO: 61;
the VH of SEQ ID NO: 94 and the VL of SEQ ID NO: 98;

the VH of SEQ ID NO: 95 and the VL of SEQ ID NO: 99; or the VH of SEQ ID NO: 95 and the VL of SEQ ID NO: 100.

An anti-idiotypic (Id) antibody is an antibody which recognizes the antigenic determinants (e.g. the paratope or CDRs) of the antibody. The Id antibody may be antigen-blocking or non-blocking. The antigen-blocking Id may be used to detect the free antibody in a sample (e.g. anti-PD-1 antibody of the invention described herein). The non-blocking Id may be used to detect the total antibody (free, partially bond to antigen, or fully bound to antigen) in a sample. An Id antibody may be prepared by immunizing an animal with the antibody to which an anti-Id is being prepared.

An anti-Id antibody may also be used as an immunogen to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity. Anti-Id antibodies may be varied (thereby producing anti-Id antibody variants) and/or derivatized by any suitable technique, such as those described elsewhere herein with respect to the antibodies that specifically bind PD-1.

Conjugates of the Antibodies that Specifically Bind PD-1 Provided Herein

The invention also provides an immunoconjugate comprising an isolated antibody or an antigen-binding fragment thereof that specifically binds PD-1 conjugated to a heterologous molecule.

In some embodiments, the heterologous molecule is a detectable label or a cytotoxic agent.

The invention also provides an antibody or an antigen-binding fragment thereof that specifically binds PD-1 conjugated to a detectable label.

The invention also provides an antibody or an antigen-binding fragment thereof that specifically binds PD-1 conjugated to a cytotoxic agent.

Antibodies or antigen-binding fragments thereof that bind PD-1 may be used to direct therapeutics to PD-1 expressing cells. Cells such as activated T cells that overexpress PD-1 may be targeted with an antibody that specifically binds PD-1 conjugated to a cytotoxic agent that kills the cell upon internalization of the PD-1 antibody. Alternatively, PD-1 expressing cells could be targeted with a PD-1 antibody coupled to a therapeutic intended to modify cell function once internalized.

In some embodiments, the detectable label is also a cytotoxic agent.

The isolated antibody that specifically binds PD-1 or the antigen-binding fragment thereof provided herein conjugated to a detectable label may be used to evaluate expression of PD-1 on a variety of samples.

Detectable label includes compositions that when conjugated to the isolated antibody that specifically binds PD-1 or the antigen-binding fragment thereof provided herein renders the latter detectable, via spectroscopic, photochemical, biochemical, immunochemical, or chemical means.

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, scintillates, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases, the detectable label emits a signal as a result of being stimulated by an external field.

Exemplary radioactive isotopes may be γ-emitting, Auger-emitting, β-emitting, an alpha-emitting or positron-emitting radioactive isotope. Exemplary radioactive isotopes include $^{3}H$, $^{11}C$, $^{13}C$, $^{15}N$, $^{18}F$, $^{19}F$, $^{55}Co$, $^{57}Co$, $^{60}Co$, $^{61}Cu$, $^{62}Cu$, $^{64}Cu$, $^{67}Cu$, $^{68}Ga$, $^{72}As$, $^{75}Br$, $^{86}Y$, $^{89}Zr$, $^{90}Sr$, $^{94m}Tc$, $^{99m}Tc$, $^{115}In$, $^{123}I$, $^{124}I$, $^{125}I$, $^{131}I$, $^{211}At$, $^{212}Bi$, $^{213}Bi$, $^{223}Ra$, $^{226}Ra$, $^{225}Ac$ and $^{227}Ac$.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e. iodine) to 83 (i.e. bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^{+}$, $Ca^{2+}$, $Cr^{2+}$, $Cr^{3+}$, $Cr^{6+}$, $Co^{2+}$, $Co^{3+}$, $Cu^{+}$, $Cu^{2+}$, $Cu^{3+}$, $Ga^{3+}$, $Gd^{3+}$, $Au^{+}$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^{+}$, $Sr^{2+}$, $Sn^{2+}$, $Sn^{4+}$, and $Zn^{2+}$. The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyanate (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The isolated antibody that specifically binds PD-1 or the antigen-binding fragment thereof provided herein conjugated to a detectable label may be used as an imaging agent.

In some embodiments, the isolated antibody that specifically binds PD-1 or the antigen-binding fragment thereof provided herein is conjugated to a cytotoxic agent.

In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

In some embodiments, the cytotoxic agent is daunomycin, doxorubicin, methotrexate, vindesine, bacterial toxins such as diphtheria toxin, ricin, geldanamycin, maytansinoids or calicheamicin. The cytotoxic agent may elicit their cytotoxic and cytostatic effects by mechanisms including tubulin binding, DNA binding, or topoisomerase inhibition.

In some embodiments, the cytotoxic agent is an enzymatically active toxin such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the cytotoxic agent is a radionuclide, such as $^{212}$Bi, $^{131}$I, $^{131}$In, $^{90}$Y, and $^{186}$Re.

In some embodiments, the cytotoxic agent is dolastatins or dolostatin peptidic analogs and derivatives, auristatin or monomethyl auristatin phenylalanine. Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45(12):3580-3584) and have anticancer and antifungal activity. The dolastatin or auristatin drug moiety may be attached to the antibody of the invention through the N (amino) terminus or the C (carboxyl) terminus of the peptidic drug moiety (WO02/088172), or via any cysteine engineered into the antibody.

The isolated antibody that specifically binds PD-1 or the antigen-binding fragment thereof provided herein may be conjugated to a detectable label using known methods.

In some embodiments, the detectable label is complexed with a chelating agent.

In some embodiments, the detectable label is conjugated to the antibody that specifically binds PD-1 or the antigen-binding fragment thereof provided herein via a linker.

The detectable label or the cytotoxic moiety may be linked directly, or indirectly, to the antibody that specifically binds PD-1 or the antigen-binding fragment thereof provided herein using known methods. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10,tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

In some embodiments, the antibody that specifically binds PD-1 or the antigen-binding fragment thereof that provided herein are removed from the blood via renal clearance.

Kits

The invention also provides a kit comprising the antibody that specifically binds PD-1 or the antigen-binding fragment thereof disclosed herein.

The kit may be used for therapeutic uses and as diagnostic kits.

The kit may be used to detect the presence of PD-1 in a sample.

In some embodiments, the kit comprises the antibody that specifically binds PD-1 or the antigen-binding fragment thereof provided herein and reagents for detecting the antibody. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody for administration; pharmaceutically acceptable carriers; and devices or other materials for administration to a subject.

In some embodiments, the kit comprises the antibody that specifically binds PD-1 or the antigen-binding fragment thereof provided herein in a container and instructions for use of the kit.

In some embodiments, the antibody in the kit is labeled.

In some embodiments, the kit comprises the antibody that specifically binds PD-1 or the antigen-binding fragment thereof comprising the VH of SEQ ID NO: 8 and the VL of SEQ ID NO: 14;
the VH of SEQ ID NO: 9 and the VL of SEQ ID NO: 15;
the VH of SEQ ID NO: 9 and the VL of SEQ ID NO: 16;
the VH of SEQ ID NO: 10 and the VL of SEQ ID NO: 16;
the VH of SEQ ID NO: 140 and the VL of SEQ ID NO: 16;
the VH of SEQ ID NO: 141 and the VL of SEQ ID NO: 16;
the VH of SEQ ID NO: 142 and the VL of SEQ ID NO: 16;
the VH of SEQ ID NO: 10 and the VL of SEQ ID NO: 143;
the VH of SEQ ID NO: 10 and the VL of SEQ ID NO: 144;
the VH of SEQ ID NO: 140 and the VL of SEQ ID NO: 143;
the VH of SEQ ID NO: 141 and the VL of SEQ ID NO: 143;
the VH of SEQ ID NO: 142 and the VL of SEQ ID NO: 143;

the VH of SEQ ID NO: 140 and the VL of SEQ ID NO: 144;

the VH of SEQ ID NO: 141 and the VL of SEQ ID NO: 144;

the VH of SEQ ID NO: 142 and the VL of SEQ ID NO: 144;

the VH of SEQ ID NO: 44 and the VL of SEQ ID NO: 60;
the VH of SEQ ID NO: 45 and the VL of SEQ ID NO: 61;
the VH of SEQ ID NO: 45 and the VL of SEQ ID NO: 62;
the VH of SEQ ID NO: 46 and the VL of SEQ ID NO: 61;
the VH of SEQ ID NO: 47 and the VL of SEQ ID NO: 61;
the VH of SEQ ID NO: 48 and the VL of SEQ ID NO: 61;
the VH of SEQ ID NO: 49 and the VL of SEQ ID NO: 61;
the VH of SEQ ID NO: 50 and the VL of SEQ ID NO: 61;
the VH of SEQ ID NO: 51 and the VL of SEQ ID NO: 61;
the VH of SEQ ID NO: 94 and the VL of SEQ ID NO: 98;
the VH of SEQ ID NO: 95 and the VL of SEQ ID NO: 99; or the VH of SEQ ID NO: 95 and the VL of SEQ ID NO: 100.

Methods of Detecting PD-1

The invention also provides a method of detecting PD-1 in a sample, comprising obtaining the sample, contacting the sample with the antibody that specifically binds PD-1 or the antigen-binding fragment thereof provided herein, and detecting the antibody bound to PD-1 in the sample.

In some embodiments, the sample may be derived from urine, blood, serum, plasma, saliva, ascites, circulating cells, synovial fluid, circulating cells, cells that are not tissue associated (i.e., free cells), tissues (e.g., surgically resected tissue, biopsies, including fine needle aspiration), histological preparations, and the like.

The antibodies or the antigen-binding fragments thereof of the invention bound to PD-1 may be detected using known methods. Exemplary methods include direct labeling of the antibodies using fluorescent or chemiluminescent labels, or radiolabels, or attaching to the antibodies of the invention a moiety which is readily detectable, such as biotin, enzymes or epitope tags. Exemplary labels and moieties are ruthenium, $^{111}$In-DOTA, $^{111}$In-diethylenetriaminepentaacetic acid (DTPA), horseradish peroxidase, alkaline phosphatase and beta-galactosidase, poly-histidine (HIS tag), acridine dyes, cyanine dyes, fluorone dyes, oxazin dyes, phenanthridine dyes, rhodamine dyes and Alexafluor® dyes.

The antibodies of the invention may be used in a variety of assays to detect PD-1 in the sample. Exemplary assays are western blot analysis, radioimmunoassay, surface plasmon resonance, immunoprecipitation, equilibrium dialysis, immunodiffusion, electrochemiluminescence (ECL) immunoassay, immunohistochemistry, fluorescence-activated cell sorting (FACS) or ELISA assay.

Methods Generating Antibodies

Antibodies that specifically bind PD-1 or antigen-binding fragments thereof provided herein may be generated using various technologies. For example, the hybridoma method of Kohler and Milstein may be used to generate monoclonal antibodies. In the hybridoma method, a mouse or other host animal, such as a hamster, rat or chicken is immunized with human and/or cyno PD-1 antigens, such as the extracellular domain of PD-1, followed by fusion of spleen cells from immunized animals with myeloma cells using standard methods to form hybridoma cells. Colonies arising from single immortalized hybridoma cells may be screened for production of antibodies with desired properties, such as specificity of binding, cross-reactivity or lack thereof, affinity for the antigen, and functionality such as agonistic activity.

Exemplary humanization techniques including selection of human acceptor frameworks include CDR grafting (U.S. Pat. No. 5,225,539), SDR grafting (U.S. Pat. No. 6,818,749), Resurfacing (Padlan, (1991) *Mol Immunol* 28:489-499), Specificity Determining Residues Resurfacing (U.S. Patent Publ. No. 2010/0261620), human framework adaptation (U.S. Pat. No. 8,748,356) or superhumanization (U.S. Pat. No. 7,709,226). In these methods, CDRs or a subset of CDR residues of parental antibodies are transferred onto human frameworks that may be selected based on their overall homology to the parental frameworks, based on similarity in CDR length, or canonical structure identity, or a combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1090/007861 and WO1992/22653, or by introducing variation at any of the CDRs for example to improve affinity of the antibody.

Transgenic animals, such as mice, rat or chicken carrying human immunoglobulin (Ig) loci in their genome may be used to generate antibodies against PD-1, and are described in for example U.S. Pat. No. 6,150,584, Int. Patent Publ. No. WO1999/45962, Int. Patent Publ. Nos. WO2002/066630, WO2002/43478, WO2002/043478 and WO1990/04036. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (http://_www_regeneron_com), Harbour Antibodies (http://_www_harbourantibodies_com), Open Monoclonal Technology, Inc. (OMT) (http://_www_omtinc_net), KyMab (http://_www_kymab_com), Trianni (http://www.trianni_com) and Ablexis (http://_www_ablexis_com) may be engaged to provide human antibodies directed against a selected antigen using technologies as described above.

Antibodies may be selected from a phage display library, where the phage is engineered to express human immunoglobulins or portions thereof such as Fabs, single chain antibodies (scFv), or unpaired or paired antibody variable regions. The antibodies of the invention may be isolated for example from phage display library expressing antibody heavy and light chain variable regions as fusion proteins with bacteriophage pIX coat protein as described in Shi et al., (2010) *J Mol Biol* 397:385-96, and Int. Patent Publ. No. WO09/085462). The libraries may be screened for phage binding to human and/or cyno PD-1 and the obtained positive clones may be further characterized, the Fabs isolated from the clone lysates, and expressed as full length IgGs.

Preparation of immunogenic antigens and monoclonal antibody production may be performed using any suitable technique, such as recombinant protein production. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

In some embodiments, the antibody that specifically binds PD-1 or the antigen-binding fragment thereof of the invention is a bispecific antibody.

In some embodiments, the antibody or the antigen-binding fragment thereof of the invention is a multispecific antibody.

The monospecific antibodies that specifically bind PD-1 provided herein may be engineered into bispecific antibodies which are also encompassed within the scope of the invention.

Full length bispecific antibodies may be generated for example using Fab arm exchange (e.g., half-molecule exchange, exchanging one heavy chain-light chain pair) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy chain disulfide bonds in the hinge regions of the parental monospecific antibodies are reduced. The resulting free cysteines of one of the parental monospecific antibodies form an inter heavy-chain disulfide bond with cysteine residues of a second parental monospecific antibody molecule and simultaneously CH3 domains of the parental antibodies release and reform by dissociation-association. The CH3 domains of the Fab arms may be engineered to favor heterodimerization over homodimerization. The resulting product is a bispecific antibody having two Fab arms or half molecules which each bind a distinct epitope.

Bispecific antibodies may also be generated using designs such as the Triomab/Quadroma (Trion Pharma/Fresenius Biotech), Knob-in-Hole (Genentech), CrossMAbs (Roche) and the electrostatically-induced CH3 interaction (Chugai, Amgen, NovoNordisk, Oncomed), the LUZ-Y (Genentech), the Strand Exchange Engineered Domain body (SEEDbody) (EMD Serono), the Biclonic (Merus) and as DuoBody® Products (Genmab A/S).

The Triomab quadroma technology may be used to generate full length bispecific antibodies. Triomab technology promotes Fab arm exchange between two parental chimeric antibodies, one parental mAb having IgG2a and the second parental mAb having rat IgG2b constant regions, yielding chimeric bispecific antibodies.

The "knob-in-hole" strategy may be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

The CrossMAb technology may be used to generate full length bispecific antibodies. CrossMAbs, in addition to utilizing the "knob-in-hole" strategy to promoter Fab arm exchange, have in one of the half arms the CH1 and the CL domains exchanged to ensure correct light chain pairing of the resulting bispecific antibody (see e.g. U.S. Pat. No. 8,242,247).

Other cross-over strategies may be used to generate full length bispecific antibodies by exchanging variable or constant, or both domains between the heavy chain and the light chain or within the heavy chain of the bispecific antibodies, either in one or both arms. These exchanges include for example VH-CH1 with VL-CL, VH with VL, CH3 with CL and CH3 with CH1 as described in Int. Patent Publ. Nos. WO2009/080254, WO2009/080251, WO2009/018386 and WO2009/080252.

Other strategies such as promoting heavy chain heterodimerization using electrostatic interactions by substituting positively charged residues at one CH3 surface and negatively charged residues at a second CH3 surface may be used, as described in US Patent Publ. No. US2010/0015133; US Patent Publ. No. US2009/0182127; US Patent Publ. No. US2010/028637 or US Patent Publ. No. US2011/0123532. In other strategies, heterodimerization may be promoted by following substitutions (expressed as modified position in the first CH3 domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Patent Publ. No. US2012/0149876 or U.S. Patent Publ. No. US2013/0195849.

LUZ-Y technology may be utilized to generate bispecific antibodies. In this technology, a leucine zipper is added into the C terminus of the CH3 domains to drive the heterodimer assembly from parental mAbs that is removed post-purification.

SEEDbody technology may be utilized to generate bispecific antibodies. SEEDbodies have, in their constant domains, select IgG residues substituted with IgA residues to promote heterodimerization as described in U.S. Patent No. US20070287170.

Bispecific antibodies may be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Int. Patent Publ. No. WO2011/131746. In the methods, the first monospecific bivalent antibody and the second monospecific bivalent antibody are engineered to have certain substitutions at the CH3 domain that promoter heterodimer stability; the antibodies are incubated together under reducing conditions sufficient to allow the cysteines in the hinge region to undergo disulfide bond isomerization; thereby generating the bispecific antibody by Fab arm exchange. Substitutions that may be used are F405L in one heavy chain and K409R in the other heavy chain in IgG1 antibodies. In IgG4 antibodies, one heavy chain may be a wild-type IgG4 having F at position 405 and R at position 409 and the other heavy chain may have F405L and R409K substitutions. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl) phosphine (TCEP), L-cysteine and beta-mercaptoethanol. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

In some embodiments, the bispecific antibodies include recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

Substitutions are typically made at the DNA level to a molecule such as the constant domain of the antibody using standard methods.

The antibodies of the invention may be engineered into various well-known antibody forms.

For example, a bispecific PD-1/CD3 antibody can be generated using the VH/VL domains of the PD-1 antibodies described herein and any VH/VL regions of published anti-CD3 antibodies.

Another embodiment of the invention is a bispecific antibody comprising a first domain that binds PD-1 and a second domain that binds CD3.

Methods of Characterizing Antibodies
Agonistic Antibodies

A typical biological activity induced by the agonistic antibodies provided herein is inhibition (e.g. suppression) of antigen-specific CD4$^+$ or CD8$^+$ T cells. Various readouts may be used to assess the agonism of the antibodies provided herein, such as reduced proliferation or reduced production of interferon-γ (IFN-γ), IL-17 IL-2, IL-6, IL-22, IL-23 or GM-CSF by antigen-specific CD4$^+$ or CD8$^+$ T cells. In an exemplary assay, the effect of antibodies on T cells from normal donor that are stimulated by allogeneic dendritic cells or specific antigens, such as Tetanus toxoid or CMV are used. In this setting, changes in T cell function with antibody treatment can be detected by measuring supernatant cytokine levels or markers of T cell activation. In an exemplary assay, PBMCs determined to be reactive to CMV antigens are used as source of antigen-specific CD4$^+$ or CD8$^+$ T cells. $1.5 \times 10^6$ cells/mL or $2 \times 10^6$ cells/mL of CMV-reactive PBMCs are plated onto culture plates and 0.1-0.2 µg/mL CMV peptides added to cultures. CMV peptides may be purchased for example from JPT Technologies. Test antibodies are added at singe dose of 10 µg/mL, plates incubated for 6 days, and cell proliferation assessed by addition of 1 µCi/well methyl-3H-thymidine (PerkinElmer) for 6 hours and radioactivity measured in each sample. Alternatively, cytokine production by cells is measured using ELISA or known multiplex assays.

Antibodies that Block PD-L1 and/or PD-L2 Binding to PD-1

The antibodies of the invention provided herein (such as agonistic antibodies that specifically bind PD-1) may be ligand blocking or non-blocking. Ability of the agonistic antibodies provided herein may be assessed for their ability to block ligand., e.g. PD-L1 or PD-L2 or both using competition assays such as cell clustering assay.

In an exemplary assay, differentially labeled HEK cells overexpressing either PD-1 or PD-L1 (or PD-L2) are mixed in a 1:1 ratio, and the ability of the antibodies to inhibit clustering of PD-1 and PD-L1 or PD-1 and PD-L2 expressing cells is quantified. Cells overexpressing human PD-1 may be labeled with Violet Cell Trace stain and cells overexpressing PD-L1 or PD-L2 may be labeled with Far Red Cell Trace Stain (Life Technologies). PD-1 expressing cells are mixed with the test antibody and after a brief incubation PD-L1 expressing cells are added into the mixture. The mixture is incubated for one hour, and the percentage of double positive events (e.g. cell clusters positive with Violet Cell Trace stain and Far Rd Cell Trace stain) is evaluated using flow cytometry. The level of clustering is measured by the percentage of double positive events, and the percentage of clustering in the presence of test antibodies is compared to positive, and negative isotype control antibodies. The antibody provided herein blocks PD-L1 (or PD-L2) binding to PD-1 when the antibody inhibits double positive events of PD-1 and PD-L1 (or PD-L2) expressing cells in a statistically significant manner when compared to the isotype control using a p value of ≤0.01 as a measure of significance. The antibody provided herein does not block PD-L1 (or PD-L2) binding to PD-1 when the antibody inhibits double positive events of PD-1 and PD-L1 (or PD-L2) in a statistically insignificant manner, e.g. p>0.01.

Antibody Affinity Measurements

The affinity of an antibody to human or non-human such as cynomolgus PD-1 may be determined experimentally using any suitable method. Such methods may utilize ProteOn XPR36, Biacore 3000 or KinExA instrumentation, ELISA or competitive binding assays known to those skilled in the art. The measured affinity of a particular antibody/PD-1 interaction may vary if measured under different conditions (e.g., osmolarity, pH). Thus, measurements of affinity and other binding parameters (e.g., $K_D$, $K_{on}$, $K_{off}$) are typically made with standardized conditions and a standardized buffer, such as the buffer described herein in Example 1. Skilled in the art will appreciate that the internal error for affinity measurements for example using Biacore 3000 or ProteOn (measured as standard deviation, SD) may typically be within 5-33% for measurements within the typical limits of detection. Therefore, the term "about" in the context of $K_D$ reflects the typical standard deviation in the assay. For example, the typical SD for a $K_D$ of $1 \times 10^{-9}$ M is up to $\pm 0.33 \times 10^{-9}$ M.

Antibodies Competing for Binding to PD-1 with a Reference Antibody

Competition between binding to PD-1 with antibodies of the invention (e.g. reference antibodies) comprising certain VH and VL sequences may be assayed in vitro on an Octet Red384 platform (Forte Bio). Histidine-tagged PD1 antigen is loaded onto HIS sensors and the sensors are exposed to 20 µg/mL reference anti-PD1 antibody, followed by exposure to an equal concentration of a test anti-PD1 antibody. Additional binding by the test antibody after saturation with the reference antibody indicates simultaneous binding of the two antibodies to PD-1, indicating the reference and the test antibody do not compete for binding to PD-1. Alternatively, no additional binding of the test antibody indicates that the two antibodies compete for binding to PD-1.

Antibodies that compete for binding to PD-1 with a reference antibody may be generated by isolating antibodies that specifically bind PD-1 using phage display libraries, and screening the generated antibodies for their ability to compete for binding to PD-1 with the aforementioned reference antibodies.

The test antibody competes with binding to PD-1 with the reference antibody when the test antibody binds PD-1 at saturating concentration of the reference antibody. Binding can be detected using bio-layer interferometry (such as Octet) by recording a wavelength shift due to the bound antibody increasing the optical density of the biosensor tip over time.

Antibody Epitope

The PD-1 epitope the antibody of the invention binds to may be resolved for example using hydrogen/deuterium exchange (H/D exchange) or by analyzing a crystal structure of the antibody in complex with PD-1. Two PD-1 antibodies "bind the same epitope on PD-1" when about 70% or more PD-1 amino acid residues protected by the antibody by at least 5% difference in deuteration levels through H/D exchange are identical between the two antibodies, or when 70% or more PD-1 surface exposed amino acid residues determined to bind the antibody in a crystal structure of a complex of the antibody and PD-1 are identical between the two antibodies. In the crystal structure of a complex of the antibody and PD-1 the epitope residues are those PD-1 residues that reside within 4 Å distance or less from any of the antibody CDR residues.

In an H/D exchange assay, PD-1 protein is incubated in the presence or absence of the antibody in deuterated water for predetermined times resulting in deuterium incorporation at exchangeable hydrogen atoms which are unprotected by the antibody, followed by protease digestion of the protein and analyses of the peptide fragments using LC-MS. In an exemplary assay, 5 µL of the test antibody (10 µg) or 5 µL of the complex of PD-1 and the test antibody (10 & 7.35 µg, respectively) is incubated with 120 µL deuterium oxide labeling buffer (50 mM phosphate, 100 mM sodium chloride at pH 7.4) for 0 sec, 60 sec, 300 sec, 1800 sec, 7200 sec, and 14400 sec. Deuterium exchange is quenched by adding 63 µL of 5 M guanidine hydrochloride and final pH is 2.5. The quenched sample is subjected to on-column pepsin/protease type XIII digestion and LC-MS analysis. For pepsin/protease type XIII digestion, 5 µg of the samples in 125 µL control buffer (50 mM phosphate, 100 mM sodium chloride at pH 7.4) are denatured by adding 63 µL of 5 M guanidine hydrochloride (final pH is 2.5) and incubating the mixture for 3 min. Then, the mixture is subjected to on-column pepsin/protease type XIII digestion and the resultant peptides analyzed using an UPLC-MS system comprised of a Waters Acquity UPLC coupled to a Q Exactive™ Hybrid Quadrupole-Orbitrap Mass Spectrometer (Thermo). Raw MS data is processed using HDX WorkBench, software for the analysis of H/D exchange MS data. The deuterium levels are calculated using the average mass difference between the deuterated peptide and its native form (t0). Peptide identification is done through searching MS/MS data against the PD-1 sequence with Mascot. The mass tolerance for the precursor and product ions is 20 ppm and 0.05 Da, respectively.

For X-ray crystallography, PD-1 and the test antibody are expressed and purified using standard protocols. The PD-1/test antibody complex is incubated overnight at 4° C., concentrated, and separated from the uncomplexed species using size-exclusion chromatography. The complex is crystallized by the vapor-diffusion method from various known test solutions for example solutions containing PEG3350, ammonium citrate and 2-(N-morpholino)ethanesulfonic acid (MES).

Antibodies binding the same epitope on PD-1 as a reference antibody may be generated by isolating antibodies binding PD-1 using phage display libraries, selecting those antibodies that compete with the reference antibody for binding to PD-1 by 100%, and identifying the antibody epitope by H/D exchange or by X-ray crystallography.

Alternatively, mice or rabbits may be immunized using peptides encompassing the epitope residues, and the generated antibodies may be evaluated for their binding within the recited region.

Polynucleotides, Vectors, Host Cells

The invention also provides an isolated polynucleotide encoding any of the antibodies of the invention.

The invention also provides an isolated polynucleotide encoding any of the antibody heavy chain variable regions, any of the antibody light chain variable regions, or any of the antibody heavy chains and/or the antibody light chains of the invention.

The invention also provides for an isolated polynucleotide encoding the VH of SEQ ID NOs: 8, 9, 10, 140, 141 or 142.

The invention also provides for an isolated polynucleotide encoding the VL of SEQ ID NOs: 14, 15, 16, 143 or 144.

The invention also provides for an isolated polynucleotide encoding the VH of SEQ ID NOs: 8, 9, 10, 140, 141 or 142 and the VL of SEQ ID NOs: 14, 15, 16, 143 or 144.

The invention also provides for an isolated polynucleotide encoding the heavy chain (HC) of SEQ ID NOs: 20, 21, 22, 150, 151 or 152.

The invention also provides for an isolated polynucleotide encoding the light chain (LC) of SEQ ID NOs: 26, 27, 28, 153 or 154.

The invention also provides for an isolated polynucleotide encoding the HC of SEQ ID NOs: 20, 21, 22, 150, 151 or 152 and the LC of SEQ ID NOs: 26, 27, 28, 153 or 154.

The invention also provides for an isolated polynucleotide comprising the polynucleotide sequence of SEQ ID NOs: 11, 12, 13, 17, 18, 19, 23, 24, 25, 29, 30, 31, 132, 133, 134, 135, 155, 156, 157, 158, 159, 160, 161, 162, 163 or 164.

The invention also provides for an isolated polynucleotide encoding the VH of SEQ ID NOs: 44, 45, 46, 47, 48, 49, 50 or 51.

The invention also provides for an isolated polynucleotide encoding the VL of SEQ ID NOs: 60, 61 or 62.

The invention also provides for an isolated polynucleotide encoding the VH of SEQ ID NOs: 44, 45, 46, 47, 48, 49, 50 or 51 and the VL of SEQ ID NOs: 60, 61 or 62.

The invention also provides for an isolated polynucleotide encoding the heavy chain of SEQ ID NOs: 66, 67, 68, 69, 70, 71, 72 or 73.

The invention also provides for an isolated polynucleotide encoding the light chain of SEQ ID NOs: 82, 83 or 84.

The invention also provides for an isolated polynucleotide encoding the HC of SEQ ID NOs: 66, 67, 68, 69, 70, 71, 72 or 73 and the LC of SEQ ID NOs: 82, 83 or 84.

The invention also provides for an isolated polynucleotide comprising the polynucleotide sequence of SEQ ID NOs: 52, 53, 54, 55, 56, 57, 58, 59, 63, 64, 65, 74, 75, 76, 77, 78, 79, 80, 81, 85, 86, 87, 136, 137, 138 or 139.

The invention also provides for an isolated polynucleotide encoding the VH of SEQ ID NOs: 94 or 95.

The invention also provides for an isolated polynucleotide encoding the VL of SEQ ID NOs: 98, 99 or 100.

The invention also provides for an isolated polynucleotide encoding the VH of SEQ ID NOs: 94 or 95 and the VL of SEQ ID NOs: 98, 99 or 100.

The invention also provides for an isolated polynucleotide encoding the HC of SEQ ID NOs: 104 or 105.

The invention also provides for an isolated polynucleotide encoding the LC of SEQ ID NOs: 108, 109 or 110.

The invention also provides for an isolated polynucleotide encoding the HC of SEQ ID NOs: 104 or 105 and the LC of SEQ ID NOs: 108, 109 or 110.

The invention also provides for an isolated polynucleotide comprising the polynucleotide sequence of SEQ ID NOs: 96, 97, 101, 102, 103, 106, 107, 111, 112 or 113.

The polynucleotide sequences encoding the VH and/or the VL or antigen binding fragments thereof of the antibodies of the invention or the heavy chain and/or the light chain of the antibodies of the invention may be operably linked to one or more regulatory elements, such as a promoter or enhancer, that allow expression of the nucleotide sequence in the intended host cell. The polynucleotide may be a cDNA.

The invention also provides for a vector comprising the polynucleotide of the invention. Such vectors may be plasmid vectors, viral vectors, vectors for baculovirus expression, transposon based vectors or any other vector suitable for introduction of the polynucleotide of the invention into a given organism or genetic background by any means. For example, polynucleotides encoding light and/or heavy chain variable regions of the antibodies of the invention, optionally linked to constant regions, are inserted into expression vectors. The light and/or heavy chains may be cloned in the same or different expression vectors. The DNA segments encoding the VH, the VL, the HC and/or the LC or antigen binding fragments thereof may be operably linked to control sequences in the expression vector(s) that ensure the expression of the polypeptides. Such control sequences include signal sequences, promoters (e.g. naturally associated or heterologous promoters), enhancer elements, and transcription termination sequences, and are chosen to be compatible with the host cell chosen to express the antibody. Once the vector has been incorporated into the appropriate host, the host is maintained under conditions suitable for high level expression of the proteins encoded by the incorporated polynucleotides.

In some embodiments, the vector comprises the polynucleotide of SEQ ID NO: 11 and/or the polynucleotide of SEQ ID NO: 17.

In some embodiments, the vector comprises the polynucleotide of SEQ ID NO: 12 and/or the polynucleotide of SEQ ID NO: 18.

In some embodiments, the vector comprises the polynucleotide of SEQ ID NO: 12 and/or the polynucleotide of SEQ ID NO: 19.

In some embodiments, the vector comprises the polynucleotide of SEQ ID NO: 13 and/or the polynucleotide of SEQ ID NO: 19.

In some embodiments, the vector comprises the polynucleotide of SEQ ID NO: 52 and/or the polynucleotide of SEQ ID NO: 63.

In some embodiments, the vector comprises the polynucleotide of SEQ ID NO: 53 and/or the polynucleotide of SEQ ID NO: 64.

In some embodiments, the vector comprises the polynucleotide of SEQ ID NO: 53 and/or the polynucleotide of SEQ ID NO: 65.

In some embodiments, the vector comprises the polynucleotide of SEQ ID NO: 54 and/or the polynucleotide of SEQ ID NO: 64.

In some embodiments, the vector comprises the polynucleotide of SEQ ID NO: 55 and/or the polynucleotide of SEQ ID NO: 64.

In some embodiments, the vector comprises the polynucleotide of SEQ ID NO: 56 and/or the polynucleotide of SEQ ID NO: 64.

In some embodiments, the vector comprises the polynucleotide of SEQ ID NO: 57 and/or the polynucleotide of SEQ ID NO: 64.

In some embodiments, the vector comprises the polynucleotide of SEQ ID NO: 58 and/or the polynucleotide of SEQ ID NO: 64.

In some embodiments, the vector comprises the polynucleotide of SEQ ID NO: 59 and/or the polynucleotide of SEQ ID NO: 64.

In some embodiments, the vector comprises the polynucleotide of SEQ ID NO: 96 and/or the polynucleotide of SEQ ID NO: 101.

In some embodiments, the vector comprises the polynucleotide of SEQ ID NO: 97 and/or the polynucleotide of SEQ ID NO: 102.

In some embodiments, the vector comprises the polynucleotide of SEQ ID NO: 97 and/or the polynucleotide of SEQ ID NO: 103.

In some embodiments, the vector comprises the polynucleotide of SEQ ID NO: 132 and/or the polynucleotide of SEQ ID NO: 133.

In some embodiments, the vector comprises the polynucleotide of SEQ ID NO: 134 and/or the polynucleotide of SEQ ID NO: 135.

In some embodiments, the vector comprises the polynucleotide of SEQ ID NO: 136 and/or the polynucleotide of SEQ ID NO: 137.

In some embodiments, the vector comprises the polynucleotide of SEQ ID NO: 138 and/or the polynucleotide of SEQ ID NO: 139.

In some embodiments, the vector comprises the polynucleotide of SEQ ID NO: 155 and/or the polynucleotide of SEQ ID NO: 19.

In some embodiments, the vector comprises the polynucleotide of SEQ ID NO: 156 and/or the polynucleotide of SEQ ID NO: 19.

In some embodiments, the vector comprises the polynucleotide of SEQ ID NO: 157 and/or the polynucleotide of SEQ ID NO: 19.

In some embodiments, the vector comprises the polynucleotide of SEQ ID NO: 13 and/or the polynucleotide of SEQ ID NO: 158.

In some embodiments, the vector comprises the polynucleotide of SEQ ID NO: 13 and/or the polynucleotide of SEQ ID NO: 159.

In some embodiments, the vector comprises the polynucleotide of SEQ ID NO: 155 and/or the polynucleotide of SEQ ID NO: 158.

In some embodiments, the vector comprises the polynucleotide of SEQ ID NO: 156 and/or the polynucleotide of SEQ ID NO: 158.

In some embodiments, the vector comprises the polynucleotide of SEQ ID NO: 157 and/or the polynucleotide of SEQ ID NO: 158.

In some embodiments, the vector comprises the polynucleotide of SEQ ID NO: 155 and/or the polynucleotide of SEQ ID NO: 159.

In some embodiments, the vector comprises the polynucleotide of SEQ ID NO: 156 and/or the polynucleotide of SEQ ID NO: 159.

In some embodiments, the vector comprises the polynucleotide of SEQ ID NO: 157 and/or the polynucleotide of SEQ ID NO: 159.

In some embodiments, the vector comprises the polynucleotide of SEQ ID NO: 160 and/or the polynucleotide of SEQ ID NO: 31.

In some embodiments, the vector comprises the polynucleotide of SEQ ID NO: 161 and/or the polynucleotide of SEQ ID NO: 31.

In some embodiments, the vector comprises the polynucleotide of SEQ ID NO: 162 and/or the polynucleotide of SEQ ID NO: 31.

In some embodiments, the vector comprises the polynucleotide of SEQ ID NO: 25 and/or the polynucleotide of SEQ ID NO: 163.

In some embodiments, the vector comprises the polynucleotide of SEQ ID NO: 25 and/or the polynucleotide of SEQ ID NO: 164.

In some embodiments, the vector comprises the polynucleotide of SEQ ID NO: 160 and/or the polynucleotide of SEQ ID NO: 163.

In some embodiments, the vector comprises the polynucleotide of SEQ ID NO: 161 and/or the polynucleotide of SEQ ID NO: 163.

In some embodiments, the vector comprises the polynucleotide of SEQ ID NO: 162 and/or the polynucleotide of SEQ ID NO: 163.

In some embodiments, the vector comprises the polynucleotide of SEQ ID NO: 160 and/or the polynucleotide of SEQ ID NO: 164.

In some embodiments, the vector comprises the polynucleotide of SEQ ID NO: 161 and/or the polynucleotide of SEQ ID NO: 164.

In some embodiments, the vector comprises the polynucleotide of SEQ ID NO: 162 and/or the polynucleotide of SEQ ID NO: 164.

Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed with the desired DNA sequences. Glutamine synthetase system may be used to express recombinant proteins such as antibodies in cells.

Suitable promoter and enhancer elements are known in the art. For expression in a eukaryotic cell, exemplary promoters include light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Selection of the appropriate vector and promoter is well within the level of ordinary skill in the art.

Large numbers of suitable vectors and promoters are known to those of skill in the art; many are commercially available for generating recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTre99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia), and pEE6.1 and pEE14.1 (Lonza).

The invention also provides for a host cell comprising one or more vectors of the invention. "Host cell" refers to a cell into which a vector has been introduced. It is understood that the term host cell is intended to refer not only to the particular subject cell but to the progeny of such a cell, and also to a stable cell line generated from the particular subject cell. Because certain modifications may occur in succeeding generations due to either mutation or environmental influences, such progeny may not be identical to the parent cell, but are still included within the scope of the term "host cell" as used herein. Such host cells may be eukaryotic cells, prokaryotic cells, plant cells or archeal cells.

*Escherichia coli*, bacilli, such as *Bacillus subtilis*, and other enterobacteriaceae, such as *Salmonella, Serratia*, and various *Pseudomonas* species are examples of prokaryotic host cells. Other microbes, such as yeast, are also useful for expression. *Saccharomyces* (e.g., *S. cerevisiae*) and *Pichia* are examples of suitable yeast host cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

The invention also provides for a method of producing the antibody of the invention comprising culturing the host cell of the invention in conditions that the antibody is expressed, and recovering the antibody produced by the host cell. Methods of making antibodies and purifying them are known. Once synthesized (either chemically or recombinantly), the whole antibodies, their dimers, individual light and/or heavy chains, or other antibody fragments such as VH and/or VL, may be purified according to standard procedures, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody may be substantially pure, e.g., at least about 80% to 85% pure, at least about 85% to 90% pure, at least about 90% to 95% pure, or at least about 98% to 99%, or more, pure, e.g., free from contaminants such as cell debris, macromolecules, etc. other than the subject antibody.

The invention also provides for a method for producing an antibody that specifically binds PD-1, comprising:
  incorporating the first polynucleotide encoding the VH of the antibody and the second polynucleotide encoding the VL of the antibody into an expression vector;
  transforming a host cell with the expression vector;
  culturing the host cell in culture medium under conditions wherein the VL and the VH are expressed and form the antibody; and
  recovering the antibody from the host cell or culture medium.

The polynucleotides encoding certain VH or VL sequences of the invention may be incorporated into vectors using standard molecular biology methods. Host cell transformation, culture, antibody expression and purification are done using well known methods.

Pharmaceutical Compositions/Administration

The invention also provides pharmaceutical compositions comprising the antibodies or the antigen binding fragments thereof of the invention and a pharmaceutically acceptable carrier. For therapeutic use, the antibodies of the invention may be prepared as pharmaceutical compositions containing an effective amount of the antibodies as an active ingredient in a pharmaceutically acceptable carrier. "Carrier" refers to a diluent, adjuvant, excipient, or vehicle with which the antibody of the invention is administered. Such vehicles may be liquids, such as water and oils, including those of petroleum, animal, vegetable or synthetic origin, such as peanut oil, soybean oil, mineral oil, sesame oil and the like. For example, 0.4% saline and 0.3% glycine may be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibodies or the antigen-binding fragments thereof of the invention in such pharmaceutical formulation may vary, from less than about 0.5%, usually to at least about 1% to as much as 15 or 20% by weight and may be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the antibodies or the antigen-binding fragments thereof of the invention may be any suitable route that delivers the antibody to a subject, such as parenteral administration, e.g., intradermal, intramuscular, intraperitoneal, intravenous or subcutaneous, pulmonary, transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intratumoral, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

The antibodies or the antigen binding fragments thereof of the invention may also be administered prophylactically in order to reduce the risk of developing an autoimmune disease and/or delay the onset of the symptoms.

The antibodies or the antigen binding fragments thereof of the invention may be lyophilized for storage and reconstituted in a suitable carrier prior to use. This technique has been shown to be effective with conventional protein preparations and well known lyophilization and reconstitution techniques can be employed.

Methods and Uses

The antibodies or the antigen binding fragments thereof of the invention have in vitro and in vivo diagnostic, as well as therapeutic and prophylactic utilities. For example, the antibodies or the antigen binding fragments thereof of the invention may be administered to cells in culture, in vitro or ex vivo, or to a subject to treat, prevent, and/or diagnose a variety of diseases, such as immune disorder or any conditions in which attenuation of PD-1 expressing T cell activity and/or downmodulation of immune response is desired.

The invention also provides a method of suppressing activation of a PD-1 expressing T cell in a subject, comprising administering to the subject the isolated antibody or the antigen binding fragment thereof of the invention for a time sufficient to suppress activation of the PD-1 expressing T cell.

In some embodiments, the PD-1 expressing T cell is an antigen-specific CD4$^+$ T cell.

In some embodiments, the PD-1 expressing T cell is an antigen-specific CD8$^+$ T cell.

"Suppress activation" refers to the ability of the antibodies provided herein to inhibit activation of PD-1 expressing T cells, for example inhibit proliferation or IFN-γ production by antigen specific CD4$^+$ and/or CD8$^+$ T cells. The antibody suppresses activation of PD-1 expressing T cells when the antibody inhibits proliferation or IFN-γ production by antigen specific CD4$^+$ and/or CD8$^+$ T cells by 20%, 30%, 40%, 45%, 50%, 55%, 60%, 65%, 70%, 75%, 80%, 85%, 90%, 95%, or 100% greater than in the absence of the antibody (e.g., negative control), or when the inhibition is statistically significant when compared to the inhibition in the absence of the antibody.

The PD-1 expressing T cell may be located at the vicinity of an inappropriate inflammatory response. The antibodies or the antigen binding fragments thereof of the invention may suppress activation of the PD-1 expressing T cell by augmenting PD-1 downstream signaling resulting in inhibition of TCR signaling and inhibition of T cell activation, proliferation and/or survival. The antibodies of the invention may alternatively mediate killing of the PD-1 positive T cells by antibody-mediated effector functions ADCC, ADCP and/or CDC.

Also provided is a method of downmodulating an immune response comprising administering to a subject in need thereof a therapeutically effective amount of the isolated antibody or the antigen binding fragment thereof of the invention to downmodulate the immune response.

Also provided is a method of treating an immune disorder comprising administering to a subject in need thereof a therapeutically effective amount of the isolated antibody or the antigen binding fragment thereof of the invention to treat the immune disorder.

The immune disorder may be chronic or acute, such as chronic inflammatory disease or acute inflammatory disease.

In some embodiments, the immune disorder is, arthritis, rheumatoid arthritis, asthma, COPD, pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, psoriatic arthritis, vasculitis, surgical adhesions, stroke, Type I Diabetes, Lyme disease, meningoencephalitis, autoimmune uveitis, multiple sclerosis, lupus (such as systemic lupus erythematosus), Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis and hypochlorhydia, infertility related to lack of fetal-maternal tolerance, Sjogren's Syndrome, vitiligo, myasthenia gravis or systemic sclerosis.

In some embodiments, the immune disorder is rheumatoid arthritis.

In some embodiments, the immune disorder is graft-versus-host disease.

In some embodiments, the immune disorder is arthritis.

In some embodiments, the immune disorder is asthma.

In some embodiments, the immune disorder is COPD.

In some embodiments, the immune disorder is pelvic inflammatory disease.

In some embodiments, the immune disorder is Alzheimer's Disease.

In some embodiments, the immune disorder is inflammatory bowel disease.

In some embodiments, the immune disorder is Crohn's disease.

In some embodiments, the immune disorder is ulcerative colitis.

In some embodiments, the immune disorder is Peyronie's Disease.

In some embodiments, the immune disorder is coeliac disease.

In some embodiments, the immune disorder is gallbladder disease.

In some embodiments, the immune disorder is Pilonidal disease.

In some embodiments, the immune disorder is peritonitis.

In some embodiments, the immune disorder is psoriasis.

In some embodiments, the immune disorder is psoriatic arthritis.

In some embodiments, the immune disorder is vasculitis.

In some embodiments, the immune disorder is surgical adhesion.

In some embodiments, the immune disorder is stroke.

In some embodiments, the immune disorder is type I diabetes.

In some embodiments, the immune disorder is lyme disease.

In some embodiments, the immune disorder is meningoencephalitis.

In some embodiments, the immune disorder is autoimmune uveitis.

In some embodiments, the immune disorder is multiple sclerosis.

In some embodiments, the immune disorder is lupus.

In some embodiments, the immune disorder is systemic lupus erythematosus.

In some embodiments, the immune disorder is Guillain-Barr syndrome.

In some embodiments, the immune disorder is Atopic dermatitis.

In some embodiments, the immune disorder is autoimmune hepatitis.

In some embodiments, the immune disorder is fibrosing alveolitis.

In some embodiments, the immune disorder is Grave's disease.

In some embodiments, the immune disorder is IgA nephropathy.

In some embodiments, the immune disorder is idiopathic thrombocytopenic purpura.

In some embodiments, the immune disorder is Meniere's disease.

In some embodiments, the immune disorder is pemphigus.

In some embodiments, the immune disorder is primary biliary cirrhosis.

In some embodiments, the immune disorder is sarcoidosis.

In some embodiments, the immune disorder is scleroderma.

In some embodiments, the immune disorder is Wegener's granulomatosis.

In some embodiments, the immune disorder is pancreatitis.

In some embodiments, the immune disorder is transplant rejection.

In some embodiments, the immune disorder is heart disease including ischaemic diseases such as myocardial infarction.

In some embodiments, the immune disorder is atherosclerosis.

In some embodiments, the immune disorder is intravascular coagulation.

In some embodiments, the immune disorder is bone resorption.

In some embodiments, the immune disorder is osteoporosis.

In some embodiments, the immune disorder is osteoarthritis.

In some embodiments, the immune disorder is periodontitis.

In some embodiments, the immune disorder is an hypochlorhydia.

In some embodiments, the immune disorder is Sjogren's Syndrome.

In some embodiments, the immune disorder is vitiligo.

In some embodiments, the immune disorder is myasthenia gravis.

In some embodiments, the immune disorder is systemic sclerosis.

Also provided is a method of treating pain associated with inflammation comprising administering to a subject in need thereof a therapeutically effective amount of the isolated antibody or the antigen binding fragment thereof of the invention to treat the pain associated with inflammation.

The invention also provides the antibody that specifically binds PD-1 of the invention for use in therapy.

The invention also provides the antibody that specifically binds PD-1 of the invention for use in treating an immune disorder.

The invention also provides the antibody that specifically binds PD-1 of the invention for use in treating rheumatoid arthritis.

The invention also provides the antibody that specifically binds PD-1 of the invention for use in treating lupus, such as systemic lupus erythematosus.

The invention also provides the antibody that specifically binds PD-1 of the invention for use in treating graft versus host disease.

The invention also provides the use of the antibody that specifically binds PD-1 of the invention in the manufacture of a medicament for the treatment or prophylaxis of an immune disorder.

Combination Therapies

The antibodies provided herein may be administered in combination with a second therapeutic agent.

The second therapeutic agent may be any known therapy for an immune disorder such as autoimmune or inflammatory diseases, including any agent or combination of agents that are known to be useful, or which have been used or are currently in use, for treatment of these diseases. Such therapies and therapeutic agents include surgery or surgical procedures (e.g. splenectomy, lymphadenectomy, thyroidectomy, plasmapheresis, leukophoresis, cell, tissue, or organ transplantation, intestinal procedures, organ perfusion, and the like), radiation therapy, therapy such as steroid therapy and non-steroidal therapy, hormone therapy, cytokine therapy, therapy with dermatological agents (for example, topical agents used to treat skin conditions such as allergies, contact dermatitis, and psoriasis), immunosuppressive therapy, and other anti-inflammatory monoclonal antibody therapy.

The second therapeutic agent may be a corticosteroid, an antimalarial drug, an immunosuppressant, a cytotoxic drug, or a B-cell modulator.

In some embodiments, the second therapeutic agent is prednisone, prednisolone, methylprednisolone, deflazcort, hydroxychloroquine, azathioprine, methotrexate, cyclophosphamide, mycophenolate mofetil (MMF), mycophenolate sodium, cyclosporine, leflunomide, tacrolimus, RITUXAN® (rituximab), or BENLYSTA® (belimumab).

In some embodiments, the antibodies of the invention are administered in combination with a second therapeutic agent. Exemplary second therapeutic agents are corticosteroids, nonsteroidal anti-inflammatory drugs (NSAIDs), salicylates, hydroxychloroquine, sulfasalazine, cytotoxic drugs, immunosuppressive drugs immunomodulatory antibodies, methotrexate, cyclophosphamide, mizoribine, chlorambucil, cyclosporine, tacrolimus (FK506; ProGrafrM), mycophenolate mofetil, and azathioprine (6-mercaptopurine), sirolimus (rapamycin), deoxysperguralin, leflunomide and its malononitriloamide analogs; anti-CTLA4 antibodies and Ig fusions, anti-B lymphocyte stimulator antibodies (e.g., LYMPHOSTAT-BTM) and CTLA4-Ig fusions (BLyS-1g), anti-CD80 antibodies, anti-T cell antibodies such as anti-CD3 (OKT3), anti-CD4, corticosteroids such as, for example, clobetasol, halobetasol, hydrocortisone, triamcinolone, betamethasone, fluocinole, fluocinonide, prednisone, prednisolone, methylprednisolone; non-steroidal anti-inflammatory drugs (NSAIDs) such as, for example, sulfasalazine, medications containing mesalamine (known as 5-ASA agents), celecoxib, diclofenac, etodolac, fenprofen, flurbiprofen, ibuprofen, ketoprofen, meclofamate, meloxicam, nabumetone, naproxen, oxaprozin, piroxicam, rofecoxib, salicylates, sulindac, and tolmetin; phosphodiesterase-4 inhibitors, anti-TNFα antibodies REMICADE® (infliximab), SIMPONI® (golimumab) and HUMIRA® (adalimumab), thalidomide or its analogs such as lenalidomide.

The antibodies of the invention may be administered in combination with a second therapeutic agent simultaneously, sequentially or separately.

Treatment effectiveness of RA may be assessed using effectiveness as measured by clinical responses defined by the American College of Rheumatology criteria, the European League of Rheumatism criteria, or any other criteria. See for example, Felson et al. (1995) Arthritis Rheum. 38: 727-35 and van Gestel et al. (1996) Arthritis Rheum. 39: 34-40.

While having described the invention in general terms, the embodiments of the invention will be further disclosed in the following examples that should not be construed as limiting the scope of the claims.

Example 1

Methods

Affinity Measurements Using Surface Plasmon Resonance (SPR)

Affinity measurements were performed using a ProteOn XPR36 system (BioRad). A biosensor surface was prepared by coupling anti-Human IgG Fc (Jackson cat #109-005-098) to the modified alginate polymer layer surface of a GLC chip (BioRad, Cat #176-5011) using the manufacturer instructions for amine-coupling chemistry. Approximately 5000 RU (response units) of mAbs were immobilized. The kinetic experiments were performed at 25° C. in running buffer (DPBS+0.01% P20+100 µg/mL BSA). To perform kinetic experiments, 200 RU of mAbs were captured followed by injections of analytes (human and cyno PD-1) at concentrations ranging from 1.563 nM to 400 nM (in a 4-fold serial dilution). The association phase was monitored for 3 minutes at 50 µL/min, then followed by 10 or 15 minutes of buffer flow (dissociation phase). The chip surface was regenerated with two 18 second pulses of 100 mM $H_3PO_4$ (Sigma, Cat #7961) at 100 µL/min.

The collected data were processed using ProteOn Manager software. First, the data was corrected for background using inter-spots. Then, double reference subtraction of the data was performed by using the buffer injection for analyte injections. The kinetic analysis of the data was performed using a Langmuir 1:1 binding model. The result for each mAb was reported in the format of ka (On-rate), kd (Off-rate) and $K_D$ (equilibrium dissociation constant).

Inhibition of Antigen Specific T Cells: Cytomegalovirus (CMV) Induced Peripheral Blood Mononuclear Cell (PBMC) Activation Assay ("CMV-PBMC")

An assay utilizing CMV-specific recall response was used to assess the ability of the generated antibodies to inhibit T cell activation measured by inhibition of cell proliferation upon treatment of CMV-reactive donors' PBMC with CMV peptide mix (JPT Technologies).

PBMC (Astarte Biologics, Hemacare, Precision for Medicine) were determined to be reactive to CMV antigens by the respective vendors. Frozen vials of PBMC were purchased from vendors and kept in liquid nitrogen. On the day of experiment an aliquot of frozen PBMC was thawed and the cells were resuspended in 10 ml of assay media (RPMI-1640/Glutamax/HEPES containing 1% Penicillin/Streptomycin, 1% sodium pyruvate, 1% non-essential amino acids (NEAA) solution, 10% heat-inactivated fetal bovine serum (all purchased from Thermo Fisher Scientific). The cells were centrifuged 200 g for 15 minutes at room temperature. After centrifugation, the supernatant was discarded, cells were resuspended in 10 ml assay media, and spun down at 250 g for 10 minutes. After centrifugation, cells were resuspended in 10 ml assay media, passed through 70 µm strainer, and counted. Cell concentration was adjusted to $1.5 \times 10^6$ cells/ml or $2 \times 10^6$ cells/mL, and the cells were plated at 100 µl/well using tissue culture treated round bottom 96-well plates (Corning). Plating cell density was donor specific and pre-determined in preliminary experiments to maximize assay window. The CMV peptide mix was prepared according to the manufacturer's instructions. Briefly, 40 µL dimethyl sulfoxide (Sigma) was added to a vial containing 25 µg CMV peptide mix lyophilized powder and pipetted gently to dissolve the reagent. DMSO stock of CMV peptide mix was diluted in PBS to prepare 50 µg/mL solution and left at room temperature for 10 min. Further dilution was prepared an assay media at 4× final concentration, and 50 µL of CMV peptide solution was added to each stimulated well; while unstimulated control wells received unsupplemented media. Final concentration was optimized for a specific donor PBMC in preliminary experiments (0.1-0.2 µg/mL). The anti-PD-1 antibody was added at singe dose of 10 µg/mL of serially diluted in assay media at 4× final concentration, and 50 µL of the antibody dilution was added to each well, while "no antibody" control wells receive 50 µl media. The plates were incubated at 37° C./5% $CO_2$ for 6 days. After incubation, 100 µL of supernatant was collected from each well, and 100 µL of assay media containing 1 µCi/well methyl-3H-thymidine (PerkinElmer) was added to each well, and the plates were incubated for 6 hours at 37° C./5% $CO_2$. The cells were harvested onto Unifilter-96, GF/C plates (PerkinElmer), which were allowed to dry overnight at room temperature. Fifty µL of Microscint-20 (PerkinElmer) was added to each well. The plates were sealed and counted using the TopCount NXT (PerkinElmer).

Inhibition of Cell Clustering to Determine Receptor-Ligand Blocking Ability of Antibodies An assay utilizing a 1:1 mixture of human embryonic kidney (HEK) cells overexpressing either PD-1 (PD-1-HEK cells) or PD-1 ligand PD-L1 (PD-L1-HEK cells) or PD-L2 (PD-L2-HEK cells) was used to assess the ability of the generated antibodies to inhibit receptor: ligand interaction in a cell based context, measured by inhibition of cell clustering as quantified by flow cytometry.

HEK cells overexpressing human PD1 (Crown Bio) were labeled with Violet Cell Trace stain (Life Technologies). HEK cells overexpressing cynomolgus monkey PD-L1 or PD-L2 were labeled with Far Red Cell Trace Stain (Life technologies). Briefly, dyes were solubilized in 20 µL DMSO to make a 5 mM stock then 5 µL was diluted into 10 mL PBS to make a 2.5 µM solution. Cells were counted and $50 \times 10^6$ cells were centrifuged at 1000 rpm for 5 minutes at room temperature. Cells were washed once in PBS, and $1 \times 10^6$ cells were set aside as unstained controls. After repeat centrifugation the supernatant was discarded, and cells were resuspended in the appropriate dye solutions described above and incubated for 15 minutes at room temperature. Next 4 mL ice cold fetal bovine serum (FBS) was added and incubated for another 5 minutes. Cells were then centrifuged as above, washed once in assay buffer (PBS, 10% FBS, 1 mM EDTA), centrifuged again and supernatant aspirated, then each cell type was resuspended in assay buffer at $3 \times 10^6$ cells/mL. Test antibodies were diluted to three times the final desired concentration (60 µg/mL) in assay buffer. To prepare the final cell/antibody samples (in triplicate), 100 µL PD-1-HEK cells were mixed with 100 µL antibody. After 10 minute incubation, 100 µL PD-L1-HEK or PD-L2-HEK cells were added and the final mixed samples were incubated on ice for one hour minimum. Finally, 5 µL propidium iodide was added and samples were mixed gently, transferred to polystyrene round bottom tubes and analyzed on an LSRII flow cytometer (BD Biosciences). After gating events on live cells, the percentage of double positive events, for Pacific Blue and APC channels, were determined using Flowjo software and graphed in GraphPad Prism 6. The level of clustering as measured by the percentage of double positive events, for anti-PD-1 mAbs was compared to positive, and negative isotype control antibodies.

Octet Epitope Binning

Epitope binning of the antibodies with a competition binding assay was performed on an Octet Red384 platform (Forte Bio), which is based on bio-layer interferometry. This technique measures binding of an initial antibody to the PD-1-coated biosensor as a wavelength shift due to the bound antibody increasing the optical density of the biosensor tip over time. Briefly, histidine-tagged PD-1 antigen was loaded onto HIS sensors. The sensors were then exposed to 20 µg/mL primary anti-PD-1 antibody, followed by exposure to an equal concentration of a second anti-PD-1 antibody. Data was processed using ForteBio Data Analysis Software. Additional binding by the second antibody after saturation with the first antibody indicates simultaneous binding of the two antibodies which necessarily have unique non-overlapping epitopes. Alternatively, no additional binding indicates that the two antibodies compete for binding to the PD-1 antigen.

Antibody-Dependent Cellular Cytotoxicity (ADCC)

Activation of Human Memory T Cells (Target Cells):

Frozen aliquots of human Memory T Cells (AllCells LLC) were thawed in 37° C. water bath and re-suspended in 40 ml culture medium (RPMI+10% FBS or 5% HuSAB+50 µM βME (1:1000). +1% GlutaMax+10 mM Hepes. The cells were centrifuged 250 g for 15 minutes at room temperature. After centrifugation, the supernatant was discarded, cells were resuspended in 10 ml culture media and spun down at 250 g for 10 minutes. After centrifugation, cells were resuspended in 10 ml assay media, and counted. Cell concentration was adjusted to $1.0 \times 10^6$ cells/ml and 10 ml s of the cell suspension was transferred to tissue culture plates pre-coated with anti CD3 antibody (eBioscience, 5 ug/ml in PBS, 1 hr at 37° C.). Culture media was supplemented with 2 µg/mL anti-CD28 Ab (eBioscience) and a cocktail of IL-2, IL-15 and IL-7 cytokines (R&D Systems and Peprotech) at 100 ng/ml conc. Preliminary experiments demonstrated that PD-1 expression peaked on day 5 post-activation and therefore this time point was chosen for the assay. Freshly isolated resting memory T Cells (not activated by CD3/CD28 stimulation) were also included in the analysis as a control, because they express low levels of PD-1.

Preparation of Effector Cells (NK92.CD16 and PBMCs):

The NK-92 cells were grown in tissue culture flasks stored upright and kept at a density of $0.5$-$1.0 \times 10^6$ cells/mL in 40 mL media (Myelocult H5100 (StemCell Technologies), 1× Sodium Pyruvate/Non-Essential Amino Acids/Pen Strep (Invitrogen), 4 µM Hydrocortisone (StemCell Technologies), 100 ng/ml rhIL-2 (R&D Systems)). Frozen PBMC cells (Hemacare) were thawed one day before the experiment and resuspended in XVIVO-10 Media (Lonza), 10% HI FBS (Invitrogen) and 100 ng/ml IL2 (R&D Systems). The cells were centrifuged 250 g for 15 minutes at room temperature. After centrifugation, the supernatant was discarded, cells were resuspended in 10 mL culture media, and spun down at 250 g for 10 minutes. After centrifugation, cells were resuspended in 10 ml culture media and counted. Cell concentration was adjusted to $1.0 \times 10^6$ cells/mL and the required number of cells were plated in TC dish.

On the day of the assay, PBMCs and NK cells were harvested and resuspended at $1 \times 10^7$ cells/mL and $4 \times 10^6$ cells/mL respectively in assay media (RPMI, 10% FBS, 1 mM Sodium pyruvate, 0.1 mM NEAA). Memory T Cells were washed once, resuspended at $1 \times 10^6$ cells/ml and labeled with 6 µL of BATDA (Perkin Elmer) per mL of cells at 37° C. for 30 min. BATDA-labeled cells were washed three times with excess cold assay media and their density adjusted to $0.2 \times 10^6$ cells/mL. Serial dilutions of the test Abs starting at 20 µg/mL were prepared in assay media were delivered (100 µL, 2× final concentration) to U-Bottom 96-Well assay plates. BATDA-labeled target cells (50 µL) were added at $0.2 \times 10^6$ cells/mL and incubated with test mAbs. PBMC (50 µL) were added at $1 \times 10^7$ cells/mL for a 50:1 Effector:Target cell ratio whereas NK cells (50 µL) were added at $4 \times 10^6$ cells/mL for a 20:1 Effector:Target cell ratio. Maximum lysis control wells containing labeled target cells and 20 µL 2% Triton X-100 were set up in triplicate. Minimum (background BATDA release) control wells containing labeled target cells in assay media were also set up in triplicate. The final volume in all assay plate wells was 200 µL. Well contents were mixed gently by pipette. Plates were spun down briefly and incubated at 37° C. in a 5% $CO_2$ incubator for 2.5 hours. Following incubation, cells were spun at 1200 rpm for 5 minutes. Supernatants (30 µL) were transferred to 96-well white opaque Nunc plates (ThermoFisher, 136101) containing 200 µL Europium solution (PerkinElmer, C135-100). Plates were covered to protect from light and mixed for 15 min on a shaker. Samples were read on an Envision MultiLabel Reader (PerkinElmer). Percent lysis was calculated as follows: 100*(Experimental release−Background release)/(Maximum release−Background release).

Complement-Dependent Cytotoxicity (CDC)

Frozen aliquots of human Pan T Cells (Biological Specialty, LSII 49301C) were thawed in 37° C. water bath and re-suspended in 40 ml prewarmed RPMI 1640+ Glutamax+ 25 mM HEPES (Life Technologies, Cat #72400-047)+10% FBS (Gibco, 160000-36). Cells were centrifuged at 250 g for 5 minutes at RT. After centrifugation, the supernatant was discarded, cells were resuspended in 10 mL-20 mL media and counted. The human Pan T Cells (Biological Specialty, LSII 49301C) were activated for 5-6 days prior to CDC assay using Human T-Activator CD3/CD28 Dynabeads™ (Life Technologies, Cat #11132D). Briefly, 75 µL prewashed Dynabeads were mixed with $6.0\times10^6$ cells/flask of T cells, added to T175 in 10-20 mL of media and incubated for 6 days in a 37° C./5% CO2 incubator. After 6 days, beads were removed from the mixture using EasySep™ Magnets (STEMCELL Technologies, 18000).

In preparation for CDC assays, cells were centrifuged at 250 g for 5 minutes at room temperature. After centrifugation, the supernatant was discarded, cells were resuspended in 10 ml serum-free culture media, and counted. Cell concentration was adjusted to $1.6\times10^6$ cells/mL in serum-free media and 50 µL/well were plated in 96-well U-Bottom plates (Falcon, 353077). Test antibodies were serially diluted 1:3 through eleven points in serum-free media, starting at 25 µg/mL (3×). 50 µL/well of test antibodies were added to the appropriate target-cell wells. 50 µL/well of serum-free media were added to background and lysis-control wells. Plates were covered and incubated for 1 hour at room temperature (RT). 50 µL/well of 10% (3×) Rabbit Complement (Invitrogen, 31038-100) diluted in serum-free media was added to test wells. 50 µL/well of serum-free media were added to background control wells. 50 µL/well of 2% Triton-X in serum-free media was added to the lysis control wells. Plates were incubated at 37° C./5% $CO_2$ for 60 minutes. Cells were spun down at 250 g for 5 minutes. 50 µL/well of supernatant was removed and transferred to a 96-well Flat-Bottom UV-Vis plates (Corning, 3635). 50 µL/well of LDH detection reagent (Roche, 11-644-793-001) was added to each sample; plates were covered and incubated for 15 minutes at RT. Absorbance at 490 and 650 nm was recorded on a SpectraMax Plus M5 (Molecular Devices). Statistical analyses were performed using Microsoft Excel and GraphPad Prism 6. The absorbance at 650 nm was subtracted from that at 490 nm to normalize for turbidity. Percent (%) Cytotoxicity was determined for each sample using the following formula:

(Experimental Value−Low Control)/(High Control−Low Control)×100

Where the high control is the average of the Triton-X lysis control wells, and the low control is the average of the 'media only' background control wells. A four-parameter logistic curve fitting model, [log(agonist) vs. response− Variable slope (four parameters)], was applied in GraphPad Prism to the log 10 of the Ab concentration versus the calculated % Cytotoxicity. Samples were run in duplicate, and the assay was performed twice.

To confirm target expression, PD-1 levels on activated Human Pan T cells were measured by flow cytometry on Day 5 or Day 6 post-activation. Briefly, the T cells were centrifuged at 250 g for 5 minutes, and resuspended at $1\times10^6$ cells/mL in BSA Stain Buffer (BD Biosciences, 554657). 100-200K cells were incubated in 100 µL total volume with saturating concentrations of PE-PD-1 Ab (Biolegend, 329906). Cells were washed 2× w/BSA Stain Buffer, and resuspended in an equal volume of buffer containing DRAQ7 live/dead stain (Cell Signaling Technology, 7406S). The Median fluorescent intensity was recorded for 5K live cell events on a MACSQuant Analyzer 10 flow cytometer. Receptor levels were determined using a standard curve generated using Quantibrite™ PE Beads (BD, 340495) and expressed as antibodies bound per cell.

Example 2

Generation of Agonistic Antibodies that Specifically Bind PD-1 and their Structural Characterization Three Balb/c and three C3H mice were immunized with extracellular domain (ECD) of human PD-1 (SEQ ID NO: 1) conjugated to Fc (huPD-1-Fc) and the hybridomas generated using standard protocols. The hybridomas were screened by ELISA for binding to recombinant PD-1 (ECD). Hits were defined as samples giving an ELISA signal greater than five times the negative control average. Positive clones were cross-screened against an irrelevant Fc fusion protein and for binding to mouse PD-1. Supernatants from single cell cloned hybridomas were tested for binding to human and cyno PD-1 protein. Hits were defined as signal greater than the average +3 S.D. of the negative controls.

Figure 1B:
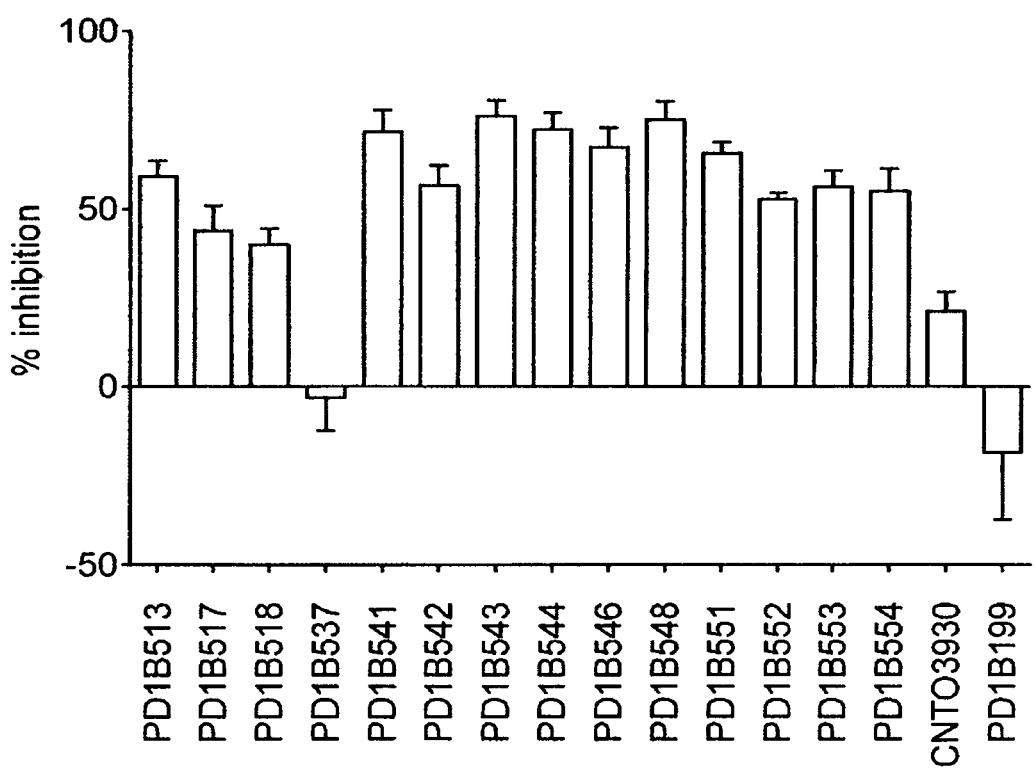
FIG. 1B shows that select generated antibodies inhibited T cell activation in CMV recall assay at a level of over 50% or more. CNT03930: isotype control. PD1B199: an antagonistic PD-1 mAb.

Select mouse antibodies were cloned as chimeric mAbs into human IgG1 and tested for their ability to inhibit antigen specific T cell activation in the CMV recall assay according to protocol described in Example 1 (CMV-PBMC assay). FIG. 1A and FIG. 1B shows that the majority of tested antibodies inhibited T cell proliferation at a level of over 50% or more. PD1B199 is an antagonistic anti-PD1 mAb. CNT03930: isotype control.

```
PD-1 ECD
                                            SEQ ID NO: 1
PGWFLDSPDRPWNPPTFSPALLVVTEGDNATFTCSFSNTSESFVLNWYRM

SPSNQTDKLAAFPEDRSQPGQDCRFRVTQLPNGRDFHMSVVRARRNDSGT

YLCGAISLAPKAQIKESLRAELRVTERRAEVPTAHPSPSPRPAGQFQTLV

FL mature PD-1
                                          SEQ ID NO: 131
PGWFLDSPDRPWNPPTFSPALLVVTEGDNATFTCSFSNTSESFVLNWYRM

SPSNQTDKLAAFPEDRSQPGQDCRFRVTQLPNGRDFHMSVVRARRNDSGT

YLCGAISLAPKAQIKESLRAELRVTERRAEVPTAHPSPSPRPAGQFQTLV

VGVVGGLLGSLVLLVWVLAVICSRAARGTIGARRTGQPLKEDPSAVPVFS

VDYGELDFQWREKTPEPPVPCVPEQTEYATIVFPSGMGTSSPARRGSADG

PRSAQPLRPEDGHCSWPL
```

Example 3

Humanization of Anti-PD-1 Antibodies

Several parental antibodies including PD1B505, PD1B506 and PD1B512 were humanized. To find the best combination of humanized VH and VL, one or more human germline heavy and light V-region sequences were selected for each of the antibodies. Human J segments for VL and VH of each parental antibody were chosen by comparing the parental J segment sequence to human J segment sequences to maximize sequence identity. All VH/VL humanized pairs of each antibody were made and tested in matrix as crude supernatants for antigen binding and protein expression. Based on these data, antibodies demonstrating comparable or improved PD-1 binding than the parental mouse antibody were purified and tested for their efficacy in the CMV-PBMC assay.

The generated antibodies were analyzed for possible unwanted post-translational modification risks. High risk deamidation motifs located in the CDRs and free cysteines anywhere in the antibody were removed by mutagenesis and the resulting antibodies tested for their binding to PD-1 and efficacy in the CMV-PBMC assay.

The humanized antibodies and their variants were cloned as IgG1.

Table 3 shows the generated antibodies. Table 4 shows the SEQ ID NOs: of the VH, the VL, the HC and the LC amino acid sequences of the antibodies. Table 5 shows the SEQ ID NOs: of the polynucleotide sequences encoding the VH, the VL, the HC and the LC of the antibodies. Table 6 shows the SEQ ID NOs: of the HCDR1, the HCDR2, the HCDR3, the LCDR1, the LCDR2 and the LCDR3 amino acid sequences of the antibodies. Table 7 shows the HCDR1, the HCDR2 and the HCDR3 amino acid sequences of the antibodies. Table 8 shows the LCDR1, the LCDR2 and the LCDR3 amino acid sequences of the antibodies. Table 9 shows the VH and the VL amino acid sequences of the antibodies. Table 10 shows the polynucleotide sequences encoding the VH of the antibodies. Table 11 shows the polynucleotide sequences encoding the VL of the antibodies. Table 12 shows the HC amino acid sequences. Table 13 shows the LC amino acid sequences. Table 14 shows the polynucleotide sequences encoding the HC of the antibodies. Table 15 shows the polynucleotide sequences encoding the LC of the antibodies.

TABLE 3

| mAb | Antibody origin | VH name | VL name |
|---|---|---|---|
| PD1B505 | Parental | PD1H93 | PD1L30 |
| PD1B742 | Humanized PD1B505 | PD1H384 | PD1L468 |
| PD1B743 | Humanized PD1B505 | PD1H384 | PD1L469 |
| PD1B878 | C84S variant of PD1B743 | PD1H405 | PD1L469 |
| PD1B506 | Parental | PD1H90 | PD1L28 |
| PD1B750 | Humanized PD1B506 | PD1H388 | PD1L470 |
| PD1B751 | Humanized PD1B506 | PD1H388 | PD1L471 |
| PD1B845 | G56A variant of PD1B750 | PD1H399 | PD1L470 |
| PD1B846 | N55D, G56A variant of PD1B750 | PD1H400 | PD1L470 |
| PD1B847 | N55Q variant of PD1B750 | PD1H401 | PD1L470 |
| PD1B848 | N55K variant of PD1B750 | PD1H402 | PD1L470 |
| PD1B849 | N55E variant of PD1B750 | PD1H403 | PD1L470 |
| PD1B850 | G56I variant of PD1B750 | PD1H404 | PD1L470 |
| PD1B512 | Parental | PD1H81 | PD1L43 |
| PD1B756 | Humanized PD1B512 | PD1H389 | PD1L472 |
| PD1B757 | Humanized PD1B512 | PD1H389 | PD1L473 |

TABLE 4

| | | | Amino acid sequence SEQ ID NOs: | | | |
|---|---|---|---|---|---|---|
| mAb | VH name | VL name | VH | VL | HC | LC |
| PD1B505 | PD1H93 | PD1L30 | 8 | 14 | 20 | 26 |
| PD1B742 | PD1H384 | PD1L468 | 9 | 15 | 21 | 27 |

TABLE 4-continued

| | | | Amino acid sequence SEQ ID NOs: | | | |
|---|---|---|---|---|---|---|
| mAb | VH name | VL name | VH | VL | HC | LC |
| PD1B743 | PD1H384 | PD1L469 | 9 | 16 | 21 | 28 |
| PD1B878 | PD1H405 | PD1L469 | 10 | 16 | 22 | 28 |
| PD1B506 | PD1H90 | PD1L28 | 44 | 60 | 66 | 82 |
| PD1B750 | PD1H388 | PD1L470 | 45 | 61 | 67 | 83 |
| PD1B751 | PD1H388 | PD1L471 | 45 | 62 | 67 | 84 |
| PD1B845 | PD1H399 | PD1L470 | 46 | 61 | 68 | 83 |
| PD1B846 | PD1H400 | PD1L470 | 47 | 61 | 69 | 83 |
| PD1B847 | PD1H401 | PD1L470 | 48 | 61 | 70 | 83 |
| PD1B848 | PD1H402 | PD1L470 | 49 | 61 | 71 | 83 |
| PD1B849 | PD1H403 | PD1L470 | 50 | 61 | 72 | 83 |
| PD1B850 | PD1H404 | PD1L470 | 51 | 61 | 73 | 83 |
| PD1B512 | PD1H81 | PD1L43 | 94 | 98 | 104 | 108 |
| PD1B756 | PD1H389 | PD1L472 | 95 | 99 | 105 | 109 |
| PD1B757 | PD1H389 | PD1L473 | 95 | 100 | 105 | 110 |

TABLE 5

| | | | Polynucleotide sequence SEQ ID NOs: | | | |
|---|---|---|---|---|---|---|
| mAb | VH name | VL name | VH | VL | HC | LC |
| PD1B505 | PD1H93 | PD1L30 | 11 | 17 | 23 | 29 |
| PD1B742 | PD1H384 | PD1L468 | 12 | 18 | 24 | 30 |
| PD1B743 | PD1H384 | PD1L469 | 12 | 19 | 24 | 31 |
| PD1B878 | PD1H405 | PD1L469 | 13 | 19 | 25 | 31 |
| PD1B506 | PD1H90 | PD1L28 | 52 | 63 | 74 | 85 |
| PD1B750 | PD1H388 | PD1L470 | 53 | 64 | 75 | 86 |
| PD1B751 | PD1H388 | PD1L471 | 53 | 65 | 75 | 87 |
| PD1B845 | PD1H399 | PD1L470 | 54 | 64 | 76 | 86 |
| PD1B846 | PD1H400 | PD1L470 | 55 | 64 | 77 | 86 |
| PD1B847 | PD1H401 | PD1L470 | 56 | 64 | 78 | 86 |
| PD1B848 | PD1H402 | PD1L470 | 57 | 64 | 79 | 86 |
| PD1B849 | PD1H403 | PD1L470 | 58 | 64 | 80 | 86 |
| PD1B850 | PD1H404 | PD1L470 | 59 | 64 | 81 | 86 |
| PD1B512 | PD1H81 | PD1L43 | 96 | 101 | 106 | 111 |
| PD1B756 | PD1H389 | PD1L472 | 97 | 102 | 107 | 112 |
| PD1B757 | PD1H389 | PD1L473 | 97 | 103 | 107 | 113 |

TABLE 6

| Antibody | HCDR1 | HCDR2 | HCDR3 | LCDR1 | LCDR2 | LCDR3 |
|---|---|---|---|---|---|---|
| PD1B505 | 2 | 3 | 4 | 5 | 6 | 7 |
| PD1B742 | 2 | 3 | 4 | 5 | 6 | 7 |
| PD1B743 | 2 | 3 | 4 | 5 | 6 | 7 |
| PD1B878 | 2 | 3 | 4 | 5 | 6 | 7 |
| PD1B506 | 32 | 33 | 40 | 41 | 42 | 43 |
| PD1B750 | 32 | 33 | 40 | 41 | 42 | 43 |
| PD1B751 | 32 | 33 | 40 | 41 | 42 | 43 |
| PD1B845 | 32 | 34 | 40 | 41 | 42 | 43 |
| PD1B846 | 32 | 35 | 40 | 41 | 42 | 43 |
| PD1B847 | 32 | 36 | 40 | 41 | 42 | 43 |
| PD1B848 | 32 | 37 | 40 | 41 | 42 | 43 |
| PD1B849 | 32 | 38 | 40 | 41 | 42 | 43 |
| PD1B850 | 32 | 39 | 40 | 41 | 42 | 43 |
| PD1B512 | 88 | 89 | 90 | 91 | 92 | 93 |
| PD1B756 | 88 | 89 | 90 | 91 | 92 | 93 |
| PD1B757 | 88 | 89 | 90 | 91 | 92 | 93 |

TABLE 7

| Antibody | HCDR1 (SEQ ID NO:) | HCDR2 (SEQ ID NO:) | HCDR3 (SEQ ID NO:) |
| --- | --- | --- | --- |
| PD1B505 | GYTFTDYSMH (SEQ ID NO: 2) | WINIETGEPT (SEQ ID NO: 3) | DYYGTYFYAMDY (SEQ ID NO: 4) |
| PD1B742 | GYTFTDYSMH (SEQ ID NO: 2) | WINIETGEPT (SEQ ID NO: 3) | DYYGTYFYAMDY (SEQ ID NO: 4) |
| PD1B743 | GYTFTDYSMH (SEQ ID NO: 2) | WINIETGEPT (SEQ ID NO: 3) | DYYGTYFYAMDY (SEQ ID NO: 4) |
| PD1B878 | GYTFTDYSMH (SEQ ID NO: 2) | WINIETGEPT (SEQ ID NO: 3) | DYYGTYFYAMDY (SEQ ID NO: 4) |
| PD1B506 | GYTFTTYWMH (SEQ ID NO: 32) | EINPNNGGIN (SEQ ID NO: 33) | DYYDYGGY (SEQ ID NO: 40) |
| PD1B750 | GYTFTTYWMH (SEQ ID NO: 32) | EINPNNGGIN (SEQ ID NO: 33) | DYYDYGGY (SEQ ID NO: 40) |
| PD1B751 | GYTFTTYWMH (SEQ ID NO: 32) | EINPNNGGIN (SEQ ID NO: 33) | DYYDYGGY (SEQ ID NO: 40) |
| PD1B845 | GYTFTTYWMH (SEQ ID NO: 32) | EINPNNAGIN (SEQ ID NO: 34) | DYYDYGGY (SEQ ID NO: 40) |
| PD1B846 | GYTFTTYWMH (SEQ ID NO: 32) | EINPNDAGIN (SEQ ID NO: 35) | DYYDYGGY (SEQ ID NO: 40) |
| PD1B847 | GYTFTTYWMH (SEQ ID NO: 32) | EINPNQGGIN (SEQ ID NO: 36) | DYYDYGGY (SEQ ID NO: 40) |
| PD1B848 | GYTFTTYWMH (SEQ ID NO: 32) | EINPNKGGIN (SEQ ID NO: 37) | DYYDYGGY (SEQ ID NO: 40) |
| PD1B849 | GYTFTTYWMH (SEQ ID NO: 32) | EINPNEGGIN (SEQ ID NO: 38) | DYYDYGGY (SEQ ID NO: 40) |
| PD1B850 | GYTFTTYWMH (SEQ ID NO: 32) | EINPNNIGIN (SEQ ID NO: 39) | DYYDYGGY (SEQ ID NO: 40) |
| PD1B512 | GFSLSTSGMGVS (SEQ ID NO: 88) | HIYWDDDKR (SEQ ID NO: 89) | KGYYDYGYVMDY (SEQ ID NO: 90) |
| PD1B756 | GFSLSTSGMGVS (SEQ ID NO: 88) | HIYWDDDKR (SEQ ID NO: 89) | KGYYDYGYVMDY (SEQ ID NO: 90) |
| PD1B757 | GFSLSTSGMGVS (SEQ ID NO: 88) | HIYWDDDKR (SEQ ID NO: 89) | KGYYDYGYVMDY (SEQ ID NO: 90) |

TABLE 8

| Antibody | LCDR1 (SEQ ID NO:) | LCDR2 (SEQ ID NO:) | LCDR3 (SEQ ID NO:) |
| --- | --- | --- | --- |
| PD1B505 | TASSSVSSSYLH (SEQ ID NO: 5) | STSNLAS (SEQ ID NO: 6) | HQYHRSPLT (SEQ ID NO: 7) |
| PD1B742 | TASSSVSSSYLH (SEQ ID NO: 5) | STSNLAS (SEQ ID NO: 6) | HQYHRSPLT (SEQ ID NO: 7) |
| PD1B743 | TASSSVSSSYLH (SEQ ID NO: 5) | STSNLAS (SEQ ID NO: 6) | HQYHRSPLT (SEQ ID NO: 7) |
| PD1B878 | TASSSVSSSYLH (SEQ ID NO: 5) | STSNLAS (SEQ ID NO: 6) | HQYHRSPLT (SEQ ID NO: 7) |
| PD1B506 | KASQNVGTNVA (SEQ ID NO: 41) | SASYRYS (SEQ ID NO: 42) | QQYNIYPYT (SEQ ID NO: 43) |
| PD1B750 | KASQNVGTNVA (SEQ ID NO: 41) | SASYRYS (SEQ ID NO: 42) | QQYNIYPYT (SEQ ID NO: 43) |
| PD1B751 | KASQNVGTNVA (SEQ ID NO: 41) | SASYRYS (SEQ ID NO: 42) | QQYNIYPYT (SEQ ID NO: 43) |

TABLE 8-continued

| Antibody | LCDR1 (SEQ ID NO:) | LCDR2 (SEQ ID NO:) | LCDR3 (SEQ ID NO:) |
|---|---|---|---|
| PD1B845 | KASQNVGTNVA (SEQ ID NO: 41) | SASYRYS (SEQ ID NO: 42) | QQYNIYPYT (SEQ ID NO: 43) |
| PD1B846 | KASQNVGTNVA (SEQ ID NO: 41) | SASYRYS (SEQ ID NO: 42) | QQYNIYPYT (SEQ ID NO: 43) |
| PD1B847 | KASQNVGTNVA (SEQ ID NO: 41) | SASYRYS (SEQ ID NO: 42) | QQYNIYPYT (SEQ ID NO: 43) |
| PD1B848 | KASQNVGTNVA (SEQ ID NO: 41) | SASYRYS (SEQ ID NO: 42) | QQYNIYPYT (SEQ ID NO: 43) |
| PD1B849 | KASQNVGTNVA (SEQ ID NO: 41) | SASYRYS (SEQ ID NO: 42) | QQYNIYPYT (SEQ ID NO: 43) |
| PD1B850 | KASQNVGTNVA (SEQ ID NO: 41) | SASYRYS (SEQ ID NO: 42) | QQYNIYPYT (SEQ ID NO: 43) |
| PD1B512 | RSSKSLLHSNGITYLN (SEQ ID NO: 91) | QMSNLAS (SEQ ID NO: 92) | AQNLELPLT (SEQ ID NO: 93) |
| PD1B756 | RSSKSLLHSNGITYLN (SEQ ID NO: 91) | QMSNLAS (SEQ ID NO: 92) | AQNLELPLT (SEQ ID NO: 93) |
| PD1B757 | RSSKSLLHSNGITYLN (SEQ ID NO: 91) | QMSNLAS (SEQ ID NO: 92) | AQNLELPLT (SEQ ID NO: 93) |

TABLE 9

| VH or VL chain name (SEQ ID NO) | Amino acid sequence |
|---|---|
| PD1H93 (SEQ ID NO: 8) | DVQLQESGPELKKPGETVKISCKASGYTFTDYSMHWVKQAP GKGLKWMGWINIETGEPTYADDFKGRFAFSLETSASTAYLQ INNLKNEDTATYFCARDYYGTYFYAMDYWGQGTTLTVSS |
| PD1H384 (SEQ ID NO: 9) | QVQLVQSGSELKKPGASVKVSCKASGYTFTDYSMHWVRQA PGQGLEWMGWINIETGEPTYAQGFTGRFVFSLDTSVSTAYL QICSLKAEDTAVYFCARDYYGTYFYAMDYWGQGTLVTVSS |
| PD1H405 (SEQ ID NO: 10) | QVQLVQSGSELKKPGASVKVSCKASGYTFTDYSMHWVRQA PGQGLEWMGWINIETGEPTYAQGFTGRFVFSLDTSVSTAYL QISSLKAEDTAVYFCARDYYGTYFYAMDYWGQGTLVTVSS |
| PD1H90 (SEQ ID NO: 44) | QVQLQQPGAELVKPGASVKLSCKASGYTFTTYWMHWVKQ RPGQGLEWIGEINPNNGGINYNEKFKKKATLTVDKSSSTAY MQLSSLTSEDSAVYYCTIDYYDYGGYWGQGTTLTVSS |
| PD1H388 (SEQ ID NO: 45) | QVQLVQSGAEVKKPGASVKVSCKASGYTFTTYWMHWVRQ APGQGLEWMGEINPNNGGINYAQKFQGRVTLTVDKSISTAY MELSRLRSDDTAVYYCTIDYYDYGGYWGQGTLVTVSS |
| PD1H399 (SEQ ID NO: 46) | QVQLVQSGAEVKKPGASVKVSCKASGYTFTTYWMHWVRQ APGQGLEWMGEINPNNAGINYAQKFQGRVTLTVDKSISTAY MELSRLRSDDTAVYYCTIDYYDYGGYWGQGTLVTVSS |
| PD1H400 (SEQ ID NO: 47) | QVQLVQSGAEVKKPGASVKVSCKASGYTFTTYWMHWVRQ APGQGLEWMGEINPNDAGINYAQKFQGRVTLTVDKSISTAY MELSRLRSDDTAVYYCTIDYYDYGGYWGQGTLVTVSS |
| PD1H401 (SEQ ID NO: 48) | QVQLVQSGAEVKKPGASVKVSCKASGYTFTTYWMHWVRQ APGQGLEWMGEINPNQGGINYAQKFQGRVTLTVDKSISTAY MELSRLRSDDTAVYYCTIDYYDYGGYWGQGTLVTVSS |
| PD1H402 (SEQ ID NO: 49) | QVQLVQSGAEVKKPGASVKVSCKASGYTFTTYWMHWVRQ APGQGLEWMGEINPNKGGINYAQKFQGRVTLTVDKSISTAY MELSRLRSDDTAVYYCTIDYYDYGGYWGQGTLVTVSS |
| PD1H403 (SEQ ID NO: 50) | QVQLVQSGAEVKKPGASVKVSCKASGYTFTTYWMHWVRQ APGQGLEWMGEINPNEGGINYAQKFQGRVTLTVDKSISTAY MELSRLRSDDTAVYYCTIDYYDYGGYWGQGTLVTVSS |

TABLE 9-continued

| VH or VL chain name (SEQ ID NO) | Amino acid sequence |
| --- | --- |
| PD1H404 (SEQ ID NO: 51) | QVQLVQSGAEVKKPGASVKVSCKASGYTFTTYWMHWVRQ APGQGLEWMGEINPNNIGINYAQKFQGRVTLTVDKSISTAY MELSRLRSDDTAVYYCTIDYYDYGGYWGQGTLVTVSS |
| PD1H81 (SEQ ID NO: 94) | QVTLKESGPGLLQPSQTLSLTCSFSGFSLSTSGMGVSWIRQPS GKGLEWLAHIYWDDDKRYNPSLKSRLTISKDTSSNQVFLKIT SVDTADTGTYYCVRKGYYDYGYVMDYWGQGTTVTVSS |
| PD1H389 (SEQ ID NO: 95) | QITLKESGPTLVKPTQTLTLTCTFSGFSLSTSGMGVSWIRQPP GKALEWLAHIYWDDDKRYSPSLKSRLTITKDTSKNQVVLT MTNMDPVDTGTYYCVRKGYYDYGYVMDYWGQGTLVTVS |
| PD1L30 (SEQ ID NO: 14) | QIVLTQSPAIMSASLGERVTMTCTASSSVSSSYLHWYQQKPG SSPKLWIYSTSNLASGVPARFSGSGSGTSYSLTISSMEAEDAA TYYCHQYHRSPLTFGAGTKLELK |
| PD1L468 (SEQ ID NO: 15) | EIVLTQSPATLSLSPGERATLSCTASSSVSSSYLHWYQQKPGL APRLLIYSTSNLASGIPDRFSGSGSGTDFTLTISRLEPEDFAVY YCHQYHRSPLTFGQGTKLEIK |
| PD1L469 (SEQ ID NO: 16) | EIVLTQSPATLSLSPGERATLSCTASSSVSSSYLHWYQQKPGL APRLLIYSTSNLASGIPDRFSGSGSGTDYTLTISRLEPEDFAVY YCHQYHRSPLTFGQGTKLEIK |
| PD1L28 (SEQ ID NO: 60) | DIVMTQSQKFMSTSVRDRVSVTCKASQNVGTNVAWYQQKP GQSPKALIYSASYRYSGVPDRFTGSGSGTDFTLTITNVQSEDL AEYFCQQYNIYPYTFGSGTKLEMK |
| PD1L470 (SEQ ID NO: 61) | DIQMTQSPSSLSASVGDRVTITCKASQNVGTNVAWYQQKPE KAPKSLIYSASYRYSGVPSRFSGSGSGTDFTLTISSLQPEDFAT YYCQQYNIYPYTFGQGTKLEIK |
| PD1L471 (SEQ ID NO: 62) | DIQMTQSPSSLSASVGDRVTITCKASQNVGTNVAWYQQKPE KAPKALIYSASYRYSGVPSRFSGSGSGTDFTLTISSLQPEDFA TYFCQQYNIYPYTFGQGTKLEIK |
| PD1L43 (SEQ ID NO: 98) | DIVMTQAALSNPVTLGTSASISCRSSKSLLHSNGITYLNWYL QKPGQSPQLLIYQMSNLASGVPDRFSSSGSGTDFTLRISRVEA EDVGVYYCAQNLELPLTFGSGTKLEMK |
| PD1L472 (SEQ ID NO: 99) | DIVMTQSPLSLPVTPGEPASISCRSSKSLLHSNGITYLNWYLQ KPGQSPQLLIYQMSNLASGVPDRFSGSGSGTDFTLKISRVEA EDVGVYYCAQNLELPLTFGGGTKVEIK |
| PD1L473 (SEQ ID NO: 100) | DIVMTQSPLSLPVTPGEPASISCRSSKSLLHSNGITYLNWYLQ KPGQSPQLLIYQMSNLASGVPDRFSSSGSGTDFTLKISRVEAE DVGVYYCAQNLELPLTFGGGTKVEIK |

TABLE 10

| VH chain (polynucleotide SEQ ID NO:) | Polynucleotide sequence |
| --- | --- |
| PD1H93 (SEQ ID NO: 11) | GATGTACAGCTTCAGGAGTCAGGACCTGAGCTGAAGAAGC CTGGAGAGACAGTCAAGATCTCCTGCAAGGCTTCTGGTTAT ACCTTCACAGACTATTCAATGCACTGGGTGAAGCAGGCTCC AGGAAAGGGTTTAAAGTGGATGGGCTGGATAAACATTGAG ACTGGTGAGCCAACATATGCAGATGACTTCAAGGGACGGTT TGCCTTCTCTTTGGAAACCTCTGCCAGCACTGCCTATTTGCA GATCAACAACCTCAAAAATGAGGACACGGCTACATATTTCT GTGCTAGAGATTACTACGGTACTTACTTCTATGCTATGGACT ACTGGGGTCAAGGCACCACTCTCACAGTCTCCTCA |

TABLE 10-continued

| VH chain (polynucleotide SEQ ID NO:) | Polynucleotide sequence |
|---|---|
| PD1H384 (SEQ ID NO: 12) | CAGGTGCAGCTGGTGCAGTCTGGAAGCGAACTGAAGAAAC CTGGAGCCTCTGTGAAAGTGTCTTGTAAGGCCAGCGGCTAC ACCTTCACCGACTACAGCATGCACTGGGTGCGGCAGGCCCC TGGACAGGGCCTGGAATGGATGGGCTGGATCAACATCGAGA CCGGCGAGCCCACCTACGCCCAGGGCTTTACCGGACGGTTC GTGTTCAGCCTGGATACATCTGTGTCTACAGCCTATCTGCAG ATCTGCTCTCTGAAGGCCGAAGATACAGCCGTGTACTTCTGC GCCCGGGACTACTACGGCACCTACTTCTACGCCATGGACTA CTGGGGCCAGGGAACACTGGTGACAGTGTCTTCT |
| PD1H405 (SEQ ID NO: 13) | CAAGTGCAGCTGGTGCAGTCTGGCAGCGAGCTGAAAAAACC TGGCGCCTCCGTGAAGGTGTCCTGCAAGGCTAGCGGCTACA CCTTTACCGACTACAGCATGCACTGGGTCCGACAGGCTCCA GGACAAGGCTTGGAATGGATGGGCTGGATCAACATCGAGAC AGGCGAGCCCACATACGCCCAGGGCTTTACCGGCAGATTCG TGTTCAGCCTGGACACCTCTGTGTCCACCGCCTACCTGCAGA TCAGCTCTCTGAAGGCCGAGGATACCGCCGTGTACTTCTGC GCCAGAGACTACTACGGCACCTACTTCTACGCCATGGATTA CTGGGGCCAGGGCACCCTGGTTACCGTTTCTTCT |
| PD1H90 (SEQ ID NO: 52) | CAGGTCCAACTGCAGCAGCCTGGGGCTGAACTTGTGAAGCC TGGGGCTTCAGTGAAGTTGTCCTGCAAGGCTTCTGGCTACAC CTTCACCACCTACTGGATGCACTGGGTGAAGCAGAGGCCTG GACAAGGCCTTGAGTGGATTGGAGAGATTAATCCTAACAAT GGTGGTATTAATTACAATGAGAAGTTCAAGAAGAAGGCCAC ACTGACTGTAGACAAATCCTCCAGCACAGCCTACATGCAGC TCAGCAGCCTGACATCTGAGGACTCTGCGGTCTATTACTGTA CAATAGACTATATGATTACGGGGGCTACTGGGGCCAAGGC ACCACTCTCACAGTCTCCTCA |
| PD1H388 (SEQ ID NO: 53) | CAGGTGCAGCTGGTGCAGTCTGGAGCCGAAGTGAAGAAAC CTGGAGCCTCTGTGAAAGTGTCTTGTAAGGCCAGCGGCTAC ACCTTCACCACCTACTGGATGCACTGGGTGCGGCAGGCCCC TGGACAGGGCCTGGAATGGATGGGCGAGATCAACCCCAAC AACGGCGGCATCAACTACGCCCAGAAATTTCAGGGACGGGT GACCCTGACAGTGGATAAGAGCATCTCTACAGCCTACATGG AACTGTCTCGGCTGCGGAGCGATGACACAGCCGTGTACTAC TGCACCATCGACTACTACGACTACGGCGGCTACTGGGGCCA GGGAACACTGGTGACAGTGTCTTCT |
| PD1H399 (SEQ ID NO: 54) | CAGGTGCAGCTGGTGCAGTCTGGAGCCGAAGTGAAGAAAC CTGGAGCCTCTGTGAAAGTGTCTTGTAAGGCCAGCGGCTAC ACCTTCACCACCTACTGGATGCACTGGGTGCGGCAGGCCCC TGGACAGGGCCTGGAATGGATGGGCGAGATCAACCCCAAC AACGCCGGCATCAACTACGCCCAGAAATTTCAGGGACGGGT GACCCTGACAGTGGATAAGAGCATCTCTACAGCCTACATGG AACTGTCTCGGCTGCGGAGCGATGACACAGCCGTGTACTAC TGCACCATCGACTACTACGACTACGGCGGCTACTGGGGCCA GGGAACACTGGTGACAGTGTCTTCT |
| PD1H400 (SEQ ID NO: 55) | CAGGTGCAGCTGGTGCAGTCTGGAGCCGAAGTGAAGAAAC CTGGAGCCTCTGTGAAAGTGTCTTGTAAGGCCAGCGGCTAC ACCTTCACCACCTACTGGATGCACTGGGTGCGGCAGGCCCC TGGACAGGGCCTGGAATGGATGGGCGAGATCAACCCCAAC GACGCCGGCATCAACTACGCCCAGAAATTTCAGGGACGGGT GACCCTGACAGTGGATAAGAGCATCTCTACAGCCTACATGG AACTGTCTCGGCTGCGGAGCGATGACACAGCCGTGTACTAC TGCACCATCGACTACTACGACTACGGCGGCTACTGGGGCCA GGGAACACTGGTGACAGTGTCTTCT |
| PD1H401 (SEQ ID NO: 56) | CAGGTGCAGCTGGTGCAGTCTGGAGCCGAAGTGAAGAAAC CTGGAGCCTCTGTGAAAGTGTCTTGTAAGGCCAGCGGCTAC ACCTTCACCACCTACTGGATGCACTGGGTGCGGCAGGCCCC TGGACAGGGCCTGGAATGGATGGGCGAGATCAACCCCAACC AGGGCGGCATCAACTACGCCCAGAAATTTCAGGGACGGGTG ACCCTGACAGTGGATAAGAGCATCTCTACAGCCTACATGGA ACTGTCTCGGCTGCGGAGCGATGACACAGCCGTGTACTACT GCACCATCGACTACTACGACTACGGCGGCTACTGGGGCCAG GGAACACTGGTGACAGTGTCTTCT |
| PD1H402 (SEQ ID NO: 57) | CAGGTGCAGCTGGTGCAGTCTGGAGCCGAAGTGAAGAAAC CTGGAGCCTCTGTGAAAGTGTCTTGTAAGGCCAGCGGCTAC ACCTTCACCACCTACTGGATGCACTGGGTGCGGCAGGCCCC TGGACAGGGCCTGGAATGGATGGGCGAGATCAACCCCAAC |

TABLE 10-continued

| VH chain (polynucleotide SEQ ID NO:) | Polynucleotide sequence |
|---|---|
| | AAGGGCGGCATCAACTACGCCCAGAAATTTCAGGGACGGGT GACCCTGACAGTGGATAAGAGCATCTCTACAGCCTACATGG AACTGTCTCGGCTGCGGAGCGATGACACAGCCGTGTACTAC TGCACCATCGACTACTACGACTACGGCGGCTACTGGGGCCA GGGAACACTGGTGACAGTGTCTTCT |
| PD1H403 (SEQ ID NO: 58) | CAGGTGCAGCTGGTGCAGTCTGGAGCCGAAGTGAAGAAAC CTGGAGCCTCTGTGAAAGTGTCTTGTAAGGCCAGCGGCTAC ACCTTCACCACCTACTGGATGCACTGGGTGCGGCAGGCCCC TGGACAGGGCCTGGAATGGATGGGCGAGATCAACCCCAAC GAGGGCGGCATCAACTACGCCCAGAAATTTCAGGGACGGGT GACCCTGACAGTGGATAAGAGCATCTCTACAGCCTACATGG AACTGTCTCGGCTGCGGAGCGATGACACAGCCGTGTACTAC TGCACCATCGACTACTACGACTACGGCGGCTACTGGGGCCA GGGAACACTGGTGACAGTGTCTTCT |
| PD1H404 (SEQ ID NO: 59) | CAGGTGCAGCTGGTGCAGTCTGGAGCCGAAGTGAAGAAAC CTGGAGCCTCTGTGAAAGTGTCTTGTAAGGCCAGCGGCTAC ACCTTCACCACCTACTGGATGCACTGGGTGCGGCAGGCCCC TGGACAGGGCCTGGAATGGATGGGCGAGATCAACCCCAAC AACATCGGCATCAACTACGCCCAGAAATTTCAGGGACGGGT GACCCTGACAGTGGATAAGAGCATCTCTACAGCCTACATGG AACTGTCTCGGCTGCGGAGCGATGACACAGCCGTGTACTAC TGCACCATCGACTACTACGACTACGGCGGCTACTGGGGCCA GGGAACACTGGTGACAGTGTCTTCT |
| PD1H81 (SEQ ID NO: 96) | CAGGTTACTCTGAAAGAGTCTGGCCCTGGGTTATTGCAGCC CTCCCAGACCCTCAGTCTGACTTGTTCTTTCTCTGGGTTTTCA CTGAGCACTTCTGGTATGGGTGTGAGCTGGATTCGTCAGCCT TCAGGAAAGGGTCTGGAGTGGCTGGCACACATTTACTGGGA TGATGACAAGCGCTATAACCCATCCCTGAAGAGCCGGCTCA CAATCTCCAAAGATACCTCCAGCAACCAGGTATTCCTCAAG ATCACCAGTGTGGACACTGCAGATACTGGCACATACTACTG TGTTCGAAAGGGCTACTATGATTACGGCTATGTAATGGACT ACTGGGGTCAAGGGACCACGGTCACCGTCTCCTCA |
| PD1H389 (SEQ ID NO: 97) | CAGATCACACTGAAAGAATCTGGACCTACACTGGTGAAACC TACACAGACCCTGACACTGACCTGTACCTTCAGCGGCTTCA GCCTGAGCACCAGCGGCATGGGCGTGAGCTGGATTCGGCAG CCTCCTGGAAAGGCCCTGGAATGGCTGGCCCACATCTACTG GGACGACGACAAGCGGTACAGCCCTAGCCTGAAGTCTCGGC TGACAATCACCAAGGATACCTCTAAGAACCAGGTGGTGCTG ACAATGACCAACATGGACCCTGTGGACACAGGCACCTACTA CTGCGTGCGGAAGGGCTACTACGACTACGGCTACGTGATGG ACTACTGGGGCCAGGGAACACTGGTGACAGTGTCTTCT |

TABLE 11

| VL name (polynucleotide SEQ ID NO:) | VL cDNA |
|---|---|
| PD1L30 (SEQ ID NO: 17) | CAAATTGTTCTCACCCAGTCTCCAGCAATCATGTCTGCATC TCTAGGGGAACGGGTCACCATGACCTGCACTGCCAGCTCA AGTGTAAGTTCCAGTTACTTGCACTGGTACCAGCAGAAGCC AGGATCCTCCCCCAAACTCTGGATTTATAGCACATCCAACC TGGCTTCTGGAGTCCCAGCTCGCTTCAGTGGCAGTGGGTCT GGGACCTCTTACTCTCTCACAATCAGCAGCATGGAGGCTGA AGATGCTGCCACTTATTACTGCCACCAGTATCATCGTTCCC CGCTCACGTTCGGTGCTGGGACCAAGCTGGAGCTGAAA |
| PD1L468 (SEQ ID NO: 18) | GAGATCGTGCTGACACAGTCTCCTGCCACACTGTCTCTGTC TCCTGGAGAACGGGCCACACTGAGCTGCACCGCCAGCAGC AGCGTGAGCAGCAGCTACCTGCACTGGTACCAGCAGAAAC CTGGACTGGCCCCTCGGCTGCTGATCTACAGCACCAGCAAC CTGGCCAGCGGCATCCCTGATCGGTTTTCTGGCAGCGGATC TGGCACAGATTTTACACTGACCATCAGCCGGCTGGAACCTG AGGATTTTGCCGTGTACTACTGCCACCAGTACCACCGGAGC CCCCTGACCTTCGGCCAGGGAACAAAGCTGGAAATCAAG |
| PD1L469 (SEQ ID | GAGATCGTGCTGACACAGTCTCCTGCCACACTGTCTCTGTC TCCTGGAGAACGGGCCACACTGAGCTGCACCGCCAGCAGC |

TABLE 11-continued

| VL name (polynucleotide SEQ ID NO:) | VL cDNA |
|---|---|
| NO: 19) | AGCGTGAGCAGCAGCTACCTGCACTGGTACCAGCAGAAAC CTGGACTGGCCCCTCGGCTGCTGATCTACAGCACCAGCAAC CTGGCCAGCGGCATCCCTGATCGGTTTTCTGGCAGCGGATC TGGCACAGATTACACACTGACCATCAGCCGGCTGGAACCT GAGGATTTTGCCGTGTACTACTGCCACCAGTACCACCGGAG CCCCCTGACCTTCGGCCAGGGAACAAAGCTGGAAATCAAG |
| PD1L28 (SEQ ID NO: 63) | GACATTGTGATGACCCAGTCTCAAAAATTCATGTCCACATC AGTAAGAGACAGGGTCAGCGTCACCTGCAAGGCCAGTCAG AATGTGGGCACTAATGTAGCCTGGTATCAACAGAAACCAG GGCAATCTCCTAAAGCACTGATTTACTCGGCATCCTACCGG TACAGTGGAGTCCCTGATCGCTTCACAGGCAGTGGATCTGG GACAGATTTCACTCTCACCATCACCAATGTGCAGTCTGAAG ACTTGGCAGAATATTTCTGTCAGCAATATAACATCTATCCG TACACGTTCGGATCGGGGACCAAGCTGGAAATGAAA |
| PD1L470 (SEQ ID NO: 64) | GACATCCAGATGACACAGTCTCCTAGCTCTCTGAGCGCCTC TGTGGGAGATCGGGTGACAATCACCTGCAAGGCCAGCCAG AACGTGGGCACCAACGTGGCCTGGTACCAGCAGAAACCTG AAAAAGCCCCTAAGAGCCTGATCTACAGCGCCAGCTACCG GTACAGCGGCGTGCCTTCTCGGTTTAGCGGCTCTGGAAGCG GAACAGATTTCACACTGACCATCTCTAGCCTGCAGCCTGAA GATTTTGCCACATACTACTGCCAGCAGTACAACATCTACCC CTACACCTTCGGCCAGGGAACAAAGCTGGAAATCAAG |
| PD1L471 (SEQ ID NO: 65) | GACATCCAGATGACACAGTCTCCTAGCTCTCTGAGCGCCTC TGTGGGAGATCGGGTGACAATCACCTGCAAGGCCAGCCAG AACGTGGGCACCAACGTGGCCTGGTACCAGCAGAAACCTG AAAAAGCCCCTAAGGCCCTGATCTACAGCGCCAGCTACCG GTACAGCGGCGTGCCTTCTCGGTTTAGCGGCTCTGGAAGCG GAACAGATTTCACACTGACCATCTCTAGCCTGCAGCCTGAA GATTTTGCCACATACTTTTGCCAGCAGTACAACATCTACCC CTACACCTTCGGCCAGGGAACAAAGCTGGAAATCAAG |

TABLE 12

| mAb | HC |
|---|---|
| PD1B505 HC (SEQ ID NO: 20) | DVQLQESGPELKKPGETVKISCKASGYTFTDYSMHWVKQAPG KGLKWMGWINIETGEPTYADDFKGRFAFSLETSASTAYLQINN LKNEDTATYFCARDYYGTYFYAMDYWGQGTTLTVSSASTKG PSVFPLAPSSKSTSGGTAALGCLVKDYFPEPVTVSWNSGALTSG VHTFPAVLQSSGLYSLSSVVTVPSSSLGTQTYICNVNHKPSNTK VDKKVEPKSCDKTHTCPPCPAPELLGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |
| PD1B742, PD1B743 HC (SEQ ID NO: 21) | QVQLVQSGSELKKPGASVKVSCKASGYTFTDYSMHWVRQAP GQGLEWMGWINIETGEPTYAQGFTGRFVFSLDTSVSTAYLQIC SLKAEDTAVYFCARDYYGTYFYAMDYWGQGTLVTVSSASTK GPSVFPLAPSSKSTSGGTAALGCLVKDYFPEPVTVSWNSGALTS GVHTFPAVLQSSGLYSLSSVVTVPSSSLGTQTYICNVNHKPSNT KVDKKVEPKSCDKTHTCPPCPAPELLGGPSVFLFPPKPKDTLMI SRTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |
| PD1B878 HC (SEQ ID NO: 22) | QVQLVQSGSELKKPGASVKVSCKASGYTFTDYSMHWVRQAP GQGLEWMGWINIETGEPTYAQGFTGRFVFSLDTSVSTAYLQISS LKAEDTAVYFCARDYYGTYFYAMDYWGQGTLVTVSSASTKG PSVFPLAPSSKSTSGGTAALGCLVKDYFPEPVTVSWNSGALTSG VHTFPAVLQSSGLYSLSSVVTVPSSSLGTQTYICNVNHKPSNTK VDKKVEPKSCDKTHTCPPCPAPELLGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |

TABLE 12-continued

| mAb | HC |
|---|---|
| PD1B506 HC (SEQ ID NO: 66) | QVQLQQPGAELVKPGASVKLSCKASGYTFTTYWMHWVKQRPGQGLEWIGEINPNNGGINYNEKFKKKATLTVDKSSSTAYMQLSSLTSEDSAVYYCTIDYYDYGGYWGQGTTLTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| PD1B750, PD1B751 HC (SEQ ID NO: 67) | QVQLVQSGAEVKKPGASVKVSCKASGYTFTTYWMHWVRQAPGQGLEWMGEINPNNGGINYAQKFQGRVTLTVDKSISTAYMELSRLRSDDTAVYYCTIDYYDYGGYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| PD1B845 HC (SEQ ID NO: 68) | QVQLVQSGAEVKKPGASVKVSCKASGYTFTTYWMHWVRQAPGQGLEWMGEINPNNAGINYAQKFQGRVTLTVDKSISTAYMELSRLRSDDTAVYYCTIDYYDYGGYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| PD1B846 HC (SEQ ID NO: 69) | QVQLVQSGAEVKKPGASVKVSCKASGYTFTTYWMHWVRQAPGQGLEWMGEINPNDAGINYAQKFQGRVTLTVDKSISTAYMELSRLRSDDTAVYYCTIDYYDYGGYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| PD1B847 HC (SEQ ID NO: 70) | QVQLVQSGAEVKKPGASVKVSCKASGYTFTTYWMHWVRQAPGQGLEWMGEINPNQGGINYAQKFQGRVTLTVDKSISTAYMELSRLRSDDTAVYYCTIDYYDYGGYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| PD1B848 HC (SEQ ID NO: 71) | QVQLVQSGAEVKKPGASVKVSCKASGYTFTTYWMHWVRQAPGQGLEWMGEINPNKGGINYAQKFQGRVTLTVDKSISTAYMELSRLRSDDTAVYYCTIDYYDYGGYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| PD1B849 HC (SEQ ID NO: 72) | QVQLVQSGAEVKKPGASVKVSCKASGYTFTTYWMHWVRQAPGQGLEWMGEINPNEGGINYAQKFQGRVTLTVDKSISTAYMELSRLRSDDTAVYYCTIDYYDYGGYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDK |

TABLE 12-continued

| mAb | HC |
|---|---|
| | KVEPKSCDKTHTCPPCPAPELLGGPSVFLFPPKPKDTLMISRTPE VTCVVVDVSHEDPEVKFNWYVDGVEVHNAKTKPREEQYNST YRVVSVLTVLHQDWLNGKEYKCKVSNKALPAPIEKTISKAKG QPREPQVYTLPPSREEMTKNQVSLTCLVKGFYPSDIAVEWESN GQPENNYKTTPPVLDSDGSFFLYSKLTVDKSRWQQGNVFSCSV MHEALHNHYTQKSLSLSPGK |
| PD1B850 HC (SEQ ID NO: 73) | QVQLVQSGAEVKKPGASVKVSCKASGYTFTTYWMHWVRQAP GQGLEWMGEINPNNIGINYAQKFQGRVTLTVDKSISTAYMELS RLRSDDTAVYYCTIDYYDYGGYWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVDK KVEPKSCDKTHTCPPCPAPELLGGPSVFLFPPKPKDTLMISRTPE VTCVVVDVSHEDPEVKFNWYVDGVEVHNAKTKPREEQYNST YRVVSVLTVLHQDWLNGKEYKCKVSNKALPAPIEKTISKAKG QPREPQVYTLPPSREEMTKNQVSLTCLVKGFYPSDIAVEWESN GQPENNYKTTPPVLDSDGSFFLYSKLTVDKSRWQQGNVFSCSV MHEALHNHYTQKSLSLSPGK |
| PD1B512 HC (SEQ ID NO: 104) | QVTLKESGPGLLQPSQTLSLTCSFSGFSLSTSGMGVSWIRQPSG KGLEWLAHIYWDDDKRYNPSLKSRLTISKDTSSNQVFLKITSV DTADTGTYYCVRKGYYDYGYVMDYWGQGTTVTVSSASTKGP SVFPLAPSSKSTSGGTAALGCLVKDYFPEPVTVSWNSGALTSG VHTFPAVLQSSGLYSLSSVVTVPSSSLGTQTYICNVNHKPSNTK VDKKVEPKSCDKTHTCPPCPAPELLGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |
| PD1B756, PD1B757 HC (SEQ ID NO: 105) | QITLKESGPTLVKPTQTLTLTCTFSGFSLSTSGMGVSWIRQPPGK ALEWLAHIYWDDDKRYSPSLKSRLTITKDTSKNQVVLTMTNM DPVDTGTYYCVRKGYYDYGYVMDYWGQGTLVTVSSASTKGP SVFPLAPSSKSTSGGTAALGCLVKDYFPEPVTVSWNSGALTSG VHTFPAVLQSSGLYSLSSVVTVPSSSLGTQTYICNVNHKPSNTK VDKKVEPKSCDKTHTCPPCPAPELLGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALPAPIEKTISK AKGQPREPQVYTLPPSREEMTKNQVSLTCLVKGFYPSDIAVEW ESNGQPENNYKTTPPVLDSDGSFFLYSKLTVDKSRWQQGNVFS CSVMHEALHNHYTQKSLSLSPGK |

TABLE 13

| mAb | LC (SEQ ID NO:) |
|---|---|
| PD1B505 LC (SEQ ID NO: 26) | QIVLTQSPAIMSASLGERVTMTCTASSSVSSSYLHWYQQKPGS SPKLWIYSTSNLASGVPARFSGSGSGTSYSLTISSMEAEDAAT YYCHQYHRSPLTFGAGTKLELKRTVAAPSVFIFPPSDEQLKSG TASVVCLLNNFYPREAKVQWKVDNALQSGNSQESVTEQDSK DSTYSLSSTLTLSKADYEKHKVYACEVTHQGLSSPVTKSFNR GEC |
| PD1B742 LC (SEQ ID NO: 27) | EIVLTQSPATLSLSPGERATLSCTASSSVSSSYLHWYQQKPGL APRLLIYSTSNLASGIPDRFSGSGSGTDFTLTISRLEPEDFAVYY CHQYHRSPLTFGQGTKLEIKRTVAAPSVFIFPPSDEQLKSGTAS VVCLLNNFYPREAKVQWKVDNALQSGNSQESVTEQDSKDST YSLSSTLTLSKADYEKHKVYACEVTHQGLSSPVTKSFNRGEC |
| PD1B743, PD1B878 LC (SEQ ID NO: 28) | EIVLTQSPATLSLSPGERATLSCTASSSVSSSYLHWYQQKPGL APRLLIYSTSNLASGIPDRFSGSGSGTDFTLTISRLEPEDFAVYY CHQYHRSPLTFGQGTKLEIKRTVAAPSVFIFPPSDEQLKSGTAS VVCLLNNFYPREAKVQWKVDNALQSGNSQESVTEQDSKDST YSLSSTLTLSKADYEKHKVYACEVTHQGLSSPVTKSFNRGEC |
| PD1B506 LC (SEQ ID NO: 82) | DIVMTQSQKFMSTSVRDRVSVTCKASQNVGTNVAWYQQKP GQSPKALIYSASYRYSGVPDRFTGSGSGTDFTLTITNVQSEDL AEYFCQQYNIYPYTFGSGTKLEMKRTVAAPSVFIFPPSDEQLK SGTASVVCLLNNFYPREAKVQWKVDNALQSGNSQESVTEQD SKDSTYSLSSTLTLSKADYEKHKVYACEVTHQGLSSPVTKSFN RGEC |
| PD1B750, PD1B845, | DIQMTQSPSSLSASVGDRVTITCKASQNVGTNVAWYQQKPEK APKSLIYSASYRYSGVPSRFSGSGSGTDFTLTISSLQPEDFATY |

TABLE 13-continued

| mAb | LC (SEQ ID NO:) |
|---|---|
| PD1B846, PD1B847, PD1B848, PD1B849, PD1B850 LC (SEQ ID NO: 83) | YCQQYNIYPYTFGQGTKLEIKRTVAAPSVFIFPPSDEQLKSGTA SVVCLLNNFYPREAKVQWKVDNALQSGNSQESVTEQDSKDS TYSLSSTLTLSKADYEKHKVYACEVTHQGLSSPVTKSFNRGEC |
| PD1B751 LC (SEQ ID NO: 84) | DIQMTQSPSSLSASVGDRVTITCKASQNVGTNVAWYQQKPEK APKALIYSASYRYSGVPSRFSGSGSGTDFTLTISSLQPEDFATY FCQQYNIYPYTFGQGTKLEIKRTVAAPSVFIFPPSDEQLKSGTA SVVCLLNNFYPREAKVQWKVDNALQSGNSQESVTEQDSKDS TYSLSSTLTLSKADYEKHKVYACEVTHQGLSSPVTKSFNRGEC |
| PD1B512 LC (SEQ ID NO: 108) | DIVMTQAALSNPVTLGTSASISCRSSKSLLHSNGITYLNWYLQ KPGQSPQLLIYQMSNLASGVPDRFSSSGSGTDFTLRISRVEAED VGVYYCAQNLELPLTFGSGTKLEMKRTVAAPSVFIFPPSDEQL KSGTASVVCLLNNFYPREAKVQWKVDNALQSGNSQESVTEQ DSKDSTYSLSSTLTLSKADYEKHKVYACEVTHQGLSSPVTKSF NRGEC |
| PD1B756 LC (SEQ ID NO: 109) | DIVMTQSPLSLPVTPGEPASISCRSSKSLLHSNGITYLNWYLQK PGQSPQLLIYQMSNLASGVPDRFSGSGSGTDFTLKISRVEAED VGVYYCAQNLELPLTFGGGTKVEIKRTVAAPSVFIFPPSDEQL KSGTASVVCLLNNFYPREAKVQWKVDNALQSGNSQESVTEQ DSKDSTYSLSSTLTLSKADYEKHKVYACEVTHQGLSSPVTKSF NRGEC |
| PD1B757 LC (SEQ ID NO: 110) | DIVMTQSPLSLPVTPGEPASISCRSSKSLLHSNGITYLNWYLQK PGQSPQLLIYQMSNLASGVPDRFSSSGSGTDFTLKISRVEAED VGVYYCAQNLELPLTFGGGTKVEIKRTVAAPSVFIFPPSDEQL KSGTASVVCLLNNFYPREAKVQWKVDNALQSGNSQESVTEQ DSKDSTYSLSSTLTLSKADYEKHKVYACEVTHQGLSSPVTKSF NRGEC |

TABLE 14

HC cDNA (SEQ ID NO:)

PD1B505 HC (SEQ ID NO: 23)
GATGTACAGCTTCAGGAGTCAGGACCTGAGCTGAAGAAGCCTGGAGAGAC
AGTCAAGATCTCCTGCAAGGCTTCTGGTTATACCTTCACAGACTATTCAA
TGCACTGGGTGAAGCAGGCTCCAGGAAAGGGTTTAAAGTGGATGGGCTGG
ATAAACATTGAGACTGGTGAGCCAACATATGCAGATGACTTCAAGGGACG
GTTTGCCTTCTCTTTGGAAACCTCTGCCAGCACTGCCTATTTGCAGATCA
ACAACCTCAAAAATGAGGACACGGCTACATATTTCTGTGCTAGAGATTAC
TACGGTACTTACTTCTATGCTATGGACTACTGGGGTCAAGGCACCACTCT
CACAGTCTCCTCAGCCTCCACCAAGGGCCCATCGGTCTTCCCCCTGGCAC
CCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCT
GACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAG
ACCTACATCTGCAACGTGAATCACAAGCCCAGCAACACCAAGGTGGACAA
GAAAGTTGAGCCCAAATCTTGTGACAAAACTCACACATGCCCACCGTGCC
CAGCACCTGAACTCCTGGGGGGACCGTCAGTCTTCCTCTTCCCCCCAAAA
CCCAAGGACACCCTCATGATCTCCCGGACCCCTGAGGTCACATGCGTGGT
GGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTG
GCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCA
CAGGTGTACACCCTGCCCCCATCCCGGGAGGAGATGACCAAGAACCAGGT
CAGCCTGACCTGCCTGGTCAAAGGCTTCTATCCCAGCGACATCGCCGTGG
AGTGGGAGAGCAATGGGCAGCCGGAGAACAACTACAAGACCACGCCTCCC
GTGCTGGACTCCGACGGCTCCTTCTTCCTCTACAGCAAGCTCACCGTGGA
CAAGAGCAGGTGGCAGCAGGGGAACGTCTTCTCATGCTCCGTGATGCATG
AGGCTCTGCACAACCACTACACGCAGAAGAGCCTCTCCCTGTCTCCGGGT
AAA

PD1B742, PD1B743 HC (SEQ ID NO: 24)
CAGGTGCAGCTGGTGCAGTCTGGAAGCGAACTGAAGAAACCTGGAGCCTC
TGTGAAAGTGTCTTGTAAGGCCAGCGGCTACACCTTCACCGACTACAGCA
TGCACTGGGTGCGGCAGGCCCCTGGACAGGGCCTGGAATGGATGGGCTGG
ATCAACATCGAGACCGGCGAGCCCACCTACGCCCAGGGCTTTACCGGACG
GTTCGTGTTCAGCCTGGACACCTCTGTGTCCACCGCCTACCTGCAGATCT
GCTCTCTGAAGGCCGAAGATACAGCCGTGTACTTCTGCGCCCGGGACTAC
TACGGCACCTACTTCTACGCCATGGACTACTGGGGCCAGGGAACACTGGT
GACAGTGTCTTCTGCCTCCACCAAGGGCCCATCGGTCTTCCCCCTGGCAC
CCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCT
GACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAG
ACCTACATCTGCAACGTGAATCACAAGCCCAGCAACACCAAGGTGGACAA
GAAAGTTGAGCCCAAATCTTGTGACAAAACTCACACATGCCCACCGTGCC
CAGCACCTCCTGGGGGAGCGTCAGTCTTCCTCTTCCCCCCAAAA
CCCAAGGACACCCTCATGATCTCCCGGACCCCTGAGGTCACATGCGTGGT
GGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTG
GCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCA
CAGGTGTACACCCTGCCCCCATCCCGGGAGGAGATGACCAAGAACCAGGT
CAGCCTGACCTGCCTGGTCAAAGGCTTCTATCCCAGCGACATCGCCGTGG
AGTGGGAGAGCAATGGGCAGCCGGAGAACAACTACAAGACCACGCCTCCC
GTGCTGGACTCCGACGGCTCCTTCTTCCTCTACAGCAAGCTCACCGTGGA
CAAGAGCAGGTGGCAGCAGGGGAACGTCTTCTCATGCTCCGTGATGCATG
AGGCTCTGCACAACCACTACACGCAGAAGAGCCTCTCCCTGTCTCCGGGT
AAA

PD1B878 HC (SEQ ID NO: 25)
CAAGTGCAGCTGGTGCAGTCTGGCAGCGAGCTGAAAAAACCTGGCGCCTC
CGTGAAGGTGTCCTGCAAGGCTAGCGGCTACACCTTTACCGACTACAGCA
TGCACTGGGTCCGACAGGCTCCAGGACAAGGCTTGGAATGGATGGGCTGG
ATCAACATCGAGACAGGCGAGCCCACATACGCCCAGGGCTTTACCGGCAG
ATTCGTGTTCAGCCTGGACACCTCTGTGTCCACCGCCTACCTGCAGATCA
GCTCTCTGAAGGCCGAGGATACCGCCGTGTACTTCTGCGCCAGAGACTAC
TACGGACCTACTTCTACGCCATGGACTACTGGGGCCAGGGAACCCTGGT
TACCGTTTCTTCTGCCTCCACCAAGGGCCCATCGGTCTTCCCCCTGGCAC
CCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCT
GACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAG
ACCTACATCTGCAACGTGAATCACAAGCCCAGCAACACCAAGGTGGACAA

TABLE 14-continued

HC cDNA (SEQ ID NO:)

GAAAGTTGAGCCCAAATCTTGTGACAAAACTCACACATGCCCACCGTGCC
CAGCACCTGAACTCCTGGGGGGACCGTCAGTCTTCGTCTTCCCCCCAAAA
CCCAAGGACACCCTCATGATCTCCCGGACCCCTGAGGTCACATGCGTGGT
GGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTG
GCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCA
CAGGTGTACACCCTGCCCCCATCCCGGGAGGAGATGACCAAGAACCAGGT
CAGCCTGACCTGCCTGGTCAAAGGCTTCTATCCCAGCGACATCGCCGTGG
AGTGGGAGAGCAATGGGCAGCCGGAGAACAACTACAAGACCACGCCTCCC
GTGCTGGACTCCGACGGCTCCTTCTTCCTCTACAGCAAGCTCACCGTGGA
CAAGAGCAGGTGGCAGCAGGGGAACGTCTTCTCATGCTCCGTGATGCATG
AGGCTCTGCACAACCACTACACGCAGAAGAGCCTCTCCCTGTCTCCGGGT
AAA

PD1B506 HC (SEQ ID NO: 74)
CAGGTCCAACTGCAGCAGCCTGGGGCTGAACTTGTGAAGCCTGGGGCTTC
AGTGAAGTTGTCCTGCAAGGCTTTCTGGCTACACCTTCACCACCTACTGA
TGCACTGGGTGAAGCAGAGGCCTGGACAAGGCCTTGAGTGGATTGGAGAG
ATTAATCCTAACAATGGTGGTATTAATTACAATGAGAAGTTCAAGAAGAA
GGCCACACTGACTGTAGACAAATCCTCCAGCACAGCCTACATGCAGCTCA
GCAGCCTGACATCTGAGGACTCTGCGGTCTATTACTGTACAATAGACTAC
TATGATTACGGGGGCTACTGGGGCCAAGGCACCACTCTCACAGTCTCCTC
AGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAAAGTTGAGCC
CAAATCTTGTGACAAAACTCACACATGCCCACCGTGCCCAGCACCTGAAC
TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAA

PD1B750, PD1B751 HC (SEQ ID NO: 75)
CAGGTGCAGCTGGTGCAGTCTGGAGCCGAAGTGAAGAAACCTGGGAGCCTC
TGTGAAAGTGTCTTGTAAGGCCAGCGGCTACACCTTCACCACCTACTGGA
TGCACTGGGTGCGGCAGGCCCCTGGACAGGGCCTGGAATGGATGGGCGAG
ATCAACCCCAACAACGCCGGCATCAACTACGCCCAGAAATTTCAGGGACG
GGTGACCCTGACAGTGGATAAGAGCATCTCTACAGCCTACATGGAACTGT
CTCGGCTGCGGAGCGATGACACAGCCGTGTACTACTGCACCATCGACTAC
TACGACTACGGCGGCTACTGGGGCCAGGGAACACTGGTGACAGTGTCTTC
TGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAAAGTTGAGCC
CAAATCTTGTGACAAAACTCACACATGCCCACCGTGCCCAGCACCTGAAC
TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAA

PD1B845 HC (SEQ ID NO: 76)
CAGGTGCAGCTGGTGCAGTCTGGAGCCGAAGTGAAGAAACCTGGGAGCCTC
TGTGAAAGTGTCTTGTAAGGCCAGCGGCTACACCTTCACCACCTACTGGA
TGCACTGGGTGCGGCAGGCCCCTGGACAGGGCCTGGAATGGATGGGCGAG
ATCAACCCCAACAACGCCGGCATCAACTACGCCCAGAAATTTCAGGGACG
GGTGACCCTGACAGTGGATAAGAGCATCTCTACAGCCTACATGGAACTGT
CTCGGCTGCGGAGCGATGACACAGCCGTGTACTACTGCACCATCGACTAC
TACGACTACGGCGGCTACTGGGGCCAGGGAACACTGGTGACAGTGTCTTC
TGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAAAGTTGAGCC
CAAATCTTGTGACAAAACTCACACATGCCCACCGTGCCCAGCACCTGAAC
TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA

TABLE 14-continued

HC cDNA (SEQ ID NO:)

ATCAACCCCAACAACGCCGGCATCAACTACGCCCAGAAATTTCAGGGACG
GGTGACCCTGACAGTGGATAAGAGCATCTCTACAGCCTACATGGAACTGT
CTCGGCTGCGGAGCGATGACACAGCCGTGTACTACTGCACCATCGACTAC
TACGACTACGGCGGCTACTGGGGCCAGGGAACACTGGTGACAGTGTCTTC
TGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAAAGTTGAGCC
CAAATCTTGTGACAAAACTCACACATGCCCACCGTGCCCAGCACCTGAAC
TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAA

PD1B846 HC (SEQ ID NO: 77)
CAGGTGCAGCTGGTGCAGTCTGGAGCCGAAGTGAAGAAACCTGGGAGCCTC
TGTGAAAGTGTCTTGTAAGGCCAGCGGCTACACCTTCACCACCTACTGGA
TGCACTGGGTGCGGCAGGCCCCTGGACAGGGCCTGGAATGGATGGGCGAG
ATCAACCCCAACGACGCCGGCATCAACTACGCCCAGAAATTTCAGGGACG
GGTGACCCTGACAGTGGATAAGAGCATCTCTACAGCCTACATGGAACTGT
CTCGGCTGCGGAGCGATGACACAGCCGTGTACTACTGCACCATCGACTAC
TACGACTACGGCGGCTACTGGGGCCAGGGAACACTGGTGACAGTGTCTTC
TGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAAAGTTGAGCC
CAAATCTTGTGACAAAACTCACACATGCCCACCGTGCCCAGCACCTGAAC
TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAA

PD1B847 HC (SEQ ID NO: 78)
CAGGTGCAGCTGGTGCAGTCTGGAGCCGAAGTGAAGAAACCTGGGAGCCTC
TGTGAAAGTGTCTTGTAAGGCCAGCGGCTACACCTTCACCACCTACTGGA
TGCACTGGGTGCGGCAGGCCCCTGGACAGGGCCTGGAATGGATGGGCGAG
ATCAACCCCAACCAGGCCGGCATCAACTACGCCCAGAAATTTCAGGGACG
GGTGACCCTGACAGTGGATAAGAGCATCTCTACAGCCTACATGGAACTGT
CTCGGCTGCGGAGCGATGACACAGCCGTGTACTACTGCACCATCGACTAC
TACGACTACGGCGGCTACTGGGGCCAGGGAACACTGGTGACAGTGTCTTC
TGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAAAGTTGAGCC
CAAATCTTGTGACAAAACTCACACATGCCCACCGTGCCCAGCACCTGAAC
TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA

TABLE 14-continued

HC cDNA (SEQ ID NO:)

ATGGGCAGCCGGAGAACAACTACAAGACCACGCCTCCCGTGCTGGACTCC
GACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAA

PD1B848 HC (SEQ ID NO: 79)
CAGGTGCAGCTGGTGCAGTCTGGAGCCGAAGTGAAGAAACCTGGAGCCTC
TGTGAAAGTGTCTTGTAAGGCCAGCGGCTACACCTTCACCACCTACTGGA
TGCACTGGGTGCGGCAGGCCCCTGGACAGGGCCTGGAATGGATGGGCGAG
ATCAACCCCAACAAGGGCGGCATCAACTACGCCCAGAAATTTCAGGGACG
GGTGACCCTGACAGTGGATAAGAGCATCTCTACAGCCTACATGGAACTGT
CTCGGCTGCGGAGCGATGACACAGCCGTGTACTACTGCACCATCGACTAC
TACGACTACGGCGGCTACTGGGGCCAGGGAACACTGGTGACAGTGTCTTC
TGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAAAGTTGAGCC
CAAATCTTGTGACAAAACTCACACATGCCCACCGTGCCCAGCACCTGAAC
TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAA

PD1B849 (SEQ ID NO: 80)
CAGGTGCAGCTGGTGCAGTCTGGAGCCGAAGTGAAGAAACCTGGAGCCTC
TGTGAAAGTGTCTTGTAAGGCCAGCGGCTACACCTTCACCACCTACTGGA
TGCACTGGGTGCGGCAGGCCCCTGGACAGGGCCTGGAATGGATGGGCGAG
ATCAACCCCAACGAGGGCGGCATCAACTACGCCCAGAAATTTCAGGGACG
GGTGACCCTGACAGTGGATAAGAGCATCTCTACAGCCTACATGGAACTGT
CTCGGCTGCGGAGCGATGACACAGCCGTGTACTACTGCACCATCGACTAC
TACGACTACGGCGGCTACTGGGGCCAGGGAACACTGGTGACAGTGTCTTC
TGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAAAGTTGAGCC
CAAATCTTGTGACAAAACTCACACATGCCCACCGTGCCCAGCACCTGAAC
TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAA

PD1B850 HC (SEQ ID NO: 81)
CAGGTGCAGCTGGTGCAGTCTGGAGCCGAAGTGAAGAAACCTGGAGCCTC
TGTGAAAGTGTCTTGTAAGGCCAGCGGCTACACCTTCACCACCTACTGGA
TGCACTGGGTGCGGCAGGCCCCTGGACAGGGCCTGGAATGGATGGGCGAG
ATCAACCCCAACAACATCGGCATCAACTACGCCCAGAAATTTCAGGGACG
GGTGACCCTGACAGTGGATAAGAGCATCTCTACAGCCTACATGGAACTGT
CTCGGCTGCGGAGCGATGACACAGCCGTGTACTACTGCACCATCGACTAC
TACGACTACGGCGGCTACTGGGGCCAGGGAACACTGGTGACAGTGTCTTC
TGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAAAGTTGAGCC
CAAATCTTGTGACAAAACTCACACATGCCCACCGTGCCCAGCACCTGAAC

TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAA

PD1B512 HC (SEQ ID NO: 106)
CAGGTTACTCTGAAAGAGTCTGGCCCTGGGTTATTGCAGCCCTCCCAGAC
CCTCAGTCTGACTTGTTCTTTCTCTGGGTTTTCACTGAGCACTTCTGGTA
TGGGTGTGAGCTGGATTCGTCAGCCTTCAGGAAAGGGTCTGGAGTGGCTG
GCACACATTTACTGGGATGATGACAAGCGCTATAACCCATCCCTGAAGAG
CCGGCTCACAATCTCCAAAGATACCTCCAGCAACCAGGTATTCCTCAAGA
TCACCAGTGTGGACACTGCAGATACTGGCACATACTACTGTGTTCGAAAG
GGCTACTATTACGGCTATGAATGGACTACTGGGGTCAAGGGACCAC
GGTCACCGTCTCCTCAGCCTCCACCAAGGGCCCATCGGTCTTCCCCCTGG
CACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGC
CCTGACCAGCGGCGTGCACACCTTCCCGGCTGTCCTACAGTCCTCAGGAC
TCTACTCCCTCAGCAGCGTGGTGACCGTGCCCTCCAGCAGCTTGGGCACC
CAGACCTACATCTGCAACGTGAATCACAAGCCCAGCAACACCAAGGTGGA
CAAGAAAGTTGAGCCCAAATCTTGTGACAAAACTCACACATGCCCACCGT
GCCCAGCACCTGAACTCCTGGGGGGACCGTCAGTCTTCCTCTTCCCCCCA
AAACCCAAGGACACCCTCATGATCTCCCGGACCCCTGAGGTCACATGCGT
GGTGGTGGACGTGAGCCACGAAGACCCTGAGGTCAAGTTCAACTGGTACG
TGGACGGCGTGGAGGTGCATAATGCCAAGACAAAGCCGCGGGAGGAGCAG
TACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCC
CAGCCCCCATCGAGAAAACCATCTCCAAAGCCAAAGGGCAGCCCCGAGAA
CCACAGGTGTACACCCTGCCCCCATCCCGGGAGGAGATGACCAAGAACCA
GGTCAGCCTGACCTGCCTGGTCAAAGGCTTCTATCCCAGCGACATCGCCG
TGGAGTGGGAGAGCAATGGGCAGCCGGAGAACAACTACAAGACCACGCCT
CCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGC
ATGAGGCTCTGCACAACCACTACACGCAGAAGAGCCTCTCCCTGTCTCCG
GGTAAA

PD1B756, PD1B757 HC (SEQ ID NO: 107)
CAGATCACACTGAAAGAATCTGGACCTACACTGGTGAAACCTACACAGAC
CCTGACACTGACCTGTACCTTCAGCGGCTTCAGCCTGAGCACCAGCGGCA
TGGGCGTGAGCTGGATTCGGCAGCCTCCTGGAAAGGCCCTGGAATGGCTG
GCCCACATCTACTGGGACGACGACAAGCGGTACAGCCCTAGCCTGAAGTC
TCGGCTGACAATCACCAAGGATACCTCTAAGAACCAGGTGGTGCTGACAA
TGACCAACATGGACCCTGTGGACACAGGCACCTACTACTGCGTGCGGAAG
GGCTACTACGACTACGGCTACGTGATGGACTACTGGGGCCAGGGAACACT
GGTGACAGTGTCTTCTGCCTCCACCAAGGGCCCATCGGTCTTCCCCCTGG
CACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGC
CCTGACCAGCGGCGTGCACACCTTCCCGGCTGTCCTACAGTCCTCAGGAC
TCTACTCCCTCAGCAGCGTGGTGACCGTGCCCTCCAGCAGCTTGGGCACC
CAGACCTACATCTGCAACGTGAATCACAAGCCCAGCAACACCAAGGTGGA
CAAGAAAGTTGAGCCCAAATCTTGTGACAAAACTCACACATGCCCACCGT
GCCCAGCACCTGAACTCCTGGGGGGACCGTCAGTCTTCCTCTTCCCCCCA
AAACCCAAGGACACCCTCATGATCTCCCGGACCCCTGAGGTCACATGCGT
GGTGGTGGACGTGAGCCACGAAGACCCTGAGGTCAAGTTCAACTGGTACG
TGGACGGCGTGGAGGTGCATAATGCCAAGACAAAGCCGCGGGAGGAGCAG
TACAACAGCACGTACCGTGTGGTCAGCGTCCTCACCGTCCTGCACCAGGA
CTGGCTGAATGGCAAGGAGTACAAGTGCAAGGTCTCCAACAAAGCCCTCC
CAGCCCCCATCGAGAAAACCATCTCCAAAGCCAAAGGGCAGCCCCGAGAA
CCACAGGTGTACACCCTGCCCCCATCCCGGGAGGAGATGACCAAGAACCA
GGTCAGCCTGACCTGCCTGGTCAAAGGCTTCTATCCCAGCGACATCGCCG
TGGAGTGGGAGAGCAATGGGCAGCCGGAGAACAACTACAAGACCACGCCT
CCCGTGCTGGACTCCGACGGCTCCTTCTTCCTCTACAGCAAGCTCACCGT
GGACAAGAGCAGGTGGCAGCAGGGGAACGTCTTCTCATGCTCCGTGATGC
ATGAGGCTCTGCACAACCACTACACGCAGAAGAGCCTCTCCCTGTCTCCG
GGTAAA

TABLE 15

| LC cDNA (SEQ ID NO:) |
| --- |

PD1B505 LC (SEQ ID NO: 29)
CAAATTGTTCTCACCCAGTCTCCAGCAATCATGTCTGCATCTCTAGGGGA

ACGGGTCACCATGACCTGCACTGCCAGCTCAAGTGTAAGTTCCAGTTACT
TGCACTGGTACCAGCAGAAGCCAGGATCCTCCCCAAACTCTGGATTTAT
AGCACATCCAACCTGGCTTCTGGAGTCCCAGCTCGCTTCAGTGGCAGTGG
GTCTGGGACCTCTTACTCTCTCACAATCAGCAGCATGGAGGCTGAAGATG
CTGCCACTTATTACTGCCACCAGTATCATCGTTCCCGCTCACGTTCGGT
GCTGGGACCAAGCTGGAGCTGAAACGTACGGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGT

PD1B742 LC (SEQ ID NO: 30)
GAGATCGTGCTGACACAGTCTCCTGCCACACTGTCTCTGTCTCCTGGAGA
ACGGGCCACACTGAGCTGCACCGCCAGCAGCAGCGTGAGCAGCAGCTACC
TGCACTGGTACCAGCAGAAACCTGGACTGGCCCCTCGGCTGCTGATCTAC
AGCACCAGCAACCTGGCCAGCGGCATCCCTGATCGGTTTCTGGCAGCGG
ATCTGGCACAGATTTTACACTGACCATCAGCCGGCTGGAACCTGAGGATT
TTGCCGTGTACTACTGCCACCAGTACCACCGGAGCCCCCTGACCTTCGGC
CAGGGAACAAAGCTGGAAATCAAGCGTACGGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGT

PD1B743, PD1B878 LC (SEQ ID NO: 31)
GAGATCGTGCTGACACAGTCTCCCGCCACACTGTCACTGTCTCCAGGCGA
AAGAGCCACACTGAGCTGTACCGCCAGCAGCTCTGTGTCCAGCAGCTACC
TGCACTGGTATCAGCAGAAGCCTGGACTGGCCCCTCGGCTGCTGATCTAC
AGCACAAGCAATCTGGCCAGCGGCATCCCCGATAGATTTTCCGGCTCTGG
AAGCGGCACCGACTACACCCTGACAATCAGCAGACTGGAACCTGAGGACT
TCGCCGTGTACTACTGCCACCAGTACCACAGAAGCCCTCTGACCTTTGGC
CAGGGCACCAAGCTGGAAATCAAGCGTACGGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGT

PD1B506 LC (SEQ ID NO: 85)
GACATTGTGATGACCCAGTCTCAAAAATTCATGTCCACATCAGTAAGAGA
CAGGGTCAGCGTCACCTGCAAGGCCAGTCAGAATGTGGGCACTAATGTAG
CCTGGTATCAACAGAAACCAGGGCAATCTCCTAAAGCACTGATTTACTCG
GCATCCTACCGGTACAGTGGAGTCCCTGATCGCTTCACAGGCAGTGGATC
TGGGACAGATTTCACTCTCACCATCACCAATGTGCAGTCTGAAGACTTGG
CAGAATATTTCTGTCAGCAATATAACATCTATCCGTACACGTTCGGATCG
GGGACCAAGCTGGAAATGAAACGTACGGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGT

PD1B750, PD1B845, PD1B846, PD1B847, PD1B848,
PD1B849, PD1B850 LC (SEQ ID NO: 86)
GACATCCAGATGACACAGTCTCCTAGCTCTCTGAGCGCCTCTGTGGGAGA
TCGGGTGACAATCACCTGCAAGGCCAGCCAGAACGTGGGCACCAACGTGG
CCTGGTACCAGCAGAAACTGAAAAAGCCCCTAAGGCCCTGATCTACAGC
GCCAGCTACCGGTACAGCGGCGTGCCTTCTCGGTTTAGCGGCTCTGGAAG
CGGAACAGATTTCACACTGACCATCTCTAGCCTGCAGCCTGAAGATTTTG
CCACATACTACTGCCAGCAGTACAACATCTACCCCTACACCTTCGGCCAG
GGAACAAAGCTGGAAATCAAGCGTACGGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGT

TABLE 15-continued

| LC cDNA (SEQ ID NO:) |
| --- |

PD1B751 LC (SEQ ID NO: 87)
GACATCCAGATGACACAGTCTCCTAGCTCTCTGAGCGCCTCTGTGGGAGA
TCGGGTGACAATCACCTGCAAGGCCAGCCAGAACGTGGGCACCAACGTGG
CCTGGTACCAGCAGAAACCTGAAAAAGCCCCTAAGGCCCTGATCTACAGC
GCCAGCTACCGGTACAGCGGCGTGCCTTCTCGGTTTAGCGGCTCTGGAAG
CGGAACAGATTTCACACTGACCATCTCTAGCCTGCAGCCTGAAGATTTTG
CCACATACTTTTGCCAGCAGTACAACATCTACCCCTACACCTTCGGCCAG
GGAACAAAGCTGGAAATCAAGCGTACGGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGT

PD1B512 LC (SEQ ID NO: 111)
GATATTGTGATGACTCAGGCTGCACTCTCCAATCCAGTCACTCTTGGAAC
ATCAGCTTCCATCTCCTGCAGGTCTAGTAAGAGTCTCCTACATAGTAATG
GCATCACTTATTTGAATTGGTATCTGCAGAAGCCAGGCCAGTCTCCTCAG
CTCCTGATTTATCAGATGTCCAACCTTGCCTCAGGAGTCCCAGACAGGTT
CAGTAGCAGTGGGTCAGGAACTGATTTCACACTGAGAATCAGCAGAGTGG
AGGCTGAGGATGTGGGTGTTTATTACTGTGCTCAAAATCTAGAACTTCCG
CTCACGTTCGGATCGGGGACCAAGCTGGAAATGAAACGTACGGTGGCTGC
ACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAA
GTACAGTGGAAGGTGGATAACGCCCTCCAATCGGGTAACTCCCAGGAGAG
TGTCACAGAGCAGGACAGCAAGGACAGCACCTACAGCCTCAGCAGCACCC
TGACGCTGAGCAAAGCAGACTACGAGAAACACAAAGTCTACGCCTGCGAA
GTCACCCATCAGGGCCTGAGCTCGCCCGTCACAAAGAGCTTCAACAGGGG
AGAGTGT

PD1B756 LC (SEQ ID NO: 112)
GACATCGTGATGACACAGTCTCCTCTGTCTCTGCCTGTGACACCTGGCGA
ACCTGCCTCTATCAGCTGCCGGAGCAGCAAGAGCCTGCTGCACAGCAACG
GCATCACCTACCTGAACTGGTACCTGCAGAAACCTGGACAGTCTCCTCAG
CTGCTGATCTACCAGATGAGCAACCTGGCCAGCGGCGTGCCTGATCGGTT
TAGCGGCTCTGGAAGCGGCACAGACTTCACACTGAAGATCTCTCGGGTGG
AAGCCGAGGACGTGGGAGTGTACTACTGCGCCCAGAACCTGGAGCTGCCC
CTGACCTTCGGAGGCGGAACAAAGGTGGAGATCAAGCGTACGGTGGCTGC
ACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAA
GTACAGTGGAAGGTGGATAACGCCCTCCAATCGGGTAACTCCCAGGAGAG
TGTCACAGAGCAGGACAGCAAGGACAGCACCTACAGCCTCAGCAGCACCC
TGACGCTGAGCAAAGCAGACTACGAGAAACACAAAGTCTACGCCTGCGAA
GTCACCCATCAGGGCCTGAGCTCGCCCGTCACAAAGAGCTTCAACAGGGG
AGAGTGT

PD1B757 LC (SEQ ID NO: 113)
GACATCGTGATGACACAGTCTCCTCTGTCTCTGCCTGTGACACCTGGCGA
ACCTGCCTCTATCAGCTGCCGGAGCAGCAAGAGCCTGCTGCACAGCAACG
GCATCACCTACCTGAACTGGTACCTGCAGAAACCTGGACAGTCTCCTCAG
CTGCTGATCTACCAGATGAGCAACCTGGCCAGCGGCGTGCCTGATCGGTT
TAGCGGCTCTGGAAGCGGCACAGACTTCACACTGAAGATCTCTCGGGTGG
AAGCCGAGGACGTGGGAGTGTACTACTGCGCCCAGAACCTGGAGCTGCCC
CTGACCTTCGGAGGCGGAACAAAGGTGGAGATCAAGCGTACGGTGGCTGC
ACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAA
GTACAGTGGAAGGTGGATAACGCCCTCCAATCGGGTAACTCCCAGGAGAG
TGTCACAGAGCAGGACAGCAAGGACAGCACCTACAGCCTCAGCAGCACCC
TGACGCTGAGCAAAGCAGACTACGAGAAACACAAAGTCTACGCCTGCGAA
GTCACCCATCAGGGCCTGAGCTCGCCCGTCACAAAGAGCTTCAACAGGGG
AGAGTGT

The cDNA sequences encoding antibody VH, VL, HC and LC provided herein can be codon optimized for expression in various cells, for example for expression in HEK or CHO cells. Additional cDNA sequences that may be used to encode and express PD1B878 and PD1B849 VH, VL, HC and LC are shown below.

PD1B878 VH cDNA
SEQ ID NO: 132
CAAGTGCAGCTGGTGCAGTCTGGCAGCGAGCTGAAAAAACCTGGCGCCTC
CGTGAAGGTGTCCTGCAAGGCTAGCGGCTACACCTTTACCGACTACAGCA
TGCACTGGGTCCGACAGGCTCCAGGACAAGGCTTGGAATGGATGGGCTGG
ATCAACATCGAGACAGGCGAGCCCACATACGCCCAGGGCTTTACCGGCAG
ATTCGTGTTCAGCCTGGACACCTCTGTGTCCACCGCCTACCTGCAGATCA
GCTCTCTGAAGGCCGAGGATACCGCCGTGTACTTCTGCGCCAGAGACTAC
TACGGCACCTACTTCTACGCCATGGATTACTGGGGCCAGGGCACCCTGGT
TACCGTTTCTTCT

PD1B878 VL cDNA
SEQ ID NO: 133
GAGATCGTGCTGACACAGTCTCCCGCCACACTGTCACTGTCTCCAGGCGA
AAGAGCCACACTGAGCTGTACCGCCAGCAGCTCTGTGTCCAGCAGCTACC
TGCACTGGTATCAGCAGAAGCCTGGACTGGCCCCTCGGCTGCTGATCTAC
AGCACAAGCAATCTGGCCAGCGGCATCCCCGATAGATTTTCCGGCTCTGG
AAGCGGCACCGACTACACCCTGACAATCAGCAGACTGGAACCCGAGGACT
TCGCCGTGTACTACTGCCACCAGTACCACAGAAGCCCTCTGACCTTTGGC
CAGGGCACCAAGCTGGAAATCAAG

PD1B878 HC cDNA
SEQ ID NO: 134
CAAGTGCAGCTGGTGCAGTCTGGCAGCGAGCTGAAAAAACCTGGCGCCTC
CGTGAAGGTGTCCTGCAAGGCTAGCGGCTACACCTTTACCGACTACAGCA
TGCACTGGGTCCGACAGGCTCCAGGACAAGGCTTGGAATGGATGGGCTGG
ATCAACATCGAGACAGGCGAGCCCACATACGCCCAGGGCTTTACCGGCAG
ATTCGTGTTCAGCCTGGACACCTCTGTGTCCACCGCCTACCTGCAGATCA
GCTCTCTGAAGGCCGAGGATACCGCCGTGTACTTCTGCGCCAGAGACTAC
TACGGCACCTACTTCTACGCCATGGATTACTGGGGCCAGGGCACCCTGGT
TACCGTTTCTTCTGCCTCCACCAAGGGCCCATCGGTCTTCCCCCTGGCAC
CCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCT
GACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAG
ACCTACATCTGCAACGTGAATCACAAGCCCAGCAACACCAAGGTGGACAA
GAAAGTTGAGCCCAAATCTTGTGACAAAACTCACACATGCCCACCGTGCC
CAGCACCTGAACTCCTGGGGGGACCGTCAGTCTTCCTCTTCCCCCCAAAA
CCCAAGGACACCCTCATGATCTCCCGGACCCCTGAGGTCACATGCGTGGT
GGTGGACGTGAGCCACGAAGACCCTGAGGTCAAGTTCAACTGGTACGTGG
ACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTG
GCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCA
CAGGTGTACACCCTGCCCCCATCCCGGGAGGAGATGACCAAGAACCAGGT
CAGCCTGACCTGCCTGGTCAAAGGCTTCTATCCCAGCGACATCGCCGTGG
AGTGGGAGAGCAATGGGCAGCCGGAGAACAACTACAAGACCACGCCTCCC
GTGCTGGACTCCGACGGCTCCTTCTTCCTCTACAGCAAGCTCACCGTGGA
CAAGAGCAGGTGGCAGCAGGGGAACGTCTTCTCATGCTCCGTGATGCATG
AGGCTCTGCACAACCACTACACGCAGAAGAGCCTCTCCCTGTCTCCGGGT
AAA

PD1B878 LC cDNA
SEQ ID NO: 135
GAGATCGTGCTGACACAGTCTCCCGCCACACTGTCACTGTCTCCAGGCGA
AAGAGCCACACTGAGCTGTACCGCCAGCAGCTCTGTGTCCAGCAGCTACC
TGCACTGGTATCAGCAGAAGCCTGGACTGGCCCCTCGGCTGCTGATCTAC
AGCACAAGCAATCTGGCCAGCGGCATCCCCGATAGATTTTCCGGCTCTGG
AAGCGGCACCGACTACACCCTGACAATCAGCAGACTGGAACCCGAGGACT
TCGCCGTGTACTACTGCCACCAGTACCACAGAAGCCCTCTGACCTTTGGC
CAGGGCACCAAGCTGGAAATCAAGCGTACGGTGGCTGCACCATCTGTCTT
CATCTTCCCGCCATCTGATGAGCAGTTGAAATCTGGAACTGCCTCTGTTG
TGTGCCTGCTGAATAACTTCTATCCCAGAGAGGCCAAAGTACAGTGGAAG
GTGGATAACGCCCTCCAATCGGGTAACTCCCAGGAGAGTGTCACAGAGCA
GGACAGCAAGGACAGCACCTACAGCCTCAGCAGCACCCTGACGCTGAGCA
AAGCAGACTACGAGAAACACAAAGTCTACGCCTGCGAAGTCACCCATCAG
GGCCTGAGCTCGCCCGTCACAAAGAGCTTCAACAGGGGAGAGTGT

PD1B849 VH cDNA
SEQ ID NO: 136
CAAGTGCAGCTGGTGCAATCTGGCGCCGAAGTGAAAAAGCCTGGCGCCTC
TGTGAAGGTGTCCTGCAAGGCCAGCGGCTACACCTTTACCACCTACTGGA
TGCACTGGGTCCGACAGGCTCCAGGACAAGGCTTGGAGTGGATGGGCGAG
ATCAACCCCAATGAAGGCGGCATCAACTACGCCCAGAAATTCCAGGGCAG
AGTGACCCTGACCGTGGACAAGAGCATCAGCACCGCCTACATGGAACTGA
GCCGGCTGAGATCCGATGACACCGCCGTGTACTACTGCACCATCGACTAC
TACGACTACGGCGGCTATTGGGGCCAGGGCACACTGGTTACAGTGTCCTC
T

PD1B849 VL cDNA
SEQ ID NO: 137
GACATCCAGATGACACAGAGCCCTAGCAGCCTGTCTGCCTCTGTGGGCGA
TAGAGTGACCATCACATGCAAGGCCAGCCAGAACGTGGGCACCAATGTGG
CCTGGTATCAGCAGAAGCCTGAGAAGGCCCCTAAGAGCCTGATCTACAGC
GCCAGCTACAGATACAGCGGCGTGCCAAGCAGATTTTCTGGAAGCGGCAG
CGGCACCGACTTCACCCTGACAATTAGTAGCCTGCAGCCTGAGGACTTCG
CCACCTACTACTGCCAGCAGTACAACATCTACCCCTACACCTTCGGCCAG
GGCACCAAGCTGGAAATCAAG

PD1B849 HC cDNA

SEQ ID NO: 138
CAAGTGCAGCTGGTGCAATCTGGCGCCGAAGTGAAAAAGCCTGGCGCCTC
TGTGAAGGTGTCCTGCAAGGCCAGCGGCTACACCTTTACCACCTACTGGA
TGCACTGGGTCCGACAGGCTCCAGGACAAGGCTTGGAGTGGATGGGCGAG
ATCAACCCCAATGAAGGCGGCATCAACTACGCCCAGAAATTCCAGGGCAG
AGTGACCCTGACCGTGGACAAGAGCATCAGCACCGCCTACATGGAACTGA
GCCGGCTGAGATCCGATGACACCGCCGTGTACTACTGCACCATCGACTAC
TACGACTACGGCGGCTATTGGGGCCAGGGCACACTGGTTACAGTGTCCTC
TGCCTCCACCAAGGGCCCATCGGTCTTCCCCCTGGCACCCTCCTCCAAGA
GCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGT
GCACACCTTCCCGGCTGTCCTACAGTCCTCAGGACTCTACTCCCTCAGCA
GCGTGGTGACCGTGCCCTCCAGCAGCTTGGGCACCCAGACCTACATCTGC
AACGTGAATCACAAGCCCAGCAACACCAAGGTGGACAAGAAAGTTGAGCC
CAAATCTTGTGACAAAACTCACACATGCCCACCGTGCCCAGCACCTGAAC
TCCTGGGGGGACCGTCAGTCTTCCTCTTCCCCCCAAAACCCAAGGACACC
CTCATGATCTCCCGGACCCCTGAGGTCACATGCGTGGTGGTGGACGTGAG
CCACGAAGACCCTGAGGTCAAGTTCAACTGGTACGTGGACGGCGTGGAGG
TGCATAATGCCAAGACAAAGCCGCGGGAGGAGCAGTACAACAGCACGTAC
CGTGTGGTCAGCGTCCTCACCGTCCTGCACCAGGACTGGCTGAATGGCAA
GGAGTACAAGTGCAAGGTCTCCAACAAAGCCCTCCCAGCCCCATCGAGA
AAACCATCTCCAAAGCCAAAGGGCAGCCCCGAGAACCACAGGTGTACACC
CTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCA
ATGGGCAGCCGGAGAACAACTACAAGACCACGCCTCCCGTGCTGGACTCC
GACGGCTCCTTCTTCCTCTACAGCAAGCTCACCGTGGACAAGAGCAGGTG
GCAGCAGGGGAACGTCTTCTCATGCTCCGTGATGCATGAGGCTCTGCACA
ACCACTACACGCAGAAGAGCCTCTCCCTGTCTCCGGGTAAA

PD1B849 LC cDNA

SEQ ID NO: 139
GACATCCAGATGACACAGAGCCCTAGCAGCCTGTCTGCCTCTGTGGGCGA
TAGAGTGACCATCACATGCAAGGCCAGCCAGAACGTGGGCACCAATGTGG
CCTGGTATCAGCAGAAGCCTGAGAAGGCCCCTAAGAGCCTGATCTACAGC
GCCAGCTACAGATACAGCGGCGTGCCAAGCAGATTTTCTGGAAGCGGCAG
CGGCACCGACTTCACCCTGACAATTAGTAGCCTGCAGCCTGAGGACTTCG
CCACCTACTACTGCCAGCAGTACAACATCTACCCCTACACCTTCGGCCAG
GGCACCAAGCTGGAAATCAAGCGTACGGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAAG
CAGACTACGAGAAACACAAAGTCTACGCCTGCGAAGTCACCCATCAGGGC
CTGAGCTCGCCCGTCACAAAGAGCTTCAACAGGGGAGAGTGT

FIG. 2A and FIG. 2B shows the alignment of the VH and the VL amino acid sequences of PD1B505 lineage mAbs, respectively.

FIG. 3A and FIG. 3B shows the alignment of the VL and the VL amino acid sequences of PD1B506 lineage mAbs, respectively.

FIG. 4A and FIG. 4B shows the alignment of the VH and the VL amino acid sequences of PD1B512 lineage mAbs, respectively.

Example 4

Humanized Anti-PD-1 Antibodies Inhibit Antigen Specific T Cells

Figure 5A:
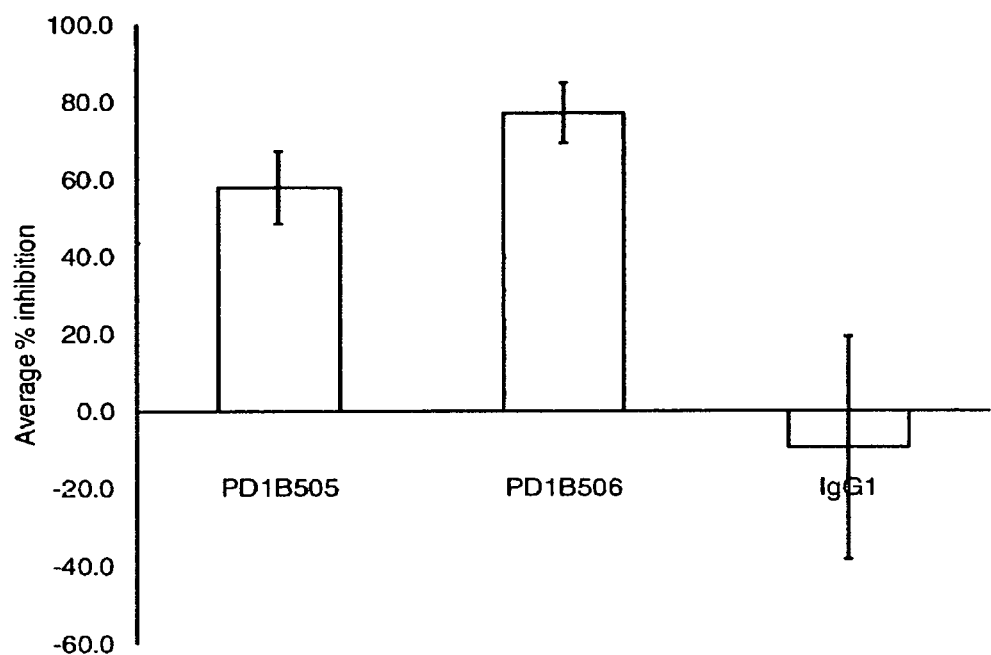
FIG. 5A shows that PD1B505 and PD1B506 inhibited activation of antigen specific T cells. The Figure shows the mean % inhibition and STDEV of T cell proliferation in CMV recall assay. IgG1: isotype control.
Figure 5B:
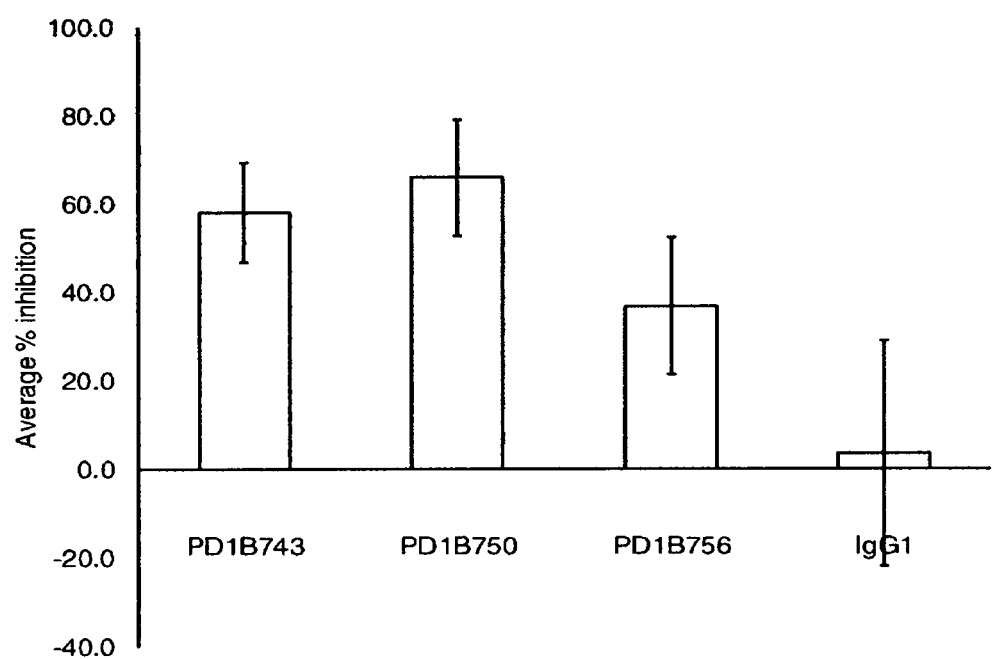
FIG. 5B shows that PD1B743, PD1B750 and PD1B756 inhibited activation of antigen specific T cells. The Figure shows the mean % inhibition and STDEV of T cell proliferation in CMV recall assay. IgG1: isotype control.
Figure 5C:
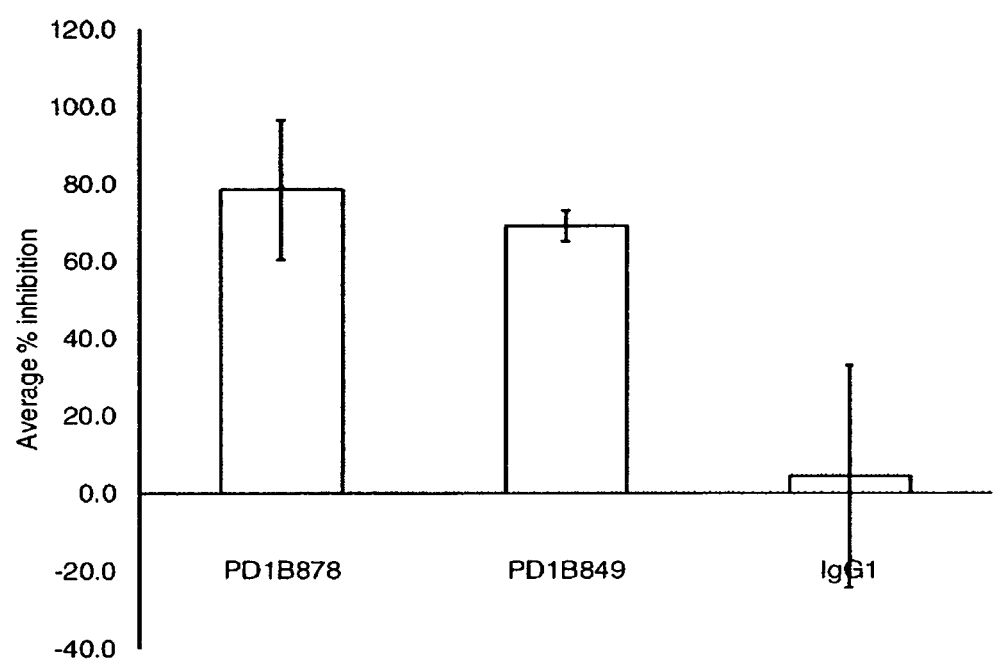
FIG. 5C shows that PD1B878 and PD1B849 inhibited activation of antigen specific T cells in a CMV-specific recall assay. The Figure shows the mean % inhibition and STDEV of T cell proliferation in CMV recall assay. IgG1: isotype control.

Select humanized antibodies were characterized for their ability to inhibit activated T cells in a CMV-specific recall assay (CMV-PBMC assay described in Example 1). The parental antibodies PD1B505 and PD1B506 demonstrated robust inhibition of activated T cells assessed across three different donors in several separate experiments as shown in Table 16, in which the results are shown as percentage (%) inhibition of T cell proliferation at 10 μg/ml of mAb. FIG. 5A shows the mean % inhibition and STDEV for PD1B505 (57.8%±9.5%) and PD1B506 (77.0%+/−7.8%) when compared to the isotype control (human IgG1) (−9.5%±28.8%). Humanized antibodies PD1B743, PD1B750 and PD1B756 also inhibited T cell activation as shown in Table 17 as % inhibition at 10 μg/ml. FIG. 5B shows the mean % inhibition and STDEV for PD1B743 (58.0%±11.3%) PD1B750 (65.9%±13.2%), PD1B756 (36.7%±15.5%), when compared to the isotype control (human IgG1) (3.5%±25.6%). Assays demonstrating over 25% STDEV were excluded from the analyses. Engineered antibodies PD1B878 and PD1B849 similarly inhibited activated T cells as shown in Table 18. FIG. 5C shows the mean % inhibition and STDEV for PD1B878 (78.3%±18.1%) and PD1B849 (69.0%±4.0%) when compared to the isotype control (human IgG1) (4.1%±28.7%).

TABLE 16

| Donor | PD1B505 | | PD1B506 | | Isotype | |
|---|---|---|---|---|---|---|
| | Mean | STDEV | Mean | STDEV | Mean | STDEV |
| D1 | 86.5 | 9.0 | 95.2 | 1.4 | 4.7 | 13.3 |
| D2 | 74.8 | 0.8 | 100.1 | 3.3 | 13.2 | 12.9 |
| D1 | 77 | 23.0 | 98 | 9.8 | 4.2 | 33.6 |
| D2 | 87.7 | 3.7 | 100.0 | 5.8 | −16.6 | 30.6 |
| D3 | 0.7 | 8.3 | 49.5 | 11.4 | 6.1 | 5.7 |
| D1 | 77.1 | 4.1 | 87.8 | 4.0 | −33.1 | 59.1 |
| D1 | 69.7 | 5.4 | 85.2 | 2.7 | 3.1 | 24.5 |
| D3 | 63.4 | 4.9 | 101.4 | 8.7 | −23.5 | 44.3 |
| D1 | 84.5 | 7.2 | 86.4 | 6.5 | −35.6 | 60.4 |
| D1 | 76.6 | 2.5 | 103.1 | 5.2 | −17.7 | 28.1 |
| D1 | 49.8 | 12.7 | 64.2 | 11.5 | −14.9 | 19.5 |
| D1 | −7.0 | 17.1 | 3.8 | 12.1 | −20.0 | 29.3 |
| D2 | 49.1 | 16.6 | 76.6 | 6.8 | −0.9 | 28.1 |
| D1 | 20.1 | 17.0 | 26.2 | 20.7 | −2.0 | 14.2 |

TABLE 17

| Do-nor | PD1B743 Mean | STDEV | PD1B750 Mean | STDEV | PD1B756 Mean | STDEV | Isotype Mean | STDEV |
|---|---|---|---|---|---|---|---|---|
| D1 | 90.1 | 3.1 | 97.2 | 10.0 | 59.3 | 18.2 | −17.7 | 28.1 |
| D3 | 21.1 | 13.8 | 74.9 | 16.7 | 27.4 | 14.2 | −6.6 | 17.7 |
| D4 | 30.5 | 23.6 | 24.2 | 15.5 | 0.3 | 17.1 | 2.7 | 7.7 |
| D5 | 64.0 | 5.9 | 75.0 | 9.9 | 69.3 | 12.8 | 14.1 | 35.6 |
| D1 | 66.7 | 14.8 | 58.1 | 19.8 | 27.4 | 15.4 | −13.1 | 45.2 |
| D3 | 35.1 | 8.2 | 55.6 | 5.8 | | | 0.5 | 20.8 |
| D1 | 84.2 | 2.2 | 72.1 | 18.8 | | | 43.1 | 17.5 |
| D1 | 58.4 | 8.4 | 64.7 | 7.3 | | | 5.8 | 31.6 |
| D1 | 72.1 | 21.4 | 71.6 | 14.8 | | | 2.5 | 25.9 |

TABLE 18

| Donor | PD1B878 Mean | STDEV | PD1B849 Mean | STDEV | Isotype Mean | STDEV |
|---|---|---|---|---|---|---|
| D1 | | | 64.3 | 2.5 | 5.8 | 31.6 |
| D1 | 78.3 | 18.1 | 73.7 | 5.6 | 2.5 | 25.9 |

Example 5

PD-1 Antibodies Bind Human PD-1 with High Affinity

Affinity of the parental and humanized antibodies to PD-1 was measured using SPR as described in Example 1.

Table 19 shows the results of the affinity measurements. The antibodies bound PD-1 with a $K_D$ ranging between about $5.2 \times 10^{-8}$ M and $2.1 \times 10^{-8}$ M.

TABLE 19

| mAb | ka (1/Ms) | kd (1/s) | $K_D$ (M) |
|---|---|---|---|
| PD1B505 | 8.11E+04 | 2.36E−03 | 2.91E−08 |
| PD1B742 | | | |
| PD1B743 | 9.15E+04 | 3.00E−03 | 3.28E−08 |
| PD1B878 | 5.98E+04 | 3.51E−03 | 5.89E−08 |
| PD1B506 | 1.95E+05 | 1.02E−02 | 5.24E−08 |
| PD1B750 | 3.59E+05 | 8.32E−03 | 2.32E−08 |
| PD1B751 | | | |
| PD1B845* | 3.51E+05 | 8.43E−03 | 2.40E−08 |
| PD1B846* | 3.49E+05 | 7.53E−03 | 2.16E−08 |
| PD1B847* | 3.03E+05 | 7.44E−03 | 2.46E−08 |
| PD1B848* | 2.53E+05 | 9.91E−03 | 3.92E−08 |
| PD1B849 | 1.88E+05 | 8.83E−03 | 4.71E−08 |
| PD1B850* | 3.13E+05 | 7.19E−03 | 2.30E−08 |
| PD1B512 | | | |
| PD1B756 | 1.18E+05 | 2.14E−03 | 1.81E−08 |
| PD1B757 | | | |

*Binding was assessed as crude supernatants

Example 6

PD-1 Antibodies Differentially Block PD-1/Ligand Interaction

Ligand blocking was assessed by evaluating the effect of the antibodies on clustering of cells overexpressing either PD-1 or PD-1 ligand (PD-L1 or PD-L2) using the protocol described in Example 1. Lower percentage (%) of recorded double positive events indicated the tested mAb blocked PD-1 binding to the tested ligand.

Figure 6A:
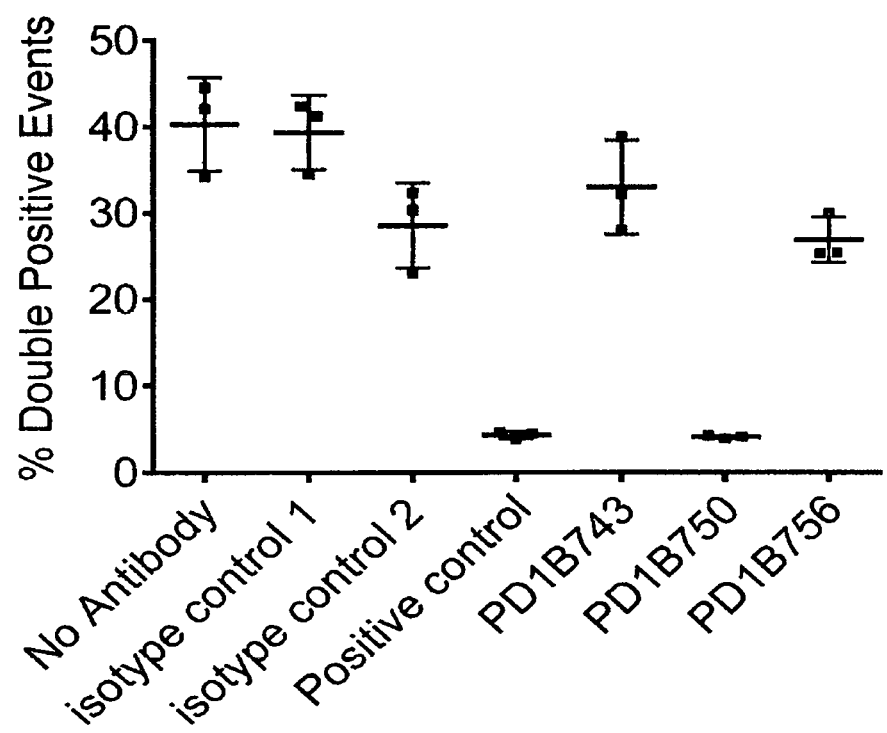
FIG. 6A shows that PD1B743 and PD1B756 did not block PD-L1 binding to PD-1 whereas PD1B750 blocked the interaction in an assay evaluating degree of clustering of PD-1 and PD-L1 expressing cells in the presence or absence of indicated antibodies using percent (%) double positive events as readout for clustering. Positive control mAb blocked PD-L1/PD-1 interaction.
Figure 6B:
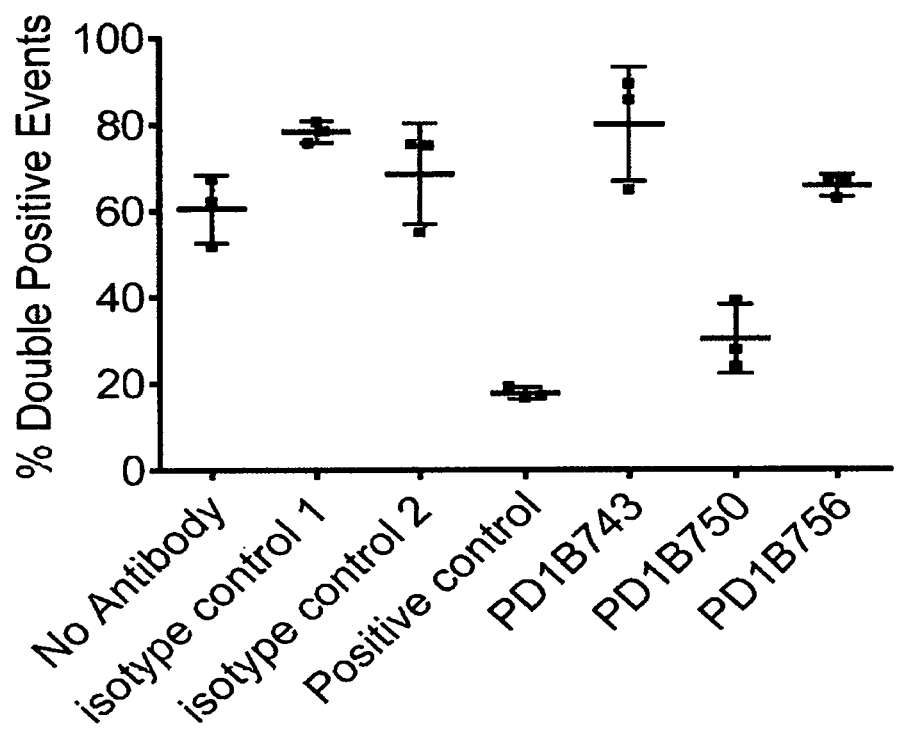
FIG. 6B shows that PD1B743 and PD1B756 did not block PD-L2 binding to PD-1 whereas PD1B750 blocked the interaction in an assay evaluating degree of clustering of PD-1 and PD-L2 expressing cells in the presence or absence of indicated antibodies using percent (%) double positive events as readout for clustering. Positive control mAb blocked PD-L2/PD-1 interaction.

FIG. 6A shows the % PD-1-HEK and PD-L1-HEK cell clusters that remained after treating cells with PD1B743, PD1B750 or PD1B756. PD1B743 and PD1B756 did not block PD-L1 binding to PD-1 whereas PD1B750 did. Similarly, PD1B743 and PD1B756 did not block PD-L2 binding to PD-1 whereas PD1B750 did (FIG. 6B). Known anti-PD-1 ligand blocking mAb was used as a positive control in the experiments.

Example 7

Epitope Binning of Antibodies

Figure 7:
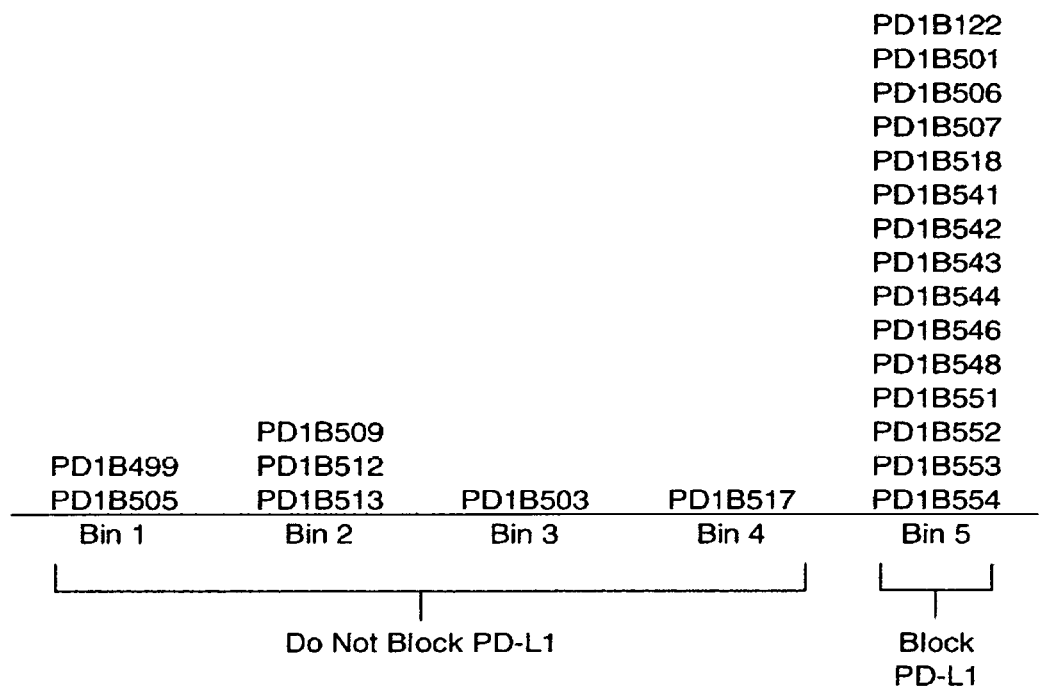
FIG. 7 shows a schematic of five distinct epitope bins of the generated PD-1 antibodies. Bin5 mAbs blocked PD-L1/PD-1 interaction whereas mAbs within bins 1-4 did not.

Five distinct epitope bins were identified in initial matrix assays using chimeric antibodies following the protocol described in Example 1. Bins 4 and 5 did not cross-compete with any other bins. Bins 1, 2 and 3 were partially overlapping; Bin 1 competed with Bin 2 and 3, and Bin 2 and 3 competed with Bin 1. Bins 1, 2, 3 and 4 did not block PD-L1 binding to PD-1, whereas Bin 5 did block PD-L1/PD-1 interaction. FIG. 7 shows the distinct epitope bins and antibodies within each bin.

A control experiment with isotype control as the first antibody added was done to demonstrate how the second antibody would bind alone to human PD-1. Then in the competition experiment, the signal (nm) of the association of the second antibody was taken at 180 seconds after the start of this step. The signal of each potentially competing antibody was compared to an average of the signal from 3 runs of the same antibody added after isotype control. A ratio of these signals was determined. If the ratio was below 0.7, then it was determined that the second antibody could not bind to human PD-1 and the two antibodies share the same epitope. If the ratio was greater than 0.7, it was determined the second antibody could bind in the presence of the first antibody, and therefore the two antibodies bound to non-competing epitopes.

Humanization and PTM engineering is not expected to result in a shift in epitope, therefore PD1B743, PD1B742 and PD1B878 is expected to bind the same epitope as the parental chimeric Bin 1 PD1B505. Similarly, PD1B750, PD1B751 and PD1B849 are expected to bind the same epitope as the parental chimeric Bin 5 PD1B506, and PD1B756 is expected to bind the same epitope as the parental chimeric Bin 2 PD1B512.

PD1B503 comprises VH and VL of SEQ ID NOs: 114 and 115, respectively.

PD1B517 comprises VH and VL of SEQ ID NOs: 116 and 117, respectively.

PD1B503 VH (PD1H96)

SEQ ID NO: 114

QVQLQQSGAELVKPGASVKLSCKASGYTFTSYDINWVRQRPEQGLEWIGW

IFPGDGSTKYNEKFKGKATLTTDKSSSTAYMQFSRLTSEDSAVYFCARGG

MRQLGRFVYWGQGTTLTVSS

PD1B503 VL (PD1L32)

SEQ ID NO: 115

DIVLTQSPSSLSASLGERVSLTCRASQEISGYLSWLQQKPDGTIKRLIYA

ASTLDSGVPKRFSGSRSGSDYSLTISSLESEDFADYYCLQYASNPYTFGG

GTKLEIK

-continued

PD1B517 VH (PD1H73)

SEQ ID NO: 116

EVQLQQSGAELVKPGASVKLSCTASGFNVKDTYFHWVKQRPDQGLEWIGR

IVSANGDTKYAPKLQDKATITTDTSSNTAYLQLSRLTSEDTAVYYCVLIY

YGFEEGDFWGQGTTLTVSS

PD1B517 VL (PD1L34)

SEQ ID NO: 117

DIVMTQSPSSLSASLGDTITITCHASQNINVWLSWYQQKPGNVPKLLIYK

ASNLHTGVPSRFSGSGSGTGFTLNISSLQPEDIATYYCQQGQSFPLTFGA

GTKLELK

Example 8

Affinity Maturation of PD1B878

To improve binding affinity of PD1B878, CDR scans were performed on both heavy and light chains. Non-combinatorial libraries were designed to diversify each position of all six CDRs (HCDR1, HCDR2, HCDR3, LCDR1, LCDR2 and LCDR3). Briefly, Fab libraries were constructed in a pIX phage Fab display system as described in WO2009/085462, Shi et al., *J Mol Biol* 397: 385-396 (2010), and Tornetta et al. *J Immunol Methods* 360: 39-46 (2010) with minor modifications to restriction enzyme sites. These libraries were panned against biotinylated Human PD-1/PDCD1 (Acro Biosystems. Cat #PD1-H82E4) according to panning schemes known in the art, such as described in WO2009/085462 and in Shi et al, J Mol Biol 397: 385-396 (2010). Phage was produced by helper phage infection. Binders were retrieved by addition of beads to form a bead/antigen/phage complex. After the final wash, phage was rescued by infection of exponentially growing TG-1 *Escherichia coli* cells.

For follow-up screening, plasmid DNA was prepared from overnight culture of the TG-1 *Escherichia coli* cells and the pIX gene was excised by NheI/SpeI digestion. After ligation, the DNA was transformed into TG-1 cells and grown on LB/Agar plates overnight. The next day, colonies were picked, grown overnight, and the cultures used for (i) colony sequencing of the V-regions, and (ii) induction of Fab production. For Fab production, the overnight culture was diluted 100 folds in new media and grown for 5-6 hours at 37° C. Fab production was induced by the addition of fresh media containing IPTG and the cultures were grown overnight at 30° C. The following day, the cultures were spun down and the supernatants, containing the soluble Fab proteins, were used for Fab ELISA. For the ELISA, the soluble Fab proteins were captured onto plates by a polyclonal anti-Fd(CH1) antibody. After washing and blocking, biotinylated Human PD-1/PDCD1 was added at 5 nM concentration. This concentration enabled ranking of the Fab variants, defined as fold change versus the parent, in which the parental Fab, present as a control in all plates, is defined as 100% binding. The biotinylated human PD-1 was detected by HRP-conjugated streptavidin with chemiluminescence measured in a plate reader. By this criterion, 3 heavy and 2 light chains binding human PD-1 at 10-fold or higher relative to parental Fab were selected.

Table 20 shows the variant with substitutions at position 57 in the HCDR2 of VH and position 29 or 30 in the LCDR1 of VL. Table 21 shows the SEQ ID NOs: of the CDRs of the antibodies. Table 22 shows the SEQ ID NOs: of the VH, the VL, the HC and the LC amino acid sequences. Table 23 shows the SEQ ID NOs: of the polynucleotides encoding the VH, the VL, the HC and the LC of the antibodies. Table 24 shows the HCDR1, the HCDR2 and the HCDR3 amino acid sequences. Table 25 shows the LCDR1, the LCDR2 and the LCDR3 amino acid sequences. Table 26 shows the VH amino acid sequences. Table 27 shows the VL amino acid sequences. The affinity matured variants are expected to bind the same epitope on PD-1 as the parental antibody PD1B878.

TABLE 20

| mAb ID | VH peptide ID | VH mutation compared to parental | VL peptide ID | VL mutation compared to parental |
| --- | --- | --- | --- | --- |
| PD1B1085 | PD1H585 | E57Y | PD1L469 | |
| PD1B1086 | PD1H586 | E57H | PD1L469 | |
| PD1B1087 | PD1H587 | E57W | PD1L469 | |
| PD1B1088 | PD1H405 | | PD1L651 | V29F |
| PD1B1089 | PD1H405 | | PD1L652 | S30P |
| PD1B1090 | PD1H585 | E57Y | PD1L651 | V29F |
| PD1B1091 | PD1H586 | E57H | PD1L651 | V29F |
| PD1B1092 | PD1H587 | E57W | PD1L651 | V29F |
| PD1B1093 | PD1H585 | E57Y | PD1L652 | S30P |
| PD1B1094 | PD1H586 | E57H | PD1L652 | S30P |
| PD1B1095 | PD1H587 | E57W | PD1L652 | S30P |

TABLE 21

| Antibody | HCDR1 | HCDR2 | HCDR3 | LCDR1 | LCDR2 | LCDR3 |
| --- | --- | --- | --- | --- | --- | --- |
| PD1B1085 | 2 | 145 | 4 | 5 | 6 | 7 |
| PD1B1086 | 2 | 146 | 4 | 5 | 6 | 7 |
| PD1B1087 | 2 | 147 | 4 | 5 | 6 | 7 |
| PD1B1088 | 2 | 3 | 4 | 148 | 6 | 7 |
| PD1B1089 | 2 | 3 | 4 | 149 | 6 | 7 |
| PD1B1090 | 2 | 145 | 4 | 148 | 6 | 7 |
| PD1B1091 | 2 | 146 | 4 | 148 | 6 | 7 |
| PD1B1092 | 2 | 147 | 4 | 148 | 6 | 7 |
| PD1B1093 | 2 | 145 | 4 | 149 | 6 | 7 |
| PD1B1094 | 2 | 146 | 4 | 149 | 6 | 7 |
| PD1B1095 | 2 | 147 | 4 | 149 | 6 | 7 |

TABLE 22

| mAb ID | VH peptide ID | VL peptide ID | VH SEQ ID NO: | VL SEQ ID NO: | HC SEQ ID NO: | LC SEQ ID NO: |
| --- | --- | --- | --- | --- | --- | --- |
| PD1B1085 | PD1H585 | PD1L469 | 140 | 16 | 150 | 28 |
| PD1B1086 | PD1H586 | PD1L469 | 141 | 16 | 151 | 28 |
| PD1B1087 | PD1H587 | PD1L469 | 142 | 16 | 152 | 28 |
| PD1B1088 | PD1H405 | PD1L651 | 10 | 143 | 22 | 153 |
| PD1B1089 | PD1H405 | PD1L652 | 10 | 144 | 22 | 154 |
| PD1B1090 | PD1H585 | PD1L651 | 140 | 143 | 150 | 153 |
| PD1B1091 | PD1H586 | PD1L651 | 141 | 143 | 151 | 153 |
| PD1B1092 | PD1H587 | PD1L651 | 142 | 143 | 152 | 153 |

TABLE 22-continued

| mAb ID | VH peptide ID | VL peptide ID | VH SEQ ID NO: | VL SEQ ID NO: | HC SEQ ID NO: | LC SEQ ID NO: |
|---|---|---|---|---|---|---|
| PD1B1093 | PD1H585 | PD1L652 | 140 | 144 | 150 | 154 |
| PD1B1094 | PD1H586 | PD1L652 | 141 | 144 | 151 | 154 |
| PD1B1095 | PD1H587 | PD1L652 | 142 | 144 | 152 | 154 |

TABLE 23

| mAb ID | VH peptide name | VL peptide name | VH cDNA SEQ ID NO: | VL cDNA SEQ ID NO: | HC cDNA SEQ ID NO: | LC cDNA SEQ ID NO: |
|---|---|---|---|---|---|---|
| PD1B1085 | PD1H585 | PD1L469 | 155 | 19 | 160 | 31 |
| PD1B1086 | PD1H586 | PD1L469 | 156 | 19 | 161 | 31 |
| PD1B1087 | PD1H587 | PD1L469 | 157 | 19 | 162 | 31 |
| PD1B1088 | PD1H405 | PD1L651 | 13 | 158 | 25 | 163 |
| PD1B1089 | PD1H405 | PD1L652 | 13 | 159 | 25 | 164 |
| PD1B1090 | PD1H585 | PD1L651 | 155 | 158 | 160 | 163 |
| PD1B1091 | PD1H586 | PD1L651 | 156 | 158 | 161 | 163 |
| PD1B1092 | PD1H587 | PD1L651 | 157 | 158 | 162 | 163 |
| PD1B1093 | PD1H585 | PD1L652 | 155 | 159 | 160 | 164 |
| PD1B1094 | PD1H586 | PD1L652 | 156 | 159 | 161 | 164 |
| PD1B1095 | PD1H587 | PD1L652 | 157 | 159 | 162 | 164 |

TABLE 24

| Antibody | HCDR1 (SEQ ID NO:) | HCDR2 (SEQ ID NO:) | HCDR3 (SEQ ID NO:) |
|---|---|---|---|
| PD1B1085 | GYTFTDYSMH (SEQ ID NO: 2) | WINIETGYPT (SEQ ID NO: 145) | DYYGTYFYAMDY (SEQ ID NO: 4) |
| PD1B1086 | GYTFTDYSMH (SEQ ID NO: 2) | WINIETGHPT (SEQ ID NO: 146) | DYYGTYFYAMDY (SEQ ID NO: 4) |
| PD1B1087 | GYTFTDYSMH (SEQ ID NO: 2) | WINIETGWPT (SEQ ID NO: 147) | DYYGTYFYAMDY (SEQ ID NO: 4) |
| PD1B1088 | GYTFTDYSMH (SEQ ID NO: 2) | WINIETGEPT (SEQ ID NO: 3) | DYYGTYFYAMDY (SEQ ID NO: 4) |
| PD1B1089 | GYTFTDYSMH (SEQ ID NO: 2) | WINIETGEPT (SEQ ID NO: 3) | DYYGTYFYAMDY (SEQ ID NO: 4) |
| PD1B1090 | GYTFTDYSMH (SEQ ID NO: 2) | WINIETGYPT (SEQ ID NO: 145) | DYYGTYFYAMDY (SEQ ID NO: 4) |
| PD1B1091 | GYTFTDYSMH (SEQ ID NO: 2) | WINIETGHPT (SEQ ID NO: 146) | DYYGTYFYAMDY (SEQ ID NO: 4) |
| PD1B1092 | GYTFTDYSMH (SEQ ID NO: 2) | WINIETGWPT (SEQ ID NO: 147) | DYYGTYFYAMDY (SEQ ID NO: 4) |
| PD1B1093 | GYTFTDYSMH (SEQ ID NO: 2) | WINIETGYPT (SEQ ID NO: 145) | DYYGTYFYAMDY (SEQ ID NO: 4) |
| PD1B1094 | GYTFTDYSMH (SEQ ID NO: 2) | WINIETGHPT (SEQ ID NO: 146) | DYYGTYFYAMDY (SEQ ID NO: 4) |
| PD1B1095 | GYTFTDYSMH (SEQ ID NO: 2) | WINIETGWPT (SEQ ID NO: 147) | DYYGTYFYAMDY (SEQ ID NO: 4) |

TABLE 25

| Antibody | LCDR1 (SEQ ID NO:) | LCDR2 (SEQ ID NO:) | LCDR3 (SEQ ID NO:) |
| --- | --- | --- | --- |
| PD1B1085 | TASSSVSSSYLH (SEQ ID NO: 5) | STSNLAS (SEQ ID NO: 6) | HQYHRSPLT (SEQ ID NO: 7) |
| PD1B1086 | TASSSVSSSYLH (SEQ ID NO: 5) | STSNLAS (SEQ ID NO: 6) | HQYHRSPLT (SEQ ID NO: 7) |
| PD1B1087 | TASSSVSSSYLH (SEQ ID NO: 5) | STSNLAS (SEQ ID NO: 6) | HQYHRSPLT (SEQ ID NO: 7) |
| PD1B1088 | TASSSFSSSYLH (SEQ ID NO: 148) | STSNLAS (SEQ ID NO: 6) | HQYHRSPLT (SEQ ID NO: 7) |
| PD1B1089 | TASSSVPSSYLH (SEQ ID NO: 149) | STSNLAS (SEQ ID NO: 6) | HQYHRSPLT (SEQ ID NO: 7) |
| PD1B1090 | TASSSFSSSYLH (SEQ ID NO: 148) | STSNLAS (SEQ ID NO: 6) | HQYHRSPLT (SEQ ID NO: 7) |
| PD1B1091 | TASSSFSSSYLH (SEQ ID NO: 148) | STSNLAS (SEQ ID NO: 6) | HQYHRSPLT (SEQ ID NO: 7) |
| PD1B1092 | TASSSFSSSYLH (SEQ ID NO: 148) | STSNLAS (SEQ ID NO: 6) | HQYHRSPLT (SEQ ID NO: 7) |
| PD1B1093 | TASSSVPSSYLH (SEQ ID NO: 149) | STSNLAS (SEQ ID NO: 6) | HQYHRSPLT (SEQ ID NO: 7) |
| PD1B1094 | TASSSVPSSYLH (SEQ ID NO: 149) | STSNLAS (SEQ ID NO: 6) | HQYHRSPLT (SEQ ID NO: 7) |
| PD1B1095 | TASSSVPSSYLH (SEQ ID NO: 149) | STSNLAS (SEQ ID NO: 6) | HQYHRSPLT (SEQ ID NO: 7) |

TABLE 26

| VH peptide name | VH amino acid sequence | SEQ ID NO: |
| --- | --- | --- |
| PD1H585 | QVQLVQSGSELKKPGASVKVSCKASGYTFTDYSMHWVRQAPGQGLEWMGWINIETGYPTYAQGFTGRFVFSLDTSVSTAYLQISSLKAEDTAVYFCARDYYGTYFYAMDYWGQGTLVTVSS | 140 |
| PD1H586 | QVQLVQSGSELKKPGASVKVSCKASGYTFTDYSMHWVRQAPGQGLEWMGWINIETGHPTYAQGFTGRFVFSLDTSVSTAYLQISSLKAEDTAVYFCARDYYGTYFYAMDYWGQGTLVTVSS | 141 |
| PD1H587 | QVQLVQSGSELKKPGASVKVSCKASGYTFTDYSMHWVRQAPGQGLEWMGWINIETGWPTYAQGFTGRFVFSLDTSVSTAYLQISSLKAEDTAVYFCARDYYGTYFYAMDYWGQGTLVTVSS | 142 |

TABLE 27

| VL peptide name | VL amino acid sequence | SEQ ID NO: |
| --- | --- | --- |
| PD1L651 | EIVLTQSPATLSLSPGERATLSCTASSSFSSSYLHWYQQKPGLAPRLLIYSTSNLASGIPDRFSGSGSGTDYTLTISRLEPEDFAVYYCHQYHRSPLTFGQGTKLEIK | 143 |
| PD1L652 | EIVLTQSPATLSLSPGERATLSCTASSSVPSSYLHWYQQKPGLAPRLLIYSTSNLASGIPDRFSGSGSGTDYTLTISRLEPEDFAVYYCHQYHRSPLTFGQGTKLEIK | 144 |

PD1B1085, PD1B1090, PD1B1093 HC

SEQ ID NO: 150

QVQLVQSGSELKKPGASVKVSCKASGYTFTDYSMHWVRQAPGQGLEWMGWINIE
TGYPTYAQGFTGRFVFSLDTSVSTAYLQISSLKAEDTAVYFCARDYYGTYFYAMD
YWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQ
KSLSLSPGK

PD1B1086, PD1B1091, PD1B1094 HC

SEQ ID NO: 151

QVQLVQSGSELKKPGASVKVSCKASGYTFTDYSMHWVRQAPGQGLEWMGWINIE
TGHPTYAQGFTGRFVFSLDTSVSTAYLQISSLKAEDTAVYFCARDYYGTYFYAMD
YWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQ
KSLSLSPGK

PD1B1087, PD1B1092, PD1B1095 HC

SEQ ID NO: 152

QVQLVQSGSELKKPGASVKVSCKASGYTFTDYSMHWVRQAPGQGLEWMGWINIE
TGWPTYAQGFTGRFVFSLDTSVSTAYLQISSLKAEDTAVYFCARDYYGTYFYAMD
YWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKA
LPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQ
KSLSLSPGK

PD1B1088, PD1B1090, PD1B1091, PD1B1092 LC

SEQ ID NO: 153

EIVLTQSPATLSLSPGERATLSCTASSSFSSSYLHWYQQKPGLAPRLLIYSTSNLASGI
PDRFSGSGSGTDYTLTISRLEPEDFAVYYCHQYHRSPLTFGQGTKLEIKRTVAAPSV
FIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC

PD1B1089, PD1B1093, PD1B1094, PD1B1095 LC

SEQ ID NO: 154

EIVLTQSPATLSLSPGERATLSCTASSSVPSSYLHWYQQKPGLAPRLLIYSTSNLASG
IPDRFSGSGSGTDYTLTISRLEPEDFAVYYCHQYHRSPLTFGQGTKLEIKRTVAAPS
VFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC

PD1H585 cDNA

```
                                           SEQ ID NO: 155
CAGGTGCAGCTGGTGCAGTCTGGAAGCGAACTGAAGAAACCTGGAGCCTCTGT

GAAAGTGTCTTGTAAGGCCAGCGGCTACACCTTCACCGACTACAGCATGCACT

GGGTGCGGCAGGCCCCTGGACAGGGCCTGGAATGGATGGGCTGGATCAACATC

GAGACCGGCTATCCCACCTACGCCCAGGGCTTTACCGGACGGTTCGTGTTCAGC

CTGGATACATCTGTGTCTACAGCCTATCTGCAGATCAGCTCTCTGAAGGCCGAA

GATACAGCCGTGTACTTCTGCGCCCGGGACTACTACGGCACCTACTTCTACGCC

ATGGACTACTGGGGCCAGGGAACACTGGTGACAGTGTCTTCT

PD1H586 cDNA
                                           SEQ ID NO: 156
CAGGTGCAGCTGGTGCAGTCTGGAAGCGAACTGAAGAAACCTGGAGCCTCTGT

GAAAGTGTCTTGTAAGGCCAGCGGCTACACCTTCACCGACTACAGCATGCACT

GGGTGCGGCAGGCCCCTGGACAGGGCCTGGAATGGATGGGCTGGATCAACATC

GAGACCGGCCATCCCACCTACGCCCAGGGCTTTACCGGACGGTTCGTGTTCAGC

CTGGATACATCTGTGTCTACAGCCTATCTGCAGATCAGCTCTCTGAAGGCCGAA

GATACAGCCGTGTACTTCTGCGCCCGGGACTACTACGGCACCTACTTCTACGCC

ATGGACTACTGGGGCCAGGGAACACTGGTGACAGTGTCTTCT

PD1H587 cDNA
                                           SEQ ID NO: 157
CAGGTGCAGCTGGTGCAGTCTGGAAGCGAACTGAAGAAACCTGGAGCCTCTGT

GAAAGTGTCTTGTAAGGCCAGCGGCTACACCTTCACCGACTACAGCATGCACT

GGGTGCGGCAGGCCCCTGGACAGGGCCTGGAATGGATGGGCTGGATCAACATC

GAGACCGGCTGGCCCACCTACGCCCAGGGCTTTACCGGACGGTTCGTGTTCAG

CCTGGATACATCTGTGTCTACAGCCTATCTGCAGATCAGCTCTCTGAAGGCCGA

AGATACAGCCGTGTACTTCTGCGCCCGGGACTACTACGGCACCTACTTCTACGC

CATGGACTACTGGGGCCAGGGAACACTGGTGACAGTGTCTTCT

PD1L651 cDNA
                                           SEQ ID NO: 158
GAGATCGTGCTGACACAGTCTCCTGCCACACTGTCTCTGTCTCCTGGAGAACGG

GCCACACTGAGCTGCACCGCCAGCAGCAGCTTCAGCAGCAGCTACCTGCACTG

GTACCAGCAGAAACCTGGACTGGCCCCTCGGCTGCTGATCTACAGCACCAGCA

ACCTGGCCAGCGGCATCCCTGATCGGTTTTCTGGCAGCGGATCTGGCACAGATT

ACACACTGACCATCAGCCGGCTGGAACCTGAGGATTTTGCCGTGTACTACTGCC

ACCAGTACCACCGGAGCCCCCTGACCTTCGGCCAGGGAACAAAGCTGGAAATC

AAG

PD1L652 cDNA
                                           SEQ ID NO: 159
GAGATCGTGCTGACACAGTCTCCTGCCACACTGTCTCTGTCTCCTGGAGAACGG

GCCACACTGAGCTGCACCGCCAGCAGCAGCGTGCCAAGCAGCTACCTGCACTG

GTACCAGCAGAAACCTGGACTGGCCCCTCGGCTGCTGATCTACAGCACCAGCA

ACCTGGCCAGCGGCATCCCTGATCGGTTTTCTGGCAGCGGATCTGGCACAGATT

ACACACTGACCATCAGCCGGCTGGAACCTGAGGATTTTGCCGTGTACTACTGCC

ACCAGTACCACCGGAGCCCCCTGACCTTCGGCCAGGGAACAAAGCTGGAAATC

AAG
```

-continued

PD1B1085, PD1B1090, PD1B1093 HC cDNA
SEQ ID NO: 160
TCTGATAAGAGTCAGAGGTAACTCCCGTTGCGGTGCTGTTAACGGTGGAGGGC

AGTGTAGTCTGAGCAGTACTCGTTGCTGCCGCGCGCGCCACCAGACATAATAG

CTGACAGACTAACAGACTGTTCCTTTCCATGGGTCTTTTCTGCAGTCACCGTCCT

TAGATCCACTAGTCCAGTGTGGTGAAGCTTGCCGCCACCATGGCTTGGGTGTGG

ACCTTGCTATTCCTGATGGCAGCTGCCCAAAGTATACAGGCCCAGGTGCAGCTG

GTGCAGTCTGGAAGCGAACTGAAGAAACCTGGAGCCTCTGTGAAAGTGTCTTG

TAAGGCCAGCGGCTACACCTTCACCGACTACAGCATGCACTGGGTGCGGCAGG

CCCCTGGACAGGGCCTGGAATGGATGGGCTGGATCAACATCGAGACCGGCTAT

CCCACCTACGCCCAGGGCTTTACCGGACGGTTCGTGTTCAGCCTGGATACATCT

GTGTCTACAGCCTATCTGCAGATCAGCTCTCTGAAGGCCGAAGATACAGCCGT

GTACTTCTGCGCCCGGGACTACTACGGCACCTACTTCTACGCCATGGACTACTG

GGGCCAGGGAACACTGGTGACAGTGTCTTCTGCCTCCACCAAGGGCCCATCGG

TCTTCCCCCTGGCACCCTCCTCCAAGAGCACCTCTGGGGGCACAGCGGCCCTGG

GCTGCCTGGTCAAGGACTACTTCCCCGAACCGGTGACGGTGTCGTGGAACTCA

GGCGCCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCACCCAG

ACCTACATCTGCAACGTGAATCACAAGCCCAGCAACACCAAGGTGGACAAGAA

AGTTGAGCCCAAATCTTGTGACAAAACTCACACATGCCCACCGTGCCCAGCAC

CTGAACTCCTGGGGGGACCGTCAGTCTTCCTCTTCCCCCCAAAACCCAAGGACA

CCCTCATGATCTCCCGGACCCCTGAGGTCACATGCGTGGTGGTGGACGTGAGCC

ACGAAGACCCTGAGGTCAAGTTCAACTGGTACGTGGACGGCGTGGAGGTGCAT

AATGCCAAGACAAAGCCGCGGGAGGAGCAGTACAACAGCACGTACCGTGTGG

TCAGCGTCCTCACCGTCCTGCACCAGGACTGGCTGAATGGCAAGGAGTACAAG

TGCAAGGTCTCCAACAAAGCCCTCCCAGCCCCCATCGAGAAAACCATCTCCAA

AGCCAAAGGGCAGCCCCGAGAACCACAGGTGTACACCCTGCCCCCATCCCGGG

AGGAGATGACCAAGAACCAGGTCAGCCTGACCTGCCTGGTCAAAGGCTTCTAT

CCCAGCGACATCGCCGTGGAGTGGGAGAGCAATGGGCAGCCGGAGAACAACT

ACAAGACCACGCCTCCCGTGCTGGACTCCGACGGCTCCTTCTTCCTCTACAGCA

AGCTCACCGTGGACAAGAGCAGGTGGCAGCAGGGGAACGTCTTCTCATGCTCC

GTGATGCATGAGGCTCTGCACAACCACTACACGCAGAAGAGCCTCTCCCTGTCT

CCGGGTAAATGATAGTTCGAATTCCTAGAAGACATGATAAGATACATTGATGA

GTTTGGACAAACCACAACTAGAATGCAGTGAAAAAAATGCTTTATTTGTGAAA

TTTGTGATGCTATTGCTTTATTTGTAACCATTATAAGCTGCAATAAACAAGTTA

ACAACAACAATTGCATTCATTTTATGTTTCAGGTTCAGGGGGAGGTGTGGGA

PD1B1086, PD1B1091, PD1B1094 HC cDNA
SEQ ID NO: 161
TCTGATAAGAGTCAGAGGTAACTCCCGTTGCGGTGCTGTTAACGGTGGAGGGC

AGTGTAGTCTGAGCAGTACTCGTTGCTGCCGCGCGCGCCACCAGACATAATAG

CTGACAGACTAACAGACTGTTCCTTTCCATGGGTCTTTTCTGCAGTCACCGTCCT

TAGATCCACTAGTCCAGTGTGGTGAAGCTTGCCGCCACCATGGCTTGGGTGTGG

-continued

```
ACCTTGCTATTCCTGATGGCAGCTGCCCAAAGTATACAGGCCCAGGTGCAGCTG

GTGCAGTCTGGAAGCGAACTGAAGAAACCTGGAGCCTCTGTGAAAGTGTCTTG

TAAGGCCAGCGGCTACACCTTCACCGACTACAGCATGCACTGGGTGCGGCAGG

CCCCTGGACAGGGCCTGGAATGGATGGGCTGGATCAACATCGAGACCGGCCAT

CCCACCTACGCCCAGGGCTTTACCGGACGGTTCGTGTTCAGCCTGGATACATCT

GTGTCTACAGCCTATCTGCAGATCAGCTCTCTGAAGGCCGAAGATACAGCCGT

GTACTTCTGCGCCCGGGACTACTACGGCACCTACTTCTACGCCATGGACTACTG

GGGCCAGGGAACACTGGTGACAGTGTCTTCTGCCTCCACCAAGGGCCCATCGG

TCTTCCCCCTGGCACCCTCCTCCAAGAGCACCTCTGGGGGCACAGCGGCCCTGG

GCTGCCTGGTCAAGGACTACTTCCCCGAACCGGTGACGGTGTCGTGGAACTCA

GGCGCCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCACCCAG

ACCTACATCTGCAACGTGAATCACAAGCCCAGCAACACCAAGGTGGACAAGAA

AGTTGAGCCCAAATCTTGTGACAAAACTCACACATGCCCACCGTGCCCAGCAC

CTGAACTCCTGGGGGGACCGTCAGTCTTCCTCTTCCCCCCAAAACCCAAGGACA

CCCTCATGATCTCCCGGACCCCTGAGGTCACATGCGTGGTGGTGGACGTGAGCC

ACGAAGACCCTGAGGTCAAGTTCAACTGGTACGTGGACGGCGTGGAGGTGCAT

AATGCCAAGACAAAGCCGCGGGAGGAGCAGTACAACAGCACGTACCGTGTGG

TCAGCGTCCTCACCGTCCTGCACCAGGACTGGCTGAATGGCAAGGAGTACAAG

TGCAAGGTCTCCAACAAAGCCCTCCCAGCCCCCATCGAGAAAACCATCTCCAA

AGCCAAAGGGCAGCCCCGAGAACCACAGGTGTACACCCTGCCCCCATCCCGGG

AGGAGATGACCAAGAACCAGGTCAGCCTGACCTGCCTGGTCAAAGGCTTCTAT

CCCAGCGACATCGCCGTGGAGTGGGAGAGCAATGGGCAGCCGGAGAACAACT

ACAAGACCACGCCTCCCGTGCTGGACTCCGACGGCTCCTTCTTCCTCTACAGCA

AGCTCACCGTGGACAAGAGCAGGTGGCAGCAGGGGAACGTCTTCTCATGCTCC

GTGATGCATGAGGCTCTGCACAACCACTACACGCAGAAGAGCCTCTCCCTGTCT

CCGGGTAAATGATAGTTCGAATTCCTAGAAGACATGATAAGATACATTGATGA

GTTTGGACAAACCACAACTAGAATGCAGTGAAAAAAATGCTTTATTTGTGAAA

TTTGTGATGCTATTGCTTTATTTGTAACCATTATAAGCTGCAATAAACAAGTTA

ACAACAACAATTGCATTCATTTTATGTTTCAGGTTCAGGGGAGGTGTGGGA
```

PD1B1087, PD1B1092, PD1B1095 HC cDNA

SEQ ID NO: 162

```
TCTGATAAGAGTCAGAGGTAACTCCCGTTGCGGTGCTGTTAACGGTGGAGGGC

AGTGTAGTCTGAGCAGTACTCGTTGCTGCCGCGCGCCACCAGACATAATAG

CTGACAGACTAACAGACTGTTCCTTTCCATGGGTCTTTTCTGCAGTCACCGTCCT

TAGATCCACTAGTCCAGTGTGGTGAAGCTTGCCGCCACCATGGCTTGGGTGTGG

ACCTTGCTATTCCTGATGGCAGCTGCCCAAAGTATACAGGCCCAGGTGCAGCTG

GTGCAGTCTGGAAGCGAACTGAAGAAACCTGGAGCCTCTGTGAAAGTGTCTTG

TAAGGCCAGCGGCTACACCTTCACCGACTACAGCATGCACTGGGTGCGGCAGG

CCCCTGGACAGGGCCTGGAATGGATGGGCTGGATCAACATCGAGACCGGCTGG

CCCACCTACGCCCAGGGCTTTACCGGACGGTTCGTGTTCAGCCTGGATACATCT

GTGTCTACAGCCTATCTGCAGATCAGCTCTCTGAAGGCCGAAGATACAGCCGT
```

```
GTACTTCTGCGCCCGGGACTACTACGGCACCTACTTCTACGCCATGGACTACTG

GGGCCAGGGAACACTGGTGACAGTGTCTTCTGCCTCCACCAAGGGCCCATCGG

TCTTCCCCCTGGCACCCTCCTCCAAGAGCACCTCTGGGGGCACAGCGGCCCTGG

GCTGCCTGGTCAAGGACTACTTCCCCGAACCGGTGACGGTGTCGTGGAACTCA

GGCGCCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCACCCAG

ACCTACATCTGCAACGTGAATCACAAGCCCAGCAACACCAAGGTGGACAAGAA

AGTTGAGCCCAAATCTTGTGACAAAACTCACACATGCCCACCGTGCCCAGCAC

CTGAACTCCTGGGGGGACCGTCAGTCTTCCTCTTCCCCCCAAAACCCAAGGACA

CCCTCATGATCTCCCGGACCCCTGAGGTCACATGCGTGGTGGTGGACGTGAGCC

ACGAAGACCCTGAGGTCAAGTTCAACTGGTACGTGGACGGCGTGGAGGTGCAT

AATGCCAAGACAAAGCCGCGGGAGGAGCAGTACAACAGCACGTACCGTGTGG

TCAGCGTCCTCACCGTCCTGCACCAGGACTGGCTGAATGGCAAGGAGTACAAG

TGCAAGGTCTCCAACAAAGCCCTCCCAGCCCCCATCGAGAAAACCATCTCCAA

AGCCAAAGGGCAGCCCCGAGAACCACAGGTGTACACCCTGCCCCCATCCCGGG

AGGAGATGACCAAGAACCAGGTCAGCCTGACCTGCCTGGTCAAAGGCTTCTAT

CCCAGCGACATCGCCGTGGAGTGGGAGAGCAATGGGCAGCCGGAGAACAACT

ACAAGACCACGCCTCCCGTGCTGGACTCCGACGGCTCCTTCTTCCTCTACAGCA

AGCTCACCGTGGACAAGAGCAGGTGGCAGCAGGGGAACGTCTTCTCATGCTCC

GTGATGCATGAGGCTCTGCACAACCACTACACGCAGAAGAGCCTCTCCCTGTCT

CCGGGTAAATGATAGTTCGAATTCCTAGAAGACATGATAAGATACATTGATGA

GTTTGGACAAACCACAACTAGAATGCAGTGAAAAAAATGCTTTATTTGTGAAA

TTTGTGATGCTATTGCTTTATTTGTAACCATTATAAGCTGCAATAAACAAGTTA

ACAACAACAATTGCATTCATTTTATGTTTCAGGTTCAGGGGGAGGTGTGGGA

PD1B1088, PD1B1090, PD1B1091, PD1B1092 LC cDNA
                                              SEQ ID NO: 163
TCTGATAAGAGTCAGAGGTAACTCCCGTTGCGGTGCTGTTAACGGTGGAGGGC

AGTGTAGTCTGAGCAGTACTCGTTGCTGCCGCGCGCCACCAGACATAATAG

CTGACAGACTAACAGACTGTTCCTTTCCATGGGTCTTTTCTGCAGTCACCGTCCT

TAGATCCACTAGTCCAGTGTGGTGAAGCTTGCCGCCACCATGGCTTGGGTGTGG

ACCTTGCTATTCCTGATGGCGGCCGCCCAAAGTATACAGGCCGAGATCGTGCTG

ACACAGTCTCCTGCCACACTGTCTCTGTCTCCTGGAGAACGGGCCACACTGAGC

TGCACCGCCAGCAGCAGCTTCAGCAGCAGCTACCTGCACTGGTACCAGCAGAA

ACCTGGACTGGCCCCTCGGCTGCTGATCTACAGCACCAGCAACCTGGCCAGCG

GCATCCCTGATCGGTTTTCTGGCAGCGGATCTGGCACAGATTACACACTGACCA

TCAGCCGGCTGGAACCTGAGGATTTTGCCGTGTACTACTGCCACCAGTACCACC

GGAGCCCCCTGACCTTCGGCCAGGGAACAAAGCTGGAAATCAAGCGTACGGTG

GCTGCACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGTCAC

AGAGCAGGACAGCAAGGACAGCACCTACAGCCTCAGCAGCACCCTGACGCTG
```

```
                 -continued
AGCAAAGCAGACTACGAGAAACACAAAGTCTACGCCTGCGAAGTCACCCATCA

GGGCCTGAGCTCGCCCGTCACAAAGAGCTTCAACAGGGGAGAGTGTTAGTGAT

TCGAATTCCTAGAAGACATGATAAGATACATTGATGAGTTTGGACAAACCACA

ACTAGAATGCAGTGAAAAAAATGCTTTATTTGTGAAATTTGTGATGCTATTGCT

TTATTTGTAACCATTATAAGCTGCAATAAACAAGTTAACAACAACAATTGCATT

CATTTTATGTTTCAGGTTCAGGGGAGGTGTGGGA

PD1B1089, PD1B1093, PD1B1094, PD1B1095 LC cDNA
                                              SEQ ID NO: 164
TCTGATAAGAGTCAGAGGTAACTCCCGTTGCGGTGCTGTTAACGGTGGAGGGC

AGTGTAGTCTGAGCAGTACTCGTTGCTGCCGCGCGCGCCACCAGACATAATAG

CTGACAGACTAACAGACTGTTCCTTTCCATGGGTCTTTTCTGCAGTCACCGTCCT

TAGATCCACTAGTCCAGTGTGGTGAAGCTTGCCGCCACCATGGCTTGGGTGTGG

ACCTTGCTATTCCTGATGGCGGCCGCCCAAAGTATACAGGCCGAGATCGTGCTG

ACACAGTCTCCTGCCACACTGTCTCTGTCTCCTGGAGAACGGGCCACACTGAGC

TGCACCGCCAGCAGCAGCGTGCCAAGCAGCTACCTGCACTGGTACCAGCAGAA

ACCTGGACTGGCCCCTCGGCTGCTGATCTACAGCACCAGCAACCTGGCCAGCG

GCATCCCTGATCGGTTTTCTGGCAGCGGATCTGGCACAGATTACACACTGACCA

TCAGCCGGCTGGAACCTGAGGATTTTGCCGTGTACTACTGCCACCAGTACCACC

GGAGCCCCCTGACCTTCGGCCAGGGAACAAAGCTGGAAATCAAGCGTACGGTG

GCTGCACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAAAGTA

CAGTGGAAGGTGGATAACGCCCTCCAATCGGGTAACTCCCAGGAGAGTGTCAC

AGAGCAGGACAGCAAGGACAGCACCTACAGCCTCAGCAGCACCCTGACGCTG

AGCAAAGCAGACTACGAGAAACACAAAGTCTACGCCTGCGAAGTCACCCATCA

GGGCCTGAGCTCGCCCGTCACAAAGAGCTTCAACAGGGGAGAGTGTTAGTGAT

TCGAATTCCTAGAAGACATGATAAGATACATTGATGAGTTTGGACAAACCACA

ACTAGAATGCAGTGAAAAAAATGCTTTATTTGTGAAATTTGTGATGCTATTGCT

TTATTTGTAACCATTATAAGCTGCAATAAACAAGTTAACAACAACAATTGCATT

CATTTTATGTTTCAGGTTCAGGGGAGGTGTGGGA
```

Affinity of the antibodies to human and cyno PD-1 was measured using SPR as described in Example 1. The antibodies bound human PD-1 with a $K_D$ ranging between $1\times10^{-8}$ M to $10\times10^{-10}$ M (Table 28) and to cyno PD-1 with a $K_D$ ranging between $7\times10^{-8}$ M to $1\times10^{-9}$ M (Table 26). The affinities of majority of the affinity matured PD1B878 variants improved about 100-fold when compared to the parental antibody.

TABLE 28

| mAb | ka (1/Ms) | kd (1/s) | KD (M) |
|---|---|---|---|
| PD1B1085 | 1.56E+05 | 1.42E−04 | 9.11E−10 |
| PD1B1086 | 1.24E+05 | 3.94E−04 | 3.19E−09 |
| PD1B1087 | 1.66E+05 | 2.39E−04 | 1.44E−09 |
| PD1B1088 | 3.13E+04 | 3.41E−04 | 1.09E−08 |
| PD1B1089 | 5.86E+04 | 4.74E−04 | 8.09E−09 |
| PD1B1090 | 1.06E+05 | 2.37E−05 | 2.23E−10 |
| PD1B1091 | 7.77E+04 | 6.44E−05 | 8.30E−10 |
| PD1B1092 | 1.40E+05 | 3.00E−05 | 2.14E−10 |
| PD1B1093 | 1.25E+05 | 4.36E−05 | 3.49E−10 |

TABLE 28-continued

| mAb | ka (1/Ms) | kd (1/s) | KD (M) |
|---|---|---|---|
| PD1B1094 | 1.05E+05 | 9.16E−05 | 8.71E−10 |
| PD1B1095 | 1.51E+05 | 7.12E−05 | 4.71E−10 |

TABLE 29

| mAb | ka (1/Ms) | kd (1/s) | KD (M) |
|---|---|---|---|
| PD1B1085 | 2.00E+05 | 1.29E−03 | 6.45E−09 |
| PD1B1086 | 1.71E+05 | 5.44E−03 | 3.18E−08 |
| PD1B1087 | 2.12E+05 | 2.47E−03 | 1.16E−08 |
| PD1B1088 | 6.61E+04 | 4.79E−03 | 7.24E−08 |
| PD1B1089 | 9.32E+04 | 8.39E−03 | 9.00E−08 |
| PD1B1090 | 1.30E+05 | 1.85E−04 | 1.43E−09 |
| PD1B1091 | 9.91E+04 | 9.24E−04 | 9.32E−09 |
| PD1B1092 | 1.29E+05 | 4.11E−04 | 3.18E−09 |

TABLE 29-continued

| mAb | ka (1/Ms) | kd (1/s) | KD (M) |
| --- | --- | --- | --- |
| PD1B1093 | 1.69E+05 | 3.68E−04 | 2.18E−09 |
| PD1B1094 | 1.35E+05 | 1.62E−03 | 1.20E−08 |
| PD1B1095 | 1.85E+05 | 7.81E−04 | 4.23E−09 |

PD1B1086, PD1B1090 and PD1B1094 were characterized for their ability to inhibit activated T cells in the CMV-specific recall assay (CMV-PBMC assay described in Example 1). Table 30 shows the mean percentage inhibition across two donors in one experiment. All tested antibodies inhibited CMV-specific recall assay by a degree of 70% or more.

TABLE 30

|  | PD1B1086 | PD1B1090 | PD1B1094 | IgG1 |
| --- | --- | --- | --- | --- |
| Mean % | 72.7 | 74.8 | 77.9 | 6.0 |

Example 9

PD-1 Agonistic Antibodies Selectively Target Chronically Activated Memory T Cells PD-1 was found mainly expressed on memory T cells (CD45RO$^+$ cells) and not on naïve T cells, and the expression was found upregulated upon T cell activation. PD-1 expression increased on memory T cells stimulated with CMV peptides (FIG. 8A).

Figure 8B:
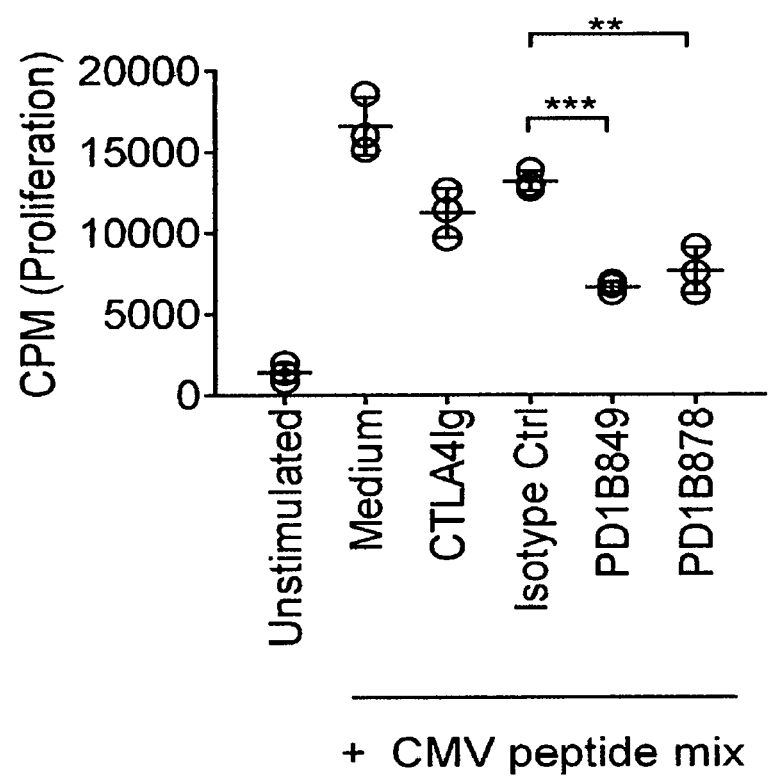
FIG. 8B shows that PD1B878 and PD1B849 inhibited activation of CMV-specific T cells in a CMV-specific recall assay. The Figure shows the mean percent (%) inhibition and STDEV of T cell proliferation in the assay.

Antibodies PD1B849 and PD1B878 were tested for their ability to inhibit activated memory CD4$^+$ or CD8$^+$ T cell proliferation utilizing CMV activated PBMCs. Both PD1B849 and PD1B878 inhibited proliferation of CMV-specific activated PBMCs in the CMV-PBMC recall assay (FIG. 8B).

Example 10

PD-1 Agonistic Antibodies Deplete Activated but not Resting Memory T Cells by ADCC PD1B849 and PD1B878 were tested for their ability to mediate ADCC of activated memory T cells or resting memory T cells using NK cells or PBMCs as effector cells. Activated memory T cells were identified to have higher expression of PD-1 when compared to resting memory T cells. The experiment was conducted according to protocol described in Example 1. PD1B849 and PD1B878 were expressed in two separate CHO cell lines, the one producing antibodies with normal CHO antibody glycosylation profile and the other producing antibodies having reduced carbohydrate fucosyl content (e.g. low fucose (LF) cell line). Antibodies expressed in the low fucose cell line had a fucosyl content of about 1-15%.

Figure 9A:
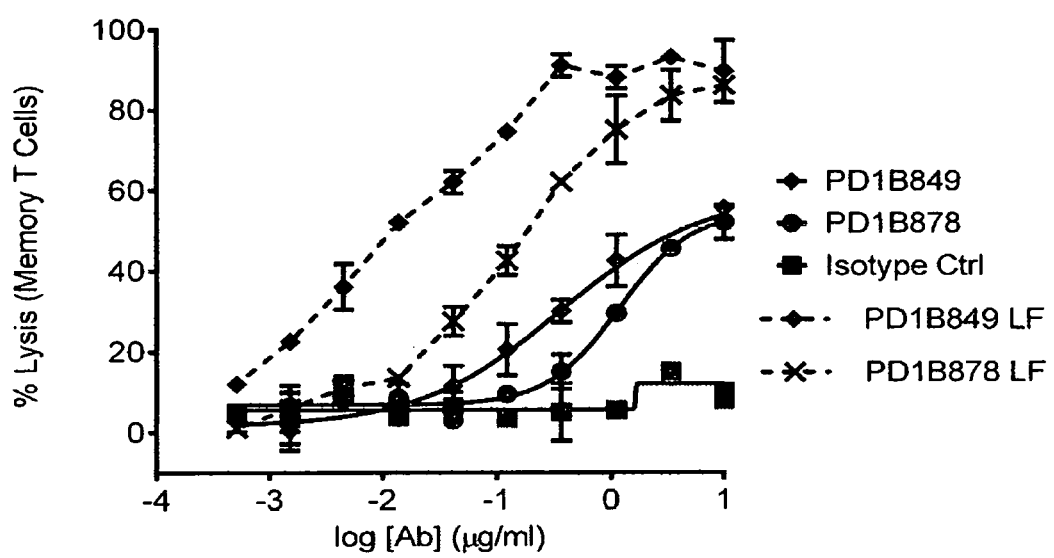
FIG. 9A shows that PD1B849 and PD1B878 elicited ADCC of activated memory T cells in the presence of NK cells as effector cells. Low fucose (LF) versions of the antibodies (PD1B849-LF and PD1B878-LF) demonstrated enhanced ADCC activity.
Figure 9B:
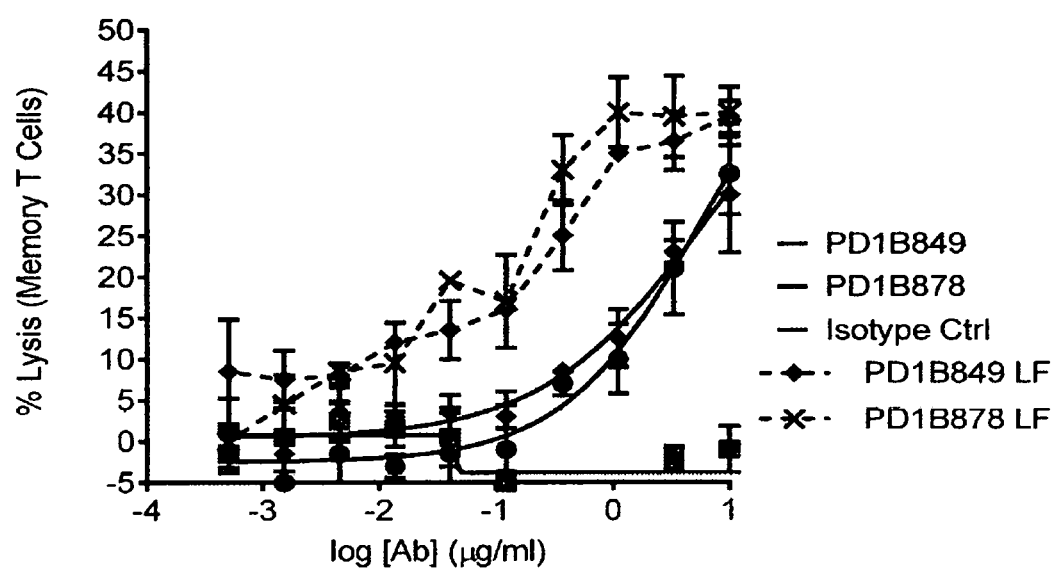
FIG. 9B shows that PD1B849 and PD1B878 elicited ADCC of activated memory T cells in the presence of PBMCs as effector cells. Low fucose (LF) versions of the antibodies (PD1B849-LF and PD1B878-LF) demonstrated enhanced ADCC activity.
Figure 10A:
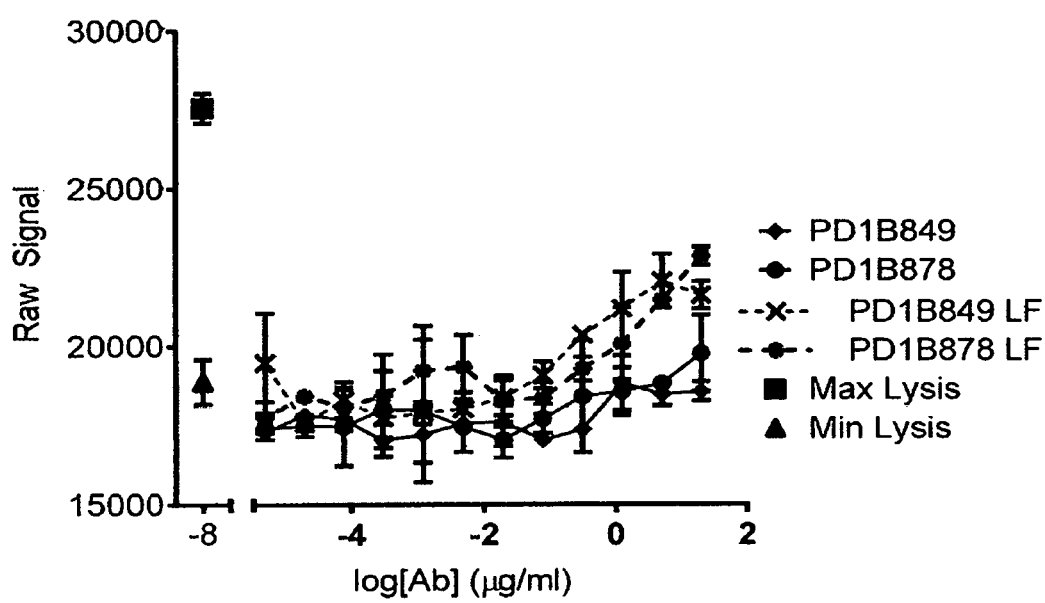
FIG. 10A shows lack of PD1B849 and PD1B878 mediated ADCC in resting memory T cells which express low levels of PD1 in the presence of NK cells as effector cells. Low fucose (LF) versions of the antibodies (PD1B849-LF and PD1B878-LF) mediated some ADCC.
Figure 10B:
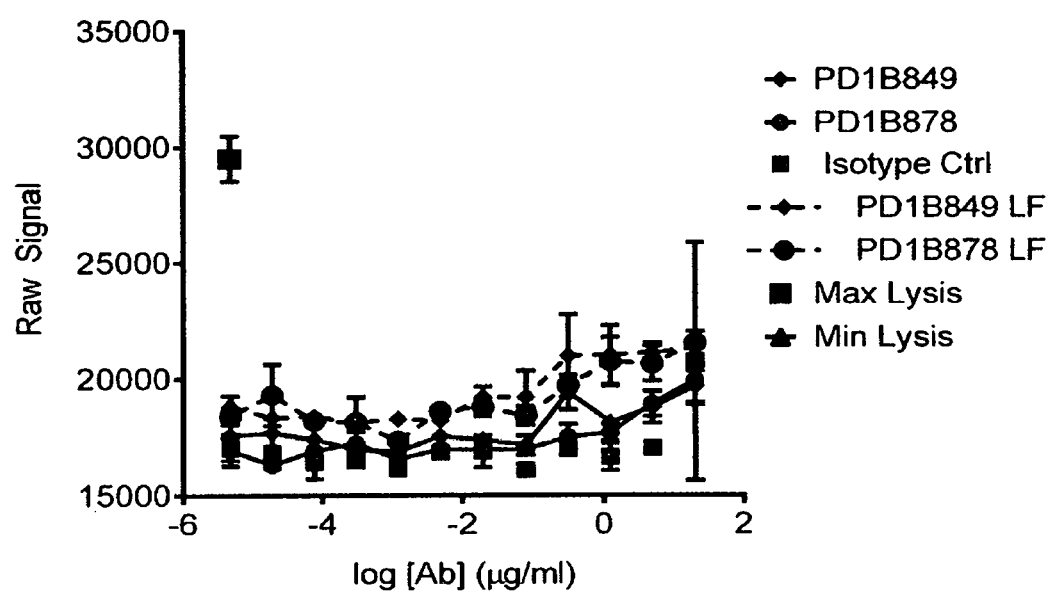
FIG. 10B shows lack of PD1B849 and PD1B878 mediated ADCC in resting memory T cells which express low levels of PD1 in the presence of PBMCs as effector cells. Low fucose (LF) versions of the antibodies (PD1B849-LF and PD1B878-LF) mediated some ADCC.

PD1B849 and PD1B878 elicited ADCC of activated memory T cells both in the presence of NK (FIG. 9A, left panel) cells and PBMC (FIG. 9A, right panel) effector cells. Antibodies with low fucose content (PD1B849-LF and PD1B878-LF) demonstrated stronger ADCC activity towards memory T cells. PD1B849 and PD1B878 were unable to elicit detectable ADCC in resting memory T Cells which express low levels of PD-1 either in the presence of NK cells (FIG. 10A, left panel) or PBMCs (FIG. 10B, right panel) effector cells. PD1B849-LF and PD1B878-LF triggered low level ADCC in the presence of either NK cells or PBMCs.

Example 11

PD-1 Agonistic Antibodies do not Elicit CDC

Figure 11:
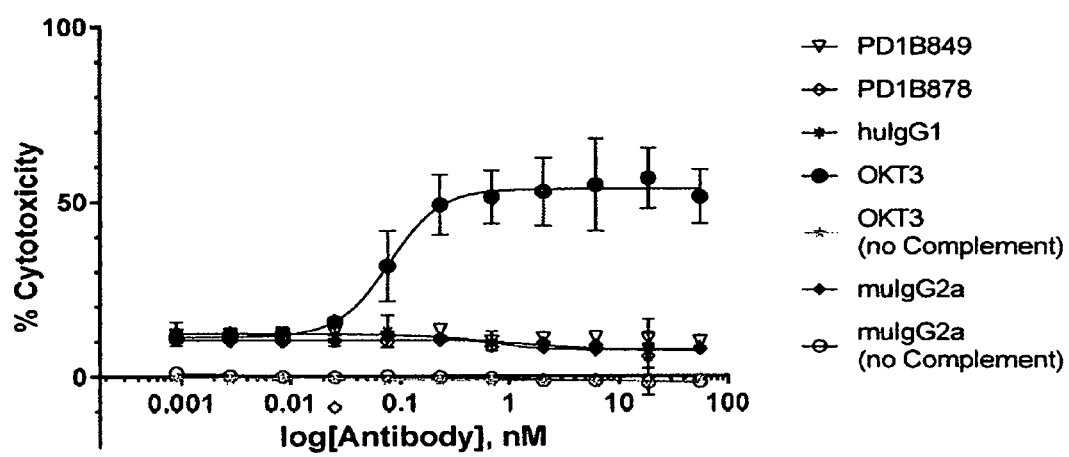
FIG. 11 shows that PD1B849 and PD1B878 did not mediate measurable CDC of activated T cells using rabbit complement. OKT3: a mouse anti-human CD3 antibody (positive control); huIgG1: isotype control, muIgG2a: isotype control.

PD1B849 and PD1B878 were tested for their ability to mediate CDC of activated pan T cells using added rabbit complement. Activated T cells have higher expression of PD-1 when compared to resting T cells. The experiment was conducted according to protocol described in Example 1. PD1B849 and PD1B878 did not elicit CDC of activated T cells at the concentrations tested (FIG. 11). The positive control OKT3 demonstrated CDC activity towards activated T cells in the presence, but not absence of complement.

Example 12

Affinity-Matured Antibodies do not Block PD-L1 Binding to PD-1

Figure 12:
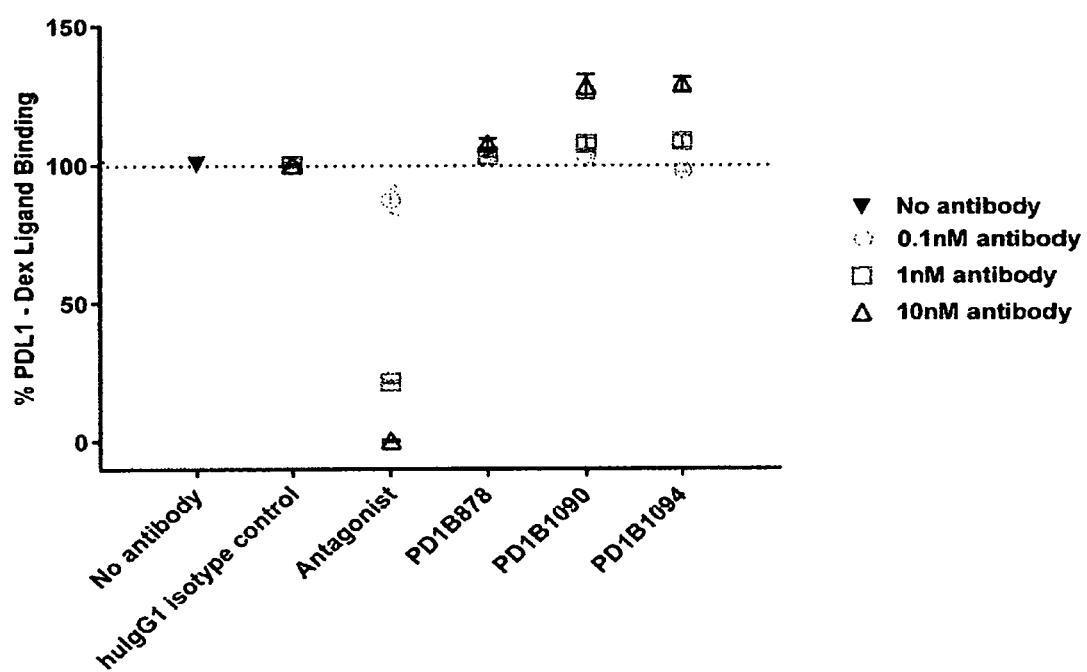
FIG. 12 shows that PD1B878, PD1B1090 and PD1B1094 did not block PD-L1 binding to PD1 on cells.

Select antibodies were tested for their ability to block binding of dextramerized PD-L1-Fc to PD-1 expressing Jurkat cells. The experiment was conducted according to protocol described below. PD1B878, PD1B1090 and PD1B1094 did not block the binding of PD-L1 at the concentrations tested (FIG. 12). As positive control, a known antagonist antibody was shown to compete with PD-L1 for binding to PD-1 in a dose dependent manner.

Method: Biotinylated PD-L1-Fc (Acro Biosystems) and SA & APC conjugated Dextramers (Immudex) were prepared at 4× concentration and were mixed at a ratio of 100 nM:10 nM in staining buffer. Biotinylated IgG1-Fc with Dextramers and Dextramers with media alone mixtures were prepared in the same manner for negative or non-specific binding controls. This mixture was covered with foil and incubated on ice for one hour while preparing the rest of the experiment. Serial dilutions of test antibodies were prepared in stain buffer at a 2× concentration of 20 nM, 2 nM and 0.2 nM. Jurkat cells over expressing PD-1 were harvested on the day of the assay and washed once with stain buffer (BD Pharmingen) by spinning the cells at 300 g for 5 minutes at 4° C. Cells were counted, checked for viability and were resuspended at 2×10$^6$ cell/mL in stain buffer. Cells were added at 25 uL/well (50000 cells/well) to U-bottom 96-well assay plate followed by the addition of prepared test antibodies at 50 µL/well. The cells with antibodies were incubated for 15 minutes on ice. Pre-mixed complexes of biotinylated PD-L1-Fc: Dextramer, biotinylated IgG1-Fc: Dextramer and Dextramers: buffer were added at 25 µL/well. This mixture of cells, antibodies and PD-L1 bound to Dextramers was incubated for 1 hour on ice and covered with foil.

Cells were washed two times by adding 150 µL stain buffer, centrifuging at 300 g for 5 minutes to pellet cells and flicking plates to remove supernatants. Cell pellet after final wash was resuspended in 40 µL of IntelliCyt running buffer (BD stain buffer supplemented with 1 mM EDTA and 0.1% Pluronic acid) containing 1:1000 dilution of Sytox green live/dead cell viability stain (ThermoFisher). Final antibody concentrations in the assay were at 10 nM, 1 nM and 0.1 nM. Final biotinylated PD-L1-Fc ligand protein concentration was at 25 nM. Final Dextramer concentration was at 2.5 nM.

Plates were run on iQue Screener (IntelliCyt). Briefly cells were gated on FCS v. SCS to eliminate debris. Singlets were gated on SCS-A vs SCS-H and from singlet population, live cells were gated on low BL1 channel for negative with Sytox green viability stain. Percent positive live cells binding to PD-L1-Fc-Dextramers was assessed by Geomeans in RL1/APC channel and compared to negative control, Fc-Dex alone binding. Using advanced metrics in ForeCyt (software program from IntelliCyt), PD-L1 positive population was calculated as % of live population. Percent specific PD-L1 binding was calculated as follows=(% positive with mAb−% positive with IgG1-Fc biotin dextramer)/(% positive with Isotype control−% positive with IgG1-Fc biotin dextramer)*100. Final results are tabulated in excel and graphed in prism showing % PD-L1 ligand binding in the presence of anti PD-1 mAbs.

Example 13

PD-1 Agonistic Antibodies are Effective in a Mouse Model of Graft vs. Host Disease (GvHD)

To study the effect of PD-1 agonist mAbs on pathogenic T cells in vivo, a xenogeneic Graft-versus-Host Disease (Xeno-GVHD) model was developed by adoptively transferring human peripheral blood mononuclear cells (PBMC) into immunocompromised NOD-scid IL-2Rγ$^{null}$ (NSG) mice. Female NSG mice (7-9 weeks of age) were obtained from Jackson Labs. The mice were quarantined in the vivarium facility for one week before use. Frozen human PBMCs isolated from buffy coats were obtained from All-Cells, Alameda, Calif. Before injection, frozen cells were quickly thawed at 37° C. in water bath and washed 3 times with sterile phosphate buffered saline (PBS) by centrifugation at 500 g for 5 min at room temperature. The cells were suspended in cold PBS to obtain a final cell concentration of $50 \times 10^6$/mL.

Animals were randomized by body weight and divided into various treatment groups (N=10/group). Following randomization conscious and freely moving mice received total body irradiation of 100 Rad (1Gy) using Gammacell® 3000 Elan Irradiator (9.72 Gy/minute). Mice were placed back into their home cages.

Each mouse received $25 \times 10^6$ human PBMCs in a volume of 500 µl intraperitoneally. Clinical scores and body weight of each animal was recorded daily according to Table 31. Mice that lost ≥20% of their body weight were sacrificed and their clinical score at end-point was recorded in accordance with institutional IACUC guidelines. All animals were euthanized on day 21. Spleens were collected for FACS analysis. Skin and colon tissue was collected for histological analyses.

TABLE 31

| Description | Clinical Score |
|---|---|
| Normal Alert and Reactive | 0 |
| Ruffled Haircoat, Decreased activity, Ocular Discharge | 1 |
| Hunched posture, Moderate Hypothermia or Hyperthermia, labored breathing during prodding | 2 |
| Labored Breathing during rest, Ataxia, tremor, Hypothermia or Hyperthermia | 3 |
| Loss of ability to ambulate with gentle prodding, unconscious | 4 |
| Death | 5 |

Mice were injected intraperitoneally with 10 mg/kg PD1B505, PD1B506, PD1B849 and PD1B878 mAbs which were cloned as chimeric mIgG2a antibodies, as well as PD-1 antagonist mAb (PD1B786 on mouse effector silent Fc), on a Q4d/Q3d regimen (dosing on days 0, 4, 7, 11, 14, and 18). CTLA-4-Ig, used as a control, was dosed on a Q3d dosing regimen (Day 0, 3, 6, 9, 12, 15 and 18) 10 mg/kg intraperitoneally.

At study termination, spleens were removed to cold RPMI1640 medium. After crushing spleens through a 70 µM filter and pelleting cells by centrifugation at 1200 rpm for 5 minutes at 4° C., red blood cells were lysed in ACK lysing buffer (Lonza) on ice for 5 minutes, and washed multiple times in in FACS buffer (PBS/0.5% BSA/2 mM EDTA). Viability of splenocytes was assessed by staining cells with ef506 viability dye (eBioscience) according to the manufacturer's instructions. Splenocytes were incubated with human and mouse Fc block (BD Biosciences) for 15 min on ice, then stained with optimal concentrations of fluorochrome conjugated mAbs ($1 \times 10^6$ cells in 100 µl Brilliant Stain buffer) in U shaped microtiter plates at 4° C. for 30 minutes, and fixed with Fixation buffer (BD Biosciences). Count Brite beads (Thermofisher) were added to each sample. FMO (fluorescence minus one) controls were prepared as negative controls for each fluorochrome. Samples were analyzed on an LSR11 instrument (BD Biosciences). The following mAbs were used for regulatory T cell analysis, anti-hCD45 peridinin chlorophyll alpha protein (PCP, clone 2D1), anti-FoxP3 allophycocyanin (APC, clone pCH101), anti-hCD3 allophycocyanin-cyanine 7 (APC-Cy7, clone HIT3a), anti-hCD4 Brilliant Violet 605 (BV605, clone OKT4), and anti-hCD25 Brilliant violet 650 (BV650, clone M-A251). Regulatory T cells were defined as hCD45+ hCD3+ hCD4+, Foxp3+ CD25+.

Figure 13A:
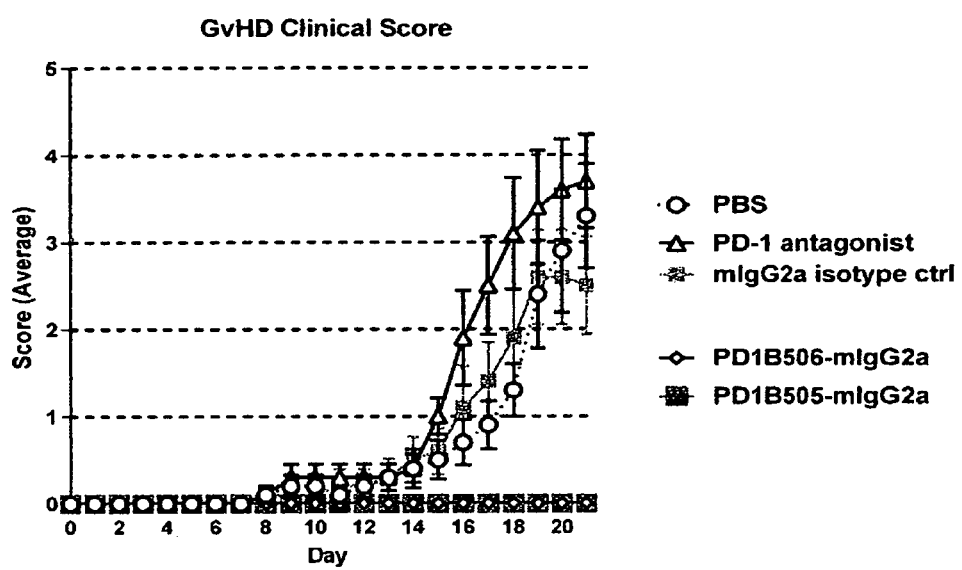
FIG. 13A shows that PD1B505-mIgG2a and PD1B506-mIgG2a prevented disease development in the mouse model of graft vs host disease (GvHD). Antibodies were dosed at 10 mg/kg i.p. on Days 0, 4, 7, 11, 14 & 18 and clinical score was recorded over time.
Figure 13B:
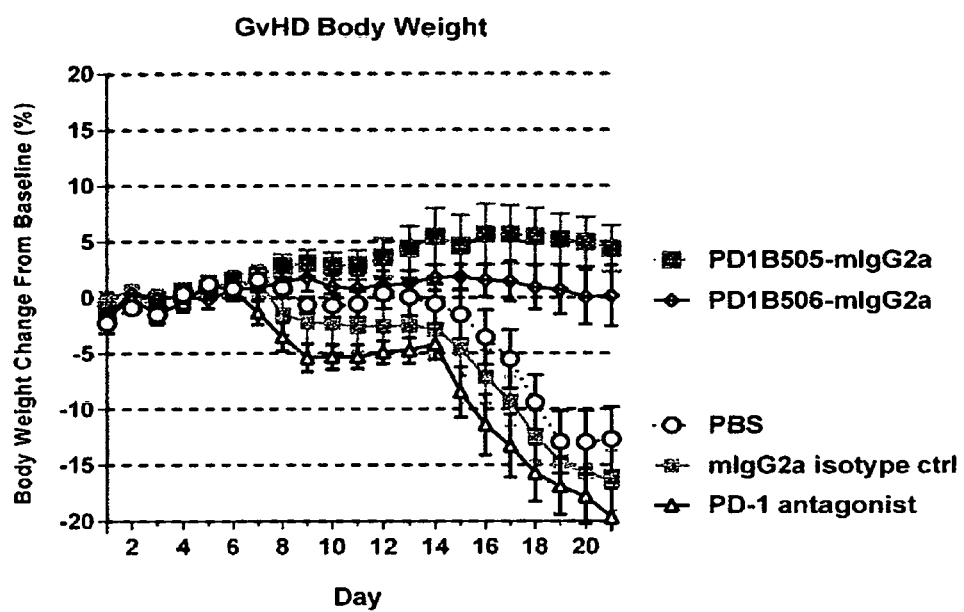
FIG. 13B shows that PD1B505-mIgG2a and PD1B506-mIgG2a mAbs (mIgG2a) prevented weight loss in the mouse model of GvHD. Antibodies were dosed at 10 mg/kg i.p. on Days 0, 4, 7, 11, 14 & 18.
Figure 14A:
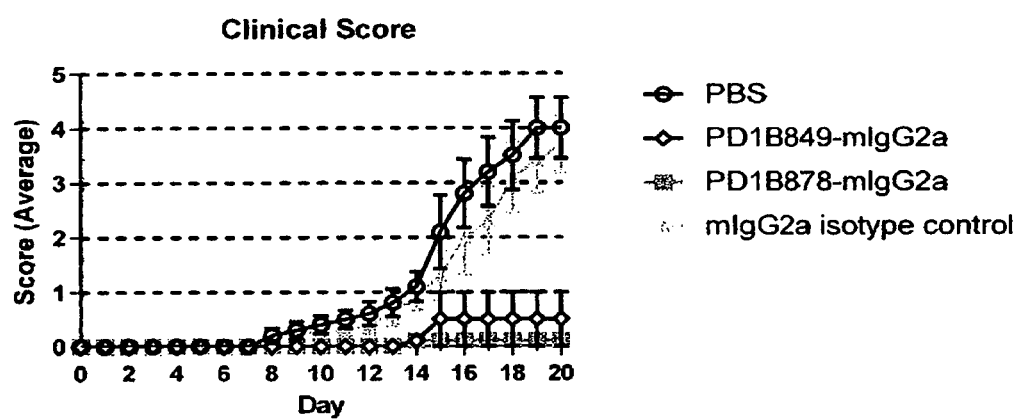
FIG. 14A shows that PD1B849-mIgG2a and PD1B878-mIgG2a prevented disease development in the mouse model of graft vs host disease (GvHD). Antibodies were dosed at 10 mg/kg i.p. on Days 0, 4, 7, 11, 14 & 18 and clinical score was recorded over time.
Figure 14B:
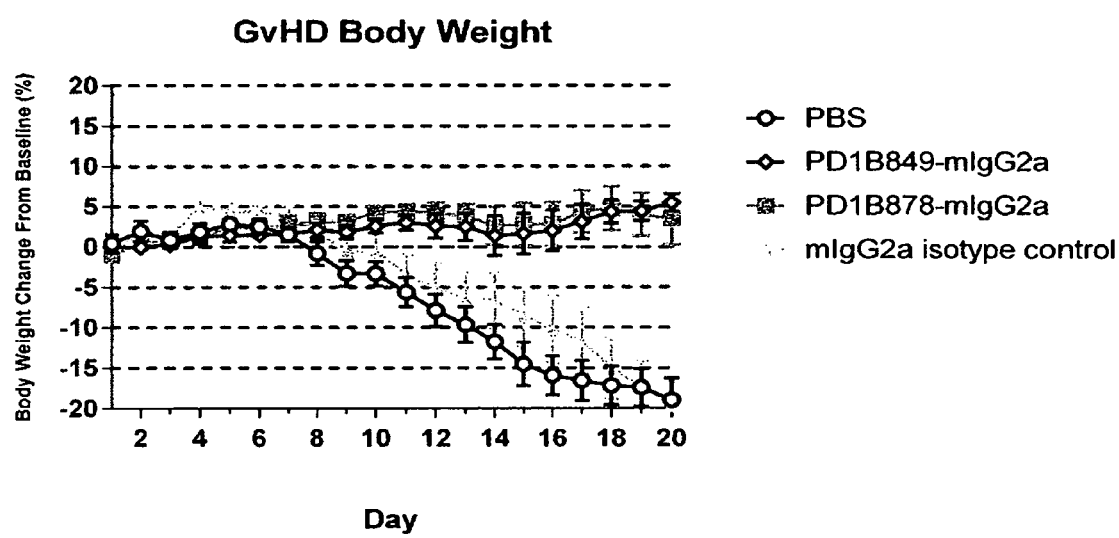
FIG. 14B shows that PD1B849-mIgG2a and PD1B878-mIgG2a prevented weight loss in the mouse model of GvHD. Antibodies were dosed at 10 mg/kg i.p. on Days 0, 4, 7, 11, 14 & 18.
Figure 15:
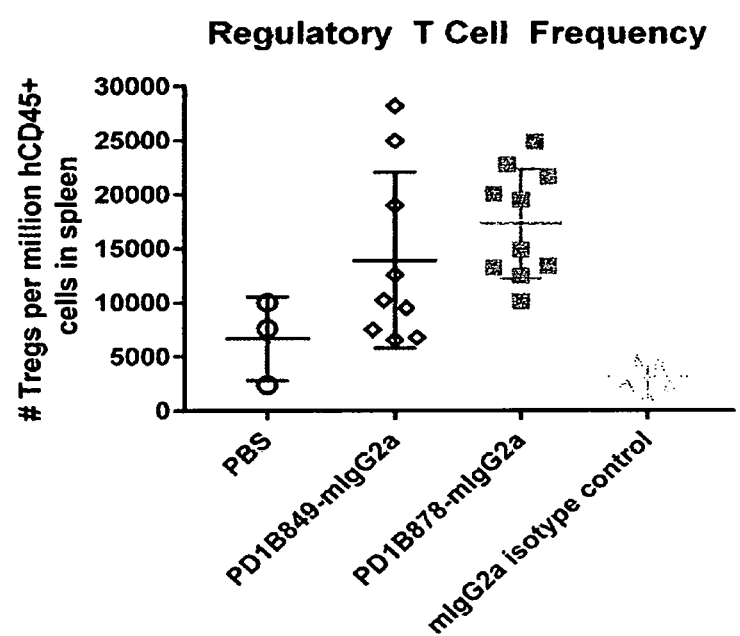
FIG. 15 shows that PD1B849-mIgG2a and PD1B878-mIgG2a increased the frequency of regulatory T cells (Tregs) in spleens in the mouse model of GvHD.

FIG. 13A shows that treatment with PD1B505-mIgG2a and PD1B506-mIgG2a prevented disease development in the mouse model of GvHD. FIG. 13B shows that treatment with PD1B505-mIgG2a and PD1B506-mIgG2a prevented weight loss in the mouse model of GvHD. FIG. 14A shows that treatment with PD1B849-mIgG2a and PD1B878-mIgG2a prevented disease development in the mouse model of GvHD. FIG. 14B shows that treatment with PD1B849-mIgG2a and PD1B878-mIgG2a prevented weight loss in the mouse model of GvHD. Inhibition of weight loss and clinical score was associated with an increase in regulatory T cells in the spleen. FIG. 15 shows the Treg frequency in spleen of animals treated with PD1B849-mIgG2a or PD1B878-mIgG2a.

Example 14

PD-1 Agonistic Antibodies Deplete T Follicular Helper (TFH) and T Peripheral Helper ($T_{PH}$) Cells Human PBMCs were retrieved from liquid nitrogen cryostorage and thawed rapidly in 37° C. water bath until just thawed. Contents of vial were transferred to a sterile 50 ml conical tube (separate tubes for each donor used) and complete RPMI media (10% FBS, 1× Penicillin/streptomycin, 1× sodium pyruvate) was added to each tube drop-wise to a total volume of 15 ml. Cells were centrifuged at 250×g for 10 min at RT then supernatant was discarded and cells were resuspended in 5-10 ml of complete media and counted using trypan blue exclusion. Cells were resuspended at $2.5 \times 10^6$ cells/ml and plated at $2.5 \times 10^5$ cells/well (=100 µl/well) in triplicate in a 96-well sterile U-bottom polystyrene plate. PD-1 mAbs or human IgG1 isotype control were diluted to 4× final concentrations and 50 µl/well were added to appropriate wells. After addition of antibodies, normal human serum was added to a final concentration of 5%. Total volume in each well was 200 µl and cells were incubated for 96 hours at 37° C., 5% $CO_2$. In addition to samples, several wells of extra cells were plated, received 5% human serum, and were incubated alongside treated samples to be used as flow cytometry staining controls.

After incubation, plates were centrifuged at 350×g for 5 min and supernatants were vacuumed off. Cells were resuspended in 200 µl PBS and replicate wells were pooled then transferred to a new 96-well U-bottom plate to stain for flow cytometry. Pooled cells were centrifuged at 350×g for 5 min, supernatants vacuumed off and fluorescent antibody cocktail was added to each sample well (see table below for antibodies used). Additional cells saved for controls were stained with FMO cocktails for critical markers such as PD-1, CXCR5, ICOS, among others, to be used in analysis for defining gates. Cells were stained for 25 min in the dark at RT then centrifuged fat 350×g for 5 min. Cells were washed twice in 200 µl PBS then 100 µl of 4% paraformaldehyde was added to each well to fix the cells. Cells were fixed for 10 min in the dark at 4° C. then washed once with PBS+1% BSA before resuspending in 200 µl PBS+1% BSA. Counting beads (Invitrogen) were added at 5 µl/well (5000 beads) for each sample prior to acquiring samples on the BD LSRII flow cytometer. Flow cytometry data was analyzed using FlowJo software. Sample counts were normalized to bead counts as such: # cells in sample=(# cells counted*5000 beads added)/(# beads counted). Samples were normalized to huIgG1 isotype control as such: (bead-normalized cell counts "sample"/bead-normalized cell counts "isotype")*100 and represented as a percentage (%). Data was graphed using GraphPad Prism v7.

During analysis, the following cell populations were described:

T follicular helper (Tfh): live, CD19−CD56−/CD4+ CD45RO+/HLADR+/CXCR5+/ICOS+PD1+;

T peripheral helper (Tph): live, CD19−CD56−/CD4+ CD45RO+/HLADR+/CXCR5−/ICOS+PD1+;

Combination Tfh/Tph population: live, CD19−CD56−/ CD4+CD45RO+/HLADR+/ICOS+PD1+.

Figure 16:
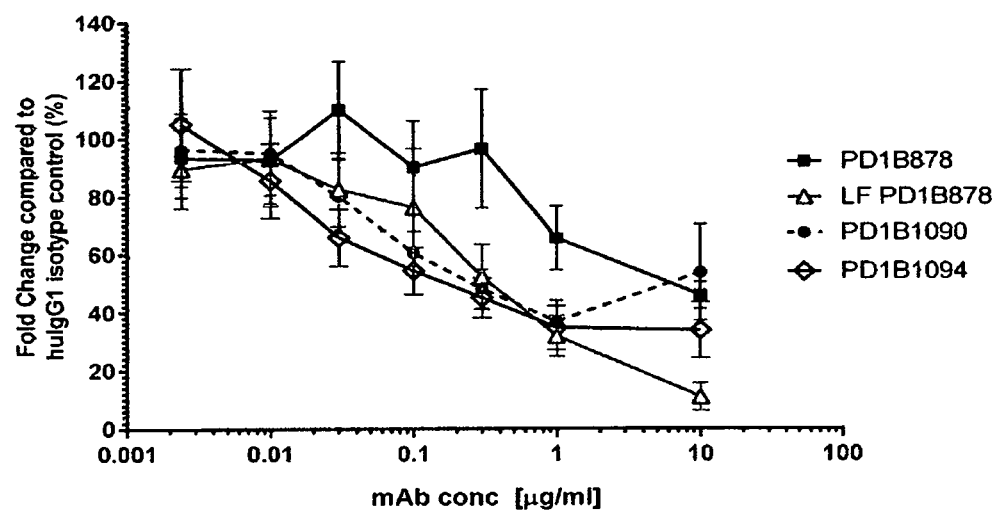
FIG. 16 shows that select anti-PD1 antibodies deplete $T_{FH}/T_{PH}$ populations. LF: low fucose.

FIG. 16 shows the dose response curve of antibody-mediated depletion of the combined $T_{HF}/T_{PH}$ population by PD1B878, PD1B878-FL (low fucose), PD1B1090 and PD1B1094. The data was represented as mean % fold change in the number of $T_{FH}/T_{PH}$ cells from isotype control using n=8 healthy human donors (n=7 for PD1B1090). PD1B878-FL were most effective in depleting the $T_{FH}/T_{PH}$ population.

---

We claim:

1. An isolated antibody that specifically binds PD-1 or an antigen binding fragment thereof, comprising a heavy chain complementarity determining region 1 (HCDR1), a HCDR2, a HCDR3, a light chain complementarity determining region 1 (LCDR1), a LCDR2 and a LCDR3 of SEQ ID NOs: 2, 165, 4, 166, 6 and 7, respectively.

2. The antibody or the antigen binding fragment thereof of claim 1, wherein the antibody or the antigen binding fragment thereof has one, two, three, four or five of the following properties:
   a) does not block PD-L1 binding to PD-1; wherein lack of blocking is measured by inability of the antibody to inhibit clustering of PD-L1 expressing and PD-1 expressing cells as described in Example 1;
   b) binds PD-1 with an equilibrium dissociation constant ($K_D$) of about $5 \times 10^{-8}$ M or less, wherein the $K_D$ is measured using a ProteOn XPR36 system at +25° C.;
   c) binds PD-1 with an association constant (ka) of about $3 \times 10^4$ l/Ms or more, wherein the ka is measured using a ProteOn XPR36 system at +25° C.;
   d) binds PD-1 with a dissociation constant (kd) of about $3 \times 10^{-3}$ l/s or less, wherein the kd is measured using a ProteOn XPR36 system at +25° C.; or
   e) inhibits proliferation of antigen specific T cells; wherein proliferation is assessed in a CMV-PBMC assay measured by inhibition of cell proliferation upon treatment of CMV-reactive donors' PBMC with CMV peptide mix.

3. The antibody or the antigen binding fragment thereof of claim 2, comprising the HCDR2 of SEQ ID NOs: 3, 145, 146 or 147 and/or the LCDR1 of SEQ ID NOs: 5, 148 or 149.

4. The antibody or the antigen binding fragment thereof of claim 3, comprising the HCDR1, the HCDR2, the HCDR3, the LCDR1, the LCDR2 and the LCDR3 of
   a) SEQ ID NOs: 2, 3, 4, 5, 6 and 7, respectively;
   b) SEQ ID NOs: 2, 145, 4, 5, 6, and 7, respectively;
   c) SEQ ID NOs: 2, 146, 4, 5, 6, and 7, respectively;
   d) SEQ ID NOs: 2, 147, 4, 5, 6, and 7, respectively;
   e) SEQ ID NOs: 2, 3, 4, 148, 6 and 7, respectively;
   f) SEQ ID NOs: 2, 3, 4, 149, 6 and 7, respectively;
   g) SEQ ID NOs: 2, 145, 4, 148, 6 and 7, respectively;
   h) SEQ ID NOs: 2, 146, 4, 148, 6 and 7, respectively;
   i) SEQ ID NOs: 2, 147, 4, 148, 6 and 7, respectively;
   j) SEQ ID NOs: 2, 145, 4, 149, 6 and 7, respectively;
   k) SEQ ID NOs: 2, 146, 4, 149, 6 and 7, respectively; or
   l) SEQ ID NOs: 2, 147, 4, 149, 6 and 7, respectively.

5. The antibody or the antigen binding fragment thereof of claim 4, comprising
   a) a heavy chain variable region (VH) framework derived from IGHV7-4-1*1 (SEQ ID NO: 125);
   b) a light chain variable region (VL) framework derived from IGKV3D-20*1 (SEQ ID NO: 126); or
   c) the VH framework derived from IGHV7-4-1*1 (SEQ ID NO: 125) and the VL framework derived from IGKV3D-20*1 (SEQ ID NO: 126).

6. The antibody or the antigen binding fragment thereof of claim 5, comprising
   a) a heavy chain variable region (VH) of SEQ ID NO: 118;
   b) a light chain variable region (VL) of SEQ ID NO: 119; or
   c) the VH and the VL of SEQ ID NOs: 118 and 119, respectively.

7. The antibody or the antigen binding fragment thereof of claim 6, comprising the VH of SEQ ID NO: 10 and the VL of SEQ ID NO:16.

8. The antibody or the antigen binding fragment thereof of claim 1, comprising
   a) the HCDR1, the HCDR2, the HCDR3, the LCDR1, the LCDR2 and the LCDR3 of SEQ ID NOs: 2, 3, 4, 5, 6 and 7, respectively;
   b) the VH of SEQ ID NO:10 and the VL of SEQ ID NO: 16; and/or
   c) a heavy chain (HC) of SEQ ID NO: 22 and a light chain (LC) of SEQ ID NO: 28.

9. The antibody or the antigen binding fragment thereof of claim 1, wherein the antibody or the antigen binding fragment thereof is an agonist of PD-1 or mediates antibody-dependent cell cytotoxicity (ADCC) of PD-1 expressing cells, or both.

10. The antibody or the antigen binding fragment thereof of claim 9, wherein the PD-1 expressing cells are activated memory T cells, T follicular helper cells ($T_{FH}$) or T peripheral helper cells ($T_{PH}$), or any combination thereof.

11. The antibody or the antigen binding fragment thereof of claim 10, wherein the antibody or the antigen binding fragment thereof is an IgG1, an IgG2, and IgG3 or an IgG4 isotype.

12. The antibody or the antigen binding fragment thereof of claim 11, wherein the antibody or the antigen binding fragment thereof comprises at least one mutation in the antibody Fc that modulates binding of the antibody to an Fc receptor (FcR).

13. The antibody or the antigen binding fragment thereof of claim 12, wherein the at least one mutation in the antibody Fc, using residue numbering according to the EU index, comprises:
   a) a S267E mutation in the antibody Fc region;
   b) a S267D mutation in the antibody Fc region;
   c) a S267E/I332E mutation in the antibody Fc region;
   d) a S267E/L328F mutation in the antibody Fc region;
   e) a G236D/S267E mutation in the antibody Fc region;
   f) a P238D mutation in the antibody Fc region; or
   g) a P238D/E233D/G237D/H268D/P271G/A330R mutation in the antibody Fc region.

14. The antibody or the antigen binding fragment thereof of claim 7, wherein the antibody comprises the HC of SEQ ID NO: 22 and the LC of SEQ ID NO: 28.

15. The antibody or the antigen binding fragment thereof of claim 14, wherein the antibody VH and the antibody VL or the antibody HC and the antibody LC are encoded by a polynucleotide comprising the polynucleotide sequence of SEQ ID NOs: 13 and 19, respectively.

16. The antibody or the antigen binding fragment thereof of claim 1, wherein the antibody or the antigen binding fragment thereof has a biantennary glycan structure with a fucose content of about between 1% to about 15%.

17. A pharmaceutical composition comprising the antibody or the antigen binding fragment thereof of claim 1.

18. A kit comprising the antibody or the antigen binding fragment thereof of claim 1.

19. An immunoconjugate comprising the antibody or the antigen binding fragment of claim 7 conjugated to a heterologous molecule.

* * * * *